US012649787B2

(12) United States Patent
Gu et al.

(10) Patent No.: US 12,649,787 B2
(45) Date of Patent: Jun. 9, 2026

(54) METHODS AND COMPOSITIONS RELATING TO ANTI-MFSD2A ANTIBODIES

(71) Applicant: PRESIDENT AND FELLOWS OF HARVARD COLLEGE, Cambridge, MA (US)

(72) Inventors: Chenghua Gu, Cambridge, MA (US); Benjamin Andreone, Cambridge, MA (US); Urs Langen, Cambridge, MA (US)

(73) Assignee: PRESIDENT AND FELLOWS OF HARVARD COLLEGE

( * ) Notice: Subject to any disclaimer, the term of this patent is extended or adjusted under 35 U.S.C. 154(b) by 516 days.

(21) Appl. No.: 18/269,018

(22) PCT Filed: Jan. 14, 2022

(86) PCT No.: PCT/US2022/012425
§ 371 (c)(1),
(2) Date: Jun. 22, 2023

(87) PCT Pub. No.: WO2022/155410
PCT Pub. Date: Jul. 21, 2022

(65) Prior Publication Data
US 2024/0117033 A1     Apr. 11, 2024

Related U.S. Application Data

(60) Provisional application No. 63/137,966, filed on Jan. 15, 2021.

(51) Int. Cl.
| | |
|---|---|
| *C07K 16/28* | (2006.01) |
| *A61K 38/00* | (2006.01) |
| *A61K 39/00* | (2006.01) |
| *A61K 47/68* | (2017.01) |
| *C07K 14/705* | (2006.01) |
| *C07K 14/725* | (2006.01) |

(52) U.S. Cl.
CPC .......... *C07K 16/28* (2013.01); *A61K 47/6849* (2017.08); *C07K 14/7051* (2013.01); *A61K 38/00* (2013.01); *A61K 39/00* (2013.01); *C07K 2317/24* (2013.01); *C07K 2317/31* (2013.01)

(58) Field of Classification Search
None
See application file for complete search history.

(56) References Cited

U.S. PATENT DOCUMENTS

| | | |
|---|---|---|
| 10,175,256 B2 | 1/2019 | Silver et al. |
| 2005/0170391 A1 | 8/2005 | Zerangue |
| 2008/0038237 A1 | 2/2008 | Sapolsky et al. |
| 2008/0287341 A1 | 11/2008 | Chen |
| 2010/0199362 A1 | 8/2010 | Mcmahon et al. |
| 2011/0123530 A1 | 5/2011 | Arron et al. |
| 2011/0287974 A1 | 11/2011 | Benvenisty et al. |

| | | |
|---|---|---|
| 2012/0058108 A1 | 3/2012 | Krohn et al. |
| 2012/0269720 A1 | 10/2012 | Silver |
| 2014/0010861 A1 | 1/2014 | Bancel et al. |
| 2016/0120893 A1* | 5/2016 | Gu ......................... A61P 25/00 514/50 |
| 2018/0238875 A1 | 8/2018 | Huang |
| 2019/0277866 A1 | 9/2019 | Silver et al. |
| 2019/0293647 A1 | 9/2019 | Huang |

FOREIGN PATENT DOCUMENTS

| | | |
|---|---|---|
| CN | 109893662 A | 6/2019 |
| WO | 2004/058146 A1 | 7/2004 |
| WO | 2015/048554 A1 | 4/2015 |
| WO | 2018196011 A1 | 11/2018 |

OTHER PUBLICATIONS

Zhang et al. MFSD2A potentiates gastric cancer response to anti-PD-1 immunotherapy by reprogramming the tumor microenvironment to activate T cell response. Cancer Communications. 2023;43:1097-111. (Year: 2023).*
Spinola et al. Research Open Access MFSD2A is a novel lung tumor suppressor gene modulating cell cycle and matrix attachment. Molecular Cancer 2010, 9:62. (Year: 2010).*
Sarkaria et al. "Is the blood-brain barrier really disrupted in all glioblastomas? A critical assessment of existing clinical data." Neuro-oncology 20(2): 184-191 (2018).
Sohet et al. "Genetic mouse models to study blood-brain barrier development and function." Fluids and Barriers of the CNS 10(1): 3 pp. 1-18 (2013).
Sprowls et al. "Improving CNS Delivery to Brain Metastases by Blood-Tumor Barrier Disruption." Trends in Cancer 5(8): 495-505 (2019).
Steele, "Tunicamycin Enhances Neuroinvasion and Pathogenicity in Mice With Venezuelan Equine Encephalitis Virus" PhD Dissertation of Uniformed Services University of the Health Sciences, published 2003.
Stolp et al., "Role of developmental inflammation and blood-brain barrier dysfunction in neurodevelopmental and neurodegenerative diseases." Neuropathology and Applied Neurobiology 35(2):132-146 (2009).
Tiwary et al. "Metastatic Brain Tumors Disrupt the Blood-Brain Barrier and Alter Lipid Metabolism by Inhibiting Expression of the Endothelial Cell Fatty Acid Transporter Mfsd2a." Scientific Reports 8(8267): 1-13 (2018).
Toufaily et al., "MFSD2a, the Syncytin-2 receptor, is important for trophoblast fusion." Placenta 34(1):85-88 (2013).

(Continued)

*Primary Examiner* — Maher M Haddad
(74) *Attorney, Agent, or Firm* — NIXON PEABODY LLP; David S. Resnick; Nicole D. Kling

(57) ABSTRACT

The technology described herein is directed to compositions comprising antibodies and antibody reagent that binds specifically to Mfsd2A and method of using such compositions, e.g., to increase blood-brain barrier permeability in therapeutic methods.

14 Claims, 39 Drawing Sheets

Specification includes a Sequence Listing.

(56)             References Cited

OTHER PUBLICATIONS

Vajdos et al. "Comprehensive Functional Maps of the Antigen-binding Site of an Anti-ErbB2 Antibody Obtained with Shotgun Scanning Mutagenesis." J. Mol. Biol. 320(2): 415-428 (2002).

Van Tellingen et al. "Overcoming the blood-brain tumor barrier for effective glioblastoma treatment." Drug Resistance Updates 19: 1-12 (2015).

Wang et al. "A Web-based design center for vector-based siRNA and siRNA cassette." Bioinformatics 20(11): 1818-1820 (2004).

Wang et al. "Mfsd2a-based pharmacological strategies for drug delivery across the blood-brain barrier." Pharmacological Research 104: 124-131 (2016).

Watts et al. "Gene silencing by siRNAs and antisense oligonucleotides in the laboratory and the clinic." J Pathol. 226 (2): 365-379 (2012).

Wu et al. Humanization of a Murine Monoclonal Antibody by Simultaneous Optimization of Framework and CDR Residues. J. Mol. Biol. 294(1): 151-162 (1999).

Yokose et al., "In vivo effects of tunicamycin on chondrocytes of rat mandibular condyles as revealed by lectin cytochemistry." Cell and Tissue Research 269(2):235-239 (1992).

Zheng et al., "Glut1/SLC2A1 is crucial for the development of the blood-brain barrier in vivo." Annals of Neurology 68 (6):835-844 (2010).

Abu-Safieh et al., "Mutation of IGFBP7 Causes Upregulation of BRAF/MEK/ERK Pathway and Familial Retinal Arterial Macroaneurysms", The American Journal of Human Genetics 89(2):313-319 (2011).

Accession No. N M_001349821.2 from the NCBI website:www.ncbi.nlm.nih.gov/nuccore/N M_001349821.2, retrieved on Sep. 1, 2020.

Accession No. NM_001136493.3 from the NCBI website: www.ncbi.nlm.nih.gov/nuccore/NM_001136493.3, retrieved on Sep. 1, 2020.

Accession No. NM_001287808.2 from the NCBI website:www.ncbi.nlm.nih.gov/nuccore/NM_001287808.2, retrieved on Sep. 1, 2020.

Accession No. NM_001287809.2from the NCBI website: www.ncbi.nim.nih.gov/nuccore/NM_001287809.2, retrieved on Sep. 1, 2020.

Accession No. NM_001349822.2 from the NCBI website: www.ncbi.nlm.nih.gov/nuccore/NM_001349822.2, retrieved on Sep. 1, 2020.

Accession No. NM_001349823.2 from the NCBI website: www.ncbi.nlm.nih.gov/nuccore/NM_001349823.2, retrieved on Sep. 1, 2020.

Accession No. NM_032793.5 from the NCBI website: www.ncbi.nlm.nih.gov/nuccore/NM_032793.5, retrieved on Sep. 1, 2020.

Accession No. NR_ 109896.2 from the NCBI website: www.ncbi.nlm.nih.gov/nuccore/NR_ 109896.2, retrieved on Sep. 1, 2020.

Alaoui-Ismaili et al. "Design of second generation therapeutic recombinant bone morphogenetic proteins." Cytokine & Growth Factor Reviews 20(5-6): 501-507 (2009).

Andreone et al. "Blood-brain barrier permeability is regulated by lipid transport-dependent suppression of caveolae-mediated transcytosis." Neuron 94.3 (2017): 581-594.

Armulik et al., "Pericytes regulate the blood-brain barrier", Nature 468(7323):557-561 (2010).

Arvanitis et al. "The blood-brain barrier and blood-tumour barrier in brain tumours and metastases." Nature Reviews Cancer 20(1): 26-41 (2020).

Arziman et al. "E-RNAi: a web application to design optimized RNAi constructs." Nucleic Acids Research 33 (suppl_2): W582-W588 (2005).

Bell et al., "Pericytes control key neurovascular functions and nueronal phenotype in the adult brain and during brain aging", Neuron 68(3):409-427 (2010).

Ben-Zvi et al., "Mfsd2a is critical for the formation and function of the blood-brain barrier." Nature. May 22, 2014;509 (7501):507-11.

doi: 10.1038/nature13324. Epub May 14, 2014. PMID: 24828040; PMCID: PMC4134871.

Berger et al., "Major Facilitator Superfamily Domain-Containing Protein 2a (MFSD2A) Has Roles in Body Growth, Motor Function, and Lipid Metabolism", PLOS One 7(11):e50629 (2012).

Bowie et al. "Deciphering the Message in Protein Sequences: Tolerance to Amino Acid Substitutions." Science 247 (4948): 1306-1310 (1990).

Burgess et al. "Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue." The Journal of Cell Biology 111(5): 2129-2138 (1990).

Casset et al. "A peptide mimetic of an anti-CD4 monoclonal antibody by rational design." Biomedical and Biophysical Research Communications 307(1): 198-205 (2003).

Chen et al. "Selection and analysis of an Optimized Anti-VEGF Antibody: Crystal Structure of an Affinity-matured Fab in Complex with Antigen." J. Mol. Biol. 293(4): 865-881 (1999).

Chesney et al., "Taurine and the renal system", Journal of Biomedical Science 17(Suppl 1):S4 (2010).

Chow et al. "Gradual suppression of transcytosis governs functional blood-retinal barrier formation." Neuron 93.6 (2017): 1325-1333.

Contessa et al., "Inhibition of N-linked glycosylation disrupts receptor tyrosine kinase signaling in tumor cells." Cancer Research 68(10):3803-3809 (2008).

Cui et al. "OptiRNAi, an RNAi design tool." Computer Methods and Programs in Biomedicine 75(1): 67-73 (2004).

Daneman et al., "Pericytes are required for blood-brain barrier integrity during embryogenesis", Nature 468 (7323):562-566 (2010).

Daneman et al., "The Mouse Blood-Brain Barrier Transcriptome: A New Resource for Understanding the Development and Function of Brain Endothelial Cells", PLoS One 5(10):e13741 (2010).

De Pascalis et al. "Grafting of "Abbreviated" Complementarity-Determining Regions Containing Specificity-Determining Residues Essential for Ligand Contact to Engineer a Less Immunogenic Humanized Monoclonal Antibody." The Journal of Immunology 169(6): 3076-3084 (2002).

Delidaki et al., "Interplay of cAMP and MAPK pathways in hCG secretion and fusogenic gene expression in a trophoblast cell line" Molecular and Cellular Endocrinology 332(1-2):213-220 (2011).

Desai et al., "Blood-brain barrier pathology in Alzheimer's and Parkinson's disease: implications for drug therapy." Cell Transplantation 16(3):285-299 (2007).

Doolittle et al. "Delivery of chemotherapeutics across the blood-brain barrier: challenges and advances." Advances in Pharmacology 71 (2014): 203-243.

Dudek et al. "TROD: T7 RNAi oligo designer." Nucleic Acids Research 32(suppl_2): W121-W123 (2004).

Echeverry et al., "Peripheral nerve injury alters blood-spinal cord barrier functional and molecular integrity through a selective inflammatory pathway." Journal of Neuroscience 31(30):10819-10828 (2011).

Finnie et al., "Effect of tunicamycin on the blood-brain barrier and on endothelial cells in vitro." Journal of Comparative Pathology 102(4):363-374 (1990).

Gerstner et al., "Increased permeability of the blood-brain barrier to chemotherapy in metastatic brain tumors: establishing a treatment paradigm." Journal of Clinical Oncology 25(16):2306-2312 (2007).

Gu, "Molecular mechanisms governing the regulation of the blood-brain barrier", Barriers of the CNS Gordon Conference (2016).

Gu, "Transcytosis regulation at the blood-brain barrier", Cell Biology of the Neuron Gordon Conference (2016).

Guo et al. "Protein tolerance to random amino acid change." PNAS 101(25): 9205-9210 (2004).

Henschel et al. "DEQOR: a web-based tool for the design and quality control of siRNAs." Nucleic Acids Research 32(suppl_2): W113-W120 (2004).

Holm et al. "Functional mapping and single chain construction of the anti-cytokeratin 8 monoclonal antibody TS1." Molecular Immunology 44(6): 1075-1084 (2007).

(56)     References Cited

OTHER PUBLICATIONS

"Daily Dose of DHA" David Perlmutter MD, dated Jan. 22, 2014, Accessed on the Internet, URL: http://www.drperimutter.com/daily-dose-dha/.

Maccallum et al. "Antibody-antigen Interactions: Contact Analysis and Binding Site Topography." J. Mol. Biol. 262 (5): 732-745 (1996).

Matsui et al., "Ammonium chloride and tunicamycin are novel toxins for dopaminergic neurons and induce Parkinson's disease-like phenotypes in medaka fish." Journal of Neurochemistry 115(5):1150-1160 (2010).

Ocak et al. "Overexpression of Mfsd2a attenuates blood brain barrier dysfunction via Cav-1/Keap-1/Nrf-2/HO-1 pathway in a rat model of surgical brain injury." Experimental Neurology 326: 113203 pp. 1-15 (2020).

Pawson et al. "Assembly of Cell Regulatory Systems Through Protein Interaction Domains." Science 300(5618): 445-452 (2003).

Phoenix et al. "Medulloblastoma genotype dictates blood brain barrier phenotype." Cancer Cell 29(4): 508-522 (2016).

Qu et al., "Mfsd2a Reverses Spatial Learning and Memory Impairment Caused by Chronic Cerebral Hypoperfusion via Protection of the Blood-Brain Barrier." Front Neurosci. Jun. 16, 2020;14:461. doi: 10.3389/fnins.2020.00461. PMID: 32612494; PMCID: PMC7308492.

Reiling et al., "A haploid genetic screen identifies the major facilitator domain containing 2A (MFSD2A) transporter as a key mediator in the response to tunicamycin." PNAS 108(29):11756-11765 (2011).

Ronaldson et al., "Targeting blood-brain barrier changes during inflammatory pain: an opportunity for optimizing CNS drug delivery." Therapeutic Delivery 2(8):1015-1041 (2011).

Rudikoff et al. "Single amino acid substitution altering antigen-binding specificity." Proc. Natl. Acad. Sci. 79(2): 1979-1983 (1982).

* cited by examiner

Relion
AutoPicking
CryoSparc
2D classification

Relion
3D classification | 460956

|  | MFSd2a (EMDB-24252) (PDB 7N98) |
| --- | --- |
| Data collection and processing | |
| Magnification | 105,000 |
| Voltage (kV) | 300 |
| Electron exposure (e–/Å$^2$) | 53 |
| Defocus range (μm) | 1.2-2.5 |
| Pixel size (Å) | 0.86 |
| Symmetry imposed | C1 |
| Initial particle images (no.) | 2,471,140 |
| Final   particle images (no.) | 90,577 |
| Map resolution (Å) | 3.50 |
| FSC threshold | 0.143 |
| Map resolution range (Å) | 11.0-2.7 |

*FIG. 14*

Refinement

| | |
|---|---|
| Initial model used (PDB code) | 4M64 |
| Model resolution (Å) | 3.98 |
| FSC threshold | 0.5 |
| Model resolution range (Å) | 200-3.35 |
| Map sharpening $B$ factor (Å$^2$) | -184 |
| Model composition | |
| Non-hydrogen atoms | 3626 |
| Protein residues | 473 |
| Ligands | 0 |
| $B$ factors (Å$^2$) | |
| Protein | 139.58 |
| Ligand | - |
| R.m.s. deviations | |
| Bond lengths (Å) | 0.004 |
| Bond angles (°) | 0.716 |
| Validation | |
| MolProbity score | 2.08 |
| Clashscore | 11.62 |
| Poor rotamers (%) | 0.27 |
| Ramachandran plot | |
| Favored (%) | 91.5 |
| Allowed (%) | 8.5 |
| Disallowed (%) | 0 |

*FIG. 14 (cont.)*

TopFluor LPC (fluorescent Wfsd2a Substrate)

Cells with or without Wfsd2a expression

Control cells

Wfsd2a cells

Wfsd2a cells + inhibitor

METHODS AND COMPOSITIONS RELATING TO ANTI-MFSD2A ANTIBODIES

CROSS-REFERENCE TO RELATED APPLICATIONS

This application is a 35 U.S.C. § 371 National Phase Entry Application of International Application No. PCT/US2022/012425 filed Jan. 14, 2022, which designates the U.S. and claims benefit under 35 U.S.C. § 119 (e) of U.S. Provisional Application No. 63/137,966 filed Jan. 15, 2021, the contents of which are incorporated herein by reference in their entireties.

GOVERNMENT SUPPORT

This invention was made with government support under NS092473 and NS116820 awarded by the National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Jan. 13, 2022, is named 002806-099170WOPT_SL.txt and is 68,598 bytes in size.

TECHNICAL FIELD

The technology described herein relates to modulation of blood-brain barrier permeability, e.g., utilizing anti-Mfsd2A reagents.

BACKGROUND

It is recognized in the art that in numerous diseases affecting the central nervous system, even when the blood-brain barrier (BBB) suffers from morphological and/or molecular perturbations, that therapeutic drugs do not cross the BBB in therapeutically-effective amounts. Drugs either accumulate at very low levels in the brain, or penetration of the brain is nearly undetectable. This is attributed to limited crossing of the BBB and rapid export from the brain. The art widely recognizes that methods and approaches to promote drug penetration across the BBB is needed. This includes strategies for disruption of the BBB, e.g., the use of mannitol to increase BBB permeability had dramatic effects on the therapeutic results of methotrexate and/or rituximab treanents. Doolittle, Nancy D et al. (Advances in pharmacology (San Diego, Calif) vol. 71 (2014): 203-43. doi: 10.1016/bs.apha.2014.06.002).

However, despite these advances, the mannitol method for BBB disruption is technically difficult. It requires general anesthesia, hypertonic mannitol arterial infusions, and has ~9% post-treatment seizures, and thus cannot be used frequently. Therefore, while serving as a proof of concept, these methods invite development of improved pharmacologic approaches.

SUMMARY

As described herein, the inventors have produced antibodies that bind specifically to Mfsd2A and can inhibit the function of Mfsd2A, thereby increasing BBB permeability. Accordingly, these antibodies and related compositions can be used in therapeutic methods that increase BBB permeability to permit therapeutic agents to enter (or more effectively enter) the brain and treat the diseases described herein.

In one aspect of any of the embodiments, provided herein is an antibody, antibody reagent, antigen-binding fragment thereof, or chimeric antigen receptor (CAR), that specifically binds a Mfsd2A polypeptide, said antibody reagent, antigen-binding portion thereof, or CAR comprising at least one heavy or light chain complementarity determining region (CDR) selected from the group consisting of:

(a) a heavy chain CDR1 having the amino acid sequence of SEQ ID NO: 4;

(b) a heavy chain CDR2 having the amino acid sequence of SEQ ID NO: 5;

(c) a heavy chain CDR3 having the amino acid sequence of SEQ ID NO: 6;

(d) a light chain CDR1 having the amino acid sequence of SEQ ID NO: 1;

(e) a light chain CDR2 having the amino acid sequence of SEQ ID NO: 2; and (f) a light chain CDR3 having the amino acid sequence of SEQ ID NO: 3;

or a conservative substitution variant of one or more of (a)-(f).

In some embodiments of any of the aspects, the antibody, antibody reagent, antigen-binding portion thereof, or CAR comprises heavy chain CDRs having the amino acid sequences of SEQ ID NOs: 4-6 or a conservative substitution variant of such amino acid sequence. In some embodiments of any of the aspects, the antibody, antibody reagent, antigen-binding portion thereof, or CAR comprises light chain CDRs having the amino acid sequences of SEQ ID NOs: 1-3 or a conservative substitution variant of such amino acid sequence. In some embodiments of any of the aspects, the antibody, antibody reagent, antigen-binding portion thereof, or CAR comprises heavy chain CDRs having the amino acid sequences of SEQ ID NOs: 4-6 and light chain CDRs having the amino acid sequences of SEQ ID NOs: 1-3 or a conservative substitution variant of such amino acid sequence.

In one aspect of any of the embodiments, provided herein a first antibody, antibody reagent, antigen-binding portion thereof, or CAR that specifically binds a Mfsd2A polypeptide, and can compete for binding of Mfsd2A with a second antibody comprising: heavy chain CDRs having the amino acid sequences of SEQ ID NOs: 4-6 and light chain CDRs having the amino acid sequences of SEQ ID NOs: 1-3 or a conservative substitution variant of such amino acid sequence. In some embodiments of any of the aspects, the antibody, antibody reagent, antigen-binding portion thereof, or CAR comprises at least one heavy or light chain complementarity determining region (CDR) selected from the group consisting of:

(a) a heavy chain CDR1 having the amino acid sequence of SEQ ID NO: 4;

(b) a heavy chain CDR2 having the amino acid sequence of SEQ ID NO: 5;

(c) a heavy chain CDR3 having the amino acid sequence of SEQ ID NO: 6;

(d) a light chain CDR1 having the amino acid sequence of SEQ ID NO: 1;

(e) a light chain CDR2 having the amino acid sequence of SEQ ID NO: 2; and (f) a light chain CDR3 having the amino acid sequence of SEQ ID NO: 3;

or a conservative substitution variant of one or more of (a)-(f).

In some embodiments of any of the aspects, the antibody, antibody reagent, antigen-binding portion thereof, or CAR comprises heavy chain CDRs having the amino acid sequences of SEQ ID NOs: 4-6 or a conservative substitution variant of such amino acid sequence. In some embodiments of any of the aspects, the antibody, antibody reagent, antigen-binding portion thereof, or CAR comprises light chain CDRs having the amino acid sequences of SEQ ID NOs: 1-3 or a conservative substitution variant of such amino acid sequence. In some embodiments of any of the aspects, the antibody, antibody reagent, antigen-binding portion thereof, or CAR heavy chain CDRs having the amino acid sequences of SEQ ID NOs: 4-6 and light chain CDRs having the amino acid sequences of SEQ ID NOs: 1-3 or a conservative substitution variant of such amino acid sequence.

In some embodiments of any of the aspects, the antibody, antibody reagent, antigen-binding portion thereof, or CAR comprises a heavy chain variable domain comprising SEQ ID NO: 12 or a light chain variable domain comprising SEQ ID NO: 11. In some embodiments of any of the aspects, the antibody, antibody reagent, antigen-binding portion thereof, or CAR comprises a heavy chain variable domain comprising SEQ ID NO: 12 and a light chain variable domain comprising SEQ ID NO: 11. In some embodiments of any of the aspects, the antibody, antibody reagent, antigen-binding portion thereof, or CAR comprises the sequence of SEQ ID NO: 7.

In some embodiments of any of the aspects, the antibody, antibody reagent, antigen-binding portion thereof, or CAR comprises a conservative substitution in a sequence not comprised by a CDR. In some embodiments of any of the aspects, the antibody, antibody reagent, antigen-binding portion thereof or CAR is fully human or fully humanized. In some embodiments of any of the aspects, the antibody, antibody reagent, antigen-binding portion thereof, or CAR is fully humanized except for the CDR sequences. In some embodiments of any of the aspects, the antibody, antibody reagent, antigen-binding portion thereof, or CAR is selected from the group consisting of: an immunoglobulin molecule, a monoclonal antibody, a chimeric antibody, a CDR-grafted antibody, a humanized antibody, a Fab, a Fab', a F(ab')2, a Fv, a disulfide linked Fv, a scFv, a single domain antibody, a diabody, a multispecific antibody, a dual specific antibody, an anti-idiotypic antibody, and a bispecific antibody.

In one aspect of any of the embodiments, provided herein is a composition, kit, or combination comprising an antibody, antibody reagent, antigen-binding portion thereof, or CAR as described herein and a central nervous system therapeutic agent. In some embodiments of any of the aspects, the antibody, antibody reagent, antigen-binding portion thereof, or CAR is conjugated to the central nervous system therapeutic agent.

In one aspect of any of the embodiments, provided herein is a nucleic acid sequence encoding the antibody, antibody reagent, antigen-binding fragment thereof, or CAR as described herein. In one aspect of any of the embodiments, provided herein is a cell comprising the antibody, antibody reagent, antigen-binding fragment thereof, CAR, or nucleic acid sequence as described herein. In one aspect of any of the embodiments, provided herein is a pharmaceutical composition comprising the antibody, antibody reagent, antigen-binding fragment thereof, CAR, composition, kit, combination, nucleic acid, or cell as described herein and a pharmaceutically acceptable carrier.

In one aspect of any of the embodiments, provided herein is a solid support comprising the antibody, antibody reagent, antigen-binding fragment thereof, or CAR as described herein. In some embodiments of any of the aspects, the antibody, antibody reagent, antigen-binding portion thereof, or CAR is detectably labeled. In some embodiments of any of the aspects, the solid support comprises a particle, a bead, a polymer, or a substrate. In one aspect of any of the embodiments, provided herein is a kit for the detection of Mfsd2A polypeptide in a sample, the kit comprising at least a first antibody, antibody reagent, antigen-binding fragment thereof, or CAR as described herein immobilized on a solid support and comprising a detectable label. In one aspect of any of the embodiments, provided herein is a molecular complex comprising at least one antibody, antibody reagent, antigen-binding fragment thereof, or CAR as described herein bound to a Mfsd2A polypeptide.

In one aspect of any of the embodiments, provided herein is a method of treatment comprising administering to a subject in need thereof an antibody, antibody reagent, antigen-binding portion thereof, CAR, composition, kit, combination, or cell as described herein. In one aspect of any of the embodiments, provided herein is an antibody, antibody reagent, antigen-binding portion thereof, CAR, composition, kit, combination, or cell as described herein for use in a method of treatment.

In some embodiments of any of the aspects, the subject is in need of treatment for a condition selected from the group consisting of: brain cancer; a brain tumor; encephalitis; hydrocephalus; Parkinson's disease; neuropathic pain; a condition treated by the administration of psychiatric drugs; a neurodegenerative disease; multiple sclerosis; Huntington's disease; Pick's disease; ALS; dementia; stroke; and Alzheimer's disease. In some embodiments of any of the aspects, the brain cancer is primary central nervous system (CNS) lymphoma (PCNSL) or glioblastoma. In some embodiments of any of the aspects, the brain tumor is a metastasis; or a metastasis of melanoma, breast, or lung cancer.

In one aspect of any of the embodiments, provided herein is a method of increasing blood-brain barrier (BBB) permeability in a subject, the method comprising administering to the subject an antibody, antibody reagent, antigen-binding portion thereof, CAR, composition, kit, combination, or cell as described herein.

BRIEF DESCRIPTION OF THE DRAWINGS

FIGS. 1A-1C depict the overall structure and functional characterization of Mfsd2a. FIG. 1A. Uptake activities of mouse Mfsd2a. The transport activity was normalized to the wild-type transporter (WT) (mean±s.e.m., n=6). FIG. 1B. The cryo-EM map of Mfsd2a, with N- and C-domains differentiated. FIG. 1C depicts the architecture of Mfsd2a. The ribbon representations of Mfsd2a are viewed from the extracellular side (top) and from the membrane (bottom). N- and C-domains are differentiated.

FIG. 2A. Mfsd2a viewed from membrane (left) or extracellular side (right). Key extracellular elements are highlighted. FIG. 2B. Uptake activities for mutations that break disulfide. The activities are normalized to that of the WT (mean±s.e.m., n=3). FIG. 2C. Slab view of Mfsd2a showing a partially outward-open conformation, viewed from membrane (left) or extracellular side (right). The central cavity and lateral openings are labeled from the extracellular view. The surface is colored by electrostatic potential ($-5$ kT e$^{-1}$; $+5$ kT e$^{-1}$). FIG. 2D. Uptake activities of Mfsd2a variants with point mutations at cavity-lining residues. The activities are normalized to that of the WT (mean±s.e.m., n=6). FIG. 2E. Residues lining cavity bottom. Residues are shown as sticks.

FIG. 3A. Cryo-EM map of Mfsd2a. The densities attributed to lipids at the lateral openings are indicated. FIG. 3B. Zoomed in view of lipid density between TM5 and TM8. The densities attributed to the lipid are shown as mesh. A LPC is tentatively modeled in the density. FIG. 3C. Uptake activities of Mfsd2a variants with point mutations in the lateral opening regions that surround the lipid density. The activities are normalized to that of the WT (mean±s.e.m., n=6). FIG. 3D. Zoomed in view of the lipid density between TM2-TM11. The densities attributed to the lipid are shown as mesh.

FIG. 4A. The proposed Na$^+$-binding site. Residues in the binding site are shown as sticks. FIG. 4B. The density map around the proposed Na$^+$-binding site. The density map is shown as mesh. The proposed Na$^+$ position is represented as a yellow circle. FIG. 4C. The aggregated sodium positions from ten MD simulations superimposed with the Mfsd2a cryo-EM structure. Na$^+$ ions bound at the Na1 site are shown as spheres and Na$^+$ ions bound at the Na2 site are shown as spheres. All other Na$^+$ ions are shown as gray spheres. The initial position of Na$^+$ in the Na1 site is shown as a circle. FIG. 4D. The coordination of the sodium bound at the Na1 site (sphere) in a representative simulation frame. The coordination is indicated by dashed lines. FIG. 4E. Uptake activities of Mfsd2a variants with point mutations in the Na$^+$-binding sites. The activities are normalized to that of the WT (mean±s.e.m., n=6; WT, D96 and control are the same as in FIG. 1A).

FIG. 5A. Close-up view of S170. S170 and R190, shown as sticks, are within hydrogen-bond distance. FIG. 5B. Zoomed-in view of S343, which is near the helical bent on TM8 that gives rise to a lateral opening. FIG. 5C. Uptake activities of mouse Mfsd2a variants with point mutations at equivalent positions to those that underlie human pathologic mutations that cause microcephaly syndromes. Uptake activities are normalized to that of the WT (mean±s.e.m., n=6).

FIGS. 6A-6D depict the biochemical and functional characterizations of Mfsd2a. FIG. 6A depicts size-exclusion chromatography profile of Mfsd2a. FIG. 6B depicts size-exclusion chromatography profile of Mfsd2a in complex with scFv. FIG. 6C. SDS-PAGE analysis of the purified Mfsd2a-scFv complex. FIG. 6D. Uptake activity of Q67H used for structural studies. The transport activity was normalized to that of the WT (mean±s.e.m., n=4).

FIGS. 7A-7F depict single-particle cryo-EM analysis of Mfsd2a. FIG. 7A. Representative cryo-EM image of Mfsd2a. FIG. 7B. 2D class averages of Mfsd2a in CryoSparc FIG. 7C. The workflow of classification and refinement. FIG. 7D. Angle distributions of the particles for the final reconstruction. FIG. 7E. Local resolution of the Mfd2a map calculated by MonoRes61. FIG. 7F Fourier shell correlation (FSC) of the final reconstruction as a function of resolution. Lighter line: gold-standard FSC curve between two half maps from masked Mfsd2a, with indicated resolution at FSC=0.143; Darker line: FSC curve between the final atomic model and the local map masked on Mfsd2a only, with indicated resolution FSC=0.5. FSC calculation performed by SAMUEL (SAM script).

FIG. 8 depicts representative cryo-EM density maps of Mfsd2a α-helices. EM map density for 12 transmembrane helices of Mfsd2a.

FIG. 11A. The minimum distance between the side chain oxygens of D92 and the sodium atom initially placed at the sodium binding pocket plotted over time for ten simulations. Unsmoothed traces are shown in gray and 20-ns moving averages are shown in black. FIG. 11B. The minimum distance between the side chain oxygens of D92 and the nearest sodium atom (excluding the sodium initially placed at the binding site) plotted over time for ten simulations. In simulation #2, a sodium ion originally in solution binds after ~0.5 µs and remains bound. Unsmoothed traces are shown in gray and 20-ns moving averages are shown in black. FIG. 11C. The aggregated sodium positions from simulation #2, which showed stable sodium binding at the Na2 site. Sodium ions bound at the Na1 site are shown as spheres and sodium ions bound at the Na2 site are shown as spheres. The initial position of Na$^+$ in the Na1 site is shown as a yellow circle. FIG. 11D. Sodium binding sites in a representative frame from simulation #2. Sodium-coordinating residues are shown as sticks. Sodium bound at the Na1 site is shown as a sphere and sodium bound at the Na2 site is shown as sphere. Oxygen atoms of water molecules are shown as spheres. FIG. 11E depict sodium binding sites in molecular dynamics simulations. Shaded regions indicate points in time during each simulation when a sodium ion was present at the Na1 site—in particular, points at which a sodium ion at a distance of 2-5 Å from the T95 side chain oxygen formed a salt bridge with D92 and/or D96. b. Shaded regions indicate points in time during each simulation when a sodium ion was present at the Na2 site—in particular, points at which a sodium ion at a distance of 5-8 Å from the T95 side chain oxygen formed a salt bridge with D92 and/or E159. Both panels show data for simulations under three conditions. In the first two conditions, a sodium ion is initially placed in the binding pocket suggested by the cryo-EM density, whereas in the third condition no sodium ions are initially placed in the binding pocket. The first and third conditions used a 9 Å nonbonded interaction cutoff, whereas the second used a 12 Å cutoff. Plots include equilibration as well as production phases of each simulation.

FIG. 12A. The cryo-EM map of the Mfsd2a-scFv complex. FIG. 12B. The ribbon representations of the Mfsd2a-scFv complex.

FIG. 14 depicts a table of cryo-EM data collection, refinement and validation statistics.

FIG. 16A) Schematic of cell-based Mfsd2a lipid transport assay. A fluorescent Mfsd2a substrate, TopFluor LPC, is added to HEK293 cells lacking Mfsd2a or HEK293 cells stably expressing mouse Mfsd2a. FIG. 16B) Anticipated results of Mfsd2a lipid transport assay. Control cells, which do not express Mfsd2a should not take up TopFluor LPC and thus have minimal fluorescent signal. Mfsd2a-expressing cells should take up TopFluor LPC and fluoresce green; TopFluor LPC signal in Mfsd2a cells+inhibitor should be reduced. FIG. 16C) TopFluor LPC uptake in control HEK293 cells. Control HEK293 or HEK 293 cells stably expressing mouse Mfsd2a were incubated with 100 nM TopFluor LPC for 30 minutes, then fixed and imaged with spinning-disk confocal microscopy. Little TopFluor LPC signal was observed in control cells, but strong TopFluor LPC signal was seen in Mfsd2a HEK293 cells. FIG. 16D) TopFluor LPC uptake in Mfsd2a HEK293 cells treated with D1 antibody. HEK293 cells stably expressing mouse Mfsd2a were incubated with 100 nM TopFluor LPC for 30 minutes, with or without 500 nM D1 antibody, then fixed and imaged with spinning-disk confocal microscopy. Robust TopFluor LPC signal was observed in untreated cells. This signal was attenuated in cells treated with D1 antibody, consistent with partial inhibition of lipid transport by Mfsd2a.

DETAILED DESCRIPTION

Figure 1A:
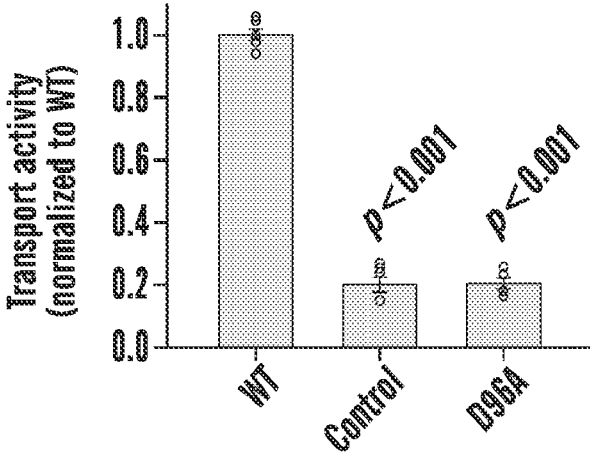

Described herein are antibody reagents that bind specifically to Mfsd2A, e.g, and inhibit Mfsd2A.

In one aspect of any of the embodiments, described herein is an antibody, antibody reagent, antigen-binding fragment thereof, or chimeric antigen receptor (CAR), that specifically binds a Mfsd2A polypeptide, said antibody reagent, antigen-binding portion thereof, or CAR comprising at least one heavy or light chain complementarity determining region (CDR) selected from the group consisting of:

- (a) a heavy chain CDR1 having the amino acid sequence of SEQ ID NO: 4;
- (b) a heavy chain CDR2 having the amino acid sequence of SEQ ID NO: 5;
- (c) a heavy chain CDR3 having the amino acid sequence of SEQ ID NO: 6;
- (d) a light chain CDR1 having the amino acid sequence of SEQ ID NO: 1;
- (e) a light chain CDR2 having the amino acid sequence of SEQ ID NO: 2; and
- (f) a light chain CDR3 having the amino acid sequence of SEQ ID NO: 3;

or a conservative substitution variant of one or more of (a)-(f).

In one aspect of any of the embodiments, described herein is a first antibody, antibody reagent, antigen-binding portion thereof, or CAR that specifically binds a Mfsd2A polypeptide, and can compete for binding of Mfsd2A with a second antibody comprising: heavy chain CDRs having the amino acid sequences of SEQ ID NOs: 4-6 and light chain CDRs having the amino acid sequences of SEQ ID NOs: 1-3 or a conservative substitution variant of such amino acid sequence.

In some embodiments of any of the aspects, an antibody, antibody reagent, antigen-binding portion thereof, or CAR described herein comprises heavy chain CDRs having the amino acid sequences of SEQ ID NOs: 4-6 or a conservative substitution variant of such amino acid sequence. In some embodiments of any of the aspects, an antibody, antibody reagent, antigen-binding portion thereof, or CAR described herein comprises heavy chain CDRs having the amino acid sequences of SEQ ID NOs: 4-6.

In some embodiments of any of the aspects, an antibody, antibody reagent, antigen-binding portion thereof, or CAR described herein comprises light chain CDRs having the amino acid sequences of SEQ ID NOs: 1-3 or a conservative substitution variant of such amino acid sequence. In some embodiments of any of the aspects, an antibody, antibody reagent, antigen-binding portion thereof, or CAR described herein comprises light chain CDRs having the amino acid sequences of SEQ ID NOs: 1-3.

In some embodiments of any of the aspects, an antibody, antibody reagent, antigen-binding portion thereof, or CAR described herein comprises heavy chain CDRs having the amino acid sequences of SEQ ID NOs: 4-6 and light chain CDRs having the amino acid sequences of SEQ ID NOs: 1-3 or a conservative substitution variant of such amino acid sequence. In some embodiments of any of the aspects, an antibody, antibody reagent, antigen-binding portion thereof, or CAR described herein comprises heavy chain CDRs having the amino acid sequences of SEQ ID NOs: 4-6 and light chain CDRs having the amino acid sequences of SEQ ID NOs: 1-3.

In some embodiments of any of the aspects, the antibody, antibody reagent, antigen-binding portion thereof, or CAR comprises a heavy chain variable domain comprising SEQ ID NO: 12 or a light chain variable domain comprising SEQ ID NO: 11. In some embodiments of any of the aspects, the antibody, antibody reagent, antigen-binding portion thereof, or CAR comprises a heavy chain variable domain comprising SEQ ID NO: 12 and a light chain variable domain comprising SEQ ID NO: 11. In some embodiments of any of the aspects, an antibody, antibody reagent, antigen-binding portion thereof, or CAR described herein comprises the sequence of SEQ ID NO: 7.

As used herein, the term "antibody" refers to immunoglobulin molecules and immunologically active portions of immunoglobulin molecules, i.e., molecules that contain an antigen binding site that immunospecifically binds an antigen. The term also refers to antibodies comprised of two immunoglobulin heavy chains and two immunoglobulin light chains as well as a variety of forms including full length antibodies and antigen-binding portions thereof, including, for example, an immunoglobulin molecule, a monoclonal antibody, a chimeric antibody, a CDR-grafted antibody, a humanized antibody, a Fab, a Fab', a F(ab')2, a Fv, a disulfide linked Fv, a scFv, a single domain antibody (dAb), a diabody, a multispecific antibody, a dual specific antibody, an anti-idiotypic antibody, a bispecific antibody, a functionally active epitope-binding portion thereof, and/or bifunctional hybrid antibodies.

Each heavy chain is composed of a variable region of said heavy chain (abbreviated here as HCVR or VH) and a constant region of said heavy chain. The heavy chain constant region consists of three domains CH1, CH2 and CH3. Each light chain is composed of a variable region of said light chain (abbreviated here as LCVR or VL) and a constant region of said light chain. The light chain constant region consists of a CL domain. The VH and VL regions may be further divided into hypervariable regions referred to as complementarity-determining regions (CDRs) and interspersed with conserved regions referred to as framework regions (FR). Each VH and VL region thus consists of three CDRs and four FRs which are arranged from the N terminus to the C terminus in the following order: FR1, CDR1, FR2, CDR2, FR3, CDR3, FR4. This structure is well known to those skilled in the art.

As used herein, the term "CDR" refers to the complementarity determining regions within antibody variable sequences. The exact boundaries of these CDRs have been defined differently according to different systems. CDRs may be defined according to the Kabat system (see Kabat, E. A. et al., 1991, "Sequences of Proteins of Immunological Interest", 5th edit., NIH Publication no. 91-3242, U.S. Department of Health and Human Services). Other systems may be used to define CDRs, which as the system devised by Chothia et al (see Chothia, C. & Lesk, A. M., 1987, "Canonical structures for the hypervariable regions of immunoglobulins", J. Mol. Biol., 196, 901-917) and the IMGT system (see Lefranc, M. P., 1997, "Unique database numbering system for immunogenetic analysis", Immunol. Today, 18, 50). An antibody typically contains 3 heavy chain CDRs and 3 light chain CDRs. The term CDR or CDRs is used here to indicate one or several of these regions. A person skilled in the art is able to readily compare the different systems of nomenclature and determine whether a particular sequence may be defined as a CDR. The methods and compositions used herein may utilize CDRs defined according to any of these systems.

The term "antigen-binding portion" of an antibody refers to one or more portions of an antibody as described herein, said one or more portions still having the binding affinities as defined above herein. Portions of a complete antibody have been shown to be able to carry out the antigen-binding function of an antibody. In accordance with the term "antigen-binding portion" of an antibody, examples of binding portions include (i) an Fab portion, i.e., a monovalent portion composed of the VL, VH, CL and CH1 domains; (ii) an F(ab')2 portion, i.e., a bivalent portion comprising two Fab portions linked to one another in the hinge region via a disulfide bridge; (iii) an Fd portion composed of the VH and CH1 domains; (iv) an Fv portion composed of the FL and VH domains of a single arm of an antibody; and (v) a dAb portion consisting of a VH domain or of VH, CH1, CH2, DH3, or VH, CH2, CH3 (dAbs, or single domain antibodies, comprising only $V_L$ domains have also been shown to specifically bind to target epitopes).

Although the two domains of the Fv portion, namely VL and VH, are encoded by separate genes, they may further be linked to one another using a synthetic linker, e.g., a poly-G4S amino acid sequence ('G4S') (SEQ ID NO: 13), and recombinant methods, making it possible to prepare them as a single protein chain in which the VL and VH regions combine in order to form monovalent molecules (known as single chain Fv (ScFv)).

The term "antigen-binding portion" of an antibody is also intended to comprise such single chain antibodies. Other forms of single chain antibodies such as "diabodies" can also be included. Diabodies are bivalent, bispecific antibodies in which VH and VL domains are expressed on a single polypeptide chain, but using a linker which is too short for the two domains being able to combine on the same chain, thereby forcing said domains to pair with complementary domains of a different chain and to form two antigen-binding sites. An immunoglobulin constant domain refers to a heavy or light chain constant domain. Human IgG heavy chain and light chain constant domain amino acid sequences are known in the art.

As used herein, the term "antibody reagent" refers to a polypeptide that includes at least one immunoglobulin variable domain or immunoglobulin variable domain sequence and which specifically binds a given antigen. An antibody reagent can comprise an antibody or a polypeptide comprising an antigen-binding domain of an antibody. In some embodiments of any of the aspects, an antibody reagent can comprise a monoclonal antibody or a polypeptide comprising an antigen-binding domain of a monoclonal antibody. For example, an antibody can include a heavy (H) chain variable region (abbreviated herein as VH), and a light (L) chain variable region (abbreviated herein as VL). In another example, an antibody includes two heavy (H) chain variable regions and two light (L) chain variable regions. The term "antibody reagent" encompasses antigen-binding fragments of antibodies (e.g., single chain antibodies, Fab and sFab fragments, F(ab')2, Fd fragments, Fv fragments, scFv, and domain antibodies (dAb) fragments as well as complete antibodies.

An antibody can have the structural features of IgA, IgG, IgE, IgD, IgM (as well as subtypes and combinations thereof). Antibodies can be from any source, including mouse, rabbit, pig, rat, and primate (human and non-human primate) and primatized antibodies. Antibodies also include midibodies, humanized antibodies, chimeric antibodies, and the like.

Furthermore, an antibody, antigen-binding portion thereof, or CAR as described herein may be part of a larger immunoadhesion molecule formed by covalent or noncovalent association of said antibody or antibody portion with one or more further proteins or peptides. Relevant to such immunoadhesion molecules are the use of the streptavidin core region in order to prepare a tetrameric scFv molecule and the use of a cystein residue, a marker peptide and a C-terminal polyhistidinyl, e.g., hexahistidinyl tag ('hexahistidinyl tag') (SEQ ID NO: 14) in order to produce bivalent and biotinylated scFv molecules.

In some embodiments of any of the aspects, the antibody, antibody reagent, antigen-binding portion thereof, or CAR described herein can be an immunoglobulin molecule, a monoclonal antibody, a chimeric antibody, a CDR-grafted antibody, a humanized antibody, a Fab, a Fab', a F(ab')2, a Fv, a disulfide linked Fv, a scFv, a single domain antibody, a diabody, a multispecific antibody, a dual specific antibody, an anti-idiotypic antibody, a bispecific antibody, and a functionally active epitope-binding portion thereof.

In some embodiments of any of the aspects, the antibody or antigen-binding portion thereof is a fully human antibody. In some embodiments of any of the aspects, the antibody, antigen-binding portion thereof, is a humanized antibody or antibody reagent. In some embodiments of any of the aspects, the antibody, antigen-binding portion thereof, is a fully humanized antibody or antibody reagent. In some embodiments of any of the aspects, the antibody or antigen-binding portion thereof, is a chimeric antibody or antibody reagent. In some embodiments of any of the aspects, the antibody, antigen-binding portion thereof, is a recombinant polypeptide. In some embodiments of any of the aspects, the CAR comprises an extracellular domain that binds Mfsd2A, wherein the extracellular domain comprises a humanized or chimeric antibody or antigen-binding portion thereof.

The term "human antibody" refers to antibodies whose variable and constant regions correspond to or are derived from immunoglobulin sequences of the human germ line, as described, for example, by Kabat et al. (see Kabat, et al. (1991) Sequences of Proteins of Immunological Interest, Fifth Edition, U.S. Department of Health and Human Services, NIH Publication No. 91-3242). However, the human antibodies can contain amino acid residues not encoded by human germ line immunoglobulin sequences (for example mutations which have been introduced by random or site-specific mutagenesis in vitro or by somatic mutation in vivo), for example in the CDRs, and in particular in CDR3. Recombinant human antibodies as described herein have variable regions and may also contain constant regions derived from immunoglobulin sequences of the human germ line (see Kabat, E. A., et al. (1991) Sequences of Proteins of Immunological Interest, Fifth Edition, U.S. Department of Health and Human Services, NIH Publication No. 91-3242).

According to particular embodiments, however, such recombinant human antibodies are subjected to in-vitro mutagenesis (or to a somatic in-vivo mutagenesis, if an animal is used which is transgenic due to human Ig sequences) so that the amino acid sequences of the VH and VL regions of the recombinant antibodies are sequences which although related to or derived from VH and VL sequences of the human germ line, do not naturally exist in vivo within the human antibody germ line repertoire. According to particular embodiments, recombinant antibodies of this kind are the result of selective mutagenesis or back mutation or of both. Preferably, mutagenesis leads to an affinity to the target which is greater, and/or an affinity to non-target structures which is smaller than that of the parent antibody.

Generating a humanized antibody from the sequences and information provided herein can be practiced by those of ordinary skill in the art without undue experimentation. In one approach, there are four general steps employed to humanize a monoclonal antibody, see, e.g., U.S. Pat. Nos. 5,585,089; 6,835,823; 6,824,989. These are: (1) determining the nucleotide and predicted amino acid sequence of the starting antibody light and heavy variable domains; (2) designing the humanized antibody, i.e., deciding which antibody framework region to use during the humanizing process; (3) the actual humanizing methodologies/techniques; and (4) the transfection and expression of the humanized antibody.

Usually the CDR regions in humanized antibodies and human antibody variants are substantially identical, and more usually, identical to the corresponding CDR regions in the mouse or human antibody from which they were derived. In some embodiments of any of the aspects, it is possible to make one or more conservative amino acid substitutions of CDR residues without appreciably affecting the binding affinity of the resulting humanized immunoglobulin or human antibody variant. In some embodiments of any of the aspects, substitutions of CDR regions can enhance binding affinity.

The term "chimeric antibody" refers to antibodies which contain sequences for the variable region of the heavy and light chains from one species and constant region sequences from another species, such as antibodies having murine heavy and light chain variable regions linked to human constant regions. Humanized antibodies have variable region framework residues substantially from a human antibody (termed an acceptor antibody) and complementarity determining regions substantially from a non-human antibody, e.g., a mouse-antibody, (referred to as the donor immunoglobulin).

The constant region(s), if present, are also substantially or entirely from a human immunoglobulin. The human variable domains are usually chosen from human antibodies whose framework sequences exhibit a high degree of sequence identity with the (murine) variable region domains from which the CDRs were derived. The heavy and light chain variable region framework residues can be substantially similar to a region of the same or different human antibody sequences. The human antibody sequences can be the sequences of naturally occurring human antibodies or can be consensus sequences of several human antibodies.

In addition, techniques developed for the production of "chimeric antibodies" by splicing genes from a mouse, or other species, antibody molecule of appropriate antigen specificity together with genes from a human antibody molecule of appropriate biological activity can be used. The variable segments of chimeric antibodies are typically linked to at least a portion of an immunoglobulin constant region (Fc), typically that of a human immunoglobulin. Human constant region DNA sequences can be isolated in accordance with well-known procedures from a variety of human cells, such as immortalized B-cells. The antibody can contain both light chain and heavy chain constant regions. The heavy chain constant region can include CH1, hinge, CH2, CH3, and, sometimes, CH4 regions. For therapeutic purposes, the CH2 domain can be deleted or omitted.

Additionally, and as described herein, a recombinant humanized antibody can be further optimized to decrease potential immunogenicity, while maintaining functional activity, for therapy in humans. In this regard, functional activity means a polypeptide capable of displaying one or more known functional activities associated with a recombinant antibody, antigen-binding portion thereof, or CAR as described herein. Such functional activities include inhibiting Mfsd2A and/or permeabilizing the BBB.

Additionally, a polypeptide having functional activity means the polypeptide exhibits activity similar, but not necessarily identical to, an activity of a reference antibody, antigen-binding portion thereof, or CAR as described herein, including mature forms, as measured in a particular assay, such as, for example, a biological assay, with or without dose dependency. In the case where dose dependency does exist, it need not be identical to that of the reference antibody, antigen-binding portion thereof, or CAR, but rather substantially similar to the dose-dependence in a given activity as compared to the reference antibody, antigen-binding portion thereof, or CAR as described herein (i.e., the candidate polypeptide will exhibit greater activity, or not more than about 25-fold less, about 10-fold less, or about 3-fold less activity relative to the antibodies, antigen-binding portions, and/or CARs described herein).

In some embodiments of any of the aspects, the antibody reagents (e.g., antibodies or CARs) described herein are not naturally-occurring biomolecules. For example, a murine antibody raised against an antigen of human origin would not occur in nature absent human intervention and manipulation, e.g., manufacturing steps carried out by a human. Chimeric antibodies are also not naturally-occurring biomolecules, e.g., in that they comprise sequences obtained from multiple species and assembled into a recombinant molecule. In certain particular embodiments, the human antibody reagents described herein are not naturally-occurring biomolecules, e.g., fully human antibodies directed against a human antigen would be subject to negative selection in nature and are not naturally found in the human body.

In some embodiments of any of the aspects, the antibody, antibody reagent, antigen-binding portion thereof, and/or CAR is an isolated polypeptide. In some embodiments of any of the aspects, the antibody, antibody reagent, antigen-binding portion thereof, and/or CAR is a purified polypeptide. In some embodiments of any of the aspects, the antibody, antibody reagent, antigen-binding portion thereof, and/or CAR is an engineered polypeptide.

In some embodiments of any of the aspects, the antibody reagent or antigen-binding fragment thereof is fully human or fully humanized. In some embodiments of any of the aspects, the antibody reagent or antigen-binding fragment thereof is fully humanized except for the CDR sequences. In some embodiments of any of the aspects, the antibody reagent or antigen-binding fragment is selected from the group consisting of: an immunoglobulin molecule, a monoclonal antibody, a chimeric antibody, a CDR-grafted antibody, a humanized antibody, a Fab, a Fab', a F(ab')2, a Fv, a disulfide linked Fv, a scFv, a single domain antibody, a diabody, a multispecific antibody, a dual specific antibody, an anti-idiotypic antibody, and a bispecific antibody.

In some embodiments of any of the aspects, the antibody, antibody reagent, antigen-binding portion thereof, or CAR can comprise one or more CDRs (e.g., one CDR, two CDRs, three CDRs, four CDRs, five CDRs, or six CDRs) having the sequence of a CDR selected from SEQ ID NOs: 1-6.

In some embodiments of any of the aspects, the antibody, antibody reagent, antigen-binding portion thereof, and/or CAR as described herein can be a variant of a sequence described herein, e.g., a conservative substitution variant of an antibody polypeptide. In some embodiments of any of the aspects, the variant is a conservatively modified variant. Conservative substitution variants can be obtained by mutations of native nucleotide sequences, for example.

A "variant," as referred to herein, is a polypeptide substantially homologous to a native or reference polypeptide, but which has an amino acid sequence different from that of the native or reference polypeptide because of one or a plurality of deletions, insertions or substitutions. Variant polypeptide-encoding DNA sequences encompass sequences that comprise one or more additions, deletions, or substitutions of nucleotides when compared to a native or reference DNA sequence, but that encode a variant protein or portion thereof that retains activity, e.g., antigen-specific binding activity for the relevant target polypeptide, e.g., Mfsd2A. A wide variety of PCR-based site-specific mutagenesis approaches are also known in the art and can be applied by the ordinarily skilled artisan.

One of skill will recognize that individual substitutions, deletions or additions to a nucleic acid, peptide, polypeptide, or protein sequence which alters a single amino acid or a small percentage of amino acids in the encoded sequence is a "conservatively modified variant" where the alteration results in the substitution of an amino acid with a chemically similar amino acid and retain the ability to specifically bind the target antigen (e.g., Mfsd2A). Such conservatively modified variants are in addition to and do not exclude polymorphic variants, interspecies homologs, and alleles consistent with the disclosure.

Examples of substitution variants include conservative substitution of amino acids, e.g., in a $V_H$ or $V_L$, domain, that do not alter the sequence of a CDR. A conservative substitution in a sequence not comprised by a CDR can be a substitution relative to a wild-type or naturally-occurring sequence, e.g., human or murine framework and/or constant regions of an antibody sequence. In some embodiments of any of the aspects, a conservatively modified variant of an antibody reagent can comprise alterations other than in the CDRs, e.g., a conservatively modified variant of an antibody, antibody reagent, antigen-binding portion thereof, or CAR can comprise CDRs having the sequence of one or more of SEQ ID NOs 1-6.

A given amino acid can be replaced by a residue having similar physiochemical characteristics, e.g., substituting one aliphatic residue for another (such as Ile, Val, Leu, or Ala for one another), or substitution of one polar residue for another (such as between Lys and Arg; Glu and Asp; or Gln and Asn). Other such conservative substitutions, e.g., substitutions of entire regions having similar hydrophobicity characteristics, are well known. Polypeptides comprising conservative amino acid substitutions can be tested in any one of the assays described herein to confirm that a desired activity, e.g., antigen-binding activity and specificity of a native or reference polypeptide is retained.

Amino acids can be grouped according to similarities in the properties of their side chains (in A. L. Lehninger, in Biochemistry, second ed., pp. 73-75, Worth Publishers, New York (1975)): (1) non-polar: Ala (A), Val (V), Leu (L), Ile (I), Pro (P), Phe (F), Trp (W), Met (M); (2) uncharged polar: Gly (G), Ser (S), Thr (T), Cys (C), Tyr (Y), Asn (N), Gln (Q); (3) acidic: Asp (D), Glu (E); (4) basic: Lys (K), Arg (R), His (H). Alternatively, naturally occurring residues can be divided into groups based on common side-chain properties: (1) hydrophobic: Norleucine, Met, Ala, Val, Leu, Ile; (2) neutral hydrophilic: Cys, Ser, Thr, Asn, Gln; (3) acidic: Asp, Glu; (4) basic: His, Lys, Arg; (5) residues that influence chain orientation: Gly, Pro; (6) aromatic: Trp, Tyr, Phe. Non-conservative substitutions will entail exchanging a member of one of these classes for another class. Particular conservative substitutions include, for example; Ala into Gly or into Ser; Arg into Lys; Asn into Gln or into H is; Asp into Glu; Cys into Ser; Gln into Asn; Glu into Asp; Gly into Ala or into Pro; His into Asn or into Gln; Ile into Leu or into Val; Leu into Ile or into Val; Lys into Arg, into Gln or into Glu; Met into Leu, into Tyr or into Ile; Phe into Met, into Leu or into Tyr; Ser into Thr; Thr into Ser; Trp into Tyr; Tyr into Trp; and/or Phe into Val, into Ile or into Leu.

A variant amino acid or DNA sequence preferably is at least 90%, at least 91%, at least 92%, at least 93%, at least 94%, at least 95%, at least 96%, at least 97%, at least 98%, at least 99%, or more, identical to a native or reference sequence. The degree of homology (percent identity) between a native and a mutant sequence can be determined, for example, by comparing the two sequences using freely available computer programs commonly employed for this purpose on the world wide web (e.g., BLASTp or BLASTn with default settings).

Alterations of the native amino acid sequence can be accomplished by any of a number of techniques known to one of skill in the art. Mutations can be introduced, for example, at particular loci by synthesizing oligonucleotides containing a mutant sequence, flanked by restriction sites enabling ligation to fragments of the native sequence. Following ligation, the resulting reconstructed sequence encodes an analog having the desired amino acid insertion, substitution, or deletion. Alternatively, oligonucleotide-directed site-specific mutagenesis procedures can be employed to provide an altered nucleotide sequence having particular codons altered according to the substitution, deletion, or insertion required.

Any cysteine residue not involved in maintaining the proper conformation of the polypeptide also can be substituted, generally with serine, to improve the oxidative stability of the molecule and prevent aberrant crosslinking. Conversely, cysteine bond(s) can be added to the polypeptide to improve its stability or facilitate oligomerization.

In particular embodiments wherein an antibody, antigen-binding portion thereof, or CAR as described herein comprises at least one CDR which is not identical to the sequence of SEQ ID NOs: 1-6, the amino acid sequence of that at least one CDR can be selected by methods well known to one of skill in the art. For example, Fujii, 2004, "Antibody affinity maturation by random mutagenesis" in Methods in Molecular Biology: Antibody Engineering 248: 345-349 (incorporated by reference herein in its entirety), particularly at FIG. 2 and Section 3.3, describes methods of generating a library for any CDR of interest. This allows one of ordinary skill in the art to identify alternative CDRs, including conservative substitution variants of the specific CDR sequences described herein, which, when present in an antibody or antigen-binding portion thereof as described herein, will result in an antigen or antigen-binding portion thereof which will specifically bind to and/or inhibit Mfsd2A. The method described in Fujii et al. also permits one of ordinary skill in the art to screen for a light chain sequence which will give the desired binding behavior when combined with a known heavy chain fragment and vice versa.

In some embodiments of any of the aspects, a conservative substitution variant has at least 80%, at least 85%, at least 90%, or at least 95% sequence identity to the applicable reference sequence (e.g., to one of the variable region sequences provided herein). In some embodiments of any of the aspects, a conservative substitution variant has at least 90% sequence identity to the applicable reference sequence (e.g., to one of the variable region sequences provided herein). In some embodiments of any of the aspects, a conservative substitution variant has at least least 95% sequence identity to the applicable reference sequence (e.g., to one of the variable region sequences provided herein). In some embodiments of any of the aspects, a conservative substitution variant has at least least 95% sequence identity to the applicable reference sequence (e.g., to one of the variable region sequences provided herein) and retains the wild-type activity of the reference sequence (e.g., the ability to bind specifically to and/or to inhibit Mfsd2A).

In some embodiments of any of the aspects, a CAR comprises an extracellular domain comprising an anti-Mfsd2A antibody or antigen-binding portion thereof that binds one or more epitopes of a Mfsd2A polypeptide; a transmembrane domain, one or more intracellular co-stimulatory signaling domains, and a primary signaling domain. Exemplary anti-Mfsd2A antibodies and antigen-binding portions thereof, as well as exemplary epitopes, are described elsewhere herein.

As used herein, "chimeric antigen receptor" or "CAR" refers to an artificially constructed hybrid polypeptide comprising an antigen-binding domain (e.g., an antigen-binding portion of an antibody (e.g., a scFV)), a transmembrane domain, and a T-cell signaling and/or T-cell activation domain. CARs have the ability to redirect T-cell specificity and reactivity toward a selected target in a non-MHC-restricted manner, exploiting the antigen-binding properties of monoclonal antibodies. The non-MHC-restricted antigen recognition gives T-cells expressing CARs the ability to recognize an antigen independent of antigen processing, thus bypassing a major mechanism of tumor escape.

Moreover, when expressed in T-cells, CARs advantageously do not dimerize with endogenous T-cell receptor (TCR) alpha and beta chains. Most commonly, the CAR's extracellular binding domain is composed of a single chain variable fragment (scFv) derived from fusing the variable heavy and light regions of a murine or humanized monoclonal antibody. Alternatively, scFvs may be used that are derived from Fab's (instead of from an antibody, e.g., obtained from Fab libraries), in various embodiments, this scFv is fused to a transmembrane domain and then to an intracellular signaling domain.

"First-generation" CARs include those that solely provide CD3zeta (CD3ζ) signals upon antigen binding, "Second-generation" CARs include those that provide both costimulation (e.g., CD28 or CD 137) and activation (CD3ζ). "Third-generation" CARs include those that provide multiple costimulatory (e.g., CD28 and CD 137) domains and activation domains (e.g., CD3ζ). In various embodiments, the CAR is selected to have high affinity or avidity for the antigen. Further discussion of CARs can be found, e.g., in Maus et al. Blood 2014 123:2624-35; Reardon et al. Neuro-Oncology 2014 16:1441-1458; Hoyos et al. Haematologica 2012 97:1622; Byrd et al. J Clin Oncol 2014 32:3039-47; Maher et al. Cancer Res 2009 69:4559-4562; and Tamada et al. Clin Cancer Res 2012 18:6436-6445; each of which is incorporated by reference herein in its entirety.

In some embodiments of any of the aspects, a CAR comprises an extracellular binding domain that comprises a humanized Mfsd2A-specific binding domain; a transmembrane domain; one or more intracellular co-stimulatory signaling domains; and a primary signaling domain. As used herein, the terms, "binding domain," "extracellular domain," "extracellular binding domain," "antigen-specific binding domain," and "extracellular antigen specific binding domain," are used interchangeably and provide a CAR with the ability to specifically bind to the target antigen of interest, e.g., Mfsd2A. The binding domain may be derived either from a natural, synthetic, semi-synthetic, or recombinant source.

In some embodiments of any of the aspects, the CARs contemplated herein may comprise linker residues between the various domains, e.g., added for appropriate spacing and conformation of the molecule. In particular embodiments the linker is a variable region linking sequence. A "variable region linking sequence," is an amino acid sequence that connects the VH and VL domains and provides a spacer function compatible with interaction of the two sub-binding domains so that the resulting polypeptide retains a specific binding affinity to the same target molecule as an antibody that comprises the same light and heavy chain variable regions. CARs contemplated herein, can comprise one, two, three, four, or five or more linkers. In particular embodiments, the length of a linker is about 1 to about 25 amino acids, about 5 to about 20 amino acids, or about 10 to about 20 amino acids, or any intervening length of amino acids. In some embodiments of any of the aspects, the linker is 1, 2, 3, 4, 5, 6, 7, 8, 9, 10, 11, 12, 13, 14, 15, 16, 17, 18, 19, 20, 21, 22, 23, 24, 25, or more amino acids long.

In particular embodiments, the binding domain of the CAR is followed by one or more "spacer domains," which refers to the region that moves the antigen binding domain away from the effector cell surface to enable proper cell/cell contact, antigen binding and activation. The hinge domain may be derived either from a natural, synthetic, semi-synthetic, or recombinant source. In certain embodiments, a spacer domain is a portion of an immunoglobulin, including, but not limited to, one or more heavy chain constant regions, e.g., CH2 and CH3. The spacer domain can include the amino acid sequence of a naturally occurring immunoglobulin hinge region or an altered immunoglobulin hinge region.

The binding domain of the CAR is generally followed by one or more "hinge domains," which plays a role in positioning the antigen binding domain away from the effector cell surface to enable proper cell/cell contact, antigen binding and activation. A CAR generally comprises one or more hinge domains between the binding domain and the transmembrane domain (TM). The hinge domain may be derived either from a natural, synthetic, semi-synthetic, or recombinant source. The hinge domain can include the amino acid sequence of a naturally occurring immunoglobulin hinge region or an altered immunoglobulin hinge region. Illustrative hinge domains suitable for use in the CARs described herein include the hinge region derived from the extracellular regions of type 1 membrane proteins such as CD8α, CD4, CD28 and CD7, which may be wild-type hinge regions from these molecules or may be altered. In another embodiment, the hinge domain comprises a CD8α hinge region.

The "transmembrane domain" is the portion of the CAR that fuses the extracellular binding portion and intracellular signaling domain and anchors the CAR to the plasma membrane of the immune effector cell. The TM domain may be derived either from a natural, synthetic, semi-synthetic, or recombinant source. The TM domain may be derived from (i.e., comprise at least the transmembrane region(s) of) the alpha, beta or zeta chain of the T-cell receptor, CD3ε, CD3ζ, CD4, CD5, CD8α, CD9, CD 16, CD22, CD27, CD28, CD33, CD37, CD45, CD64, CD80, CD86, CD 134, CD137, CD152, CD 154, and PD1.

In some embodiments of any of the aspects, CARs contemplated herein comprise an intracellular signaling domain. An "intracellular signaling domain," refers to the part of a CAR that participates in transducing the message of effective CAR binding to a target antigen into the interior of the immune effector cell to elicit effector cell function, e.g., activation, cytokine production, proliferation and cytotoxic activity, including the release of cytotoxic factors to the CAR-bound targeT-cell, or other cellular responses elicited with antigen binding to the extracellular CAR domain. In some embodiments of any of the aspects, a CAR contemplated herein comprises an intracellular signaling domain that comprises one or more "co-stimulatory signaling domain" and a "primary signaling domain."

Primary signaling domains regulate primary activation of the TCR complex either in a stimulatory way, or in an inhibitory way. Primary signaling domains that act in a stimulatory manner may contain signaling motifs which are known as immunoreceptor tyrosine-based activation motifs or ITAMs. Illustrative examples of ITAM containing primary signaling domains that are of particular use in the invention include those derived from TCRζ, FcRγ, FcRβ, CD3γ, CD3δ, CD3ε, CD3ζ, CD22, CD79a, CD79b, and CD66d.

As used herein, the term, "co-stimulatory signaling domain," or "co-stimulatory domain", refers to an intracellular signaling domain of a co-stimulatory molecule. Co-stimulatory molecules are cell surface molecules other than antigen receptors or Fc receptors that provide a second signal required for efficient activation and function of T lymphocytes upon binding to antigen. Illustrative examples of such co-stimulatory molecules include CARD11, CD2, CD7, CD27, CD28, CD30, CD40, CD54 (ICAM), CD83, CD134 (OX40), CD137 (4-1BB), CD150 (SLAMF1), CD152 (CTLA4), CD223 (LAG3), CD270 (HVEM), CD273 (PD-L2), CD274 (PD-L1), CD278 (ICOS), DAP10, LAT, NKD2C SLP76, TRIM, and ZAP70. In one embodiment, a CAR comprises one or more co-stimulatory signaling domains selected from the group consisting of CD28, CD137, and CD134, and a CD3ζ primary signaling domain.

As described herein, the inventors have determined the residues and/or epitopes of Mfsd2A that are bound by inhibitory antibodies. Those residues and/or epitopes can comprise one or more of A223; V224; V225; S227; N458; Q460; Q462; S465; Q466; P467; E468; K75; V76; E77; P136; D137; F138; P139; S140; G141; T142; E143; Q234; S235; T236; A237; S238; and L239, e.g., with respect to SEQ ID NO: 9. Accordingly, in one aspect of any of the embodiments, provided herein is an antibody, antibody reagent, antigen-binding fragment thereof, or chimeric antigen receptor (CAR), that specifically binds a Mfsd2A polypeptide at one or more epitope residues selected from the group consisting of: A223; V224; V225; S227; N458; Q460;

Q462; S465; Q466; P467; E468; K75; V76; E77; P136; D137; F138; P139; S140; G141; T142; E143; Q234; S235; T236; A237; S238; and L239.

In some embodiments of any of the aspects, the one or more epitope residues comprise, consist of, or consist essentially of: A223; V224; V225; S227; N458; Q460; Q462; S465; Q466; P467; E468; K75; V76; E77; P136; D137; F138; P139; S140; G141; T142; E143; Q234; S235; T236; A237; S238; and L239. In some embodiments of any of the aspects, the one or more epitope residues comprise, consist of, or consist essentially of: A223; V224; V225; S227; N458; Q460; Q462; S465; Q466; P467; E468; K75; E77; P136; D137; F138; T142; E143; Q234; S235; T236; A237; and L239. In some embodiments of any of the aspects, the one or more epitope residues comprise, consist of, or consist essentially of: 223; V224; V225; S227; N458; Q460; Q462; S465; Q466; P467; and E468. In some embodiments of any of the aspects, the one or more epitope residues comprise, consist of, or consist essentially of: 223; V224; V225; S227; N458; Q460; Q462; S465; Q466; P467; and E468. In some embodiments of any of the aspects, the one or more epitope residues comprise, consist of, or consist essentially of: K75, V76, E77, P136, D137, F138, P139, S140, G141, T142, E143, Q234, S235, T236, A237, S238, and L239.

In some embodiments of any of the aspects, an antibody-drug conjugate is provided. In particular embodiments, an antibody-drug conjugate comprises an antibody, antibody reagent, or antigen-binding portion thereof as described herein. The drug can be, e.g., a central nervous system (CNS) therapeutic agent molecule as described elsewhere herein. In some embodiments of any of the aspects, the antibody-drug conjugate comprises a central nervous system (CNS) therapeutic agent directly conjugated and/or bound to an antibody or antigen-binding portion thereof. In some embodiments of any of the aspects, binding can be non-covalent, e.g., by hydrogen bonding, electrostatic, or van der Waals interactions; however, binding may also be covalent. By "conjugated" is meant the covalent linkage of at least two molecules. In some embodiments of any of the aspects, the composition can be an antibody-drug conjugate.

In some embodiments of any of the aspects, an antibody, antibody reagent, or antigen-binding portion thereof can be bound to and/or conjugated to multiple central nervous system (CNS) therapeutic agent molecules. In some embodiments of any of the aspects, an antibody-drug conjugate can be bound to and/or conjugated to multiple central nervous system (CNS) therapeutic agent molecules. In some embodiments of any of the aspects, the ratio of a given central nervous system (CNS) therapeutic agent molecule to an antibody or antigen-binding portion thereof can be from about 1:1 to about 1,000:1, e.g., a single antibody reagent molecule can be linked to, conjugated to, etc. from about 1 to about 1,000 individual central nervous system (CNS) therapeutic agent molecules.

In some embodiments of any of the aspects, an antibody, or antigen-binding portion thereof, and the central nervous system (CNS) therapeutic agent can be present in a scaffold material. Scaffold materials suitable for use in therapeutic compositions are known in the art and can include, but are not limited to, a nanoparticle; a matrix; a hydrogel; and a biomaterial, biocompatible, and/or biodegradable scaffold material. As used herein, the term "nanoparticle" refers to particles that are on the order of about $10^{-9}$ or one to several billionths of a meter. The term "nanoparticle" includes nanospheres; nanorods; nanoshells; and nanoprisms; these nanoparticles may be part of a nanonetwork.

The term "nanoparticles" also encompasses liposomes and lipid particles having the size of a nanoparticle. As used herein, the term "matrix" refers to a 3-dimensional structure comprising the components of a composition described herein (e.g., an antibody or antigen-binding portion thereof). Non-limiting examples of matrix structures include foams; hydrogels; electrospun fibers; gels; fiber mats; sponges; 3-dimensional scaffolds; non-woven mats; woven materials; knit materials; fiber bundles; and fibers and other material formats (See, e.g., Rockwood et al. Nature Protocols 2011 6:1612-1631 and US Patent Publications 2011/0167602; 2011/0009960; 2012/0296352; and U.S. Pat. No. 8,172,901; each of which is incorporated by reference herein in its entirety). The structure of the matrix can be selected by one of skill in the art depending upon the intended application of the composition, e.g., electrospun matrices can have greater surface area than foams.

In some embodiments of any of the aspects, the scaffold is a hydrogel. As used herein, the term "hydrogel" refers to a three-dimensional polymeric structure that is insoluble in water but which is capable of absorbing and retaining large quantities of water to form a stable, often soft and pliable, structure. In some embodiments of any of the aspects, water can penetrate in between the polymer chains of the polymer network, subsequently causing swelling and the formation of a hydrogel. In general, hydrogels are superabsorbent. Hydrogels have many desirable properties for biomedical applications. For example, they can be made nontoxic and compatible with tissue, and they are highly permeable to water, ions, and small molecules. Hydrogels are super-absorbent (they can contain over 99% water) and can be comprised of natural (e.g., silk) or synthetic polymers, e.g., PEG.

As used herein, "biomaterial" refers to a material that is biocompatible and biodegradable. As used herein, the term "biocompatible" refers to substances that are not toxic to cells. In some embodiments of any of the aspects, a substance is considered to be "biocompatible" if its addition to cells in vitro results in less than or equal to approximately 20% cell death. In some embodiments of any of the aspects, a substance is considered to be "biocompatible" if its addition to cells in vivo does not induce inflammation and/or other adverse effects in vivo. As used herein, the term "biodegradable" refers to substances that are degraded under physiological conditions. In some embodiments of any of the aspects, a biodegradable substance is a substance that is broken down by cellular machinery. In some embodiments of any of the aspects, a biodegradable substance is a substance that is broken down by chemical processes.

The central nervous system (CNS) therapeutic agent can be any agent for the treatment of any disease, provided that it is desired that the CNS therapeutic agent reaches the central nervous system. In some embodiments of any of the aspects, methods which comprise administering an antibody, antibody reagent, antigen-binding fragment thereof, or CAR as described herein, e.g., an inhibitor of Mfsd2A, to a subject can further comprise administering a CNS therapeutic agent to the subject. Non-limiting examples of such CNS therapeutic agents can include, antibiotics, antibodies, gabapentin, chemotherapeutics, anti-inflammatories, neurotransmitters, morphines, peptides, polypeptides, nucleic acids (e.g. RNAi-based therapies), psychiatric dugs, and/or therapeutic agents for the treatment of brain cancer; encephalitis; hydrocephalus; Parkinson's disease; neuropathic pain; and a condition treated by the administration of psychiatric drugs. The identity of such CNS therapeutic agents are known in the art and described, e.g. in Ghose et al. J Comb Chem 1999

1:55-68 and Pardridge. NeuroRx 2005 2:3-14; each of which is incorporated by reference herein in its entirety. In some embodiments of any of the aspects, a central nervous system therapeutic agent can inhibit the activity and/or expression of a therapeutic target gene associated with a central nervous system disease (e.g. examples of such genes are described below herein), e.g. it can be an inhibitory nucleic acid or an inhibitory antibody reagent.

In some embodiments of any of the aspects, the central nervous system therapeutic reagent is less than about 500 kDa in size. In some embodiments of any of the aspects, the central nervous system therapeutic reagent is less than 500 kDa in size. In some embodiments of any of the aspects, the central nervous system therapeutic reagent is less than about 300 kDa in size. In some embodiments of any of the aspects, the central nervous system therapeutic reagent is less than 300 kDa in size. In some embodiments of any of the aspects, the central nervous system therapeutic reagent is less than about 200 kDa in size. In some embodiments of any of the aspects, the central nervous system therapeutic reagent is less than 200 kDa in size. In some embodiments of any of the aspects, the central nervous system therapeutic reagent is less than about 70 kDa in size. In some embodiments of any of the aspects, the central nervous system therapeutic reagent is less than 70 kDa in size. In some embodiments of any of the aspects, the central nervous system therapeutic reagent can be, e.g. an enzyme, an antibody reagent, a sugar, and/or a small molecule.

In some embodiments of any of the aspects, the CNS therapeutic agent is an agent that does not normally cross the BBB. In some embodiments of any of the aspects, the CNS therapeutic agent is an agent that inefficiently crosses the BBB, e.g. a therapeutically effective dose of the agent is unable to cross the BBB when administered systemically. In some embodiments of any of the aspects, the CNS therapeutic agent is an agent that does efficiently cross the BBB, e.g. a therapeutically effective dose of the agent is able to cross the BBB when administered systemically. Administration of administering an antibody, antibody reagent, antigen-binding fragment thereof, or CAR as described herein can increase the permeability of the BBB such that, e.g. a therapeutically effective dose of the CNS therapeutic agent is able to reach the CNS or the necessary dose of the CNS therapeutic agent can be lowered.

In some embodiments of any of the aspects, the composition comprises a bi-specific antibody, e.g. an antibody that can specifically bind to both Mfsd2A and a therapeutic target. The therapeutic target can vary depending upon the disease to be treated. Targets for various diseases of the CNS are known in the art, see, e.g. Corbo and Alsono Adel. Prog Mol Biol Transl Sci 2011 98:47-83 and "Emerging Drugs and Targets for Alzheimer's Disease" Martinez (ed), 2010, RSC Press for discussion of Alzheimer's targets; Hickey and Stacy. Drug Des Devel Thera 2011 5:241-254; Coune et al. Cold Spring Harb Perspect Med 2012 2:a009431; and Douglas. Expert Review of Neurotherapeutics 2013 13:695-705 for discussion of Parkinson's disease targets. In some embodiments of any of the aspects, the subject is in need of treatment for Alzheimer's, and the therapeutic target is beta-secretase 1. In some embodiments of any of the aspects, the subject is in need of treatment for cancer or a cancer tumor and the CNS therapeutic agent is a chemotherapeutic molecule or immune checkpoint inhibitor, e.g., carboplatin; carmustine; cisplatin; cyclophosphamide; etoposide; irinotecan; lomustine; methotrexate; procarbazine; rituximab; temozolomide; bevacizumab; nivolumab; permbrolizumab; cediranib; aflibercept; cilengitide; erdafitinib; crizotinib; onartuzumab; cabozantinib; erlotinib; gefitinib; cetuximab; afatinib; dacomatinib; vemurafenib; dabrafenib; encorafenib; sorafenib; trametinib; cobimetinib; selumetinib; pimasertib; binimetinib; buparlisib; depatux-M; rinodopeptimut; temsirolimus; and vincristine. In some embodiments of any of the aspects, the subject is in need of treatment for cancer or a cancer tumor and the CNS therapeutic agent is a CAR or CAR-T cell, oncolytic virus, or a vaccine. See, e.g., Khaddour et al. Pharmaceuticals 2020 13:389; which is incorporated by reference herein in its entirety.

In some embodiments of any of the aspects, the technology described herein relates to a nucleic acid encoding an antibody, antibody reagent, antigen-binding portion thereof, or CAR as described herein. In some embodiments of any of the aspects, the nucleic acid is a cDNA.

As used herein, the term "nucleic acid" or "nucleic acid sequence" refers to a polymeric molecule incorporating units of ribonucleic acid, deoxyribonucleic acid or an analog thereof. The nucleic acid can be either single-stranded or double-stranded. A single-stranded nucleic acid can be one strand nucleic acid of a denatured double-stranded DNA. In some embodiments of any of the aspects, the nucleic acid can be a cDNA, e.g., a nucleic acid lacking introns.

Nucleic acid molecules encoding amino acid sequence variants of antibodies are prepared by a variety of methods known in the art. These methods include, but are not limited to preparation by oligonucleotide-mediated (or site-directed) mutagenesis, PCR mutagenesis, and cassette mutagenesis of an earlier prepared variant or a non-variant version of the antibody. A nucleic acid sequence encoding at least one antibody, portion or polypeptide as described herein can be recombined with vector DNA in accordance with conventional techniques, including blunt-ended or staggered-ended termini for ligation, restriction enzyme digestion to provide appropriate termini, filling in of cohesive ends as appropriate, alkaline phosphatase treatment to avoid undesirable joining, and ligation with appropriate ligases. Techniques for such manipulations can be used to construct nucleic acid sequences which encode a monoclonal antibody molecule, antibody reagent, antigen binding region thereof, or CAR.

A nucleic acid molecule, such as DNA, is said to be "capable of expressing" a polypeptide if it contains nucleotide sequences which contain transcriptional and translational regulatory information and such sequences are "operably linked" to nucleotide sequences which encode the polypeptide. An operable linkage is a linkage in which the regulatory DNA sequences and the DNA sequence sought to be expressed are connected in such a way as to permit gene expression as peptides or antibody portions in recoverable amounts. The precise nature of the regulatory regions needed for gene expression may vary from organism to organism, as is well known in the analogous art.

In some embodiments of any of the aspects, a nucleic acid encoding an antibody, antibody reagent, antigen-binding portion thereof, or CAR as described herein is comprised by a vector. In some of the aspects described herein, a nucleic acid sequence encoding an antibody, antibody reagent, antigen-binding portion thereof, or CAR as described herein, or any module thereof, is operably linked to a vector. The term "vector", as used herein, refers to a nucleic acid construct designed for delivery to a host cell or for transfer between different host cells. As used herein, a vector can be viral or non-viral. The term "vector" encompasses any genetic element that is capable of replication when associated with the proper control elements and that can transfer gene sequences to cells. A vector can include, but is not limited to, a cloning vector, an expression vector, a plasmid, phage, transposon, cosmid, chromosome, virus, virion, etc.

As used herein, the term "expression vector" refers to a vector that directs expression of an RNA or polypeptide from sequences linked to transcriptional regulatory sequences on the vector. The sequences expressed will often, but not necessarily, be heterologous to the cell. An expression vector may comprise additional elements, for example, the expression vector may have two replication systems, thus allowing it to be maintained in two organisms, for example in human cells for expression and in a prokaryotic host for cloning and amplification. The term "expression" refers to the cellular processes involved in producing RNA and proteins and as appropriate, secreting proteins, including where applicable, but not limited to, for example, transcription, transcript processing, translation and protein folding, modification and processing. "Expression products" include RNA transcribed from a gene, and polypeptides obtained by translation of mRNA transcribed from a gene. The term "gene" means the nucleic acid sequence which is transcribed (DNA) to RNA in vitro or in vivo when operably linked to appropriate regulatory sequences. The gene may or may not include regions preceding and following the coding region, e.g., 5' untranslated (5'UTR) or "leader" sequences and 3' UTR or "trailer" sequences, as well as intervening sequences (introns) between individual coding segments (exons).

As used herein, the term "viral vector" refers to a nucleic acid vector construct that includes at least one element of viral origin and has the capacity to be packaged into a viral vector particle. The viral vector can contain the nucleic acid encoding an antibody, antigen-binding portion thereof, or CAR as described herein in place of non-essential viral genes. The vector and/or particle may be utilized for the purpose of transferring any nucleic acids into cells either in vitro or in vivo. Numerous forms of viral vectors are known in the art.

By "recombinant vector" is meant a vector that includes a heterologous nucleic acid sequence, or "transgene" that is capable of expression in vivo. It should be understood that the vectors described herein can, in some embodiments, be combined with other suitable compositions and therapies. In some embodiments of any of the aspects, the vector is episomal. The use of a suitable episomal vector provides a means of maintaining the nucleotide of interest in the subject in high copy number extra chromosomal DNA thereby eliminating potential effects of chromosomal integration.

In one aspect of any of the embodiments, described herein is a cell comprising an antibody, antibody reagent, antigen-binding portion thereof, or CAR as described herein, or a nucleic acid encoding such an antibody, antibody reagent, antigen-binding portion thereof, or CAR.

The expression of an antibody, antibody reagent, antigen-binding portion thereof, or CAR as described herein can occur in either prokaryotic or eukaryotic cells. Suitable hosts include bacterial or eukaryotic hosts, including yeast, insects, fungi, bird and mammalian cells either in vivo, or in situ, or host cells of mammalian, insect, bird or yeast origin. The mammalian cell or tissue can be of human, primate, hamster, rabbit, rodent, cow, pig, sheep, horse, goat, dog or cat origin, but any other mammalian cell may be used. Further, by use of, for example, the yeast ubiquitin hydrolase system, in vivo synthesis of ubiquitin-transmembrane polypeptide fusion proteins can be accomplished. The fusion proteins so produced can be processed in vivo or purified and processed in vitro, allowing synthesis of an antibody or portion thereof as described herein with a specified amino terminus sequence.

Moreover, problems associated with retention of initiation codon-derived methionine residues in direct yeast (or bacterial) expression may be avoided. Any of a series of yeast gene expression systems incorporating promoter and termination elements from the actively expressed genes coding for glycolytic enzymes produced in large quantities when yeast is grown in mediums rich in glucose can be utilized to obtain recombinant antibodies or antigen-binding portions thereof as described herein. Known glycolytic genes can also provide very efficient transcriptional control signals. For example, the promoter and terminator signals of the phosphoglycerate kinase gene can be utilized.

Production of antibodies or antigen-binding portions thereof as described herein in insects can be achieved. For example, by infecting the insect host with a baculovirus engineered to express a transmembrane polypeptide by methods known to those of ordinary skill in the art.

In some embodiments of any of the aspects, the introduced nucleotide sequence is incorporated into a plasmid or viral vector capable of autonomous replication in the recipient host. Any of a wide variety of vectors can be employed for this purpose and are known and available to those or ordinary skill in the art. Factors of importance in selecting a particular plasmid or viral vector include: the ease with which recipient cells that contain the vector may be recognized and selected from those recipient cells which do not contain the vector; the number of copies of the vector which are desired in a particular host; and whether it is desirable to be able to "shuttle" the vector between host cells of different species.

Exemplary prokaryotic vectors known in the art include plasmids such as those capable of replication in *E. coli*, for example. Other gene expression elements useful for the expression of cDNA encoding antibodies, antigen-binding portions thereof, or CARs include, but are not limited to (a) viral transcription promoters and their enhancer elements, such as the SV40 early promoter, Rous sarcoma virus LTR, and Moloney murine leukemia virus; (b) splice regions and polyadenylation sites such as those derived from the SV40 late region, and (c) polyadenylation sites such as in SV40. Immunoglobulin cDNA genes can be expressed, e.g., using as expression elements the SV40 early promoter and its enhancer, the mouse immunoglobulin H chain promoter enhancers, SV40 late region mRNA splicing, rabbit S-globin intervening sequence, immunoglobulin and rabbit S-globin polyadenylation sites, and SV40 polyadenylation elements.

For immunoglobulin genes comprised of part cDNA, part genomic DNA, the transcriptional promoter can be human cytomegalovirus, the promoter enhancers can be cytomegalovirus and mouse/human immunoglobulin, and mRNA splicing and polyadenylation regions can be the native chromosomal immunoglobulin sequences.

In some embodiments of any of the aspects, for expression of cDNA genes in rodent cells, the transcriptional promoter is a viral LTR sequence, the transcriptional promoter enhancers are either or both the mouse immunoglobulin heavy chain enhancer and the viral LTR enhancer, the splice region contains an intron of greater than 31 bp, and the polyadenylation and transcription termination regions are derived from the native chromosomal sequence corresponding to the immunoglobulin chain being synthesized. In other embodiments, cDNA sequences encoding other proteins are combined with the above-recited expression elements to achieve expression of the proteins in mammalian cells.

A gene is assembled in, or inserted into, an expression vector. Recipient cells capable of expressing the chimeric immunoglobulin chain gene product are then transfected singly with an antibody, antigen-binding portion thereof, or CAR, or chimeric H or chimeric L chain-encoding gene, or are co-transfected with a chimeric H and a chimeric L chain gene. The transfected recipient cells are cultured under conditions that permit expression of the incorporated genes and the expressed immunoglobulin chains or intact antibodies or fragments are recovered from the culture.

In some embodiments of any of the aspects, the genes encoding the antibody, antigen-binding portion thereof, CAR, or chimeric H and L chains, or portions thereof are assembled in separate expression vectors that are then used to co-transfect a recipient T-cell. Each vector can contain two selectable genes, a first selectable gene designed for selection in a bacterial system and a second selectable gene designed for selection in a eukaryotic system, wherein each vector has a different pair of genes. This strategy results in vectors which first direct the production, and permit amplification, of the genes in a bacterial system. The genes so produced and amplified in a bacterial host are subsequently used to co-transfect a eukaryotic cell, and allow selection of a co-transfected cell carrying the desired transfected genes.

Non-limiting examples of selectable genes for use in a bacterial system are the gene that confers resistance to ampicillin and the gene that confers resistance to chloramphenicol. Selectable genes for use in eukaryotic transfectants include the xanthine guanine phosphoribosyl transferase gene (designated gpt) and the phosphotransferase gene from Tn5 (designated neo). Alternatively, the genes can be assembled on the same expression vector.

For transfection of the expression vectors and production of the antibodies, antibody reagents, antigen-binding portions thereof, or CARs described herein, the recipient T-cell line can be a myeloma cell. Myeloma cells can synthesize, assemble and secrete immunoglobulins encoded by transfected immunoglobulin genes and possess the mechanism for glycosylation of the immunoglobulin. For example, In some embodiments of any of the aspects, the recipienT-cell is the recombinant Ig-producing myeloma cell SP2/0 (ATCC #CRL 8287). SP2/0 cells produce only immunoglobulin encoded by the transfected genes. Myeloma cells can be grown in culture or in the peritoneal cavity of a mouse, where secreted immunoglobulin can be obtained from ascites fluid. Other suitable recipient cells include lymphoid cells such as B lymphocytes of human or non-human origin, hybridoma cells of human or non-human origin, or interspecies heterohybridoma cells.

An expression vector carrying a chimeric, humanized, or composite human antibody construct, antibody, antigen-binding portion thereof, and/or CAR as described herein can be introduced into an appropriate host cell by any of a variety of suitable means, including such biochemical means as transformation, transfection, conjugation, protoplast fusion, calcium phosphate-precipitation, and application with polycations such as diethylaminoethyl (DEAE) dextran, and such mechanical means as electroporation, direct microinjection, and microprojectile bombardment, as known to one of ordinary skill in the art.

Traditionally, monoclonal antibodies have been produced as native molecules in murine hybridoma lines. In addition to that technology, the methods and compositions described herein provide for recombinant DNA expression of monoclonal antibodies. This allows the production of humanized antibodies as well as a spectrum of antibody derivatives and fusion proteins in a host species of choice. The production of antibodies in bacteria, yeast, transgenic animals and chicken eggs are also alternatives for hybridoma-based production systems. The main advantages of transgenic animals are potential high yields from renewable sources.

In one aspect, a cell comprising an isolated antibody, antigen-binding portion thereof, or CAR as described herein is provided. In some embodiments of any of the aspects, the isolated antibody, antigen-binding portion thereof, or CAR as described herein is expressed on the cell surface. In some embodiments of any of the aspects, the cell comprises a nucleic acid encoding an isolated antibody, antigen-binding portion thereof, or CAR as described herein.

In some embodiments of any of the aspects, the cell is an immune cell. As used herein, "immune cell" refers to a cell that plays a role in the immune response. Immune cells are of hematopoietic origin, and include lymphocytes, such as B-cells and T-cells; natural killer cells; myeloid cells, such as monocytes, macrophages, eosinophils, mast cells, basophils, and granulocytes. In some embodiments of any of the aspects, the cell is a T-cell; a NK cell; a NKT-cell; lymphocytes, such as B-cells and T-cells; and myeloid cells, such as monocytes, macrophages, eosinophils, mast cells, basophils, and granulocytes.

In particular embodiments, a cell (e.g., an immune cell) is transduced with a retroviral vector, e.g., a lentiviral vector, encoding a CAR. For example, an immune effector cell is transduced with a vector encoding a CAR that comprises an anti-Mfsd2A antibody or antigen binding portion thereof that binds a Mfsd2A polypeptide, with an intracellular signaling domain of CD3ζ, CD28, 4-1BB, Ox40, or any combinations thereof. Thus, these transduced cells can elicit a CAR-mediated cytotoxic response.

Retroviruses are a common tool for gene delivery. In particular embodiments, a retrovirus is used to deliver a polynucleotide encoding a chimeric antigen receptor (CAR) to a cell. As used herein, the term "retrovirus" refers to an RNA virus that reverse transcribes its genomic RNA into a linear double-stranded DNA copy and subsequently covalently integrates its genomic DNA into a host genome. Once the virus is integrated into the host genome, it is referred to as a "provirus." The provirus serves as a template for RNA polymerase II and directs the expression of RNA molecules which encode the structural proteins and enzymes needed to produce new viral particles.

Illustrative retroviruses suitable for use in particular embodiments, include, but are not limited to: Moloney murine leukemia virus (M-MuLV), Moloney murine sarcoma virus (MoMSV), Harvey murine sarcoma virus (Ha-MuSV), murine mammary tumor virus (MuMTV), gibbon ape leukemia virus (GaLV), feline leukemia virus (FLV), spumavirus, Friend murine leukemia virus, Murine Stem Cell Virus (MSCV) and Rous Sarcoma Virus (RSV)) and lentivirus.

As used herein, the term "lentivirus" refers to a group (or genus) of complex retroviruses. Illustrative lentiviruses include, but are not limited to: HIV (human immunodeficiency virus; including HIV type 1, and HIV type 2); visna-maedi virus (VMV) virus; the caprine arthritis-encephalitis virus (CAEV); equine infectious anemia virus (EIAV); feline immunodeficiency virus (FIV); bovine immune deficiency virus (BIV); and simian immunodeficiency virus (SIV). In one embodiment, HIV based vector backbones (i.e., HIV cis-acting sequence elements) are preferred. In particular embodiments, a lentivirus is used to deliver a polynucleotide comprising a CAR to a cell.

Retroviral vectors and more particularly lentiviral vectors may be used in practicing particular embodiments of the present invention. Accordingly, the term "retrovirus" or "retroviral vector", as used herein is meant to include "lentivirus" and "lentiviral vectors" respectively.

In one aspect, described herein is a kit comprising a composition as described herein, e.g., a composition comprising an antibody, antibody reagent, antigen-binding portion thereof, or CAR as described herein, or a nucleic acid or cell as described herein. A kit is any manufacture (e.g., a package or container) comprising at least one reagent, e.g., an antibody, the manufacture being promoted, distributed, or sold as a unit for performing the methods described herein. In some embodiments of any of the aspects, the antibody, antibody reagent, antigen-binding fragment thereof as described herein or a nucleic acid or cell as described herein is immobilized on a solid support. In some embodiments of any of the aspects, the solid support comprises a particle, a bead, a polymer, or a substrate. In some embodiments of any of the aspects, the antibody, antibody reagent or antigen-binding fragment thereof or a nucleic acid or cell as described herein is detectably labeled.

In some embodiments of any of the aspects, the kit can further comprise a central nervous system therapeutic agent. In some embodiments of any of the aspects, the antibody, antibody reagent, antigen-binding fragment thereof, or CAR is conjugated to a central nervous system therapeutic agent.

The kits described herein can optionally comprise additional components useful for performing the methods described herein. By way of example, the kit can comprise fluids (e.g., buffers) suitable for composition comprising an antibody, antigen-binding portion thereof, or CAR as described herein, an instructional material which describes performance of a method as described herein, and the like. A kit can further comprise devices and/or reagents for delivery of the composition as described herein. Additionally, the kit may comprise an instruction leaflet and/or may provide information as to the relevance of the obtained results.

In one aspect of any of the embodiments, described herein is a composition comprising an antibody, antibody reagent, antigen-binding portion thereof, or CAR as described herein or a nucleic acid encoding an antibody, antibody reagent, antigen-binding portion thereof, or CAR as described herein or a cell as described herein. In some embodiments of any of the aspects, the composition is a pharmaceutical composition. As used herein, the term "pharmaceutical composition" refers to the active agent in combination with a pharmaceutically acceptable carrier accepted for use in the pharmaceutical industry. The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The preparation of a pharmacological composition that contains active ingredients dissolved or dispersed therein is well understood in the art and need not be limited based on formulation. Typically, such compositions are prepared as injectable either as liquid solutions or suspensions, however, solid forms suitable for solution, or suspensions, in liquid prior to use can also be prepared. The preparation can also be emulsified or presented as a liposome composition. The active ingredient can be mixed with excipients which are pharmaceutically acceptable and compatible with the active ingredient and in amounts suitable for use in the therapeutic methods described herein. Suitable excipients are, for example, water, saline, dextrose, glycerol, ethanol or the like and combinations thereof. In addition, if desired, the composition can contain minor amounts of auxiliary substances such as wetting or emulsifying agents, pH buffering agents and the like which enhance or maintain the effectiveness of the active ingredient.

The therapeutic composition as described herein can include pharmaceutically acceptable salts of the components therein. Pharmaceutically acceptable salts include the acid addition salts (formed with the free amino groups of the polypeptide) that are formed with inorganic acids such as, for example, hydrochloric or phosphoric acids, or such organic acids as acetic, tartaric, mandelic and the like. Salts formed with the free carboxyl groups can also be derived from inorganic bases such as, for example, sodium, potassium, ammonium, calcium or ferric hydroxides, and such organic bases as isopropylamine, trimethylamine, 2-ethyl-amino ethanol, histidine, procaine and the like.

Physiologically tolerable carriers are well known in the art. Exemplary liquid carriers are sterile aqueous solutions that contain no materials in addition to the active ingredients and water, or contain a buffer such as sodium phosphate at physiological pH value, physiological saline or both, such as phosphate-buffered saline. Still further, aqueous carriers can contain more than one buffer salt, as well as salts such as sodium and potassium chlorides, dextrose, polyethylene glycol and other solutes. Liquid compositions can also contain liquid phases in addition to and to the exclusion of water. Exemplary of such additional liquid phases are glycerin, vegetable oils such as cottonseed oil, and water-oil emulsions. The amount of an active agent used in the invention that will be effective in the treatment of a particular disorder or condition will depend on the nature of the disorder or condition, and can be determined by standard clinical techniques.

In some embodiments of any of the aspects, the composition comprising an antibody, antibody reagent, antigen-binding portion thereof, or CAR as described herein or a nucleic acid encoding an antibody, antibody reagent, antigen-binding portion thereof, or CAR as described herein can be a lyophilisate.

In some embodiments of any of the aspects, the technology described herein relates to a syringe or catheter, including an organ-specific catheter, comprising a therapeutically effective amount of a composition described herein.

As used herein, the phrase "therapeutically effective amount", "effective amount" or "effective dose" refers to an amount that provides a therapeutic or aesthetic benefit in the treatment, prevention, or management of condition/disorder, e.g., an amount that provides a statistically significant decrease in at least one symptom, sign, or marker of the condition/disorder. Determination of a therapeutically effective amount is well within the capability of those skilled in the art. Generally, a therapeutically effective amount can vary with the subject's history, age, condition, sex, as well as the severity and type of the medical condition in the subject, and administration of other pharmaceutically active agents.

In one aspect, the technology described herein relates to a method comprising administering an antibody, antibody reagent, antigen-binding portion thereof, or CAR as described herein or a nucleic acid encoding an antibody, antibody reagent, antigen-binding portion thereof, or CAR as described herein to a subject. In some embodiments of any of the aspects, the subject is in need of treatment for brain cancer; a brain tumor; encephalitis; hydrocephalus; Parkinson's disease; neuropathic pain; a condition treated by the administration of psychiatric drugs; a neurodegenerative disease; multiple sclerosis; Huntington's disease; Pick's disease; ALS; dementia; stroke; or Alzheimer's disease. In some embodiments of any of the aspects, the method is a method of treating a subject. In some embodiments of any of the aspects, the method is a method of treating brain cancer; a brain tumor; encephalitis; hydrocephalus; Parkinson's disease; neuropathic pain; a condition treated by the administration of psychiatric drugs; a neurodegenerative disease; multiple sclerosis; Huntington's disease; Pick's disease; ALS; dementia; stroke; and Alzheimer's disease in a subject. In some embodiments of any of the aspects, the method is a method of increasing BBB permeability in a subject.

In some embodiments of any of the aspects, the methods described herein relate to treating a subject having or diagnosed as having a disease affecting the CNS, e.g. a neurodegenerative disease or a condition treated by delivering therapeutic agents to the CNS. Subjects having a disease affecting the CNS can be identified by a physician using current methods of diagnosing such conditions. Symptoms and/or complications of such conditions which characterize these conditions and aid in diagnosis are well known in the art and include but are not limited to, lost of neural function (e.g. lack of coordination, lack of sensation, altered behaviors, inflammation of the CNS, headaches, etc). Tests that may aid in a diagnosis of such conditions can include, but are not limited to, CT scan, MRI scan, spinal tap, brain biopsy, electroencephalogram (EEG), lumbar puncture, and/or blood tests. For some conditions, a family history of the condition, or exposure to risk factors for the condition can also aid in determining if a subject is likely to have the condition or in making a diagnosis.

As used herein, the term "cancer" relates generally to a class of diseases or conditions in which abnormal cells divide without control and can invade nearby tissues. Cancer cells can also spread to other parts of the body through the blood and lymph systems. There are several main types of cancer. Carcinoma is a cancer that begins in the skin or in tissues that line or cover internal organs. Sarcoma is a cancer that begins in bone, cartilage, fat, muscle, blood vessels, or other connective or supportive tissue. Leukemia is a cancer that starts in blood-forming tissue such as the bone marrow, and causes large numbers of abnormal blood cells to be produced and enter the blood. Lymphoma and multiple myeloma are cancers that begin in the cells of the immune system. Central nervous system cancers are cancers that begin in the tissues of the brain and spinal cord.

In some embodiments of any of the aspects, the cancer is a primary cancer. In some embodiments of any of the aspects, the cancer is a malignant cancer. As used herein, the term "malignant" refers to a cancer in which a group of tumor cells display one or more of uncontrolled growth (i.e., division beyond normal limits), invasion (i.e., intrusion on and destruction of adjacent tissues), and metastasis (i.e., spread to other locations in the body via lymph or blood). As used herein, the term "metastasize" refers to the spread of cancer from one part of the body to another. A tumor formed by cells that have spread is called a "metastatic tumor" or a "metastasis." The metastatic tumor contains cells that are like those in the original (primary) tumor. As used herein, the term "benign" or "non-malignant" refers to tumors that may grow larger but do not spread to other parts of the body. Benign tumors are self-limited and typically do not invade or metastasize.

A "cancer cell" or "tumor cell" refers to an individual cell of a cancerous growth or tissue. A tumor refers generally to a swelling or lesion formed by an abnormal growth of cells, which may be benign, pre-malignant, or malignant. Most cancer cells form tumors, but some, e.g., leukemia, do not necessarily form tumors. For those cancer cells that form tumors, the terms cancer (cell) and tumor (cell) are used interchangeably. As used herein the term "neoplasm" refers to any new and abnormal growth of tissue, e.g., an abnormal mass of tissue, the growth of which exceeds and is uncoordinated with that of the normal tissues. Thus, a neoplasm can be a benign neoplasm, premalignant neoplasm, or a malignant neoplasm.

A subject that has a cancer or a tumor is a subject having objectively measurable cancer cells present in the subject's body. Included in this definition are malignant, actively proliferative cancers, as well as potentially dormant tumors or micrometastases. Cancers which migrate from their original location and seed other vital organs can eventually lead to the death of the subject through the functional deterioration of the affected organs.

Examples of cancer include but are not limited to, carcinoma, lymphoma, blastoma, sarcoma, leukemia, basal cell carcinoma, biliary tract cancer; bladder cancer; bone cancer; brain and CNS cancer; breast cancer; cancer of the peritoneum; cervical cancer; choriocarcinoma; colon and rectum cancer; connective tissue cancer; cancer of the digestive system; endometrial cancer; esophageal cancer; eye cancer; cancer of the head and neck; gastric cancer (including gastrointestinal cancer); glioblastoma (GBM); hepatic carcinoma; hepatoma; intra-epithelial neoplasm; kidney or renal cancer; larynx cancer; leukemia; liver cancer; lung cancer (e.g., small-cell lung cancer, non-small cell lung cancer, adenocarcinoma of the lung, and squamous carcinoma of the lung); lymphoma including Hodgkin's and non-Hodgkin's lymphoma; melanoma; myeloma; neuroblastoma; oral cavity cancer (e.g., lip, tongue, mouth, and pharynx); ovarian cancer; pancreatic cancer; prostate cancer; retinoblastoma; rhabdomyosarcoma; rectal cancer; cancer of the respiratory system; salivary gland carcinoma; sarcoma; skin cancer; squamous cell cancer; stomach cancer; testicular cancer; thyroid cancer; uterine or endometrial cancer; cancer of the urinary system; vulval cancer; as well as other carcinomas and sarcomas; as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia); chronic lymphocytic leukemia (CLL); acute lymphoblastic leukemia (ALL); Hairy cell leukemia; chronic myeloblastic leukemia; and post-transplant lymphoproliferative disorder (PTLD), as well as abnormal vascular proliferation associated with phakomatoses, edema (such as that associated with brain tumors), and Meigs' syndrome A "cancer cell" is a cancerous, pre-cancerous, or transformed cell, either in vivo, ex vivo, or in tissue culture, that has spontaneous or induced phenotypic changes that do not necessarily involve the uptake of new genetic material. Although transformation can arise from infection with a transforming virus and incorporation of new genomic nucleic acid, or uptake of exogenous nucleic acid, it can also arise spontaneously or following exposure to a carcinogen, thereby mutating an endogenous gene. Transformation/cancer is associated with, e.g., morphological changes, immortalization of cells, aberrant growth control, foci formation, anchorage independence, malignancy, loss of contact inhibition and density limitation of growth, growth factor or serum independence, tumor specific markers, invasiveness or metastasis, and tumor growth in suitable animal hosts such as nude mice.

In some embodiments of any of the aspects, the brain cancer is primary central nervous system (CNS) lymphoma (PCNSL) or glioblastoma. In some embodiments of any of the aspects, the brain cancer is primary central nervous system (CNS) lymphoma (PCNSL). In some embodiments of any of the aspects, the brain cancer glioblastoma. In some embodiments of any of the aspects, the brain tumor is a metastasis; or a metastasis of melanoma, breast, or lung cancer.

In one aspect, described herein is a method of treating brain cancer; a brain tumor; encephalitis; hydrocephalus; Parkinson's disease; neuropathic pain; a condition treated by the administration of psychiatric drugs; a neurodegenerative disease; multiple sclerosis; Huntington's disease; Pick's disease; ALS; dementia; stroke; or Alzheimer's disease in a subject in need thereof, the method comprising administering a cell as described herein, e.g., a cell comprising an antibody, antibody reagent, antigen-binding portion thereof, or CAR as described herein. In some embodiments of any of the aspects, the cell is an immune cell. In one aspect, described herein is a method of brain cancer; a brain tumor; encephalitis; hydrocephalus; Parkinson's disease; neuropathic pain; a condition treated by the administration of psychiatric drugs; a neurodegenerative disease; multiple sclerosis; Huntington's disease; Pick's disease; ALS; dementia; stroke; or Alzheimer's disease in a subject in need thereof, the method comprising administering a nucleic acid as described herein or an immune cell comprising the nucleic acid to the subject, wherein the subject's immune cells are caused to express the polypeptide encoded by the nucleic acid. In some embodiments of any of the aspects, the immune cell is a T-cell or is mediated by one or more T-cells. Nucleic acids can be targeted to particular cell types by, e.g., use of a cell-type specific promoter and/or a composition that selectively binds to the desired cell type. For example, conjugation of a nucleic acid to an aptamer can permit targeted delivery (McNamara, J O., et al. (2006) Nat. Biotechnol. 24:1005-1015).

In an alternative embodiment, the nucleic acid can be delivered using drug delivery systems such as a nanoparticle, a dendrimer, a polymer, liposomes, or a cationic delivery system. Positively charged cationic delivery systems facilitate binding of a nucleic acid molecule (negatively charged) and also enhance interactions at the negatively charged cell membrane to permit efficient uptake of a nucleic acid by the cell. Cationic lipids, dendrimers, or polymers can either be bound to a nucleic acid, or induced to form a vesicle or micelle (see e.g., Kim S H., et al. (2008) Journal of Controlled Release 129(2):107-116) that encases a nucleic acid. The formation of vesicles or micelles further prevents degradation of the nucleic acid when administered systemically.

Methods for making and administering cationic-nucleic acid complexes are well within the abilities of one skilled in the art. Some non-limiting examples of drug delivery systems useful for systemic delivery of nucleic acids include DOTAP Oligofectamine, "solid nucleic acid lipid particles", cardiolipin, polyethyleneimine, Arg-Gly-Asp (RGD) peptides, and polyamidoamines. In some embodiments of any of the aspects, a nucleic acid forms a complex with cyclodextrin for systemic administration. Methods for administration and pharmaceutical compositions of nucleic acids and cyclodextrins can be found in U.S. Pat. No. 7,427,605, which is herein incorporated by reference in its entirety. Targeted delivery of nucleic acids is described, for example in Ikeda and Taira Pharmaceutical Res 2006 23:1631-1640; Soutschek et al., Nature 2004 432:173-8 and Lorenze et al. Bioorg. Med. Chem. Lett. 14, 4975-4977 (2004); each of which is incorporated by reference herein in its entirety. By way of example, the nucleic acid can be targeted to immune cells by encapsulating the inhibitor in a liposome comprising ligands of receptors expressed on immune cells, e.g., TCRs. In some embodiments of any of the aspects, the liposome can comprise aptamers specific for immune cells.

In some embodiments of any of the aspects, the methods described herein relate to CAR-T-cell therapy. CAR-T-cell and related therapies relate to adoptive cell transfer of immune cells (e.g., T-cells) expressing a CAR that binds specifically to a targeted cell type (e.g., overactive immune or inflammatory cells) to treat a subject. In some embodiments of any of the aspects, the cells administered as part of the therapy can be autologous to the subject. In some embodiments of any of the aspects, the cells administered as part of the therapy are not autologous to the subject. In some embodiments of any of the aspects, the cells are engineered and/or genetically modified to express the CAR. Further discussion of CAR-T therapies can be found, e.g., in Maus et al. Blood 2014 123:2624-35; Reardon et al. Neuro-Oncology 2014 16:1441-1458; Hoyos et al. Haematologica 2012 97:1622; Byrd et al. J Clin Oncol 2014 32:3039-47; Maher et al. Cancer Res 2009 69:4559-4562; and Tamada et al. Clin Cancer Res 2012 18:6436-6445; each of which is incorporated by reference herein in its entirety.

A subject can be one who has been previously diagnosed with or identified as suffering from or having a condition in need of treatment (e.g., brain cancer; a brain tumor; encephalitis; hydrocephalus; Parkinson's disease; neuropathic pain; a condition treated by the administration of psychiatric drugs; a neurodegenerative disease; multiple sclerosis; Huntington's disease; Pick's disease; ALS; dementia; stroke; or Alzheimer's disease) or one or more complications related to such a condition, and optionally, but need not have already undergone treatment for a condition or the one or more complications related to the condition. Alternatively, a subject can also be one who has not been previously diagnosed as having a condition in need of treatment or one or more complications related to such a condition. For example, a subject can be one who exhibits one or more risk factors for a condition or one or more complications related to a condition or a subject who does not exhibit risk factors. A "subject in need" of treatment for a particular condition can be a subject having that condition, diagnosed as having that condition, or at risk of developing that condition.

As used herein, the terms "treat," "treatment," "treating," or "amelioration" when used in reference to a disease, disorder or medical condition, refer to therapeutic treatments for a condition, wherein the object is to reverse, alleviate, ameliorate, inhibit, slow down or stop the progression or severity of a symptom or condition. The term "treating" includes reducing or alleviating at least one adverse effect or symptom of a condition. Treatment is generally "effective" if one or more symptoms or clinical markers are reduced. Alternatively, treatment is "effective" if the progression of a condition is reduced or halted. That is, "treatment" includes not just the improvement of symptoms or markers, but also a cessation or at least slowing of progress or worsening of symptoms that would be expected in the absence of treatment. Beneficial or desired clinical results include, but are not limited to, alleviation of one or more symptom(s), diminishment of extent of the deficit, stabilized (i.e., not worsening) state of a immune response, delay or slowing of disease progression, and an increased lifespan as compared to that expected in the absence of treatment.

As used herein, the term "administering," refers to the placement of an agent, including but not limited to, an antibody, antibody reagent, antigen-binding portion thereof, or CAR as described herein or a nucleic acid encoding an antibody, antibody reagent, antigen-binding portion thereof, or CAR, or a cell comprising such an agent, as described herein into a subject by a method or route which results in at least partial localization of the agents at a desired site. The pharmaceutical composition comprising an antibody, antibody reagent, antigen-binding portion thereof, or CAR as described herein or a nucleic acid encoding an antibody, antibody reagent, antigen-binding portion thereof, or CAR, or a cell comprising such an agent as described herein disclosed herein can be administered by any appropriate route which results in an effective treatment in the subject.

The administration of the compositions contemplated herein may be carried out in any convenient manner, including by aerosol inhalation, injection, ingestion, transfusion, implantation or transplantation. In a preferred embodiment, compositions are administered parenterally. The phrases "parenteral administration" and "administered parenterally" as used herein refers to modes of administration other than enteral and topical administration, usually by injection, and includes, without limitation, intravascular, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion. In one embodiment, the compositions contemplated herein are administered to a subject by direct injection into, e.g., the CNS.

It can generally be stated that a pharmaceutical composition comprising the cells, e.g., T-cells or immune cells, described herein may be administered at a dosage of $10^2$ to $10^{10}$ cells/kg body weight, preferably $10^5$ to $10^6$ cells/kg body weight, including all integer values within those ranges. The number of cells will depend upon the ultimate use for which the composition is intended as will the type of cells included therein. For uses provided herein, the cells are generally in a volume of a liter or less, can be 500 mLs or less, even 250 mLs or 100 mLs or less. Hence the density of the desired cells is typically greater than $10^6$ cells/ml and generally is greater than $10^7$ cells/ml, generally $10^8$ cells/ml or greater. The clinically relevant number of immune cells can be apportioned into multiple infusions that cumulatively equal or exceed $10^5$, $10^6$, $10^7$, $10^8$, $10^9$, $10^{10}$, $10^{11}$, or $10^{12}$ cells.

In some aspects of the present invention, particularly since all the infused cells will be redirected to a particular target antigen, lower numbers of cells, in the range of $10^6$/kilogram ($10^6$-$10^{11}$ per patient) may be administered. CAR expressing cell compositions may be administered multiple times at dosages within these ranges. In some embodiments of any of the aspects, the dosage can be from about $1\times10^5$ cells to about $1\times10^8$ cells per kg of body weight. In some embodiments of any of the aspects, the dosage can be from about $1\times10^6$ cells to about $1\times10^7$ cells per kg of body weight. In some embodiments of any of the aspects, the dosage can be about $1\times10^6$ cells per kg of body weight. In some embodiments of any of the aspects, one dose of cells can be administered. In some embodiments of any of the aspects, the dose of cells can be repeated, e.g., once, twice, or more. In some embodiments of any of the aspects, the dose of cells can be administered on, e.g., a daily, weekly, or monthly basis.

The dosage ranges for the agent depend upon the potency, and encompass amounts large enough to produce the desired effect e.g., slowing of disease progression or a reduction in disease activity. The dosage should not be so large as to cause unacceptable adverse side effects. Generally, the dosage will vary with the age, condition, and sex of the patient and can be determined by one of skill in the art. The dosage can also be adjusted by the individual physician in the event of any complication. In some embodiments of any of the aspects, the dosage ranges from 0.001 mg/kg body weight to 0.5 mg/kg body weight. In some embodiments of any of the aspects, the dose range is from 5 µg/kg body weight to 100 µg/kg body weight. Alternatively, the dose range can be titrated to maintain serum levels between 1 µg/mL and 1000 µg/mL. For systemic administration, subjects can be administered a therapeutic amount, such as, e.g., 0.1 mg/kg, 0.5 mg/kg, 1.0 mg/kg, 2.0 mg/kg, 2.5 mg/kg, 5 mg/kg, 10 mg/kg, 15 mg/kg, 20 mg/kg, 25 mg/kg, 30 mg/kg, 40 mg/kg, 50 mg/kg, or more.

Administration of the doses recited above can be repeated. In some embodiments of any of the aspects, the doses are given once a day, or multiple times a day, for example but not limited to three times a day. In some embodiments of any of the aspects, the doses recited above are administered daily for several weeks or months. The duration of treatment depends upon the subject's clinical progress and responsiveness to therapy.

In some embodiments of any of the aspects, the dose can be from about 2 mg/kg to about 15 mg/kg. In some embodiments of any of the aspects, the dose can be about 2 mg/kg. In some embodiments of any of the aspects, the dose can be about 4 mg/kg. In some embodiments of any of the aspects, the dose can be about 5 mg/kg. In some embodiments of any of the aspects, the dose can be about 6 mg/kg. In some embodiments of any of the aspects, the dose can be about 8 mg/kg. In some embodiments of any of the aspects, the dose can be about 10 mg/kg. In some embodiments of any of the aspects, the dose can be about 15 mg/kg. In some embodiments of any of the aspects, the dose can be from about 100 mg/m$^2$ to about 700 mg/m$^2$. In some embodiments of any of the aspects, the dose can be about 250 mg/m$^2$. In some embodiments of any of the aspects, the dose can be about 375 mg/m$^2$. In some embodiments of any of the aspects, the dose can be about 400 mg/m$^2$. In some embodiments of any of the aspects, the dose can be about 500 mg/m$^2$.

In some embodiments of any of the aspects, the dose can be administered intravenously. In some embodiments of any of the aspects, the intravenous administration can be an infusion occurring over a period of from about 10 minute to about 3 hours. In some embodiments of any of the aspects, the intravenous administration can be an infusion occurring over a period of from about 30 minutes to about 90 minutes. In some embodiments of any of the aspects, the doses are given twice a week, once a week, bikweekly, or monthly.

In some embodiments of any of the aspects, the dose can be from about 1 mg to about 2000 mg. In some embodiments of any of the aspects, the dose can be about 3 mg. In some embodiments of any of the aspects, the dose can be about 10 mg. In some embodiments of any of the aspects, the dose can be about 30 mg. In some embodiments of any of the aspects, the dose can be about 1000 mg. In some embodiments of any of the aspects, the dose can be about 2000 mg. In some embodiments of any of the aspects, the dose can be about 3 mg given by intravenous infusion daily. In some embodiments of any of the aspects, the dose can be about 10 mg given by intravenous infusion daily. In some embodiments of any of the aspects, the dose can be about 30 mg given by intravenous infusion three times per week.

A therapeutically effective amount is an amount of an agent that is sufficient to produce a statistically significant, measurable change in disease activity, disease progression, etc. Such effective amounts can be gauged in clinical trials as well as animal studies.

An agent can be administered intravenously by injection or by gradual infusion over time. Given an appropriate formulation for a given route, for example, agents useful in the methods and compositions described herein can be administered intravenously, intranasally, by inhalation, intraperitoneally, intramuscularly, subcutaneously, intracavity, and can be delivered by peristaltic means, if desired, or by other means known by those skilled in the art. It is preferred that the compounds used herein are administered orally, intravenously or intramuscularly to a patient having an autoimmune or autoinflammatory response, condition, or disorder. Local administration directly to affected sites is also specifically contemplated.

Therapeutic compositions containing at least one agent can be conventionally administered in a unit dose, for example. The term "unit dose" when used in reference to a therapeutic composition refers to physically discrete units suitable as unitary dosage for the subject, each unit containing a predetermined quantity of active material calculated to produce the desired therapeutic effect in association with the required physiologically acceptable diluent, i.e., carrier, or vehicle.

The compositions are administered in a manner compatible with the dosage formulation, and in a therapeutically effective amount. The quantity to be administered and timing depends on the subject to be treated, capacity of the subject's system to utilize the active ingredient, and degree of therapeutic effect desired.

Precise amounts of active ingredient required to be administered depend on the judgment of the practitioner and are particular to each individual. However, suitable dosage ranges for systemic application are disclosed herein and depend on the route of administration. Suitable regimes for administration are also variable, but are typified by an initial administration followed by repeated doses at one or more hour intervals by a subsequent injection or other administration. Alternatively, continuous intravenous infusion sufficient to maintain concentrations in the blood in the ranges specified for in vivo therapies are contemplated.

In some embodiments of any of the aspects, the methods further comprise administering the pharmaceutical composition described herein along with one or more central nervous system therapeutic agents, cancer therapeutic agents, biologics, drugs, or treatments as part of a combinatorial therapy. Examples of central nervous system therapeutic agents and cancer therapeutic agents are provided elsewhere herein.

In some embodiments of the methods described herein, the methods further comprise administering one or more central nervous system therapeutic agents, cancer therapeutic agents, biologics, drugs, or treatments agents to the subject being administered the pharmaceutical composition described herein.

The efficacy of a given treatment for, e.g., cancer, can be determined by the skilled clinician. However, a treatment is considered "effective treatment," as the term is used herein, if any one or all of the signs or symptoms of e.g., the cancer is treated and/or managed in a beneficial manner or other clinically accepted symptoms are improved, e.g., by at least 10% following treatment with an agent as described herein. Efficacy can also be measured by a failure of an individual to worsen as assessed by hospitalization or need for medical interventions (i.e., progression of the disease is halted). Methods of measuring these indicators are known to those of skill in the art and/or described herein. An effective amount for the treatment of a disease means that amount which, when administered to a mammal in need thereof, is sufficient to result in effective treatment as that term is defined herein, for that disease. Efficacy of an agent can be determined by assessing physical indicators of disease progression, disease activity, etc.

The compositions and methods described herein can be administered to a subject having or diagnosed as having a disease affecting the CNS. In some embodiments of any of the aspects, the methods described herein comprise administering an effective amount of compositions described herein, to a subject in order to alleviate a symptom of a disease affecting the CNS. As used herein, "alleviating a symptom" is ameliorating any condition or symptom associated with the disease affecting the CNS. As compared with an equivalent untreated control, such reduction is by at least 5%, 10%, 20%, 40%, 50%, 60%, 80%, 90%, 95%, 99% or more as measured by any standard technique. A variety of means for administering the compositions described herein to subjects are known to those of skill in the art. Such methods can include, but are not limited to oral, parenteral, intravenous, intramuscular, subcutaneous, transdermal, airway (aerosol), pulmonary, cutaneous, injection, or intratumoral administration. Administration can be local or systemic.

The term "effective amount" as used herein refers to the amount of a composition needed to alleviate at least one or more symptom of the disease or disorder, and relates to a sufficient amount of pharmacological composition to provide the desired effect. The term "therapeutically effective amount" therefore refers to an amount of a composition that is sufficient to provide a particular effect when administered to a typical subject. An effective amount as used herein, in various contexts, would also include an amount sufficient to delay the development of a symptom of the disease, alter the course of a symptom disease (for example but not limited to, slowing the progression of a symptom of the disease), or reverse a symptom of the disease. Thus, it is not generally practicable to specify an exact "effective amount". However, for any given case, an appropriate "effective amount" can be determined by one of ordinary skill in the art using only routine experimentation.

Effective amounts, toxicity, and therapeutic efficacy can be determined by standard pharmaceutical procedures in cell cultures or experimental animals, e.g., for determining the LD50 (the dose lethal to 50% of the population) and the ED50 (the dose therapeutically effective in 50% of the population). The dosage can vary depending upon the dosage form employed and the route of administration utilized. The dose ratio between toxic and therapeutic effects is the therapeutic index and can be expressed as the ratio LD50/ED50. Compositions and methods that exhibit large therapeutic indices are preferred. A therapeutically effective dose can be estimated initially from cell culture assays. Also, a dose can be formulated in animal models to achieve a circulating plasma concentration range that includes the IC50 (i.e., the concentration of the active agent which achieves a half-maximal inhibition of symptoms) as determined in cell culture, or in an appropriate animal model. Levels in plasma can be measured, for example, by high performance liquid chromatography. The effects of any particular dosage can be monitored by a suitable bioassay, e.g., assay for BBB permeability, among others. The dosage can be determined by a physician and adjusted, as necessary, to suit observed effects of the treatment.

In some embodiments of any of the aspects, the technology described herein relates to a pharmaceutical composition comprising an antibody, antibody reagent, antigen-binding fragment thereof, nucleic acid, or cell as described herein, and optionally a pharmaceutically acceptable carrier. In some embodiments of any of the aspects, the active ingredients of the pharmaceutical composition comprise an antibody, antibody reagent, antigen-binding fragment thereof, nucleic acid, or cell as described herein. In some embodiments of any of the aspects, the active ingredients of the pharmaceutical composition consist essentially of an antibody, antibody reagent, antigen-binding fragment thereof, nucleic acid, or cell as described herein. In some embodiments of any of the aspects, the active ingredients of the pharmaceutical composition consist of an antibody, antibody reagent, antigen-binding fragment thereof, nucleic acid, or cell as described herein. Pharmaceutically acceptable carriers and diluents include saline, aqueous buffer solutions, solvents and/or dispersion media. The use of such carriers and diluents is well known in the art. Some non-limiting examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) lubricating agents, such as magnesium stearate, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol (PEG); (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; (22) $C_2$-$C_{12}$ alcohols, such as ethanol; and (23) other non-toxic compatible substances employed in pharmaceutical formulations. Wetting agents, coloring agents, release agents, coating agents, sweetening agents, flavoring agents, perfuming agents, preservative and antioxidants can also be present in the formulation. The terms such as "excipient", "carrier", "pharmaceutically acceptable carrier" or the like are used interchangeably herein. In some embodiments of any of the aspects, the carrier inhibits the degradation of the active agent as described herein.

In some embodiments of any of the aspects, the pharmaceutical composition comprising an antibody, antibody reagent, antigen-binding fragment thereof, nucleic acid, or cell as described herein can be a parenteral dose form. Since administration of parenteral dosage forms typically bypasses the patient's natural defenses against contaminants, parenteral dosage forms are preferably sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions. In addition, controlled-release parenteral dosage forms can be prepared for administration of a patient, including, but not limited to, DUROS®-type dosage forms and dose-dumping.

Suitable vehicles that can be used to provide parenteral dosage forms are well known to those skilled in the art. Examples include, without limitation: sterile water; water for injection USP; saline solution; glucose solution; aqueous vehicles such as but not limited to, sodium chloride injection, Ringer's injection, dextrose Injection, dextrose and sodium chloride injection, and lactated Ringer's injection; water-miscible vehicles such as, but not limited to, ethyl alcohol, polyethylene glycol, and propylene glycol; and non-aqueous vehicles such as, but not limited to, corn oil, cottonseed oil, peanut oil, sesame oil, ethyl oleate, isopropyl myristate, and benzyl benzoate. Compounds that alter or modify the solubility of a pharmaceutically acceptable salt of agents as disclosed herein can also be incorporated into the parenteral dosage forms of the disclosure, including conventional and controlled-release parenteral dosage forms.

Pharmaceutical compositions comprising an antibody, antibody reagent, antigen-binding fragment thereof, nucleic acid, or cell can also be formulated to be suitable for oral administration, for example as discrete dosage forms, such as, but not limited to, tablets (including without limitation scored or coated tablets), pills, caplets, capsules, chewable tablets, powder packets, cachets, troches, wafers, aerosol sprays, or liquids, such as but not limited to, syrups, elixirs, solutions or suspensions in an aqueous liquid, a non-aqueous liquid, an oil-in-water emulsion, or a water-in-oil emulsion. Such compositions contain a predetermined amount of the pharmaceutically acceptable salt of the disclosed compounds, and may be prepared by methods of pharmacy well known to those skilled in the art. See generally, Remington: The Science and Practice of Pharmacy, 21st Ed., Lippincott, Williams, and Wilkins, Philadelphia PA. (2005).

Conventional dosage forms generally provide rapid or immediate drug release from the formulation. Depending on the pharmacology and pharmacokinetics of the drug, use of conventional dosage forms can lead to wide fluctuations in the concentrations of the drug in a patient's blood and other tissues. These fluctuations can impact a number of parameters, such as dose frequency, onset of action, duration of efficacy, maintenance of therapeutic blood levels, toxicity, side effects, and the like. Advantageously, controlled-release formulations can be used to control a drug's onset of action, duration of action, plasma levels within the therapeutic window, and peak blood levels. In particular, controlled- or extended-release dosage forms or formulations can be used to ensure that the maximum effectiveness of a drug is achieved while minimizing potential adverse effects and safety concerns, which can occur both from under-dosing a drug (i.e., going below the minimum therapeutic levels) as well as exceeding the toxicity level for the drug. In some embodiments of any of the aspects, the antibody, antibody reagent, antigen-binding fragment thereof, nucleic acid, or cell can be administered in a sustained release formulation.

Controlled-release pharmaceutical products have a common goal of improving drug therapy over that achieved by their non-controlled release counterparts. Ideally, the use of an optimally designed controlled-release preparation in medical treatment is characterized by a minimum of drug substance being employed to cure or control the condition in a minimum amount of time. Advantages of controlled-release formulations include: 1) extended activity of the drug; 2) reduced dosage frequency; 3) increased patient compliance; 4) usage of less total drug; 5) reduction in local or systemic side effects; 6) minimization of drug accumulation; 7) reduction in blood level fluctuations; 8) improvement in efficacy of treatment; 9) reduction of potentiation or loss of drug activity; and 10) improvement in speed of control of diseases or conditions. Kim, Cherng-ju, Controlled Release Dosage Form Design, 2 (Technomic Publishing, Lancaster, Pa.: 2000).

Most controlled-release formulations are designed to initially release an amount of drug (active ingredient) that promptly produces the desired therapeutic effect, and gradually and continually release other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, ionic strength, osmotic pressure, temperature, enzymes, water, and other physiological conditions or compounds.

A variety of known controlled- or extended-release dosage forms, formulations, and devices can be adapted for use with the salts and compositions of the disclosure. Examples include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; 5,733,566; and 6,365,185 B1; each of which is incorporated herein by reference. These dosage forms can be used to provide slow or controlled-release of one or more active ingredients using, for example, hydroxypropylmethyl cellulose, other polymer matrices, gels, permeable membranes, osmotic systems (such as OROS® (Alza Corporation, Mountain View, Calif USA)), or a combination thereof to provide the desired release profile in varying proportions.

In some embodiments of any of the aspects, the antibody, antibody reagent, antigen-binding fragment thereof, nucleic acid, or cell described herein is administered as a monotherapy, e.g., another treatment for the condition is not administered to the subject.

In vitro and animal model assays are provided herein which allow the assessment of a given dose of an antibody, antibody reagent, antigen-binding fragment thereof, nucleic acid, or cell. By way of non-limiting example, the effects of a dose of an antibody, antibody reagent, antigen-binding fragment thereof, nucleic acid, or cell can be assessed by assays for BBB permeability and/or advancement of a condition described herein, e.g., cancer tumor growth. The efficacy of a given dosage combination can also be assessed in an animal model, e.g. a mouse model of cancer.

In one aspect, described herein is a method of detecting Mfsd2A, the method comprising contacting a biological sample with an antibody, antibody reagent, or antigen-binding portion thereof as described herein, wherein reaction of the antibody or antigen-binding portion thereof with Mfsd2A indicates the presence of Mfsd2A. In some embodiments of any of the aspects, a detectable signal is generated by the antibody or antigen-binding portion thereof when a Mfsd2A molecule is present. In some embodiments of any of the aspects, the antibody or antigen-binding portion thereof is detectably labeled or capable of generating a detectable signal. In some embodiments of any of the aspects, the level of the Mfsd2A is determined using a method selected from the group consisting of: Western blot; immunoprecipitation; enzyme-linked immunosorbent assay (ELISA); radioimmunological assay (RIA); sandwich assay; fluorescence in situ hybridization (FISH); immunohistological staining; radioimmunometric assay; immunofluorescence assay; mass spectroscopy; FACS; and immunoelectrophoresis assay. In some embodiments of any of the aspects, the antibody or antigen-binding portion thereof is detectably labeled or generates a detectable signal. In some embodiments of any of the aspects, the expression level of Mfsd2A is normalized relative to the expression level of one or more reference genes or reference proteins. In some embodiments of any of the aspects, the reference level of Mfsd2A is the expression level of Mfsd2A in a prior sample obtained from the subject.

In some embodiments of any of the aspects, the level of Mfsd2A can be the level of Mfsd2A polypeptide. Detection of Mfsd2A polypeptides can be according to any method known in the art. Immunological methods to detect Mfsd2A polypeptides in accordance with the present technology include, but are not limited to antibody techniques such as immunohistochemistry, immunocytochemistry, flow cytometry, fluorescence-activated cell sorting (FACS), immunoblotting, radioimmunoassays, western blotting, immunoprecipitation, enzyme-linked immunosorbent assays (ELISA), and derivative techniques that make use of antibody reagents as described herein.

Immunochemical methods require the use of an antibody reagent specific for the target molecule (e.g., the antigen or in the embodiments described herein, a Mfsd2A polypeptide. In some embodiments of any of the aspects, the assays, methods, and/or systems described herein can comprise: an anti-Mfsd2A antibody reagent. In some embodiments of any of the aspects, the antibody reagent can be detectably labeled. In some embodiments of any of the aspects, the antibody reagent can be attached to a solid support (e.g., bound to a solid support). In some embodiments of any of the aspects, the solid support can comprise a particle (including, but not limited to an agarose or latex bead or particle or a magnetic particle), a bead, a nanoparticle, a polymer, a substrate, a slide, a coverslip, a plate, a dish, a well, a membrane, and/or a grating. The solid support can include many different materials including, but not limited to, polymers, plastics, resins, polysaccharides, silicon or silica based materials, carbon, metals, inorganic glasses, and membranes.

In one embodiment, an assay, method, and/or system as described herein can comprise an ELISA. In an exemplary embodiment, a first antibody reagent can be immobilized on a solid support (usually a polystyrene micro titer plate). The solid support can be contacted with a sample obtained from a subject, and the antibody reagent will bind ("capture") antigens for which it is specific (e.g., Mfsd2A). The solid support can then be contacted with a second labeled antibody reagent (e.g., a detection antibody reagent). The detection antibody reagent can, e.g., comprise a detectable signal, be covalently linked to an enzyme, or can itself be detected by a secondary antibody which is linked to an enzyme through bio-conjugation. The presence of a signal indicates that both the first antibody reagent immobilized on the support and the second "detection" antibody reagent have bound to an antigen, i.e., the presence of a signal indicated the presence of a Mfsd2A molecule. Between each step the plate is typically washed with a mild detergent solution to remove any proteins or antibodies that are not specifically bound. After the final wash step, the plate is developed by adding an enzymatic substrate to produce a visible signal, which indicates the quantity of Mfsd2A polypeptides in the sample. Older ELISAs utilize chromogenic substrates, though newer assays employ fluorogenic substrates with much higher sensitivity. There are other different forms of ELISA, which are well known to those skilled in the art.

In one embodiment, the assays, systems, and methods described herein can comprise a lateral flow immunoassay test (LFIA), also known as the immunochromatographic assay, or strip test to measure or determine the level of Mfsd2A polypeptide in a sample. LFIAs are a simple device intended to detect the presence (or absence) of Mfsd2A in a sample. There are currently many LFIA tests used for medical diagnostics either for home testing, point of care testing, or laboratory use. LFIA tests are a form of immunoassay in which the test sample flows along a solid substrate via capillary action. After the sample is applied to the test strip it encounters a colored antibody reagent which mixes with the sample, and if bound to a portion of the sample, transits the substrate encountering lines or zones which have been pretreated with a second antibody reagent. Depending upon the level of Mfsd2A present in the sample the colored antibody reagent can become bound at the test line or zone. LFIAs are essentially immunoassays adapted to operate along a single axis to suit the test strip format or a dipstick format. Strip tests are extremely versatile and can be easily modified by one skilled in the art for detecting an enormous range of antigens from fluid samples such as urine, blood, water samples etc. Strip tests are also known as dip stick test, the name bearing from the literal action of "dipping" the test strip into a fluid sample to be tested. LFIA strip test are easy to use, require minimum training and can easily be included as components of point-of-care test (POCT) diagnostics to be used on site in the field. LFIA tests can be operated as either competitive or sandwich assays. Sandwich LFIAs are similar to sandwich ELISA. The sample first encounters colored particles which are labeled with antibody reagents specific for a target (e.g., a Mfsd2A-specific antibody reagent). The test line will also contain antibody reagents (e.g., a Mfsd2A-specific antibody reagent). The test line will show as a colored band in positive samples. In some embodiments of any of the aspects, the lateral flow immunoassay can be a double antibody sandwich assay, a competitive assay, a quantitative assay or variations thereof. There are a number of variations on lateral flow technology. It is also possible to apply multiple capture zones to create a multiplex test.

A typical test strip consists of the following components: (1) sample application area comprising an absorbent pad (i.e. the matrix or material) onto which the test sample is applied; (2) conjugate or reagent pad—this contains antibody reagent(s) specific to the target which can be conjugated to colored particles (usually colloidal gold particles, or latex microspheres); (3) test results area comprising a reaction membrane—typically a hydrophobic nitrocellulose or cellulose acetate membrane onto which antibody reagents are immobilized in a line across the membrane as a capture zone or test line (a control zone may also be present, containing antibodies specific for the antibody reagents conjugated to the particles or microspheres); and (4) optional wick or waste reservoir—a further absorbent pad designed to draw the sample across the reaction membrane by capillary action and collect it. The components of the strip are usually fixed to an inert backing material and may be presented in a simple dipstick format or within a plastic casing with a sample port and reaction window showing the capture and control zones. While not strictly necessary, most tests will incorporate a second line which contains an antibody that picks up free latex/gold in order to confirm the test has operated correctly.

The use of "dip sticks" or LFIA test strips and other solid supports has been described in the art in the context of an immunoassay for a number of antigen biomarkers. U.S. Pat. Nos. 4,943,522; 6,485,982; 6,187,598; 5,770,460; 5,622,871; 6,565,808, U.S. patent application Ser. No. 10/278,676; U.S. Ser. No. 09/579,673 and U.S. Ser. No. 10/717,082, which are incorporated herein by reference in their entirety, are non-limiting examples of such lateral flow test devices. Three U.S. patents (U.S. Pat. No. 4,444,880, issued to H. Tom; U.S. Pat. No. 4,305,924, issued to R. N. Piasio; and U.S. Pat. No. 4,135,884, issued to J. T. Shen) describe the use of "dip stick" technology to detect soluble antigens via immunochemical assays. The apparatuses and methods of these three patents broadly describe a first component fixed to a solid surface on a "dip stick" which is exposed to a solution containing a soluble antigen that binds to the component fixed upon the "dip stick," prior to detection of the component-antigen complex upon the stick. It is within the skill of one in the art to modify the teaching of these "dip stick" technologies as necessary for the detection of Mfsd2A polypeptides. In some embodiments of any of the aspects, the dip stick (or LFIA) can be suitable for use with urine samples. In some embodiments of any of the aspects, a dip stick can be suitable for use with blood samples.

Immunochemistry is a family of techniques based on the use of a specific antibody, wherein antibodies are used to specifically target molecules inside or on the surface of cells. In some embodiments of any of the aspects, immunohistochemistry ("IHC") and immunocytochemistry ("ICC") techniques can be used to detect or measure the levels of Mfsd2A polypeptide. IHC is the application of immunochemistry to tissue sections, whereas ICC is the application of immunochemistry to cells or tissue imprints after they have undergone specific cytological preparations such as, for example, liquid-based preparations. In some instances, signal amplification may be integrated into the particular protocol, wherein a secondary antibody, that includes a label, follows the application of an antibody reagent specific for platelets or leukocytes. Typically, for immunohistochemistry, tissue obtained from a subject and fixed by a suitable fixing agent such as alcohol, acetone, and paraformaldehyde, is sectioned and reacted with an antibody. Conventional methods for immunohistochemistry are described in Buchwalow and Bocker (Eds) "Immunohistochemistry: Basics and Methods" Springer (2010): Lin and Prichard "Handbook of Practical Immunohistochemistry" Springer (2011); which are incorporated by reference herein in their entireties. In some embodiments of any of the aspects, immunocytochemistry may be utilized where, in general, tissue or cells obtained from a subject are fixed by a suitable fixing agent such as alcohol, acetone, and paraformaldehyde, to which is reacted an antibody. Methods of immunocytological staining of human samples is known to those of skill in the art and described, for example, in Burry "Immunocytochemistry: A Practical Guide for Biomedical Research" Springer (2009); which is incorporated by reference herein in its entirety.

In some embodiments of any of the aspects, one or more of the antibody reagents described herein can comprise a detectable label and/or comprise the ability to generate a detectable signal (e.g., by catalyzing a reaction converting a compound to a detectable product). Detectable labels can comprise, for example, a light-absorbing dye, a fluorescent dye, or a radioactive label. Detectable labels, methods of detecting them, and methods of incorporating them into an antibody reagent are well known in the art.

In some embodiments of any of the aspects, detectable labels can include labels that can be detected by spectroscopic, photochemical, biochemical, immunochemical, electromagnetic, radiochemical, or chemical means, such as fluorescence, chemifluorescence, or chemiluminescence, or any other appropriate means. The detectable labels used in the methods described herein can be primary labels (where the label comprises a moiety that is directly detectable or that produces a directly detectable moiety) or secondary labels (where the detectable label binds to another moiety to produce a detectable signal, e.g., as is common in immunological labeling using secondary and tertiary antibodies). The detectable label can be linked by covalent or non-covalent means to the antibody reagent. Alternatively, a detectable label can be linked such as by directly labeling a molecule that achieves binding to the antibody reagent via a ligand-receptor binding pair arrangement or other such specific recognition molecules. Detectable labels can include, but are not limited to radioisotopes, bioluminescent compounds, chromophores, antibodies, chemiluminescent compounds, fluorescent compounds, metal chelates, and enzymes.

In other embodiments, the detection antibody is labeled with a fluorescent compound. When the fluorescently labeled antibody is exposed to light of the proper wavelength, its presence can then be detected due to fluorescence. In some embodiments of any of the aspects, a detectable label can be a fluorescent dye molecule, or fluorophore including, but not limited to fluorescein, phycoerythrin, phycocyanin, o-phthaldehyde, fluorescamine, Cy3™, Cy5™, allophycocyanine, Texas Red, peridenin chlorophyll, cyanine, tandem conjugates such as phycoerythrin-Cy5™, green fluorescent protein, rhodamine, fluorescein isothiocyanate (FITC) and Oregon Green™, rhodamine and derivatives (e.g., Texas red and tetrarhodimine isothiocynate (TRITC)), biotin, phycoerythrin, AMCA, CyDyes™, 6-carboxyfhiorescein (commonly known by the abbreviations FAM and F), 6-carboxy-2',4',7',4,7-hexachlorofiuorescein (HEX), 6-carboxy-4',5'-dichloro-2',7'-dimethoxyfluorescein (JOE or J), N,N,N',N'-tetramethyl-6carboxyrhodamine (TAMRA or T), 6-carboxy-X-rhodamine (ROX or R), 5-carboxyrhodamine-6G (R6G5 or G5), 6-carboxyrhodamine-6G (R6G6 or G6), and rhodamine 110; cyanine dyes, e.g., Cy3, Cy5 and Cy7 dyes; coumarins, e.g umbelliferone; benzimide dyes, e.g., Hoechst 33258; phenanthridine dyes, e.g., Texas Red; ethidium dyes; acridine dyes; carbazole dyes; phenoxazine dyes; porphyrin dyes; polymethine dyes, e.g., cyanine dyes such as Cy3, Cy5, etc; BODIPY dyes and quinoline dyes.

In some embodiments of any of the aspects, a detectable label can be a radiolabel including, but not limited to $^{3}H$, $^{125}$, $^{35}S$, $^{14}C$, $^{32}P$, and $^{33}P$.

In some embodiments of any of the aspects, a detectable label can be an enzyme including, but not limited to horseradish peroxidase and alkaline phosphatase. An enzymatic label can produce, for example, a chemiluminescent signal, a color signal, or a fluorescent signal. Enzymes contemplated for use to detectably label an antibody reagent include, but are not limited to, malate dehydrogenase, staphylococcal nuclease, delta-V-steroid isomerase, yeast alcohol dehydrogenase, alpha-glycerophosphate dehydrogenase, triose phosphate isomerase, horseradish peroxidase, alkaline phosphatase, asparaginase, glucose oxidase, beta-galactosidase, ribonuclease, urease, catalase, glucose-VI-phosphate dehydrogenase, glucoamylase and acetylcholinesterase.

In some embodiments of any of the aspects, a detectable label is a chemiluminescent label, including, but not limited to lucigenin, luminol, luciferin, isoluminol, theromatic acridinium ester, imidazole, acridinium salt and oxalate ester. In some embodiments of any of the aspects, a detectable label can be a spectral colorimetric label including, but not limited to colloidal gold or colored glass or plastic (e.g., polystyrene, polypropylene, and latex) beads.

In some embodiments of any of the aspects, antibodies can also be labeled with a detectable tag, such as c-Myc, HA, VSV-G, HSV, FLAG, V5, HIS, or biotin. Other detection systems can also be used, for example, a biotin-streptavidin system. In this system, the antibodies immunoreactive (i. e. specific for) with the biomarker of interest is biotinylated. Quantity of biotinylated antibody bound to the biomarker is determined using a streptavidin-peroxidase conjugate and a chromagenic substrate. Such streptavidin peroxidase detection kits are commercially available, e. g. from DAKO; Carpinteria, CA.

An antibody reagent can also be detectably labeled using fluorescence emitting metals such as $^{152}$Eu, or others of the lanthanide series. These metals can be attached to the antibody reagent using such metal chelating groups as diethylenetriaminepentaacetic acid (DTPA) or ethylenediaminetetraacetic acid (EDTA).

The term "sample" or "test sample" as used herein denotes a sample taken or isolated from an organism, e.g., a blood or BBB sample from a subject. Exemplary biological samples include, but are not limited to, a biofluid sample; serum; plasma; urine; saliva; and/or joint fluid sample, etc. The term also includes a mixture of the above-mentioned samples. The term "test sample" also includes untreated or pretreated (or pre-processed) biological samples. In some embodiments of any of the aspects, a test sample can comprise cells from a subject. As used herein, the term "biofluid" refers to any fluid obtained from a biological source and includes, but is not limited to, blood, urine, and bodily secretions.

The test sample can be obtained by removing a sample from a subject, but can also be accomplished by using a previously isolated sample (e.g., isolated at a prior timepoint and isolated by the same or another person). In addition, the test sample can be freshly collected or a previously collected sample.

In some embodiments of any of the aspects, the test sample can be an untreated test sample. As used herein, the phrase "untreated test sample" refers to a test sample that has not had any prior sample pre-treatment except for dilution and/or suspension in a solution. Exemplary methods for treating a test sample include, but are not limited to, centrifugation, filtration, sonication, homogenization, heating, freezing and thawing, and combinations thereof. In some embodiments of any of the aspects, the test sample can be a frozen test sample, e.g., a frozen tissue. The frozen sample can be thawed before employing methods, assays and systems described herein. After thawing, a frozen sample can be centrifuged before being subjected to methods, assays and systems described herein. In some embodiments of any of the aspects, the test sample is a clarified test sample, for example, prepared by centrifugation and collection of a supernatant comprising the clarified test sample. In some embodiments of any of the aspects, a test sample can be a pre-processed test sample, for example, supernatant or filtrate resulting from a treatment selected from the group consisting of centrifugation, filtration, thawing, purification, and any combinations thereof. In some embodiments of any of the aspects, the test sample can be treated with a chemical and/or biological reagent. Chemical and/or biological reagents can be employed to protect and/or maintain the stability of the sample, including biomolecules (e.g., nucleic acid and protein) therein, during processing. One exemplary reagent is a protease inhibitor, which is generally used to protect or maintain the stability of protein during processing. The skilled artisan is well aware of methods and processes appropriate for pre-processing of biological samples required for determination of the level of Mfsd2A as described herein.

In one aspect of any of any of the embodiments, described herein is an antibody, antibody reagent, or antigen-binding portion thereof as described herein conjugated to or coupled to a detectable label.

In one aspect of any of any of the embodiments, described herein is a solid support comprising an antibody, antibody reagent, antigen-binding fragment thereof as described herein. In some embodiments of any of the aspects, the antibody, antibody reagent or antigen-binding fragment thereof is detectably labeled. In some embodiments of any of the aspects, the solid support comprises a particle, a bead, a polymer, or a substrate.

In one aspect of any of the embodiments, described herein is a molecular complex comprising at least one antibody, antibody reagent, antigen-binding fragment thereof, or CAR of as described herein bound to an Mfsd2A polypeptide.

For convenience, the meaning of some terms and phrases used in the specification, examples, and appended claims, are provided below. Unless stated otherwise, or implicit from context, the following terms and phrases include the meanings provided below. The definitions are provided to aid in describing particular embodiments, and are not intended to limit the claimed invention, because the scope of the invention is limited only by the claims. Unless otherwise defined, all technical and scientific terms used herein have the same meaning as commonly understood by one of ordinary skill in the art to which this invention belongs. If there is an apparent discrepancy between the usage of a term in the art and its definition provided herein, the definition provided within the specification shall prevail.

For convenience, certain terms employed herein, in the specification, examples and appended claims are collected here.

As described herein, "Mfsd2A" or "major facilitator superfamily domain-containing 2A" refers to a transmembrane protein believed to mediate the uptake and transport of tunicamycin. Mfsd2A has a 12 transmembrane alpha-helical domain structure with similarity to the bacterial Na$^+$/melibiose symporters. The sequences of Mfsd2A polypeptides and nucleic acids encoding such polypeptides are known in the art for a number of species, e.g. human Mfsd2A (NCBI Gene ID: 84879 (polypeptide; NCBI Ref Seq: NP_001129965; SEQ ID NO: 9) (mRNA; NCBI Ref Seq: NM_001136493; SEQ ID NO:10)

A Mfsd2A polypeptide can comprise SEQ ID NO: 9 or a homolog, variant, and/or functional fragment thereof. A nucleic acid encoding a Mfsd2A polypeptide can comprise SEQ ID NO: 10 or a homolog or variant thereof. The polypeptide sequences and nucleic acid sequences encoding any of the other BBB key regulatory genes described herein can readily by obtained by searching the "Gene" Database of the NCBI (available on the World Wide Web at ncbi.nlm-.nih.gov/) using the common name or NCBI Gene ID number as the query and selecting the first returned *Homo sapiens* gene.

As used herein, a "functional fragment" of, e.g. SEQ ID NO: 9, is a fragment or segment of that polypeptide which can promote formation of the BBB at least 10% as strongly as the reference polypeptide (i.e. SEQ ID NO: 9), e.g. at least 10%, at least 20%, at least 30%, at least 40%, at least 50%, at least 75%, at least 90%, at least 100% as strongly, or more strongly. Assays for measuring the formation of the BBB are known in the art, e.g., by way of non-limiting example, the migration of tracer dyes out of vessels in the brain using the embryonic models described in US Publication 2016/0120893 can be used to quantitate the formation and/or integrity of the BBB. A functional fragment can comprise conservative substitutions of the sequences disclosed herein. The foregoing references are incorporated by reference herein in their entireties.

The terms "decrease", "reduced", "reduction", or "inhibit" are all used herein to mean a decrease by a statistically significant amount. In some embodiments of any of the aspects, "reduce," "reduction" or "decrease" or "inhibit" typically means a decrease by at least 10% as compared to a reference level (e.g. the absence of a given treatment or agent) and can include, for example, a decrease by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, at least about 99%, or more. As used herein, "reduction" or "inhibition" does not encompass a complete inhibition or reduction as compared to a reference level. "Complete inhibition" is a 100% inhibition as compared to a reference level. A decrease can be preferably down to a level accepted as within the range of normal for an individual without a given disorder.

As described herein, an "inhibitor" of target, e.g. an inhibitor of Mfsd2A, refers to an agent which can decrease the expression and/or activity of the targeted expression product (e.g. mRNA encoding the target or a target polypeptide), e.g. by at least 10% or more, e.g. by 10% or more, 50% or more, 70% or more, 80% or more, 90% or more, 95% or more, or 98% or more. The efficacy of an inhibitor of, for example, Mfsd2A, e.g. its ability to decrease the level and/or activity of Mfsd2A can be determined, e.g. by measuring the level of an expression product of Mfsd2A and/or the activity of Mfsd2A (e.g. the permeability of the BBB, the measurement of which is described elsewhere herein). Methods for measuring the level of a given mRNA and/or polypeptide are known to one of skill in the art, e.g. RTPCR with primers can be used to determine the level of RNA and Western blotting with an antibody (e.g. an anti-Mfsd2A antibody, e.g. Cat No. ab105399; Abcam; Cambridge, MA) can be used to determine the level of a polypeptide. The activity of, e.g., Mfsd2A can be determined using methods known in the art and described above herein.

The terms "increased", "increase", "enhance", or "activate" are all used herein to mean an increase by a statically significant amount. In some embodiments of any of the aspects, the terms "increased", "increase", "enhance", or "activate" can mean an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level. In the context of a marker or symptom, a "increase" is a statistically significant increase in such level.

As used herein, a "subject" means a human or animal. Usually the animal is a vertebrate such as a primate, rodent, domestic animal or game animal. Primates include chimpanzees, cynomolgous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. In some embodiments of any of the aspects, the subject is a mammal, e.g., a primate, e.g., a human. The terms, "individual," "patient" and "subject" are used interchangeably herein.

Preferably, the subject is a mammal. The mammal can be a human, non-human primate, mouse, rat, dog, cat, horse, or cow, but is not limited to these examples. Mammals other than humans can be advantageously used as subjects that represent animal models of the conditions or diseases described herein. A subject can be male or female.

A subject can be one who has been previously diagnosed with or identified as suffering from or having a condition in need of treatment or one or more complications related to such a condition, and optionally, have already undergone treatment for the condition or the one or more complications related to the condition. Alternatively, a subject can also be one who has not been previously diagnosed as having the condition or one or more complications related to the condition. For example, a subject can be one who exhibits one or more risk factors for the condition or one or more complications related to the condition or a subject who does not exhibit risk factors.

A "subject in need" of treatment for a particular condition can be a subject having that condition, diagnosed as having that condition, or at risk of developing that condition.

As used herein, the terms "protein" and "polypeptide" are used interchangeably herein to designate a series of amino acid residues, connected to each other by peptide bonds between the alpha-amino and carboxy groups of adjacent residues. The terms "protein", and "polypeptide" refer to a polymer of amino acids, including modified amino acids (e.g., phosphorylated, glycated, glycosylated, etc.) and amino acid analogs, regardless of its size or function. "Protein" and "polypeptide" are often used in reference to relatively large polypeptides, whereas the term "peptide" is often used in reference to small polypeptides, but usage of these terms in the art overlaps. The terms "protein" and "polypeptide" are used interchangeably herein when referring to a gene product and fragments thereof. Thus, exemplary polypeptides or proteins include gene products, naturally occurring proteins, homologs, orthologs, paralogs, fragments and other equivalents, variants, fragments, and analogs of the foregoing. The terms also refer to fragments or variants of the polypeptide that maintain at least 50% of the activity or effect of the full length polypeptide. Conservative substitution variants that maintain the activity of the wildtype reference will include a conservative substitution as defined herein. The identification of amino acids most likely to be tolerant of conservative substitution while maintaining at least 50% of the activity of the wildtype is guided by, for example, sequence alignment with homologs or paralogs from other species. Amino acids that are identical between homologs are less likely to tolerate change, while those showing conservative differences are obviously much more likely to tolerate conservative change in the context of an artificial variant. Similarly, positions with non-conservative differences are less likely to be critical to function and more likely to tolerate conservative substitution in an artificial variant. Variants, fragments, and/or fusion proteins can be tested for activity, for example, by administering the variant to an appropriate animal model of the BBB or diseases or conditions as described herein.

In some embodiments of any of the aspects, a polypeptide, can be a variant of a sequence described herein. In some embodiments of any of the aspects, the variant is a conservative substitution variant. Variants can be obtained by mutations of native nucleotide sequences, for example. A "variant," as referred to herein, is a polypeptide substantially homologous to a native or reference polypeptide, but which has an amino acid sequence different from that of the native or reference polypeptide because of one or a plurality of deletions, insertions or substitutions. Polypeptide-encoding DNA sequences encompass sequences that comprise one or more additions, deletions, or substitutions of nucleotides when compared to a native or reference DNA sequence, but that encode a variant protein or fragment thereof that retains the relevant biological activity relative to the reference protein, e.g., at least 50% of wildtype activity. As to amino acid sequences, one of skill will recognize that individual substitutions, deletions or additions to a nucleic acid, peptide, polypeptide, or protein sequence which alters a single amino acid or a small percentage, (i.e. 5% or fewer, e.g. 4% or fewer, or 3% or fewer, or 1% or fewer) of amino acids in the encoded sequence is a "conservatively modified variant" where the alteration results in the substitution of an amino acid with a chemically similar amino acid. It is contemplated that some changes can potentially improve the relevant activity, such that a variant, whether conservative or not, has more than 100% of the activity of wildtype, e.g. 110%, 125%, 150%, 175%, 200%, 500%, 1000% or more.

One method of identifying amino acid residues which can be substituted is to align, for example, a human polypeptide to a homolog from one or more non-human species. Alignment can provide guidance regarding not only residues likely to be necessary for function but also, conversely, those residues likely to tolerate change. Where, for example, an alignment shows two identical or similar amino acids at corresponding positions, it is more likely that that site is not important functionally. Where, conversely, alignment shows residues in corresponding positions to differ significantly in size, charge, hydrophobicity, etc., it is more likely that that site can tolerate variation in a functional polypeptide. The variant amino acid or DNA sequence can be at least 90%, at least 95%, at least 96%, at least 97%, at least 98%, at least 99%, or more, identical to a native or reference sequence, or a nucleic acid encoding one of those amino acid sequences. The degree of homology (percent identity) between a native and a mutant sequence can be determined, for example, by comparing the two sequences using freely available computer programs commonly employed for this purpose on the world wide web. The variant amino acid or DNA sequence can be at least 90%, at least 91%, at least 92%, at least 93%, at least 94%, at least 95%, at least 96%, at least 97%, at least 98%, at least 99%, or more, similar to the sequence from which it is derived (referred to herein as an "original" sequence). The degree of similarity (percent similarity) between an original and a mutant sequence can be determined, for example, by using a similarity matrix. Similarity matrices are well known in the art and a number of tools for comparing two sequences using similarity matrices are freely available online, e.g. BLASTp or BLASTn (available on the world wide web at blast.ncbi.nlm.nih.gov), with default parameters set.

In the various embodiments described herein, it is further contemplated that variants (naturally occurring or otherwise), alleles, homologs, conservatively modified variants, and/or conservative substitution variants of any of the particular polypeptides described are encompassed. As to amino acid sequences, one of skill will recognize that individual substitutions, deletions or additions to a nucleic acid, peptide, polypeptide, or protein sequence which alters a single amino acid or a small percentage of amino acids in the encoded sequence is a "conservatively modified variant" where the alteration results in the substitution of an amino acid with a chemically similar amino acid and retains the desired activity of the polypeptide. Such conservatively modified variants are in addition to and do not exclude polymorphic variants, interspecies homologs, and alleles consistent with the disclosure.

A given amino acid can be replaced by a residue having similar physiochemical characteristics, e.g., substituting one aliphatic residue for another (such as Ile, Val, Leu, or Ala for one another), or substitution of one polar residue for another (such as between Lys and Arg; Glu and Asp; or Gln and Asn). Other such conservative substitutions, e.g., substitutions of entire regions having similar hydrophobicity characteristics, are well known. Polypeptides comprising conservative amino acid substitutions can be tested in any one of the assays described herein to confirm that a desired activity, and specificity of a native or reference polypeptide is retained.

A given amino acid can be replaced by a residue having similar physiochemical characteristics, e.g., substituting one aliphatic residue for another (such as Ile, Val, Leu, or Ala for one another), or substitution of one polar residue for another (such as between Lys and Arg; Glu and Asp; or Gln and Asn). Other such conservative substitutions, e.g., substitutions of entire regions having similar hydrophobicity characteristics, are well known. Polypeptides comprising conservative amino acid substitutions can be tested in any one of the assays described herein to confirm that a desired activity of a native or reference polypeptide is retained. Conservative substitution tables providing functionally similar amino acids are well known in the art. Such conservatively modified variants are in addition to and do not exclude polymorphic variants, interspecies homologs, and alleles consistent with the disclosure.

Amino acids can be grouped according to similarities in the properties of their side chains (in A. L. Lehninger, in Biochemistry, second ed., pp. 73-75, Worth Publishers, New York (1975)): (1) non-polar: Ala (A), Val (V), Leu (L), Ile (I), Pro (P), Phe (F), Trp (W), Met (M); (2) uncharged polar: Gly (G), Ser (S), Thr (T), Cys (C), Tyr (Y), Asn (N), Gln (Q); (3) acidic: Asp (D), Glu (E); (4) basic: Lys (K), Arg (R), His (H). Alternatively, naturally occurring residues can be divided into groups based on common side-chain properties: (1) hydrophobic: Norleucine, Met, Ala, Val, Leu, Ile; (2) neutral hydrophilic: Cys, Ser, Thr, Asn, Gln; (3) acidic: Asp, Glu; (4) basic: His, Lys, Arg; (5) residues that influence chain orientation: Gly, Pro; (6) aromatic: Trp, Tyr, Phe. Non-conservative substitutions will entail exchanging a member of one of these classes for another class. Particular conservative substitutions include, for example; Ala into Gly or into Ser; Arg into Lys; Asn into Gln or into His; Asp into Glu; Cys into Ser; Gln into Asn; Glu into Asp; Gly into Ala or into Pro; His into Asn or into Gln; Ile into Leu or into Val; Leu into Ile or into Val; Lys into Arg, into Gln or into Glu;

Met into Leu, into Tyr or into Ile; Phe into Met, into Leu or into Tyr; Ser into Thr; Thr into Ser; Trp into Tyr; Tyr into Trp; and/or Phe into Val, into Ile or into Leu. Typically conservative substitutions for one another also include: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)).

In some embodiments of any of the aspects, the polypeptide described herein (or a nucleic acid encoding such a polypeptide) can be a functional fragment of one of the amino acid sequences described herein. As used herein, a "functional fragment" is a fragment or segment of a peptide which retains at least 50% of the wildtype reference polypeptide's activity according to the assays described below herein. A functional fragment can comprise conservative substitutions of the sequences disclosed herein.

In some embodiments of any of the aspects, the polypeptide described herein can be a variant of a sequence described herein. In some embodiments of any of the aspects, the variant is a conservatively modified variant. Conservative substitution variants can be obtained by mutations of native nucleotide sequences, for example. A "variant," as referred to herein, is a polypeptide substantially homologous to a native or reference polypeptide, but which has an amino acid sequence different from that of the native or reference polypeptide because of one or a plurality of deletions, insertions or substitutions. Variant polypeptide-encoding DNA sequences encompass sequences that comprise one or more additions, deletions, or substitutions of nucleotides when compared to a native or reference DNA sequence, but that encode a variant protein or fragment thereof that retains activity. A wide variety of PCR-based site-specific mutagenesis approaches are known in the art and can be applied by the ordinarily skilled artisan.

In some embodiments of any of the aspects, a polypeptide can comprise one or more amino acid substitutions or modifications. In some embodiments of any of the aspects, the substitutions and/or modifications can prevent or reduce proteolytic degradation and/or prolong half-life of the polypeptide in a subject. In some embodiments of any of the aspects, a polypeptide can be modified by conjugating or fusing it to other polypeptide or polypeptide domains such as, by way of non-limiting example, transferrin (WO06096515A2), albumin (Yeh et al., 1992), growth hormone (US2003104578AA); cellulose (Levy and Shoseyov, 2002); and/or Fc fragments (Ashkenazi and Chamow, 1997). The references in the foregoing paragraph are incorporated by reference herein in their entireties.

In some embodiments of any of the aspects, a polypeptide as described herein can comprise at least one peptide bond replacement. A polypeptide as described herein can comprise one type of peptide bond replacement or multiple types of peptide bond replacements, e.g. 2 types, 3 types, 4 types, 5 types, or more types of peptide bond replacements. Non-limiting examples of peptide bond replacements include urea, thiourea, carbamate, sulfonyl urea, trifluoroethylamine, ortho-(aminoalkyl)-phenylacetic acid, para-(aminoalkyl)-phenylacetic acid, meta-(aminoalkyl)-phenylacetic acid, thioamide, tetrazole, boronic ester, olefinic group, and derivatives thereof.

In some embodiments of any of the aspects, a polypeptide as described herein can comprise naturally occurring amino acids commonly found in polypeptides and/or proteins produced by living organisms, e.g. Ala (A), Val (V), Leu (L), Ile (I), Pro (P), Phe (F), Trp (W), Met (M), Gly (G), Ser (S), Thr (T), Cys (C), Tyr (Y), Asn (N), Gln (Q), Asp (D), Glu (E), Lys (K), Arg (R), and His (H). In some embodiments of any of the aspects, a polypeptide as described herein can comprise alternative amino acids. Non-limiting examples of alternative amino acids include, D-amino acids; beta-amino acids; homocysteine, phosphoserine, phosphothreonine, phosphotyrosine, hydroxyproline, gamma-carboxyglutamate; hippuric acid, octahydroindole-2-carboxylic acid, statine, 1,2,3,4-tetrahydroisoquinoline-3-carboxylic acid, penicillamine (3-mercapto-D-valine), ornithine, citruline, alpha-methyl-alanine, para-benzoylphenylalanine, para-amino phenylalanine, p-fluorophenylalanine, phenylglycine, propargylglycine, sarcosine, and tert-butylglycine), diaminobutyric acid, 7-hydroxy-tetrahydroisoquinoline carboxylic acid, naphthylalanine, biphenylalanine, cyclohexylalanine, amino-isobutyric acid, norvaline, norleucine, tert-leucine, tetrahydroisoquinoline carboxylic acid, pipecolic acid, phenylglycine, homophenylalanine, cyclohexylglycine, dehydroleucine, 2,2-diethylglycine, 1-amino-1-cyclopentanecarboxylic acid, 1-amino-1-cyclohexanecarboxylic acid, amino-benzoic acid, amino-naphthoic acid, gamma-aminobutyric acid, difluorophenylalanine, nipecotic acid, alpha-amino butyric acid, thienyl-alanine, t-butylglycine, trifluorovaline; hexafluoroleucine; fluorinated analogs; azide-modified amino acids; alkyne-modified amino acids; cyano-modified amino acids; and derivatives thereof.

In some embodiments of any of the aspects, a polypeptide can be modified, e.g. by addition of a moiety to one or more of the amino acids that together comprise the peptide. In some embodiments of any of the aspects, a polypeptide as described herein can comprise one or more moiety molecules, e.g. 1 or more moiety molecules per polypeptide, 2 or more moiety molecules per polypeptide, 5 or more moiety molecules per polypeptide, 10 or more moiety molecules per polypeptide or more moiety molecules per polypeptide. In some embodiments of any of the aspects, a polypeptide as described herein can comprise one more types of modifications and/or moieties, e.g. 1 type of modification, 2 types of modifications, 3 types of modifications or more types of modifications. Non-limiting examples of modifications and/or moieties include PEGylation; glycosylation; HESylation; ELPylation; lipidation; acetylation; amidation; end-capping modifications; cyano groups; phosphorylation; albumin, and cyclization. In some embodiments of any of the aspects, an end-capping modification can comprise acetylation at the N-terminus, N-terminal acylation, and N-terminal formylation. In some embodiments of any of the aspects, an end-capping modification can comprise amidation at the C-terminus, introduction of C-terminal alcohol, aldehyde, ester, and thioester moieties. The half-life of a polypeptide can be increased by the addition of moieties, e.g. PEG, albumin, or other fusion partners (e.g. Fc fragment of an immunoglobin).

Any cysteine residue not involved in maintaining the proper conformation of the polypeptide also can be substituted, generally with serine, to improve the oxidative stability of the molecule and prevent aberrant crosslinking. Conversely, cysteine bond(s) can be added to the polypeptide to improve its stability or facilitate oligomerization.

Alterations of the native amino acid sequence can be accomplished by any of a number of techniques known to one of skill in the art. Mutations can be introduced, for example, at particular loci by synthesizing oligonucleotides containing a mutant sequence, flanked by restriction sites enabling ligation to fragments of the native sequence. Following ligation, the resulting reconstructed sequence encodes an analog having the desired amino acid insertion, substitution, or deletion. Alternatively, oligonucleotide-directed site-specific mutagenesis procedures can be employed to provide an altered nucleotide sequence having particular codons altered according to the substitution, deletion, or insertion required. Techniques for making such alterations are very well established. Alterations of the original amino acid sequence can be accomplished by any of a number of techniques known to one of skill in the art. Mutations can be introduced, for example, at particular loci by synthesizing oligonucleotides containing a mutant sequence, flanked by restriction sites permitting ligation to fragments of the native sequence. Following ligation, the resulting reconstructed sequence encodes an analog having the desired amino acid insertion, substitution, or deletion. Alternatively, oligonucleotide-directed site-specific mutagenesis procedures can be employed to provide an altered nucleotide sequence having particular codons altered according to the substitution, deletion, or insertion required. Techniques for making such alterations include those disclosed by Khudyakov et al. "Artificial DNA: Methods and Applications" CRC Press, 2002; Braman "In Vitro Mutagenesis Protocols" Springer, 2004; and Rapley "The Nucleic Acid Protocols Handbook" Springer 2000; which are herein incorporated by reference in their entireties. In some embodiments of any of the aspects, a polypeptide as described herein can be chemically synthesized and mutations can be incorporated as part of the chemical synthesis process.

As used herein, the term "nucleic acid" or "nucleic acid sequence" refers to any molecule, preferably a polymeric molecule, incorporating units of ribonucleic acid, deoxyribonucleic acid or an analog thereof. The nucleic acid can be either single-stranded or double-stranded. A single-stranded nucleic acid can be one nucleic acid strand of a denatured double-stranded DNA. Alternatively, it can be a single-stranded nucleic acid not derived from any double-stranded DNA. In one aspect, the nucleic acid can be DNA. In another aspect, the nucleic acid can be RNA. Suitable DNA can include, e.g., genomic DNA or cDNA. Suitable RNA can include, e.g., mRNA.

The term "expression" refers to the cellular processes involved in producing RNA and proteins and as appropriate, secreting proteins, including where applicable, but not limited to, for example, transcription, transcript processing, translation and protein folding, modification and processing. Expression can refer to the transcription and stable accumulation of sense (mRNA) or antisense RNA derived from a nucleic acid fragment or fragments of the invention and/or to the translation of mRNA into a polypeptide.

"Expression products" include RNA transcribed from a gene, and polypeptides obtained by translation of mRNA transcribed from a gene. The term "gene" means the nucleic acid sequence which is transcribed (DNA) to RNA in vitro or in vivo when operably linked to appropriate regulatory sequences. The gene may or may not include regions preceding and following the coding region, e.g. 5' untranslated (5'UTR) or "leader" sequences and 3' UTR or "trailer" sequences, as well as intervening sequences (introns) between individual coding segments (exons).

"Operably linked" refers to an arrangement of elements wherein the components so described are configured so as to perform their usual function. Thus, control elements operably linked to a coding sequence are capable of effecting the expression of the coding sequence. The control elements need not be contiguous with the coding sequence, so long as they function to direct the expression thereof. Thus, for example, intervening untranslated yet transcribed sequences can be present between a promoter sequence and the coding sequence and the promoter sequence can still be considered "operably linked" to the coding sequence.

In some embodiments of any of the aspects, the methods described herein relate to measuring, detecting, or determining the level of at least one marker. As used herein, the term "detecting" or "measuring" refers to observing a signal from, e.g. a probe, label, or target molecule to indicate the presence of an analyte in a sample. Any method known in the art for detecting a particular label moiety can be used for detection. Exemplary detection methods include, but are not limited to, spectroscopic, fluorescent, photochemical, biochemical, immunochemical, electrical, optical or chemical methods. In some embodiments of any of the aspects, measuring can be a quantitative observation.

In some embodiments of any of the aspects, a polypeptide, nucleic acid, or cell as described herein can be engineered. As used herein, "engineered" refers to the aspect of having been manipulated by the hand of man. For example, a polypeptide is considered to be "engineered" when at least one aspect of the polypeptide, e.g., its sequence, has been manipulated by the hand of man to differ from the aspect as it exists in nature. As is common practice and is understood by those in the art, progeny of an engineered cell are typically still referred to as "engineered" even though the actual manipulation was performed on a prior entity.

In some embodiments of any of the aspects, a agent (e.g., an antibody, antibody reagent, antigen-binding fragment thereof, CAR, cell, nucleic acid, or therapeutic agent) described herein is exogenous. In some embodiments of any of the aspects, the agent described herein is ectopic. In some embodiments of any of the aspects, the agent described herein is not endogenous.

The term "exogenous" refers to a substance present in a cell other than its native source. The term "exogenous" when used herein can refer to a nucleic acid (e.g. a nucleic acid encoding a polypeptide) or a polypeptide that has been introduced by a process involving the hand of man into a biological system such as a cell or organism in which it is not normally found and one wishes to introduce the nucleic acid or polypeptide into such a cell or organism. Alternatively, "exogenous" can refer to a nucleic acid or a polypeptide that has been introduced by a process involving the hand of man into a biological system such as a cell or organism in which it is found in relatively low amounts and one wishes to increase the amount of the nucleic acid or polypeptide in the cell or organism, e.g., to create ectopic expression or levels. In contrast, the term "endogenous" refers to a substance that is native to the biological system or cell. As used herein, "ectopic" refers to a substance that is found in an unusual location and/or amount. An ectopic substance can be one that is normally found in a given cell, but at a much lower amount and/or at a different time. Ectopic also includes substance, such as a polypeptide or nucleic acid that is not naturally found or expressed in a given cell in its natural environment.

In some embodiments of any of the aspects, a nucleic acid encoding a polypeptide as described herein is comprised by a vector. In some of the aspects described herein, a nucleic acid sequence encoding a given polypeptide as described herein, or any module thereof, is operably linked to a vector. The term "vector", as used herein, refers to a nucleic acid construct designed for delivery to a host cell or for transfer between different host cells. As used herein, a vector can be viral or non-viral. The term "vector" encompasses any genetic element that is capable of replication when associated with the proper control elements and that can transfer gene sequences to cells. A vector can include, but is not limited to, a cloning vector, an expression vector, a plasmid, phage, transposon, cosmid, chromosome, virus, virion, etc.

In some embodiments of any of the aspects, the vector is recombinant, e.g., it comprises sequences originating from at least two different sources. In some embodiments of any of the aspects, the vector comprises sequences originating from at least two different species. In some embodiments of any of the aspects, the vector comprises sequences originating from at least two different genes, e.g., it comprises a fusion protein or a nucleic acid encoding an expression product which is operably linked to at least one non-native (e.g., heterologous) genetic control element (e.g., a promoter, suppressor, activator, enhancer, response element, or the like).

In some embodiments of any of the aspects, the vector or nucleic acid described herein is codon-optimized, e.g., the native or wild-type sequence of the nucleic acid sequence has been altered or engineered to include alternative codons such that altered or engineered nucleic acid encodes the same polypeptide expression product as the native/wild-type sequence, but will be transcribed and/or translated at an improved efficiency in a desired expression system. In some embodiments of any of the aspects, the expression system is an organism other than the source of the native/wild-type sequence (or a cell obtained from such organism). In some embodiments of any of the aspects, the vector and/or nucleic acid sequence described herein is codon-optimized for expression in a mammal or mammalian cell, e.g., a mouse, a murine cell, or a human cell. In some embodiments of any of the aspects, the vector and/or nucleic acid sequence described herein is codon-optimized for expression in a human cell. In some embodiments of any of the aspects, the vector and/or nucleic acid sequence described herein is codon-optimized for expression in a yeast or yeast cell. In some embodiments of any of the aspects, the vector and/or nucleic acid sequence described herein is codon-optimized for expression in a bacterial cell. In some embodiments of any of the aspects, the vector and/or nucleic acid sequence described herein is codon-optimized for expression in an *E. coli* cell.

As used herein, the term "expression vector" refers to a vector that directs expression of an RNA or polypeptide from sequences linked to transcriptional regulatory sequences on the vector. The sequences expressed will often, but not necessarily, be heterologous to the cell. An expression vector may comprise additional elements, for example, the expression vector may have two replication systems, thus allowing it to be maintained in two organisms, for example in human cells for expression and in a prokaryotic host for cloning and amplification.

As used herein, the term "viral vector" refers to a nucleic acid vector construct that includes at least one element of viral origin and has the capacity to be packaged into a viral vector particle. The viral vector can contain the nucleic acid encoding a polypeptide as described herein in place of non-essential viral genes. The vector and/or particle may be utilized for the purpose of transferring any nucleic acids into cells either in vitro or in vivo. Numerous forms of viral vectors are known in the art.

It should be understood that the vectors described herein can, in some embodiments, be combined with other suitable compositions and therapies. In some embodiments of any of the aspects, the vector is episomal. The use of a suitable episomal vector provides a means of maintaining the nucleotide of interest in the subject in high copy number extra chromosomal DNA thereby eliminating potential effects of chromosomal integration.

As used herein, the terms "treat," "treatment," "treating," or "amelioration" refer to therapeutic treatments, wherein the object is to reverse, alleviate, ameliorate, inhibit, slow down or stop the progression or severity of a condition associated with a disease or disorder, e.g. cancer. The term "treating" includes reducing or alleviating at least one adverse effect or symptom of a condition, disease or disorder. Treatment is generally "effective" if one or more symptoms or clinical markers are reduced. Alternatively, treatment is "effective" if the progression of a disease is reduced or halted. That is, "treatment" includes not just the improvement of symptoms or markers, but also a cessation of, or at least slowing of, progress or worsening of symptoms compared to what would be expected in the absence of treatment. Beneficial or desired clinical results include, but are not limited to, alleviation of one or more symptom(s), diminishment of extent of disease, stabilized (i.e., not worsening) state of disease, delay or slowing of disease progression, amelioration or palliation of the disease state, remission (whether partial or total), and/or decreased mortality, whether detectable or undetectable. The term "treatment" of a disease also includes providing relief from the symptoms or side-effects of the disease (including palliative treatment).

In some embodiments of any of the aspects, described herein is a prophylactic method of treatment. As used herein "prophylactic" refers to the timing and intent of a treatment relative to a disease or symptom, that is, the treatment is administered prior to clinical detection or diagnosis of that particular disease or symptom in order to protect the patient from the disease or symptom. Prophylactic treatment can encompass a reduction in the severity or speed of onset of the disease or symptom, or contribute to faster recovery from the disease or symptom. Accordingly, the methods described herein can be prophylactic relative to, e.g., metastasis or further tumor growth. In some embodiments of any of the aspects, prophylactic treatment is not prevention of all symptoms or signs of a disease.

As used herein, the term "pharmaceutical composition" refers to the active agent in combination with a pharmaceutically acceptable carrier e.g. a carrier commonly used in the pharmaceutical industry. The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. In some embodiments of any of the aspects, a pharmaceutically acceptable carrier can be a carrier other than water. In some embodiments of any of the aspects, a pharmaceutically acceptable carrier can be a cream, emulsion, gel, liposome, nanoparticle, and/or ointment. In some embodiments of any of the aspects, a pharmaceutically acceptable carrier can be an artificial or engineered carrier, e.g., a carrier that the active ingredient would not be found to occur in in nature.

As used herein, the term "administering," refers to the placement of a compound as disclosed herein into a subject by a method or route which results in at least partial delivery of the agent at a desired site. Pharmaceutical compositions comprising the compounds disclosed herein can be administered by any appropriate route which results in an effective treatment in the subject. In some embodiments of any of the aspects, administration comprises physical human activity, e.g., an injection, act of ingestion, an act of application, and/or manipulation of a delivery device or machine. Such activity can be performed, e.g., by a medical professional and/or the subject being treated.

As used herein, "contacting" refers to any suitable means for delivering, or exposing, an agent to at least one cell. Exemplary delivery methods include, but are not limited to, direct delivery to cell culture medium, perfusion, injection, or other delivery method well known to one skilled in the art. In some embodiments of any of the aspects, contacting comprises physical human activity, e.g., an injection; an act of dispensing, mixing, and/or decanting; and/or manipulation of a delivery device or machine.

The term "statistically significant" or "significantly" refers to statistical significance and generally means a two standard deviation (2SD) or greater difference.

Other than in the operating examples, or where otherwise indicated, all numbers expressing quantities of ingredients or reaction conditions used herein should be understood as modified in all instances by the term "about." The term "about" when used in connection with percentages can mean $\pm 1\%$.

As used herein, the term "comprising" means that other elements can also be present in addition to the defined elements presented. The use of "comprising" indicates inclusion rather than limitation.

The term "consisting of" refers to compositions, methods, and respective components thereof as described herein, which are exclusive of any element not recited in that description of the embodiment.

As used herein the term "consisting essentially of" refers to those elements required for a given embodiment. The term permits the presence of additional elements that do not materially affect the basic and novel or functional characteristic(s) of that embodiment of the invention.

As used herein, an "epitope" can be formed on a polypeptide both from contiguous amino acids, or noncontiguous amino acids juxtaposed by tertiary folding of a protein. Epitopes formed from contiguous amino acids are typically retained on exposure to denaturing solvents, whereas epitopes formed by tertiary folding are typically lost on treatment with denaturing solvents. An epitope typically includes at least 3, and more usually, at least 5, about 9, or about 8-10 amino acids in a unique spatial conformation. An "epitope" includes the unit of structure conventionally bound by an immunoglobulin VH/VL pair. Epitopes define the minimum binding site for an antibody, and thus represent the target of specificity of an antibody. In the case of a single domain antibody, an epitope represents the unit of structure bound by a variable domain in isolation. The terms "antigenic determinant" and "epitope" can also be used interchangeably herein. In certain embodiments, epitope determinants include chemically active surface groupings of molecules such as amino acids, sugar side chains, phosphoryl, or sulfonyl, and, in certain embodiments, may have specific three dimensional structural characteristics, and/or specific charge characteristics.

"Avidity" is the measure of the strength of binding between an antigen-binding molecule (such as an antibody or antigen-binding portion thereof described herein) and the pertinent antigen. Avidity is related to both the affinity between an antigenic determinant and its antigen binding site on the antigen-binding molecule, and the number of pertinent binding sites present on the antigen-binding molecule. Typically, antigen-binding proteins (such as an antibody or portion of an antibody as described herein) will bind to their cognate or specific antigen with a dissociation constant (KD of $10^{-5}$ to $10^{-12}$ moles/liter or less, such as $10^{-7}$ to $10^{-12}$ moles/liter or less, or $10^{-8}$ to $10^{-12}$ moles/liter (i.e., with an association constant (KA) of $10^5$ to $10^{12}$ liter/moles or more, such as $10^7$ to $10^{12}$ liter/moles or $10^8$ to $10^{12}$ liter/moles). Any KD value greater than $10^{-4}$ mol/liter (or any KA value lower than $10^4$ $M^{-1}$) is generally considered to indicate non-specific binding. The KD for biological interactions which are considered meaningful (e.g., specific) are typically in the range of $10^{-10}$ M (0.1 nM) to $10^{-5}$ M (10000 nM). The stronger an interaction, the lower is its KD. For example, a binding site on an antibody or portion thereof described herein will bind to the desired antigen with an affinity less than 500 nM, such as less than 200 nM, or less than 10 nM, such as less than 500 pM. Specific binding of an antigen-binding protein to an antigen or antigenic determinant can be determined in any suitable manner known per se, including, for example, Scatchard analysis and/or competitive binding assays, such as radioimmunoassays (RIA), enzyme immunoassays (EIA) and sandwich competition assays, and the different variants thereof known per se in the art; as well as other techniques as mentioned herein.

As used herein, the term "specific binding" refers to a chemical interaction between two molecules, compounds, cells and/or particles wherein the first entity binds to the second, target entity with greater specificity and affinity than it binds to a third entity which is a non-target. In some embodiments of any of the aspects, specific binding can refer to an affinity of the first entity for the second target entity which is at least 10 times, at least 50 times, at least 100 times, at least 500 times, at least 1000 times or greater than the affinity for the third nontarget entity. A reagent specific for a given target is one that exhibits specific binding for that target under the conditions of the assay being utilized.

In some embodiments of any of the aspects, a reagent that binds specifically has the ability to bind to a target, such as an antigen present on the cell-surface, with a KD $10^{-5}$ M (10000 nM) or less, e.g., $10^{-6}$ M, $10^{-7}$ M, $10^{-8}$ M, $10^{-9}$ M, $10^{-10}$ M, $10^{-11}$ M, $10^{-12}$ M, or less. Specific binding can be influenced by, for example, the affinity and avidity of the polypeptide agent and the concentration of polypeptide agent. The person of ordinary skill in the art can determine appropriate conditions under which the polypeptide agents described herein selectively bind the targets using any suitable methods, such as titration of a polypeptide agent in a suitable cell binding assay. A polypeptide specifically bound to a target is not displaced by a non-similar competitor. In certain embodiments, an antibody, antigen-binding portion thereof, or CAR is said to specifically bind an antigen when it preferentially recognizes its target antigen in a complex mixture of proteins and/or macromolecules.

In some embodiments of any of the aspects, an antibody, antigen-binding portion thereof, and/or CAR as described herein binds to Mfsd2A with a dissociation constant ($K_D$) of $10^{-5}$ M (10000 nM) or less, e.g., $10^{-6}$ M, $10^{-7}$ M, $10^{-8}$ M, $10^{-9}$ M, $10^{-10}$ M, $10^{-11}$ M, $10^{-12}$ M, or less. In some embodiments of any of the aspects, an antibody, antigen-binding portion thereof, and/or CAR as described herein binds to Mfsd2A with a dissociation constant ($K_D$) of from about $10^{-5}$ M to $10^{-6}$ M. In some embodiments of any of the aspects, an antibody, antigen-binding portion thereof, and/or CAR as described herein binds to Mfsd2A with a dissociation constant ($K_D$) of from about $10^{-6}$ M to $10^{-7}$ M. In some embodiments of any of the aspects, an antibody, antigen-binding portion thereof, and/or CAR as described herein binds to Mfsd2A with a dissociation constant ($K_D$) of from about $10^{-7}$ M to $10^{-8}$ M. In some embodiments of any of the aspects, an antibody, antigen-binding portion thereof, and/or CAR as described herein binds to Mfsd2A with a dissociation constant ($K_D$) of from about $10^{-8}$ M to $10^{-9}$ M. In some embodiments of any of the aspects, an antibody, antigenbinding portion thereof, and/or CAR as described herein binds to Mfsd2A with a dissociation constant ($K_D$) of from about $10^{-9}$ M to $10^{-10}$ M. In some embodiments of any of the aspects, an antibody, antigen-binding portion thereof, and/or CAR as described herein binds to Mfsd2A with a dissociation constant ($K_D$) of from about $10^{-10}$ M to $10^{-11}$ M. In some embodiments of any of the aspects, an antibody, antigen-binding portion thereof, and/or CAR as described herein binds to Mfsd2A with a dissociation constant ($K_D$) of from about $10^{-11}$ M to $10^{-12}$ M. In some embodiments of any of the aspects, an antibody, antigen-binding portion thereof, and/or CAR as described herein binds to Mfsd2A with a dissociation constant ($K_D$) of less than $10^{-12}$ M.

The singular terms "a," "an," and "the" include plural referents unless context clearly indicates otherwise. Similarly, the word "or" is intended to include "and" unless the context clearly indicates otherwise. Although methods and materials similar or equivalent to those described herein can be used in the practice or testing of this disclosure, suitable methods and materials are described below. The abbreviation, "e.g." is derived from the Latin exempli gratia, and is used herein to indicate a non-limiting example. Thus, the abbreviation "e.g." is synonymous with the term "for example."

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

Unless otherwise defined herein, scientific and technical terms used in connection with the present application shall have the meanings that are commonly understood by those of ordinary skill in the art to which this disclosure belongs. It should be understood that this invention is not limited to the particular methodology, protocols, and reagents, etc., described herein and as such can vary. The terminology used herein is for the purpose of describing particular embodiments only, and is not intended to limit the scope of the present invention, which is defined solely by the claims. Definitions of common terms in immunology and molecular biology can be found in The Merck Manual of Diagnosis and Therapy, 20th Edition, published by Merck Sharp & Dohme Corp., 2018 (ISBN 0911910190, 978-0911910421); Robert S. Porter et al. (eds.), The Encyclopedia of Molecular Cell Biology and Molecular Medicine, published by Blackwell Science Ltd., 1999-2012 (ISBN 9783527600908); and Robert A. Meyers (ed.), Molecular Biology and Biotechnology: a Comprehensive Desk Reference, published by VCH Publishers, Inc., 1995 (ISBN 1-56081-569-8); Immunology by Werner Luttmann, published by Elsevier, 2006; Janeway's Immunobiology, Kenneth Murphy, Allan Mowat, Casey Weaver (eds.), W. W. Norton & Company, 2016 (ISBN 0815345054, 978-0815345053); Lewin's Genes XI, published by Jones & Bartlett Publishers, 2014 (ISBN-1449659055); Michael Richard Green and Joseph Sambrook, Molecular Cloning: A Laboratory Manual, 4th ed., Cold Spring Harbor Laboratory Press, Cold Spring Harbor, N.Y., USA (2012) (ISBN 1936113414); Davis et al., Basic Methods in Molecular Biology, Elsevier Science Publishing, Inc., New York, USA (2012) (ISBN 044460149X); Laboratory Methods in Enzymology: DNA, Jon Lorsch (ed.) Elsevier, 2013 (ISBN 0124199542); Current Protocols in Molecular Biology (CPMB), Frederick M. Ausubel (ed.), John Wiley and Sons, 2014 (ISBN 047150338X, 9780471503385), Current Protocols in Protein Science (CPPS), John E. Coligan (ed.), John Wiley and Sons, Inc., 2005; and Current Protocols in Immunology (CPI) (John E. Coligan, ADA M Kruisbeek, David H Margulies, Ethan M Shevach, Warren Strobe, (eds.) John Wiley and Sons, Inc., 2003 (ISBN 0471142735, 9780471142737), the contents of which are all incorporated by reference herein in their entireties.

One of skill in the art can readily identify a chemotherapeutic agent of use (e.g. see Physicians' Cancer Chemotherapy Drug Manual 2014, Edward Chu, Vincent T. DeVita Jr., Jones & Bartlett Learning; Principles of Cancer Therapy, Chapter 85 in Harrison's Principles of Internal Medicine, 18th edition; Therapeutic Targeting of Cancer Cells: Era of Molecularly Targeted Agents and Cancer Pharmacology, Chs. 28-29 in Abeloff's Clinical Oncology, 2013 Elsevier; and Fischer D S (ed): The Cancer Chemotherapy Handbook, 4th ed. St. Louis, Mosby-Year Book, 2003).

Non-limiting examples of cancer therapies for use in the methods and compositions described herein can include radiation therapy, surgery, gemcitabine, cisplastin, paclitaxel, carboplatin, bortezomib, AMG479, vorinostat, rituximab, temozolomide, rapamycin, ABT-737, PI-103; alkylating agents such as thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gamma1I and calicheamicin omega1I (see, e.g., Agnew, Chem. Intl. Ed. Engl., 33: 183-186 (1994)); dynemicin, including dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin;

anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL® paclitaxel (Bristol-Myers Squibb Oncology, Princeton, N.J.), ABRAXANE® Cremophor-free, albumin-engineered nanoparticle formulation of paclitaxel (American Pharmaceutical Partners, Schaumberg, Ill.), and TAXOTERE® doxetaxel (Rhone-Poulenc Rorer, Antony, France); chloranbucil; GEMZAR® gemcitabine; 6-thioguanine; mercaptopurine; methotrexate; platinum analogs such as cisplatin, oxaliplatin and carboplatin; vinblastine; platinum; etoposide (VP-16); ifosfamide; mitoxantrone; vincristine; NAVELBINE® vinorelbine; novantrone; teniposide; edatrexate; daunomycin; aminopterin; xeloda; ibandronate; irinotecan (Camptosar, CPT-11) (including the treatment regimen of irinotecan with 5-FU and leucovorin); topoisomerase inhibitor RFS 2000; difluoromethylornithine (DMFO); retinoids such as retinoic acid; capecitabine; combretastatin; leucovorin (LV); oxaliplatin, including the oxaliplatin treatment regimen (FOLFOX); lapatinib (Tykerb®); inhibitors of PKC-alpha, Raf, H-Ras, EGFR (e.g., erlotinib (Tarceva®)) and VEGF-A that reduce cell proliferation and pharmaceutically acceptable salts, acids or derivatives of any of the above.

Other terms are defined herein within the description of the various aspects of the invention.

All patents and other publications; including literature references, issued patents, published patent applications, and co-pending patent applications; cited throughout this application are expressly incorporated herein by reference for the purpose of describing and disclosing, for example, the methodologies described in such publications that might be used in connection with the technology described herein. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The description of embodiments of the disclosure is not intended to be exhaustive or to limit the disclosure to the precise form disclosed. While specific embodiments of, and examples for, the disclosure are described herein for illustrative purposes, various equivalent modifications are possible within the scope of the disclosure, as those skilled in the relevant art will recognize. For example, while method steps or functions are presented in a given order, alternative embodiments may perform functions in a different order, or functions may be performed substantially concurrently. The teachings of the disclosure provided herein can be applied to other procedures or methods as appropriate. The various embodiments described herein can be combined to provide further embodiments. Aspects of the disclosure can be modified, if necessary, to employ the compositions, functions and concepts of the above references and application to provide yet further embodiments of the disclosure. Moreover, due to biological functional equivalency considerations, some changes can be made in protein structure without affecting the biological or chemical action in kind or amount. These and other changes can be made to the disclosure in light of the detailed description. All such modifications are intended to be included within the scope of the appended claims.

Specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

In some embodiments, the present technology may be defined in any of the following numbered paragraphs:

1. An antibody, antibody reagent, antigen-binding fragment thereof, or chimeric antigen receptor (CAR), that specifically binds a Mfsd2A polypeptide, said antibody reagent, antigen-binding portion thereof, or CAR comprising at least one heavy or light chain complementarity determining region (CDR) selected from the group consisting of:
   (a) a heavy chain CDR1 having the amino acid sequence of SEQ ID NO: 4;
   (b) a heavy chain CDR2 having the amino acid sequence of SEQ ID NO: 5;
   (c) a heavy chain CDR3 having the amino acid sequence of SEQ ID NO: 6;
   (d) a light chain CDR1 having the amino acid sequence of SEQ ID NO: 1;
   (e) a light chain CDR2 having the amino acid sequence of SEQ ID NO: 2; and
   (f) a light chain CDR3 having the amino acid sequence of SEQ ID NO: 3;
   or a conservative substitution variant of one or more of (a)-(f).

2. The antibody, antibody reagent, antigen-binding portion thereof, or CAR of paragraph 1, which comprises heavy chain CDRs having the amino acid sequences of SEQ ID NOs: 4-6 or a conservative substitution variant of such amino acid sequence.

3. The antibody, antibody reagent, antigen-binding portion thereof, or CAR of any one of paragraphs 1-2, which comprises light chain CDRs having the amino acid sequences of SEQ ID NOs: 1-3 or a conservative substitution variant of such amino acid sequence.

4. The antibody, antibody reagent, antigen-binding portion thereof, or CAR of any one of paragraphs 1-3, which comprises:
   heavy chain CDRs having the amino acid sequences of SEQ ID NOs: 4-6 and light chain CDRs having the amino acid sequences of SEQ ID NOs: 1-3 or a conservative substitution variant of such amino acid sequence.

5. A first antibody, antibody reagent, antigen-binding portion thereof, or CAR that specifically binds a Mfsd2A polypeptide, and can compete for binding of Mfsd2A with a second antibody comprising: heavy chain CDRs having the amino acid sequences of SEQ ID NOs: 4-6 and light chain CDRs having the amino acid sequences of SEQ ID NOs: 1-3 or a conservative substitution variant of such amino acid sequence.

6. The first antibody, antibody reagent, antigen-binding fragment thereof, or chimeric antigen receptor (CAR) of paragraph 5, comprising at least one heavy or light chain complementarity determining region (CDR) selected from the group consisting of:
    (a) a heavy chain CDR1 having the amino acid sequence of SEQ ID NO: 4;
    (b) a heavy chain CDR2 having the amino acid sequence of SEQ ID NO: 5;
    (c) a heavy chain CDR3 having the amino acid sequence of SEQ ID NO: 6;
    (d) a light chain CDR1 having the amino acid sequence of SEQ ID NO: 1;
    (e) a light chain CDR2 having the amino acid sequence of SEQ ID NO: 2; and
    (f) a light chain CDR3 having the amino acid sequence of SEQ ID NO: 3;
    Or a conservative substitution variant of one or more of (a)-(f).

7. The antibody, antibody reagent, antigen-binding portion thereof, or CAR of any one of paragraphs 5-6, which comprises heavy chain CDRs having the amino acid sequences of SEQ ID NOs: 4-6 or a conservative substitution variant of such amino acid sequence.

8. The antibody, antibody reagent, antigen-binding portion thereof, or CAR of any one of paragraphs 5-7, which comprises light chain CDRs having the amino acid sequences of SEQ ID NOs: 1-3 or a conservative substitution variant of such amino acid sequence.

9. The antibody, antibody reagent, antigen-binding portion thereof, or CAR of any one of paragraphs 5-8, which comprises:
    heavy chain CDRs having the amino acid sequences of SEQ ID NOs: 4-6 and light chain CDRs having the amino acid sequences of SEQ ID NOs: 1-3 or a conservative substitution variant of such amino acid sequence.

10. The antibody, antibody reagent, antigen-binding portion thereof, or CAR of any one of paragraphs 1-9, comprising the sequence of SEQ ID NO: 7.

11. The antibody, antibody reagent, antigen-binding portion thereof, or CAR of any one of paragraphs 1-10, further comprising a conservative substitution in a sequence not comprised by a CDR.

12. The antibody, antibody reagent, antigen-binding portion thereof, or CAR of any one of paragraphs 1-11, wherein the antibody reagent or antigen-binding fragment thereof is fully human or fully humanized.

13. The antibody, antibody reagent, antigen-binding portion thereof, or CAR of any one of paragraphs 1-12, wherein the antibody reagent or antigen-binding fragment thereof is fully humanized except for the CDR sequences.

14. The antibody, antibody reagent, antigen-binding portion thereof, or CAR of any one of paragraphs 1-13, wherein the antibody reagent or antigen-binding fragment is selected from the group consisting of:
    an immunoglobulin molecule, a monoclonal antibody, a chimeric antibody, a CDR-grafted antibody, a humanized antibody, a Fab, a Fab', a F(ab')2, a Fv, a disulfide linked Fv, a scFv, a single domain antibody, a diabody, a multispecific antibody, a dual specific antibody, an anti-idiotypic antibody, and a bispecific antibody.

15. A composition, kit, or combination comprising:
    (i) the antibody, antibody reagent, antigen-binding portion thereof, or CAR of any one of paragraphs 1-14; and
    (ii) a central nervous system therapeutic agent.

16. The composition, kit, or combination of paragraph 15, wherein the antibody, antibody reagent, or antigen-binding portion thereof is conjugated to the central nervous system therapeutic agent.

17. A nucleic acid sequence encoding the antibody, antibody reagent, antigen-binding fragment thereof, or CAR of any one of paragraphs 1-14.

18. A cell comprising the antibody, antibody reagent, antigen-binding fragment thereof, or CAR of any one of paragraphs 1-14 or the nucleic acid sequence of paragraph 17.

19. A pharmaceutical composition comprising the antibody, antibody reagent, antigen-binding fragment thereof, or CAR of any one of paragraphs 1-14; or the composition, kit, or combination of any one of paragraphs 15-16; or the nucleic acid sequence of paragraph 17; or the cell of paragraph 18 and a pharmaceutically acceptable carrier.

20. A solid support comprising the antibody, antibody reagent, antigen-binding fragment thereof, or CAR of any one of paragraphs 1-14.

21. The solid support of paragraph 20, wherein the antibody, antibody reagent or antigen-binding fragment thereof is detectably labeled.

22. The solid support of any one of paragraphs 20-21, wherein the solid support comprises a particle, a bead, a polymer, or a substrate.

23. A kit for the detection of Mfsd2A polypeptide in a sample, the kit comprising at least a first antibody, antibody reagent, antigen-binding fragment thereof, or CAR of any one of paragraphs 1-14 immobilized on a solid support and comprising a detectable label.

24. A molecular complex comprising at least one antibody, antibody reagent, antigen-binding fragment thereof, or CAR of any one of paragraphs 1-14 bound to a Mfsd2A polypeptide.

25. A method of treatment comprising administering to a subject in need thereof:
    (i) the antibody, antibody reagent, antigen-binding portion thereof, or CAR of any one of paragraphs 1-14;
    (ii) the composition kit, or combination of any one of paragraphs 15-16; and/or
    (iii) the cell of paragraph 18.

26. The method of paragraph 25, wherein the subject is in need of treatment for a condition selected from the group consisting of:
    brain cancer; a brain tumor; encephalitis; hydrocephalus; Parkinson's disease; neuropathic pain; a condition treated by the administration of psychiatric drugs; a neurodegenerative disease; multiple sclerosis; Huntington's disease; Pick's disease; ALS; dementia; stroke; and Alzheimer's disease.

27. The method of paragraph 26, wherein the brain cancer is primary central nervous system (CNS) lymphoma (PCNSL) or glioblastoma.

28. The method of paragraph 26, wherein the brain tumor is a metastasis; or a metastasis of melanoma, breast, or lung cancer.

29. A method of increasing blood-brain barrier (BBB) permeability in a subject, the method comprising administering to the subject:
   (i) the antibody, antibody reagent, antigen-binding portion thereof, or CAR of any one of paragraphs 1-14;
   (ii) the composition kit, or combination of any one of paragraphs 15-16; and/or
   (iii) the cell of paragraph 26.

30. The antibody, antibody reagent, antigen-binding fragment thereof, chimeric antigen receptor (CAR), nucleic acid, cell, composition, kit, or combination of any of paragraphs 1-19 for use in a method of treating a subject or increasing BBB permeability in a subject, the method comprising administering the antibody, antibody reagent, antigen-binding fragment thereof, chimeric antigen receptor (CAR), nucleic acid, cell, composition, kit, or combination to the subject.

31. The antibody, antibody reagent, antigen-binding fragment thereof, chimeric antigen receptor (CAR), nucleic acid, cell, composition, kit, or combination of paragraph 30, wherein the subject is in need of treatment for a condition selected from the group consisting of: brain cancer; a brain tumor; encephalitis; hydrocephalus; Parkinson's disease; neuropathic pain; a condition treated by the administration of psychiatric drugs; a neurodegenerative disease; multiple sclerosis; Huntington's disease; Pick's disease; ALS; dementia; stroke; and Alzheimer's disease.

32. The antibody, antibody reagent, antigen-binding fragment thereof, chimeric antigen receptor (CAR), nucleic acid, cell, composition, kit, or combination of paragraph 31, wherein the brain cancer is primary central nervous system (CNS) lymphoma (PCNSL) or glioblastoma.

33. The antibody, antibody reagent, antigen-binding fragment thereof, chimeric antigen receptor (CAR), nucleic acid, cell, composition, kit, or combination of paragraph 31, wherein the brain tumor is a metastasis; or a metastasis of melanoma, breast, or lung cancer.

The technology described herein is further illustrated by the following examples which in no way should be construed as being further limiting.

EXAMPLES

Example 1—Structure and Mechanism of Blood-Brain Barrier Lysophosphatidylcholine Transporter Mfsd2a Mfsd2a is a sodium-dependent lysophosphatidylcholine symporter that is responsible for docosahexaenoic acid (DHA) uptake into the brain thus crucial for normal brain development. Mfsd2a's ability to transport lipid is also a key mechanism underlying its function as a transcytosis inhibitor to regulate the BBB. Thus, Mfsd2a also represents an attractive target for modulating BBB permeability for therapy or drug delivery. Described herein is the cryo-electron microscopy structure of Mfsd2a. This structure defines this important transporter's architecture, reveals its unique extracellular domain and uncovers the substrate binding cavity. The structure, together with the functional studies, identifies a conserved sodium-binding site, reveals a potential lipid entry pathway, and helps rationalize Mfsd2a mutations that underlie microcephaly syndromes. These results shed light on Mfsd2a's critical lipid transport function and relate to specific modulators for therapeutic purposes.

The blood-brain barrier (BBB) controls solute flux between the central nervous system (CNS) and the blood to support normal brain function[1-3]. Historically, the restricted permeability of brain vasculature has been attributed to specialized tight junctions between adjacent endothelial cells that prohibit paracellular passage of water-soluble molecules[4-6]. Recent evidence shows that CNS endothelial cells also actively inhibit transcytosis to ensure BBB integrity and that full barrier integrity requires restriction of both paracellular and transcellular leakage. Specifically, a BBB-specific lipid transporter, Mfsd2a, was found to be a key inhibitor of transcytosis for BBB function[7-9]. In CNS endothelial cells, Mfsd2a-translocated phospholipids give the plasma membrane a unique composition that inhibits caveolae vesicle formation and thereby suppresses transcytosis[8,10]. The lipid transport function of Mfsd2a thus plays a central role in ensuring BBB integrity, making Mfsd2a a highly promising target for manipulating BBB's permeability to deliver drugs into CNS[8,11].

Mfsd2a translocates lysophosphatidylcholine (LPC)-conjugated long chain fatty acids in a sodium-dependent manner. It is required for docosahexaenoic acid (DHA) uptake into brain[12,13], where DHA is abundant but the levels of de novo synthesis are extremely low[14-16]. The critical requirement for DHA in normal brain development and cognitive performance[17-20] underscores the important role Mfsd2a plays in brain growth and function. The effects of Mfsd2a mutations likewise attest to its importance: they cause progressive or lethal microcephaly syndromes in both humans and mice, with the severity of the disease correlating with the degree to which Mfsd2a function is impaired[21,22].

As a lipid transporter[12,13], Mfsd2a is unique among the known mammalian members of the ubiquitous MFS superfamily transporters, whose members are typically involved in transporting diverse soluble substrates such as solutes and ions[23]. Moreover, Mfsd2a lacks significant sequence similarity to MFS transporters with known structures: its closest homolog with a structure, a bacterial melibiose transporter MelB, shares only ~25% identify and is not involved in lipid transport[24,25]. The lack of a reliable structural model impedes the mechanistic understanding of Mfsd2a functions, leaving fundamental questions to be answered. For example, how does Mfsd2a mediate lipid transport, and how is the transport coupled to sodium?

To elucidate the structural basis of the Mfsd2a transporter and to gain insight into its transport mechanisms, structural and functional studies were performed. Described herein is the structure of mouse Mfsd2a as determined by single-particle cryo-electron microscope (cryo-EM). The structure together with functional characterizations and molecular dynamics (MD) simulations reveals the architecture of this important transporter and provides a blueprint to understand the lipid translocation pathway and the mechanism of sodium-dependent transport.

Structural determination and functional characterization. To understand the structure and transport mechanism of Mfsd2a, mouse Mfsd2a was focused on. This Mfsd2a has been extensively characterized as a model system to establish Mfsd2a's physiological functions[7,8,10]. In addition to having optimal biochemical properties, mouse Mfsd2a shares high sequence similarity with its human counterpart (84% sequence identity and 90% similarity). The transporter's activity was measured using an uptake assay of Top-Fluor LPC, a fluorescent LPC previously shown as an Mfsd2a substrate[12,13]. Cells that overexpress wild-type mouse Mfsd2a show significant uptake activity above the control (that does not overexpress Mfsd2a) (FIG. 1A). Substituting D96, a residue critical for transport activity[12], substantially reduced the uptake activity. These results indicate that mouse Mfsd2a is a LPC transporter with properties comparable to human Mfsd2a.

Figure 1B:
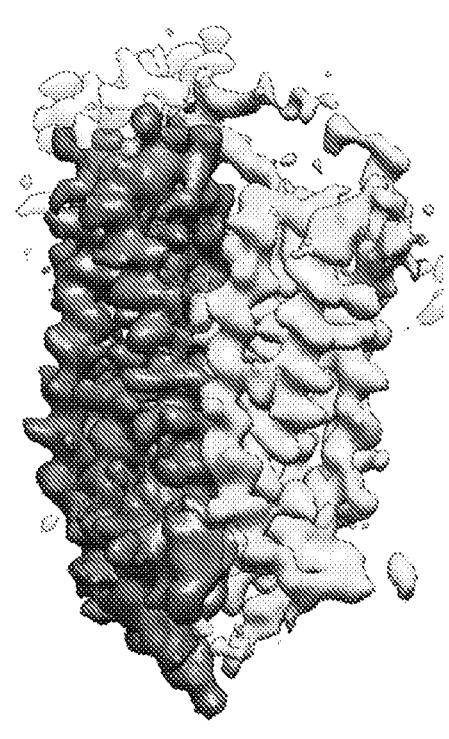
Figure 6B:
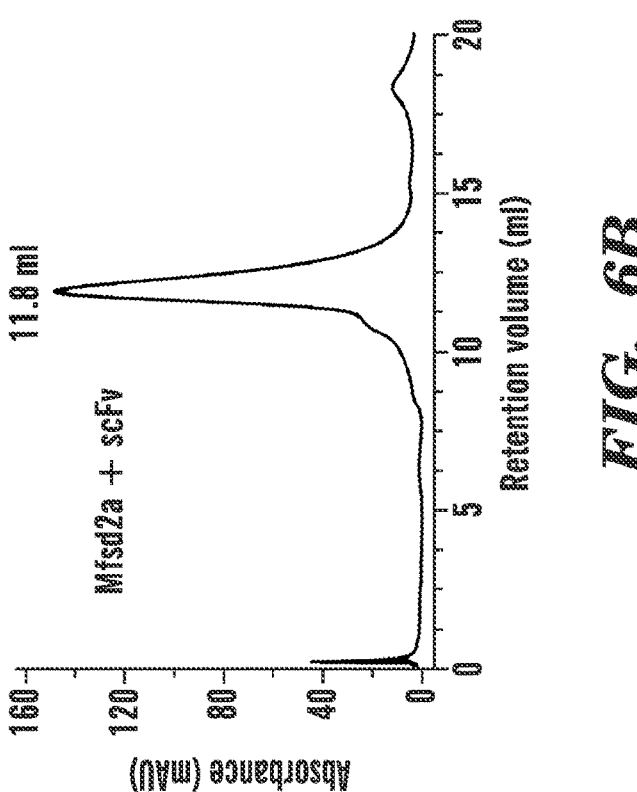
Figure 6A:
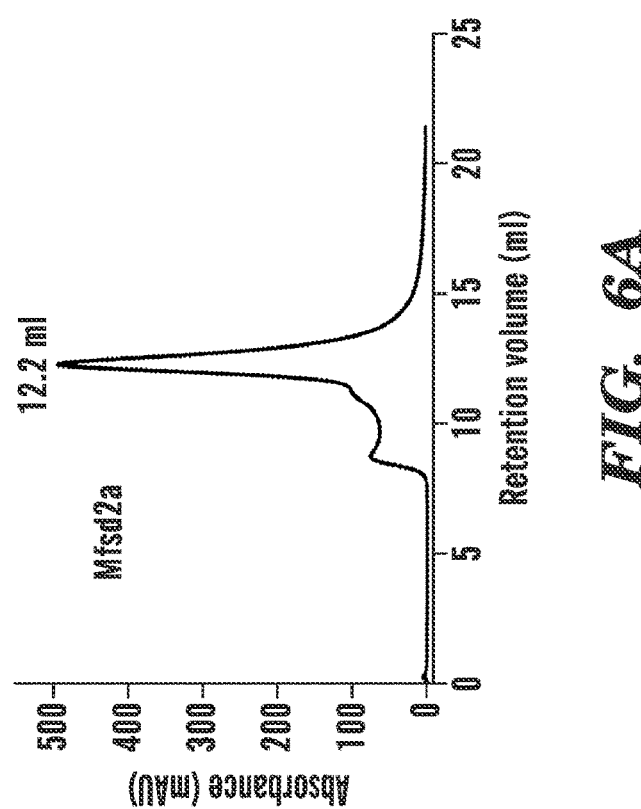
Figure 6D:
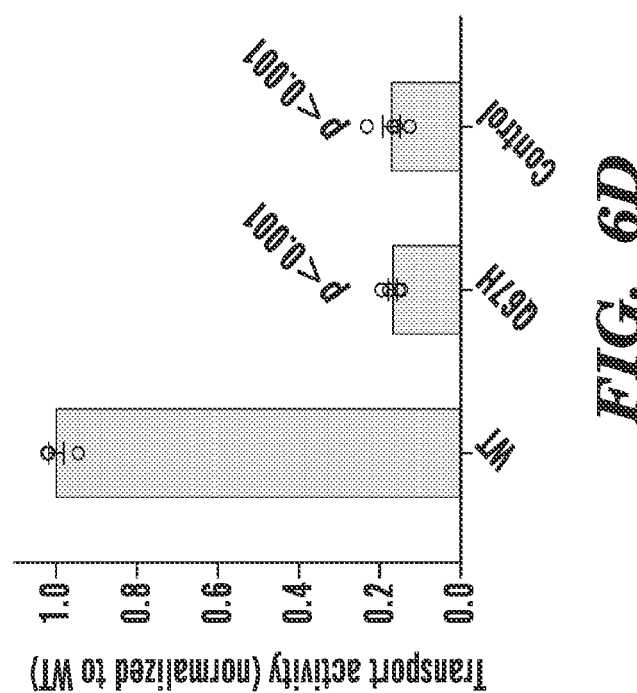
Figure 6C:
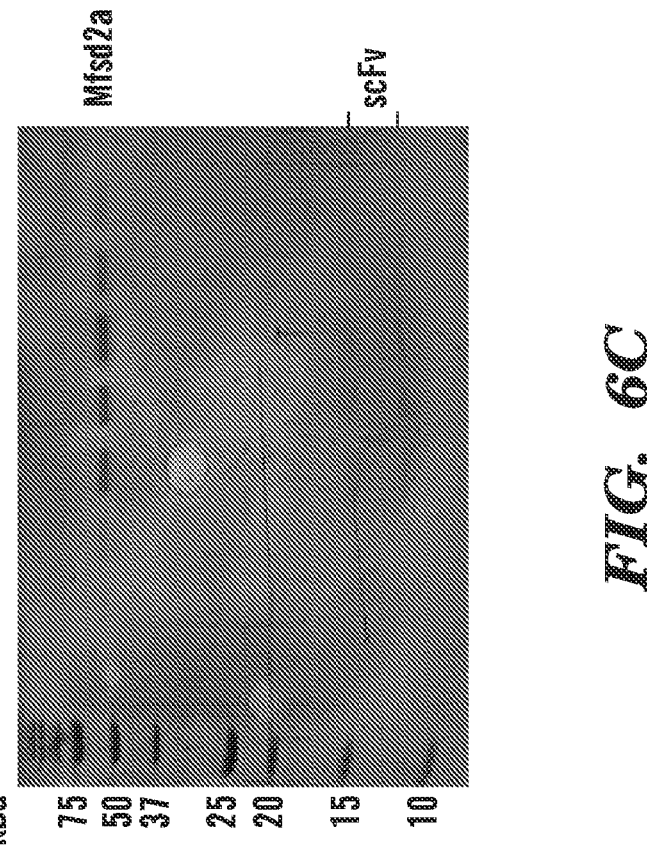
Figures 7A, 7B:
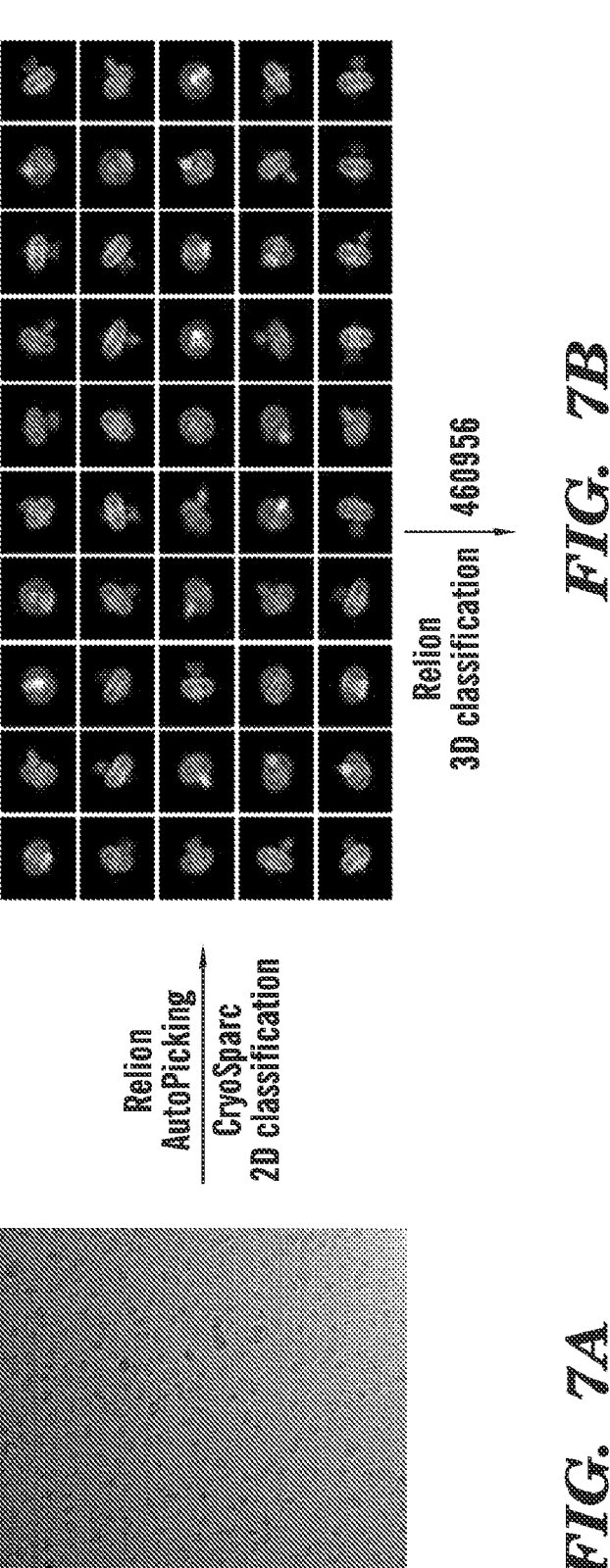
Figure 7C:
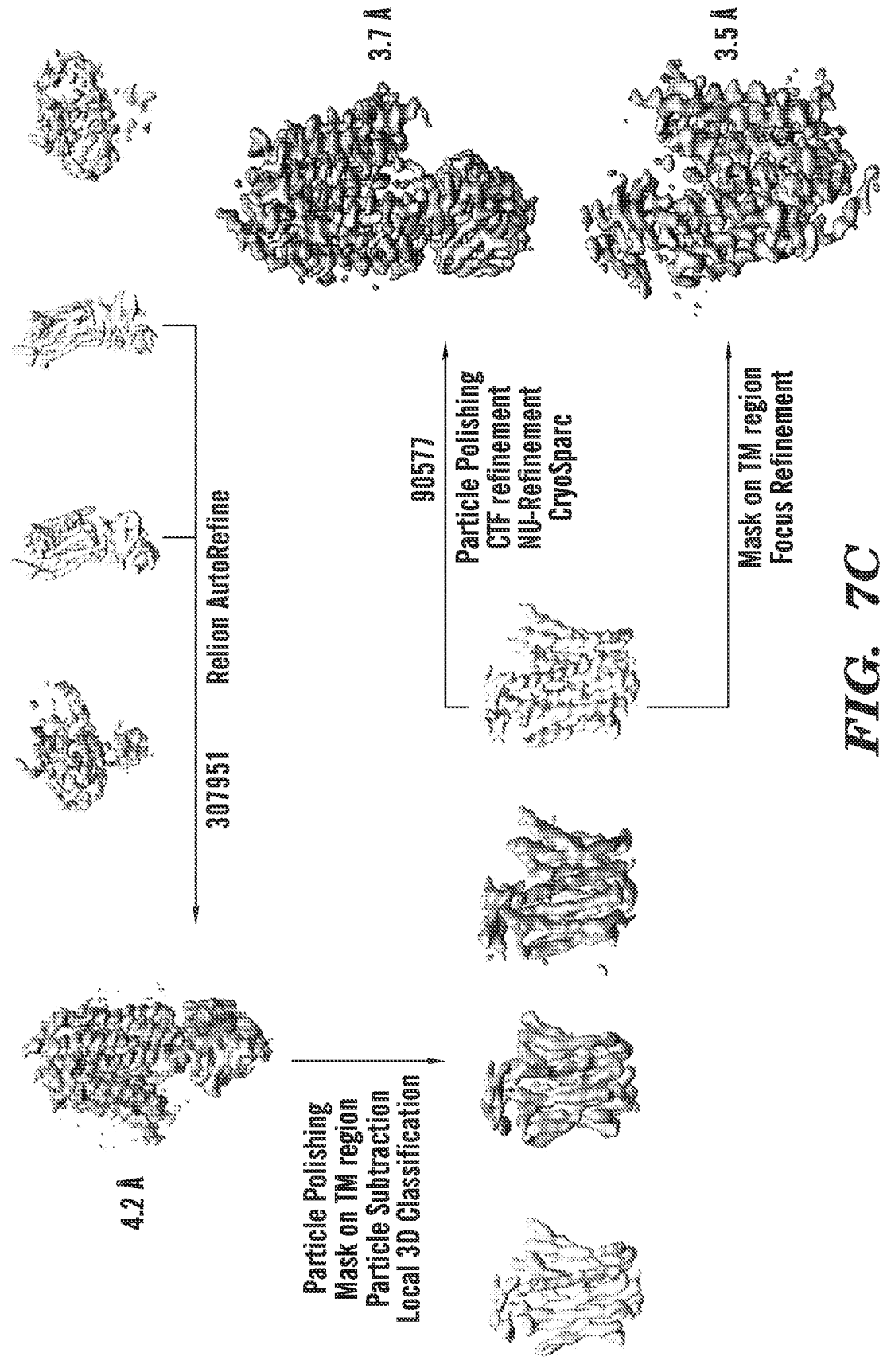
Figures 7D, 7E, 7F:
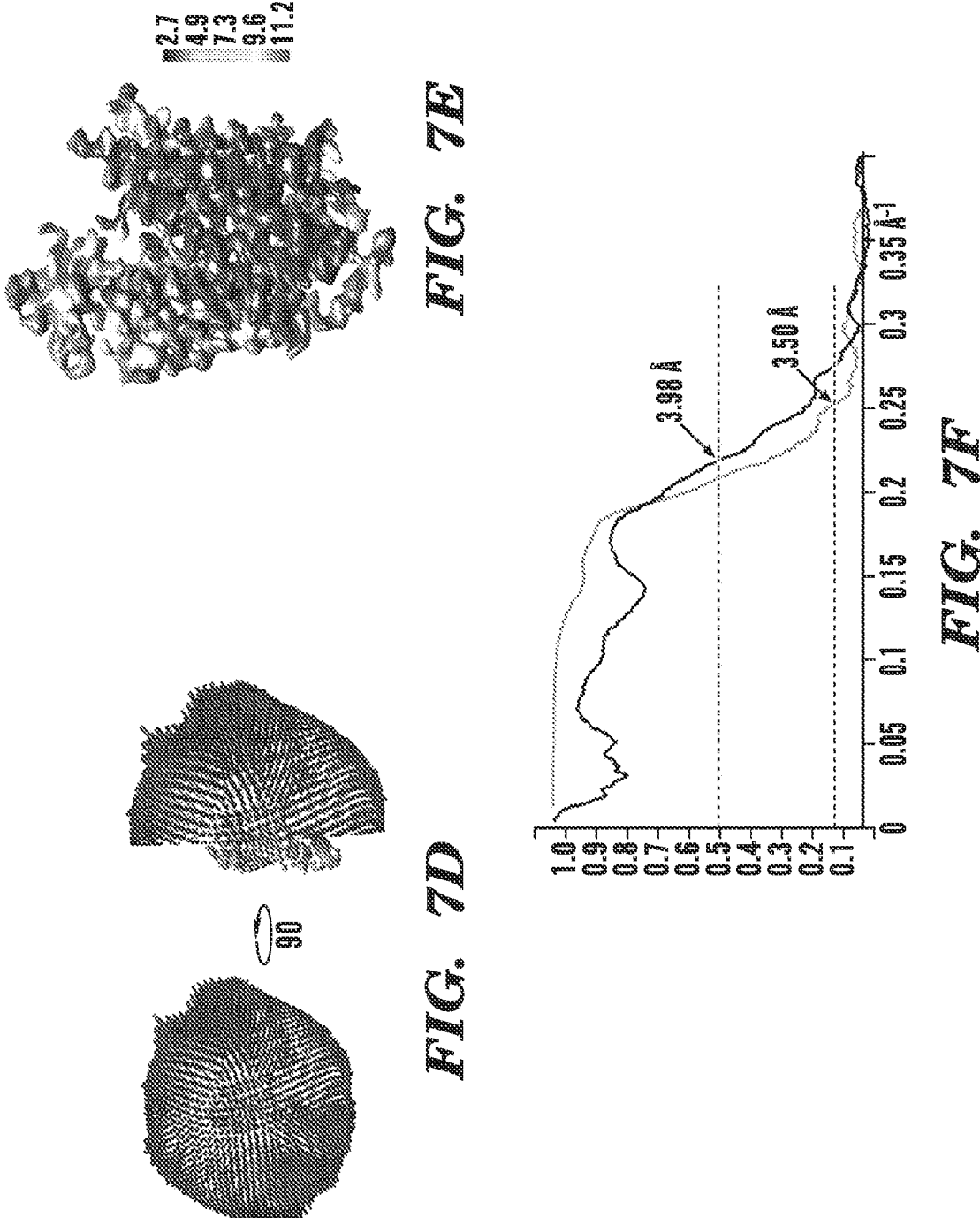
Figure 8:
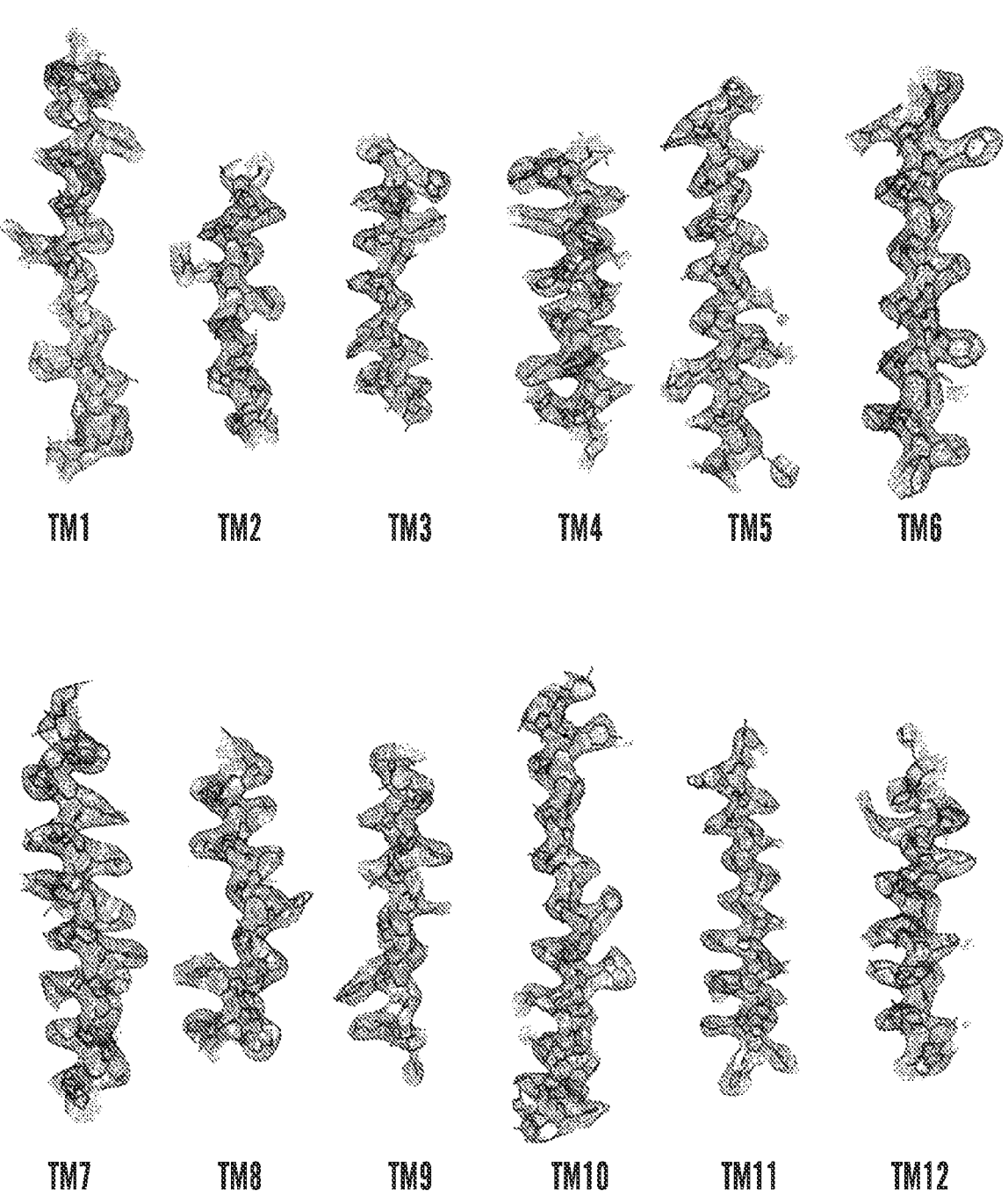
Figure 9:
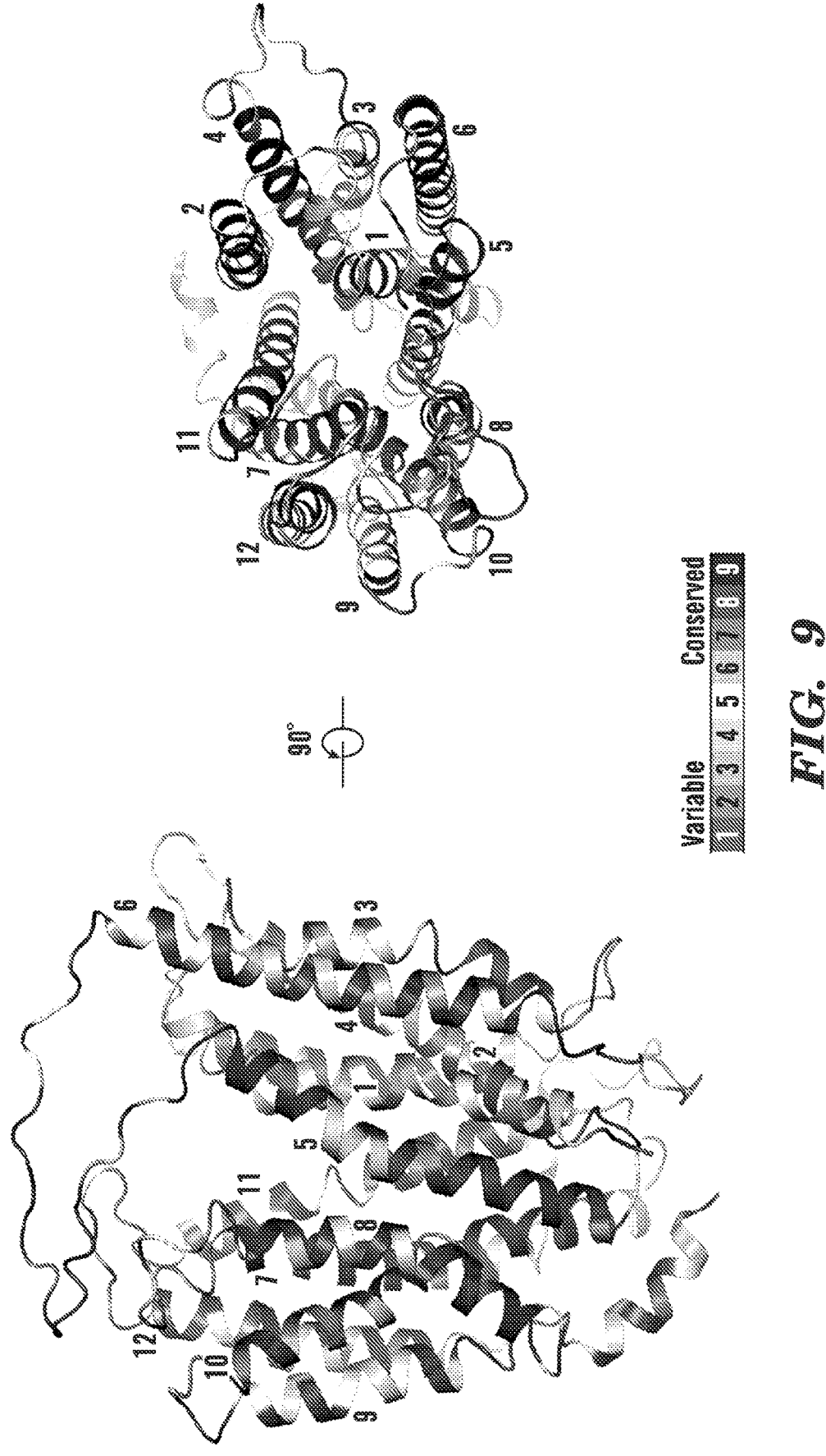
FIG. 9 depicts conservation analysis of mouse Mfsd2a structure. Residues are colored from variable to conserved according to the palette below the structure.

Mouse Mfsd2a was over-expressed in HEK293 cells and purified for structural studies. A fortuitous loss-of-function single point mutation Q67H (FIG. 6D) was identified that presumably arrests the transporter in an outward-facing conformation based on its location near the typical extracellular gate area in MFS transporters. It was theorized that this might reduce conformational heterogeneity and selected this variant for structural studies. The purified protein was biochemically stable and appeared monodisperse on size exclusion chromatography (FIG. 6A). To obtain the most homogenous samples for cryo-EM studies, the proteins were screened after being purified under various conditions. Mfsd2a purified in lauryl maltose neopentyl glycol/cholesteryl hemisuccinate/glycol-diosgenin (LMNG/CHS/GDN) detergent mixture was selected for further structural studies as particles appeared to be homogeneous in size and shape. Since Mfsd2a is small in size (59 kDa) with few features outside the micelle, it presents challenges for cryo-EM studies. To aid the particle alignment, we used a single-chain variable fragment (scFv) of antibody that binds to the extracellular side of Mfsd2a as a fiducial mark. This strategy permitted determination of the cryo-EM structure of Mfsd2a at 3.5 Å resolution (FIG. 1B; FIGS. 7A-7F). The high-quality EM map shows clear side chain densities that allowed unambiguous sequence register assignment and model building of Mfsd2a (FIG. 8).

Figure 1C:
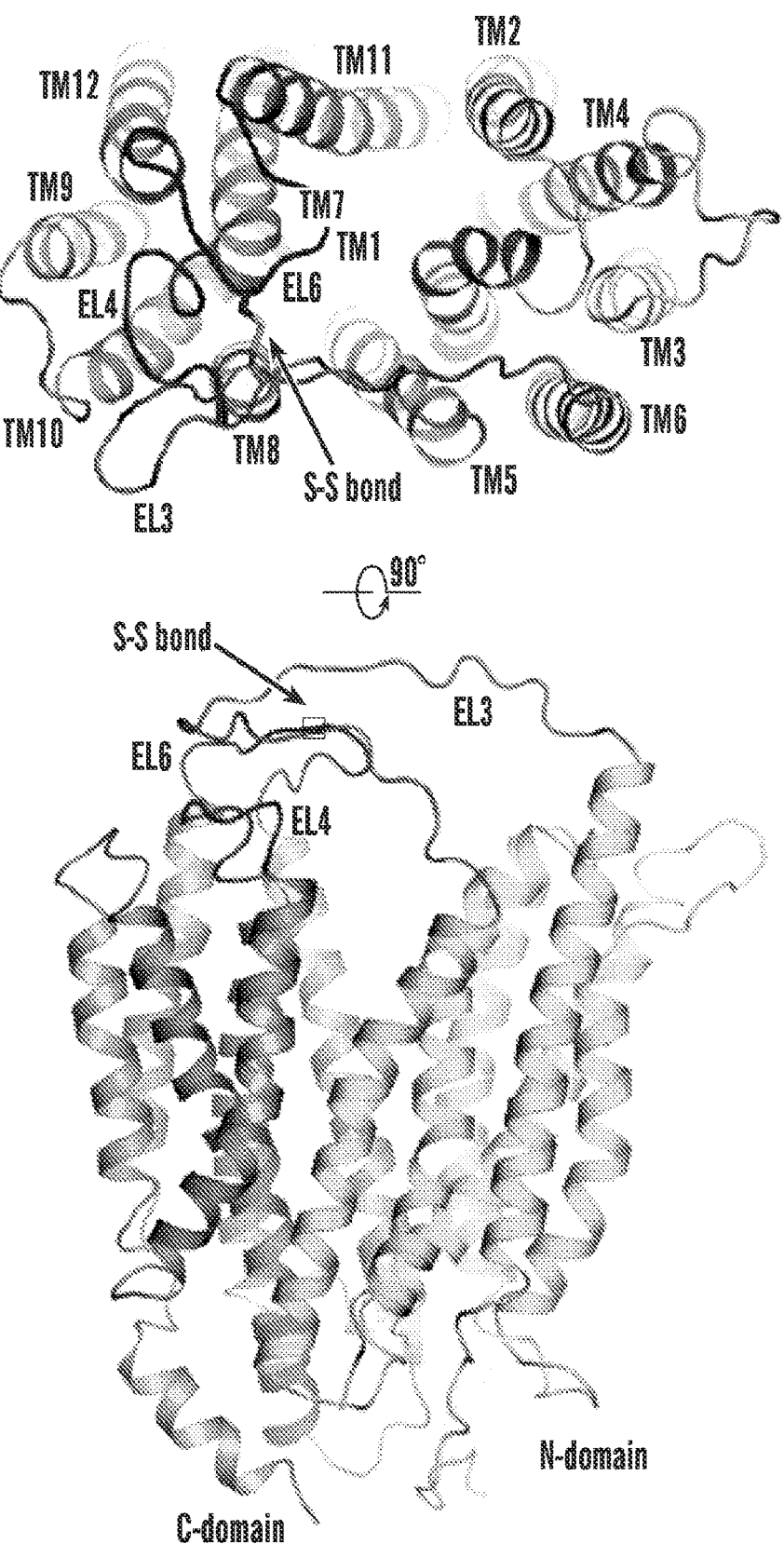
Figure 2A:
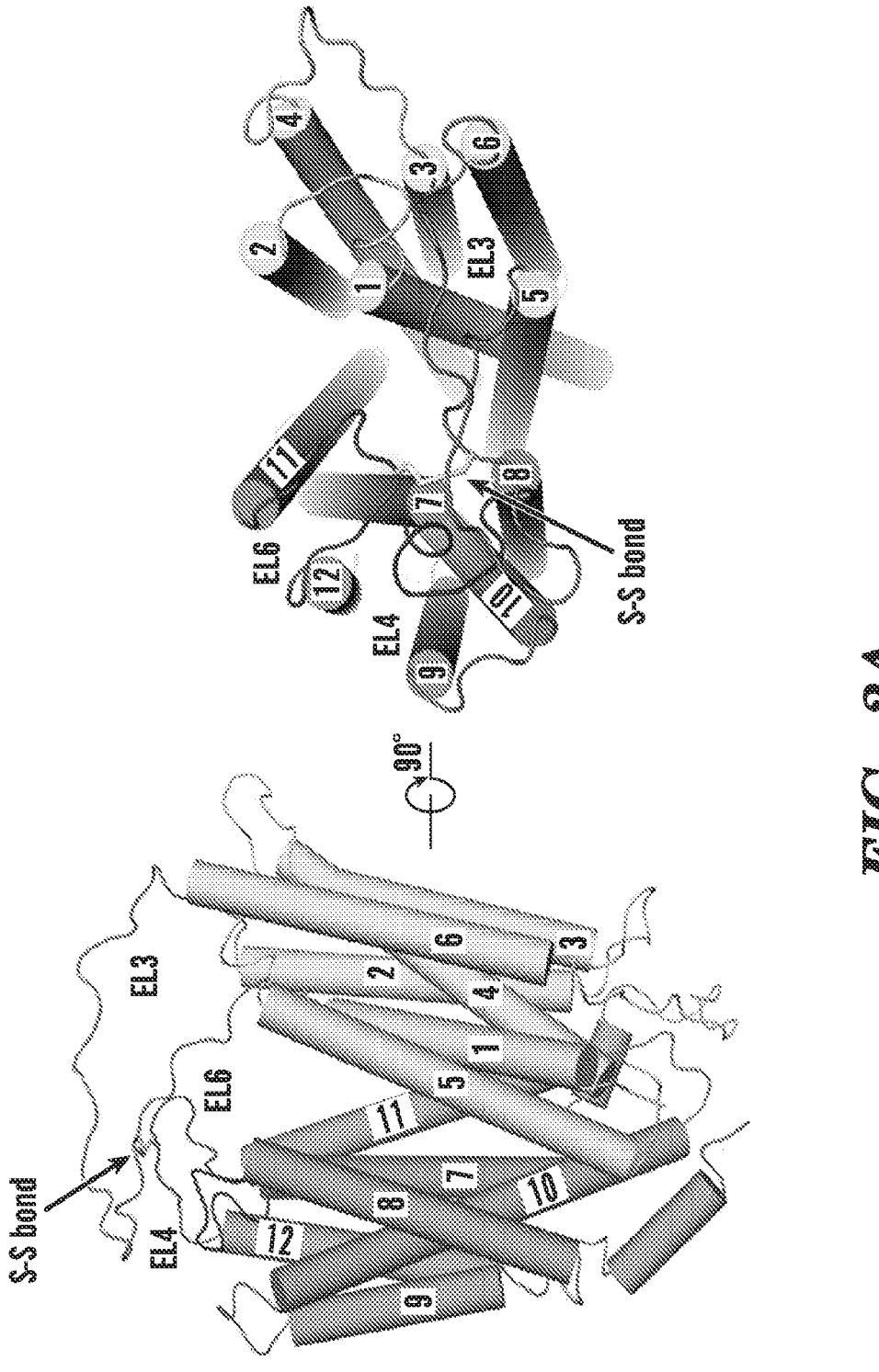
FIGS. 2A-2E depict the extracellular domain and substrate translocation pathway.
Figure 2B:
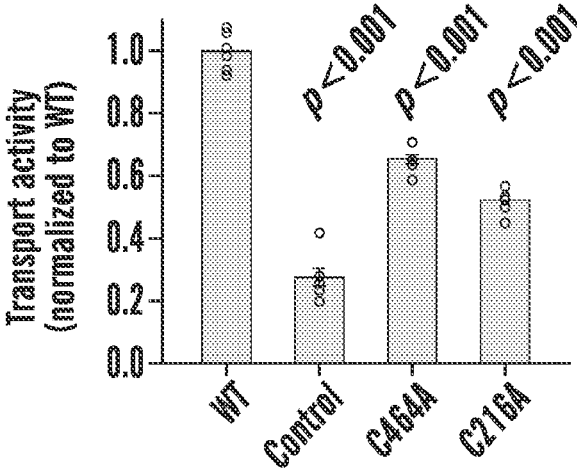
Figure 2C:
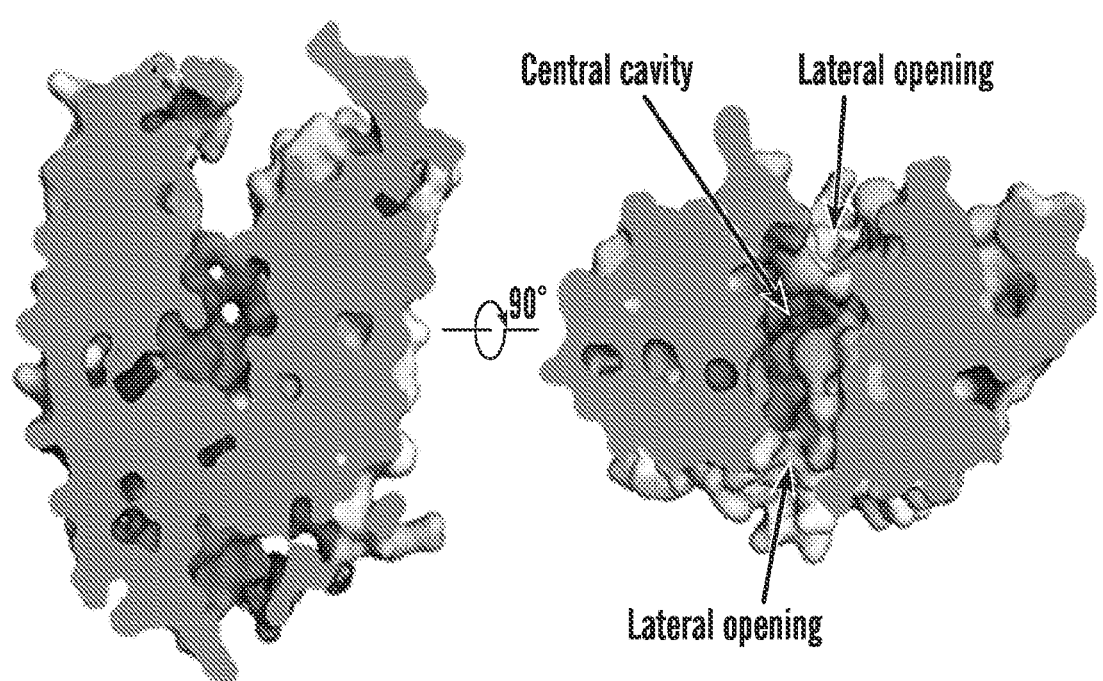
Figure 10:
FIG. 10 depicts intracellular elements of Mfsd2a. Ribbon representation (left) and cylindrical representation (right) of Mfsd2a viewed from the intracellular side. N- and C-domains are indicated, respectively. IL=intracellular linker. The helix after the last transmembrane helix is also indicated.

Overall structure. Mfsd2a adopts a canonical MFS structural fold consisting of twelve TM helices (TM1-TM12) that form two structurally related domains, the N-domain (TM1-6) and C-domain (TM7-12) (FIG. 1C). In this structure, Mfsd2a was captured in an outward-facing conformation. The N- and C-domains closely interact with each other on the intracellular side, while they are more separated on the extracellular side with an opening to the solution. The two domains form a cavity at their interface that is accessible from the extracellular solution to around the middle of the membrane (FIG. 2C). One unique feature of Mfsd2a is its extracellular domain, which is mainly formed by two structural elements—an elongated and ordered loop between TM5 and TM6 (EL3) and a loop between TM11 and TM12 (EL6) (FIG. 2A. EL3 reaches across the N- and C-domain interface and interacts with both EL6 and EL4 (between TM7 and TM8). A conserved disulfide bridge is formed between C216 on EL3 and C464 on EL6, providing a covalent linkage (FIG. 2A). The extracellular domain is mainly on one side of the transporter and may potentially impose constrains on the relative movement between N- and C-domains. Mutating either C216 or C464 to alanine substantially reduced the transport activity (FIG. 2B), indicating an important role of the extracellular domain that is stabilized by the disulfide bridge. On the intracellular side, the N- and C-domains are connected by a long linker between TM6 and TM7 (FIG. 10) that interacts with both domains and may contribute to stabilizing the outward-open conformation. After the last TM, there is a short helix at the C-terminus that reaches from the C-domain to the domain interface on the intracellular surface. This could help to stabilize the close conformation on the intracellular side. In contrast to the sugar transporter family within the MFS superfamily[26-28], no helical bundle domain is formed on Mfsd2a's intracellular side.

Figure 2D:
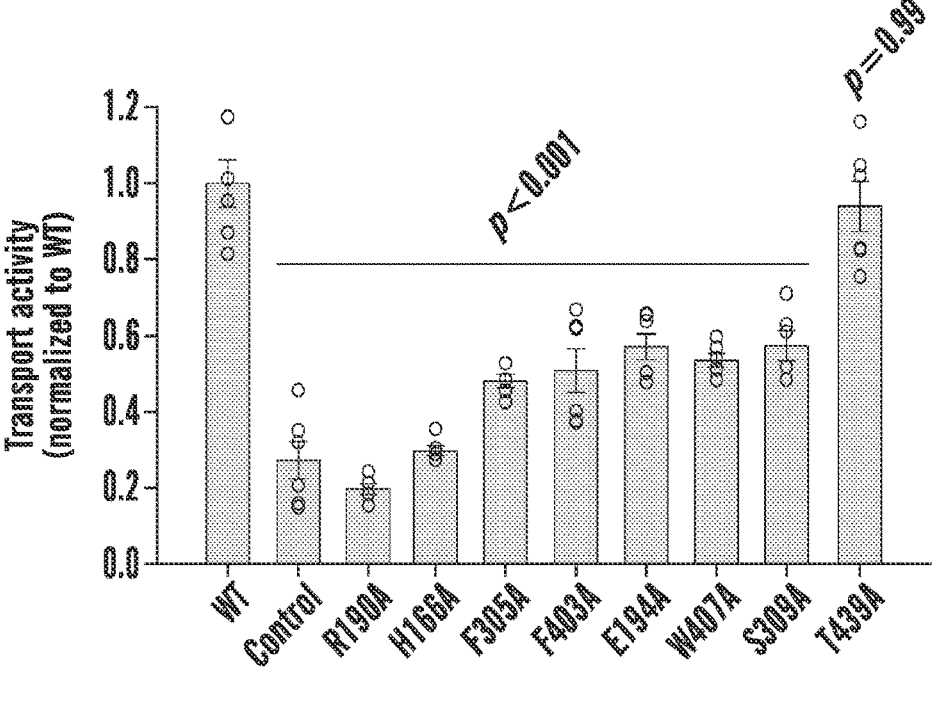

Translocation pathway. In the outward-facing conformation, the solvent-accessible cavity extends into the transmembrane domain, traversing around half of the membrane. The cavity is surrounded mainly by TM1, TM2, TM4, TM5, TM7, TM8, TM10 and TM11 (FIG. 2A), which likely form a substrate translocation pathway. The bottom half of the cavity has an overall highly negative electrostatic surface that becomes more neutral near the mouth of the cavity (FIG. 2C). This electrostatic distribution along the cavity can thus accommodate the amphipathic nature of its substrate LPC in such an orientation that the positively charged group at one end of LPC settles in the bottom of the cavity and its hydrophobic tail points to the extracellular side. Multiple charged residues and hydrophilic residues are located near the bottom of the cavity; these may interact with zwitterionic phosphatidylcholine headgroups. Together, these structural features raise the possibility that, in Mfsd2a's outward-facing conformation, LPC anchors in the cavity with its head group at the bottom. To assess the functional roles of the residues that line the deeper part of the central cavity, mutagenesis studies were carried out (FIG. 2D). Mutating R190 or H166 to alanine abolished transport activity. Alanine substitution for S309, W407, E194, F305 also significantly reduced transport activity, but to a lesser extent. In contrast, mutating T439 has no apparent effect on transport activity. These results indicate the important roles of the central pocket residues that are on both N- and C-domains. It is conceivable that potentially charged residues that are highly conserved across Mfsd2a and near the bottom of the cavity, such as H166, might directly interact with the zwitterionic phosphatidylcholine headgroups on LPC.

Figure 3B:
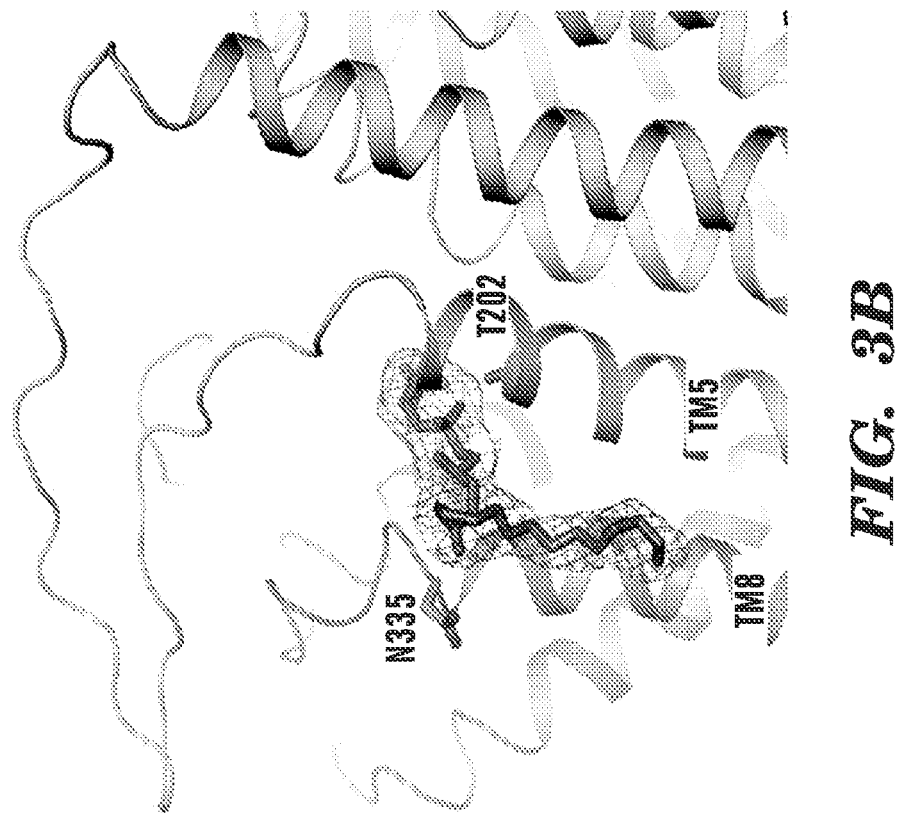
FIGS. 3A-3D depict lateral side openings.
Figure 3A:
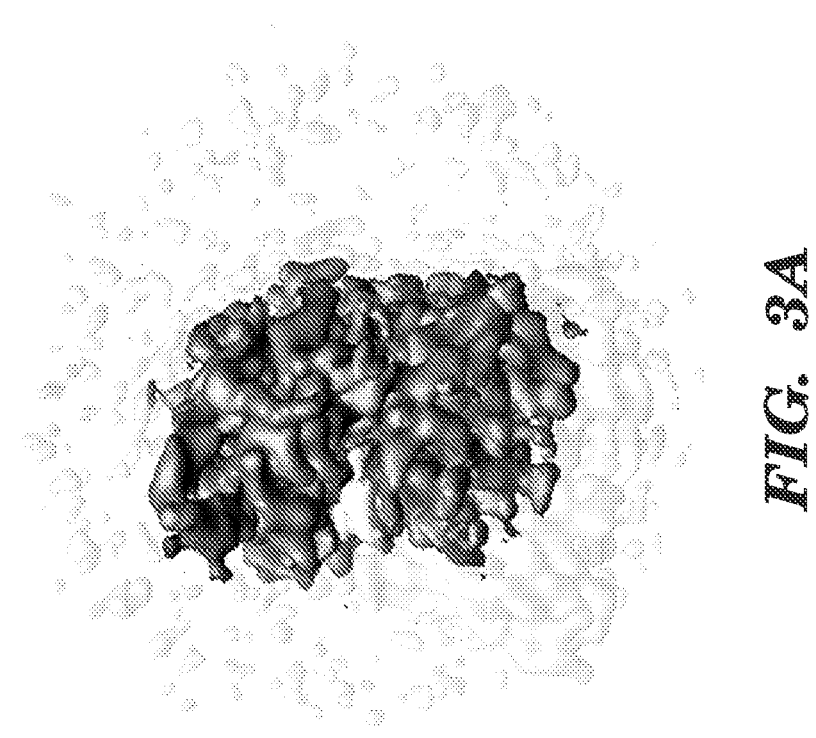
Figure 3C:
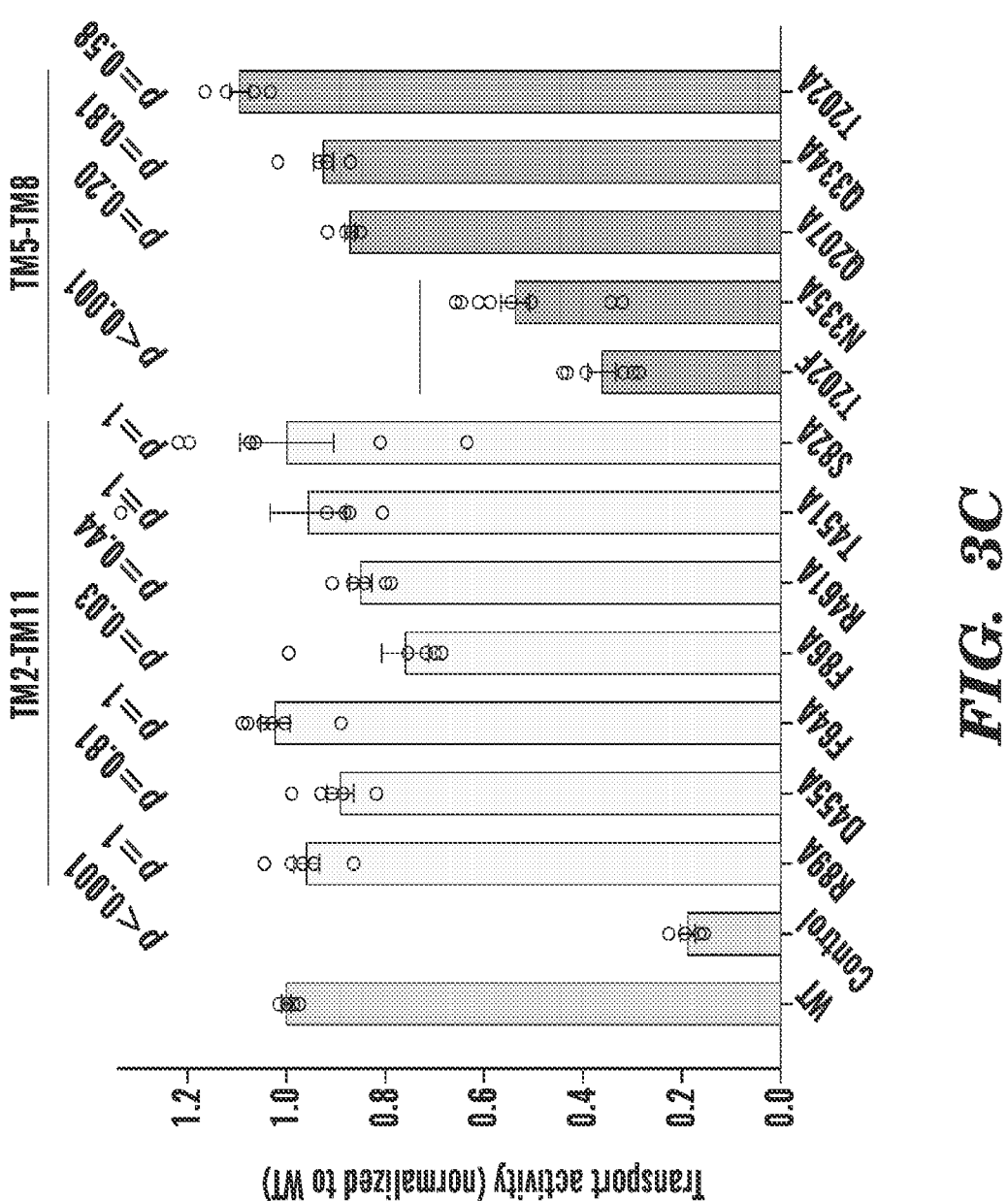
Figure 3D:
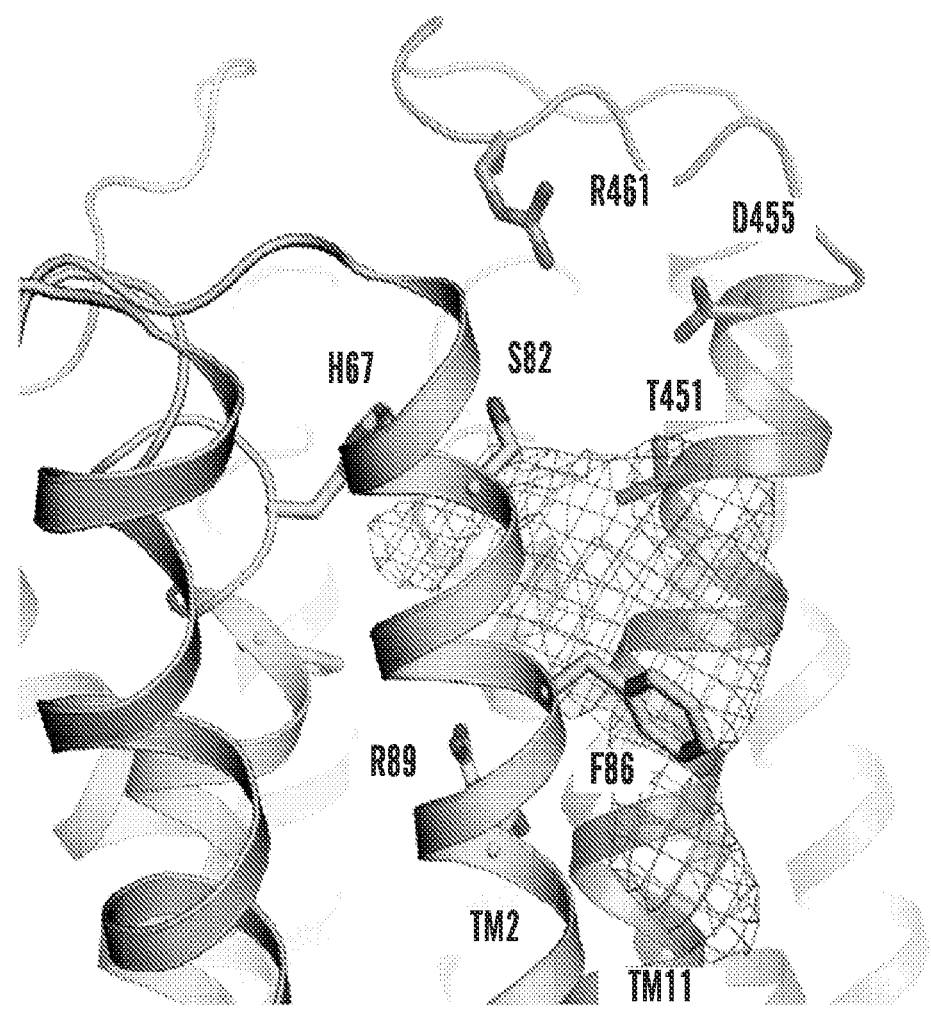

Lateral side entry and lipid binding site. In the extracellular half of the membrane, N- and C-domains only loosely interact, leaving lateral openings to the membrane on both sides of the transporter (FIG. 2C). The "V"-shaped openings are formed between TM5 and TM8 on one side and between TM2 and TM11 on the other side. Intriguingly, extra lipid-like density wedged in both openings was found (FIG. 3A). The lipid density between TM5 and TM8 is stronger than that between TM2 and TM11, indicating more stable interactions. Although the local resolution is not sufficient to unambiguously resolve the identity of the lipid, LPC can be placed with a reasonably good fit into the lipid density between TM5 and TM8 (FIG. 3B). In this case, the LPC head group points to the cavity's center and its C-terminal acyl chain extends outside the transporter, parallel to the TM helices, matching well with the chemical environment of the lipid bilayer. The density between TM2 and TM11 shows some flatness feature in parts (FIG. 3D); its identity is less clear. To probe the importance of residues that constitute the potential lipid binding sites at these two lateral side openings, mutagenesis studies were carried out (FIG. 3C). N335 on TM8 lies at the entrance of the lateral opening and is in proximity to the kink of the tentatively modelled LPC. Mutating N335 abolished transport activity, consistent with its potential important role for lipid docking. The sidechain of T202 on TM5 points towards the lipid density. Trimming its sidechain by an alanine substitution did not affect transport activity, but mutating to a bulky residue (T202F) substantially impaired the transport activity. It is conceivable that a bulky sidechain at this position might sterically hinder lipid binding. In contrast, Q334 on TM8 or Q207 on TM5 have sidechains that point away from the lipid density, and mutating them had only a modest effect on transport activity. Likewise, mutating residues that are near the lipid density on TM2 and TM11 produced negligible effect (F64A, S82A, R89A, T451A) or only had modest impacts on transport activity (F86A, D455A, R461A). These results infivstr that the lateral opening between TM5 and TM8 is substantially more important from a functional standpoint than the one between TM2 and TM11. It is therefore contemplated herein that the lateral opening between TM5 and TM8 constitutes a LPC binding site en route to the central cavity, which can facilitate LPC diffusion into/from the membrane. This is consistent with the potentially more stable lipid binding there and the overall good fit of the LPC in the density.

Figures 4A, 4B:
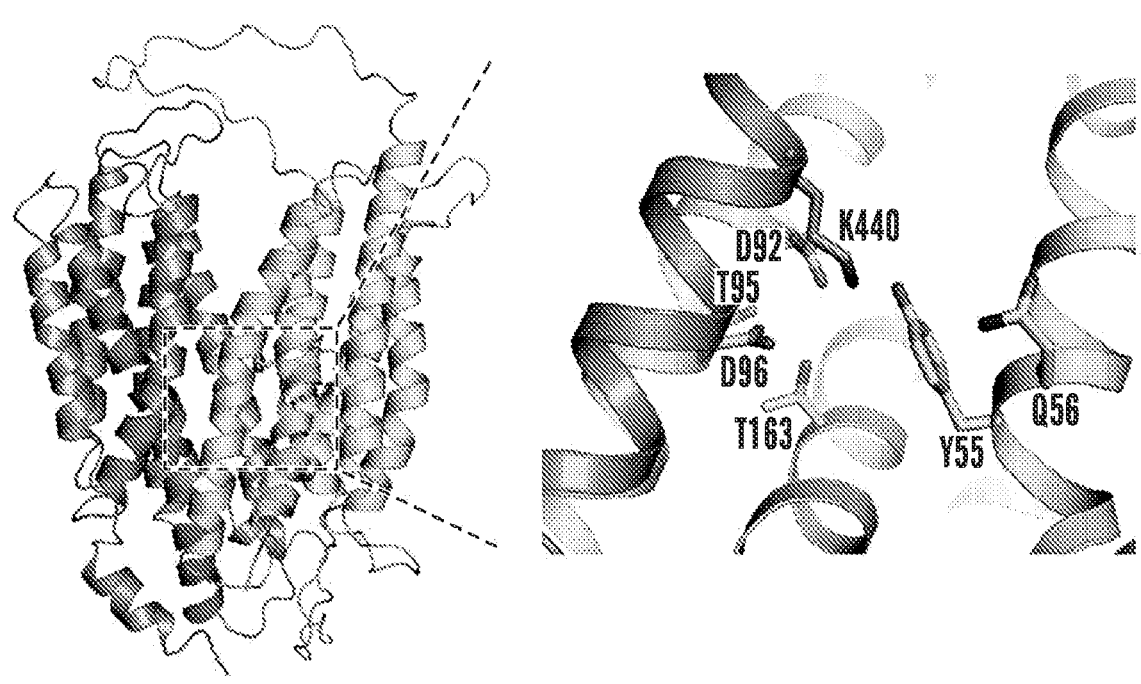
FIGS. 4A-4E depict the Na$^+$-binding site.

Sodium ion binding site. It has been shown that Mfsd2a's LPC transport activity depends on sodium[12,13]. Within the MFS superfamily, the melibiose transporter MelB has been well-characterized as a $Na^+$-coupled symporter[24,25]. Based on the structural comparison, several key residues in MelB's $Na^+$-binding site are conserved in Mfsd2a, whose equivalent region likely also forms a sodium binding site (FIG. 4A). In particular, side-chain oxygens of D92, D96, T95 and T163 form a pocket that is well-positioned to coordinate sodium at the center. In this region of the cryo-EM map, there is extra density above the background level (FIG. 4B). This is compatible with $Na^+$ in this region given the sample was prepared in the presence of 150 mM NaCl. The resolution is not sufficient to place the ion unambiguously, however.

Figure 4C:
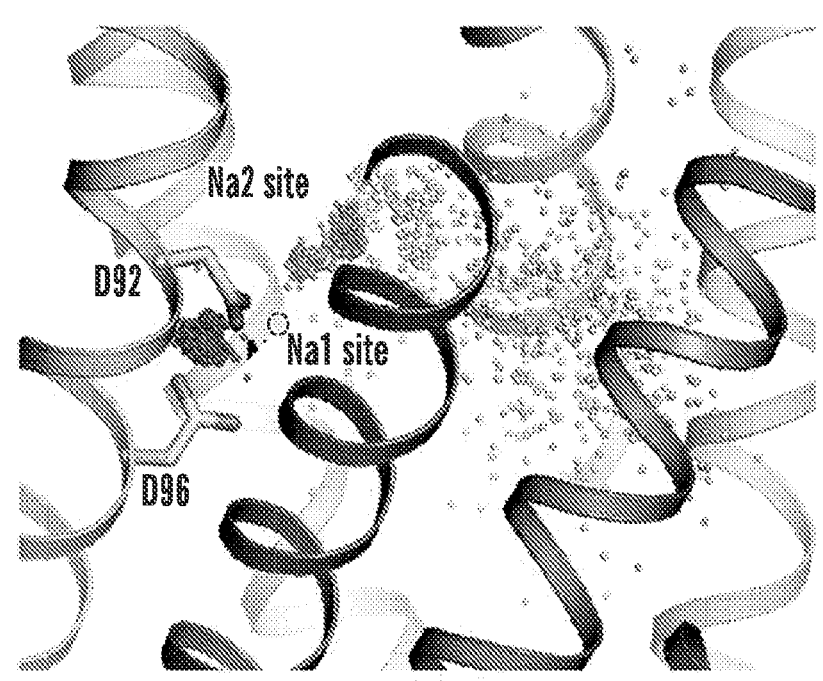
Figure 4D:
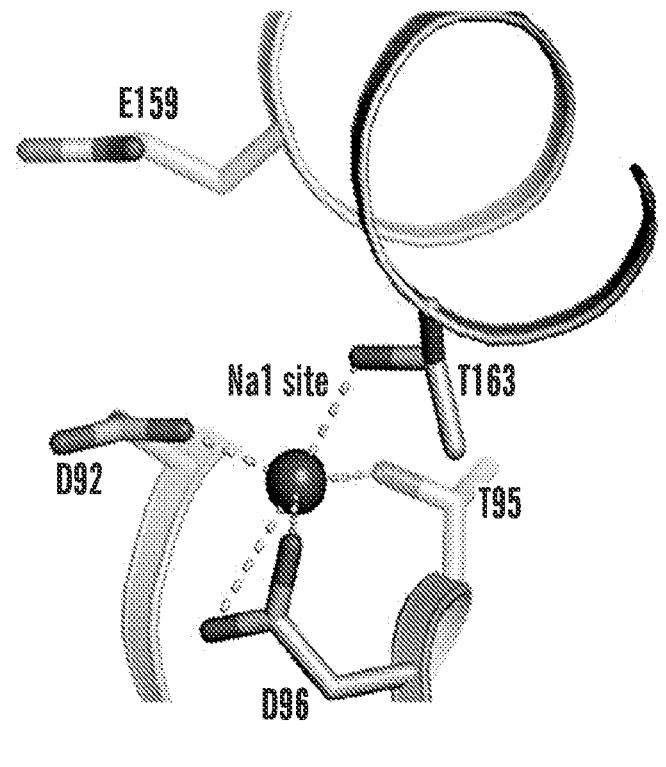
Figure 11A:
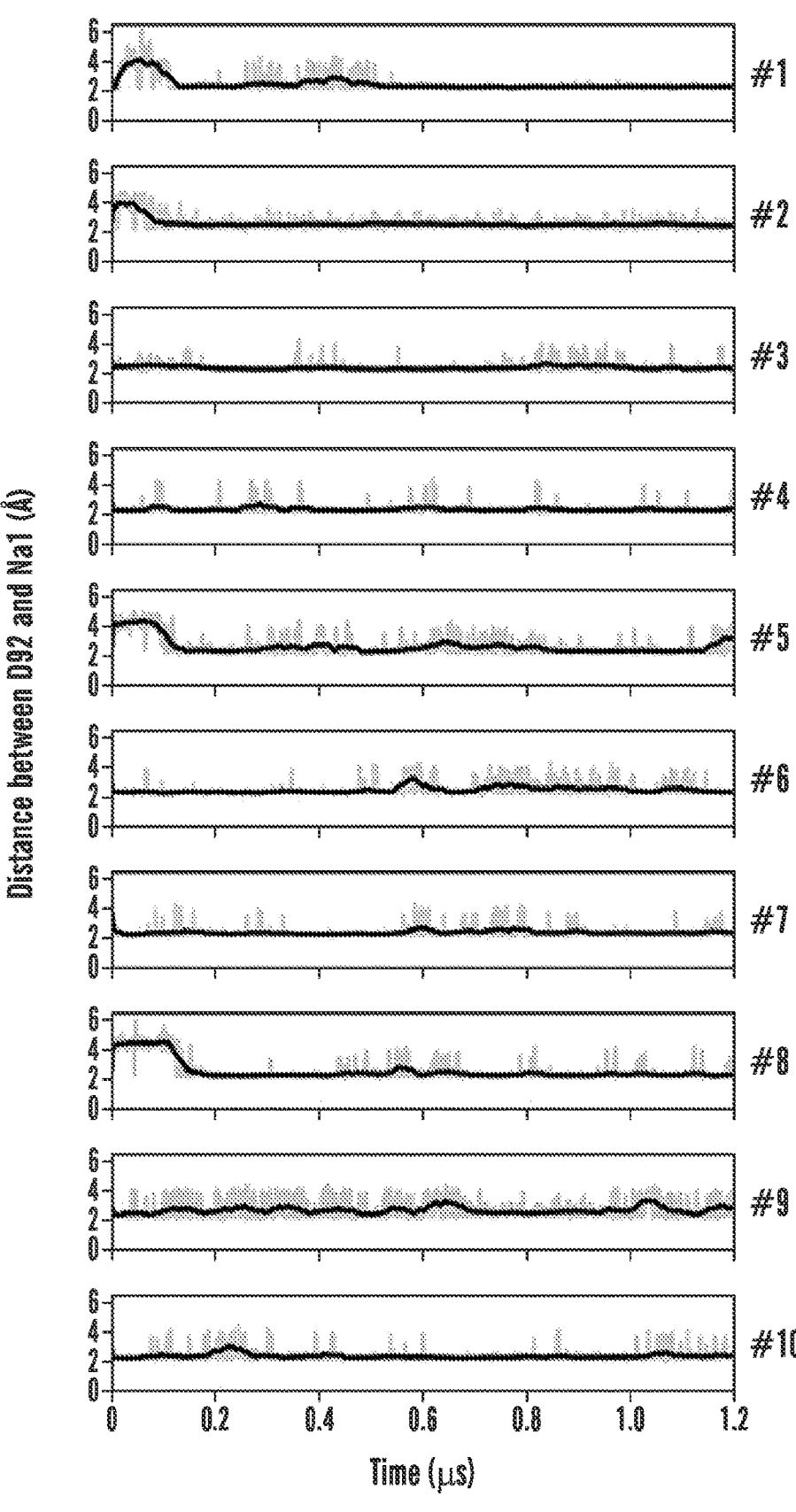
FIGS. 11A-11E depict sodium binding sites in molecular dynamics simulations.
Figure 11B:
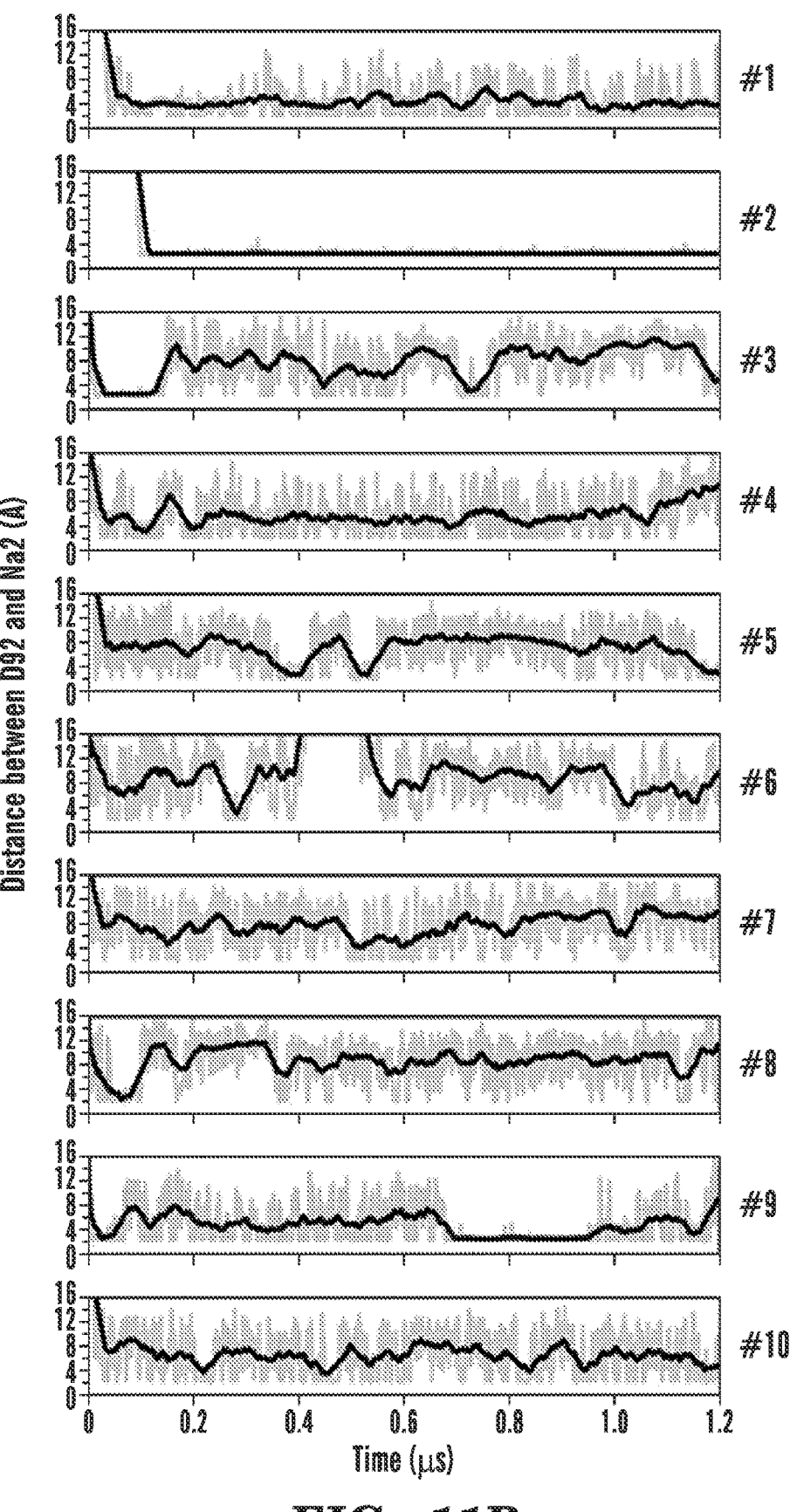
Figure 11D:
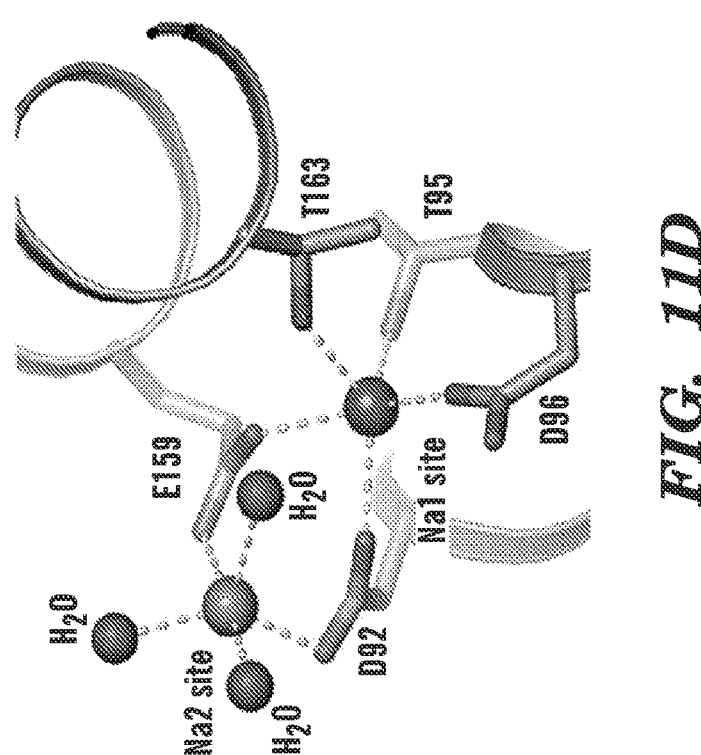

To better understand the potential sodium binding site, all-atom molecular dynamics (MD) simulations were carried out. Simulations were initiated with a sodium placed roughly at the center of the pocket. During the course of all ten simulations (~1.2 μs each) (Extended Data FIG. 11A), the initially placed sodium shifted its position to coordinate with D96, D92, T95 and T163 (Na1 site), and remained stably bound in the pocket (FIG. 4C-4D). The coordination distance and geometry at the Na1 site are consistent with those typically observed for sodium binding[29]. These observations support the notion that the pocket constitutes a sodium binding site. In addition, sodium from the outside solution diffuses through the central cavity to the edge of the pocket (Na2 site), where it tends to reside transiently (FIG. 4C). Sodium binds at the Na2 site much less stably than at the Na1 site (FIGS. 11A-11B). When bound at the putative Na2 site, sodium interacts with D92 and E159 and water molecules provide additional coordination (FIG. 11D). In this case, D92 and E159 interact with both Na1 and Na2, forming a connected binding network. The Na2 site may represent a transient site for sodium, given the relatively transient binding and its exposure to solution.

Figure 4E:
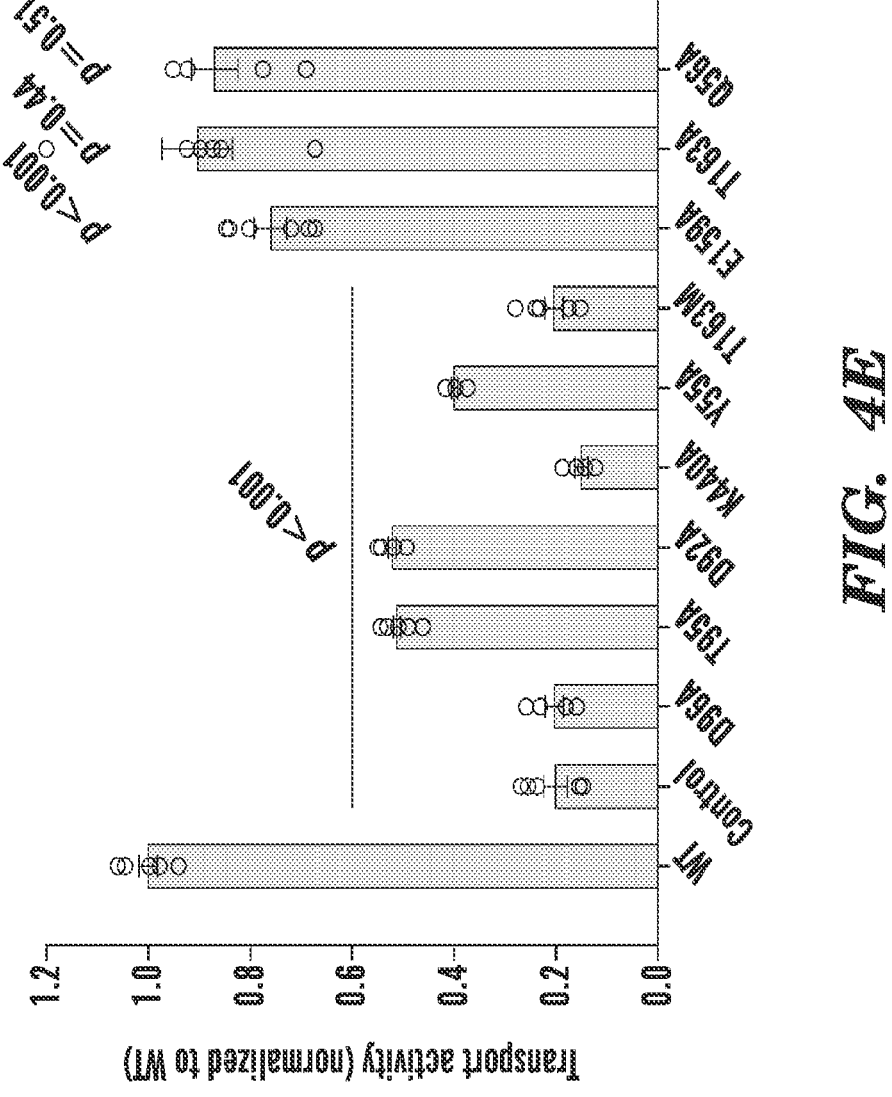

To further probe the proposed $Na^+$-binding sites, mutagenesis studies were carried out (FIG. 4E). For the Na1 site, substituting alanine at D96 abolished transport activity, corroborating previous findings[12]. This is consistent with the observation that D96 provides strong coordination for $Na^+$ bound at the Na1 site; both oxygens of its carboxylate group interact with $Na^+$. Mutating D92 or T95 also significantly impaired uptake, consistent with their important roles in coordinating $Na^+$. It was found that substituting alanine for T163 to trim its side chain had little effect, while substituting methionine abolished transport activity. This is probably because T163 mutation is not sufficient to disrupt the $Na^+$ coordination while a longer side chain interferes with the $Na^+$ binding. In control experiments, mutating Q56 (faces the central cavity) produced little effect on transport activity. Together, these mutagenesis results suggest the Na1 site is a functionally important $Na^+$ binding site and corroborate several critical residues found in human Mfsd2a[13]. For the Na2 site, mutating E159 had only a modest effect on transport activity. This indicates that the Na2 site likely is not involved directly in coupled transport of $Na^+$ and lipid, consistent with the transient nature of the binding. Sequence conservation analysis on Mfsd2a and its close relative Mfsd2b further supports the $Na^+$-binding sites: D92 is strictly conserved in Mfsd2a, but in Mfsd2b—a $Na^+$-independent sphingosine 1-phosphate transporter[30,31]—it is substituted by glycine. This is consistent with the differing requirement for $Na^+$ in these two transporters. It is noteworthy that K440 is next to the Na1 site, where it forms electrostatic interactions with D96 and D92. This stabilizes closely spaced carboxylate groups of D96 and D92 and thus helps to uphold the Na1 site. It was found that mutating K440 abolished transport activity (FIG. 4E), consistent with its important role in stabilizing the $Na^+$ binding site. Likewise, mutating Y55 significantly reduced transport activity. Y55 is within distance to interact with K440, which might help to further stabilize the Na1 site.

Figure 5A:
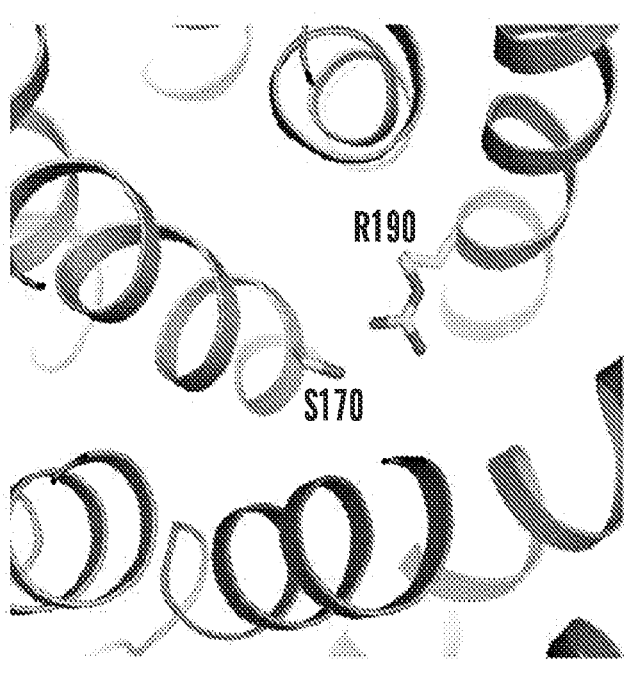
FIGS. 5A-5C depict the structural mapping of disease-causing mutations.
Figure 5B:
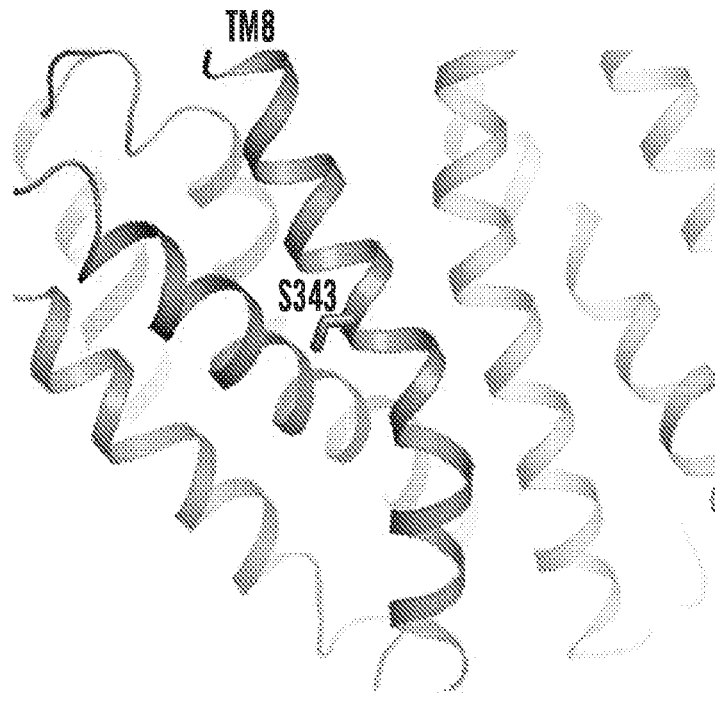
Figure 5C:
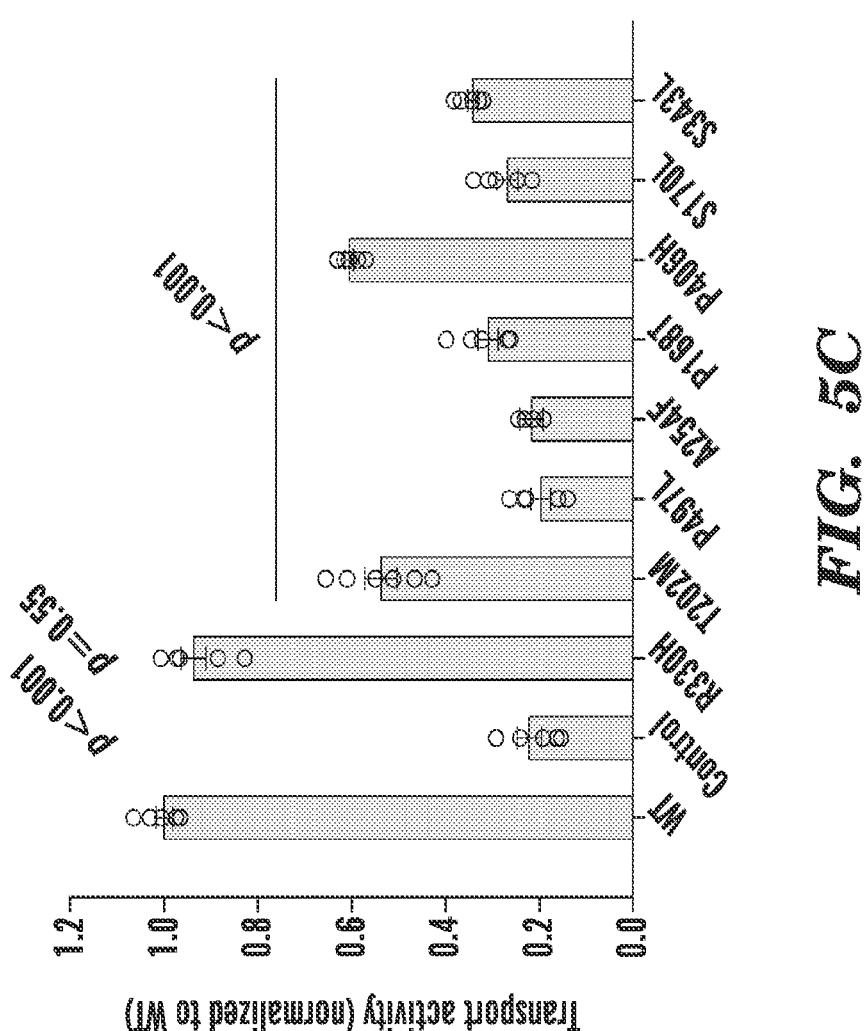

Disease-causing mutations. The structure allows us to probe the molecular basis underlying disease-causing mutations in Mfsd2a. To date, three Mfsd2a mutations are documented to cause either a lethal microcephaly syndrome (patients do not live beyond a few years of age) or a progressive microcephaly syndrome that results in intellectual disability, spastic quadriparesis, and inability to speak[21, 22]. T159M or S166L mutations (equivalent to T163M and S170L in mouse Mfsd2a) underlie a lethal microcephaly syndrome. The structure reveals that T163 is part of the Na1 site. Its mutation to methionine thus likely disrupts $Na^+$ binding and impedes transport (FIGS. 4D, 4E). S170 is found right below the bottom of the central cavity at the interface between the N- and C-domains (FIG. 5A). It forms a hydrogen bond with R190 and is in close contact with W407. As S170 contributes to the formation of the central binding pocket and possibly the closing of the intracellular gate, its mutation is thus expected to disrupt the transport function. Indeed, the S170L mutation reduced transport activity close to the background level (FIG. 5C). The third mutation, S339L (equivalent to S343L in mouse Mfsd2a). This mutation may affect the helical bend of TM8 (FIG. 5B), which mediates the N- and C-domain interaction, thereby affecting the conformational transition between states. The functional studies showed that the S343L mutation substantially reduced activity (FIG. 5C), albeit to a lesser extent than T163M. This is consistent with decreased LPC uptake in the brains of patients and a milder progressive microcephaly syndrome[22]. These results corroborate that the mouse Mfsd2a structure provides a faithful model to interpret function and disease-causing mutations of human Mfsd2a[13,22].

Discussion MFS transporters are generally thought to operate by a rocker-switch model[32]. Following a similar mechanism, the structurally similar N- and C-domains of Mfsd2a rock to alternately expose the central binding pocket to the extracellular solution and the outer membrane leaflet, or to the intracellular solution and the inner membrane leaflet. In this case, the open or close of Mfsd2a's lateral openings on both sides is expected to accompany the open or close of the central cavity to the solution. For a $Na^+$-coupled transporter, a central mechanistic question is how $Na^+$ is coupled to the transport cycle. The structural analyses, MD simulations and functional studies have revealed a relatively stable and functionally important $Na^+$ binding site, Na1 at a strategic position right around the TM2 helical kink, which is encompassed by $Na^+$-binding residues D92 and D96. As TM2's kink gives rise to the "V"-shape lateral opening between TM2 and TM11, this raises the possibility that $Na^+$ binding can be linked directly to the open or close of the lateral opening, thus coupling it to the state transition between the outward- and inward-open conformations. In addition, the interaction between K440 on the C-domain and the Na1 site residue D92 and D96 on the N-domain plays an important role for stabilizing the $Na^+$-binding site. This also provides a potential link between $Na^+$-binding and the conformational state transition that involves relative rocking movement between N- and C-domains. Moreover, the $Na^+$-binding sites are beside the central cavity, near its bottom. This raises the possibility that the LPC head group, which presumably binds near the bottom of the cavity, can be in close proximity to the $Na^+$-binding sites. The binding of LPC or sodium might induce local conformational changes, thereby affecting binding of the other substrate and giving rise to coupling in their transport. The exact mechanisms of coupled transport between sodium and LPC still need future investigation.

The structure of Mfsd2a represents the first for a eukaryotic lipid transporter within MFS, the largest secondary active transporter superfamily[23]. Compared with the majority of known MFS transporters, whose soluble substrates can diffuse directly into the cavity from the solution, it remains unknown how the lipids enter and leave Mfsd2a. The structure reveals lateral openings to the membrane bilayer and densities for bound lipids. This suggests a possible two-step mechanism: After lipid diffuses laterally from the membrane to Mfsd2a, it first docks onto the lipid binding site at the lateral entry and then moves into the central cavity. We observed lateral openings on both sides of Mfsd2a, at the interface of the N- and C-domains. The opening between TM5 and TM8 is more likely to serve as the LPC entrance in an outward-facing conformation: lipid density there matches well with a LPC molecule, the relatively strong density indicates a stable interaction and the surrounding residues are functionally important. In an inward-facing conformation, it is likely that the lateral opening at the N- and C-domain interface serves the same purpose. The simplest scenario would be for the lateral opening on the same side (between TM5 and TM8) to also serve as the LPC entrance in an inward-open conformation. This would potentially allow the tail of LPC to be retained in the lipid bilayer without being fully buried in the pocket during the transport cycle. This would help to explain how LPC with relatively long tails can be transported[12,13]. It is interesting to note that many other MFS transporters, such as the sugar porter GLUT3 (also in an outward-facing conformation)[33], have central cavities that are better shielded from the membrane and lack much lateral opening. This might reflect their different need for the pathway of substrate entry.

Figure 12B:
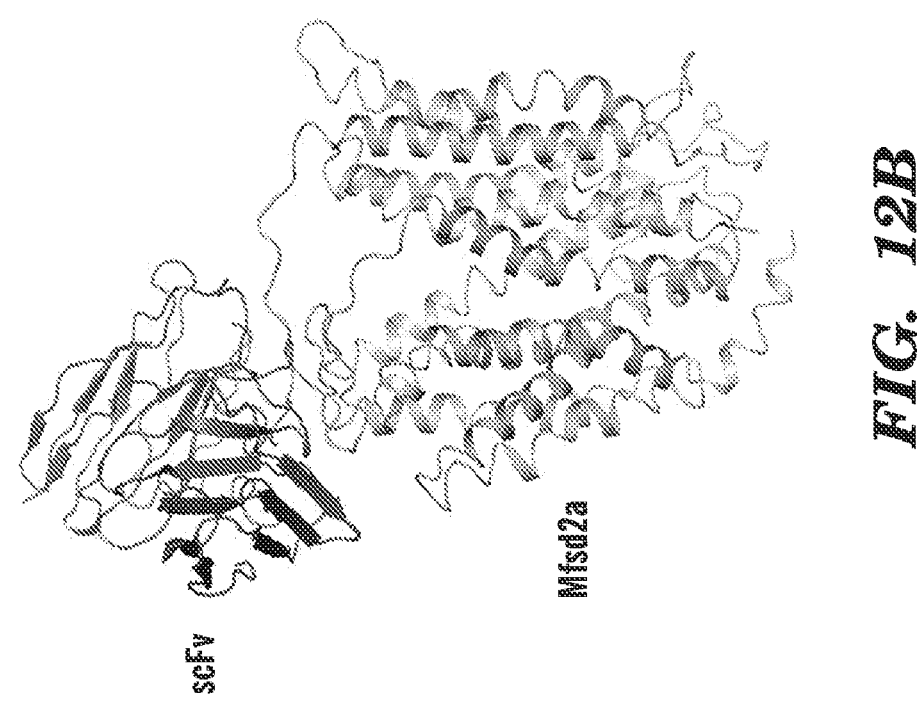
FIGS. 12A-12B depict the structure of Mfsd2a in complex with scFv.
Figure 12A:
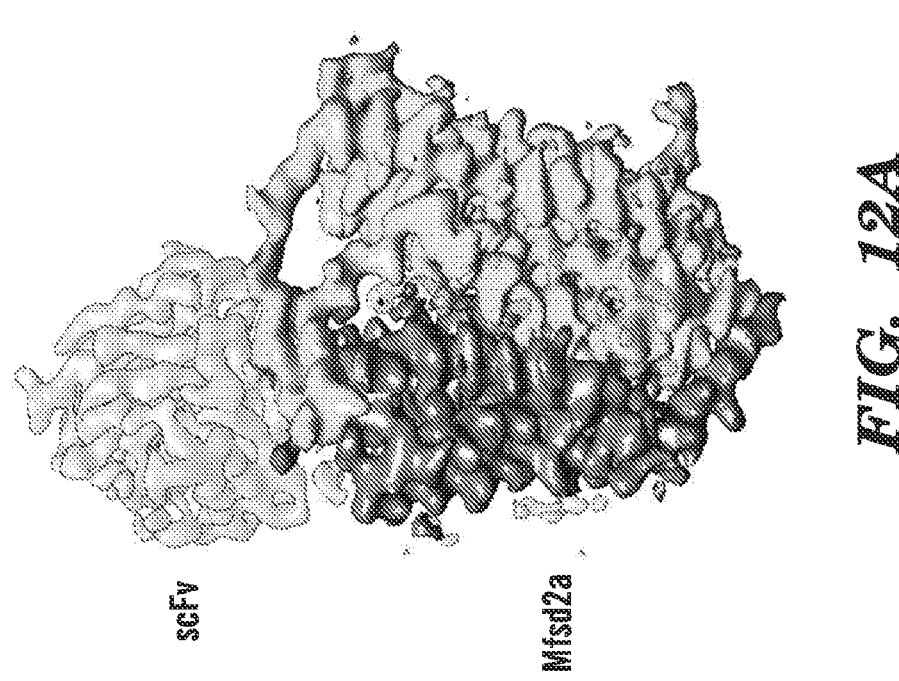

A major hurdle in developing therapeutics for CNS disorders is the extremely limited permeability across the BBB for most drug molecules[34,35]. Since lipids transported by Mfsd2a lead to transcytosis suppression in CNS endothelial cells, which ensures the BBB's restrictive permeability, inhibiting Mfsd2a represents an attractive strategy for drug delivery into CNS. The structure of Mfsd2a in an outward-facing conformation provides a blueprint for structure-based discovery of Mfsd2a inhibitors. In silico docking of small molecules from large libraries into the central cavity revealed in our structure can lead to molecules that either compete with substrate or hinder the conformational transitions to stall the transport. Finally, demonstrated herein is a proof of principle in developing an extracellular surface binder against Mfsd2a (FIG. 12). This category of biologics warrants further investigations; they have the potential to inhibit the transport by impeding the relative movement of N- and C-domains that underlies the transport cycle or by restraining other conformational changes important for transport function.

REFERENCES

1 Andreone, B. J., Lacoste, B. & Gu, C. Neuronal and vascular interactions. *Annu. Rev. Neurosci.* 38, 25-46 (2015).

2 Weiss, N., Miller, F., Cazaubon, S. & Couraud, P. O. The blood-brain barrier in brain homeostasis and neurological diseases. *Biochim. Biophys. Acta* 1788, 842-857 (2009).

3 Keaney, J. & Campbell, M. The dynamic blood-brain barrier. *FEBS J.* 282, 4067-4079 (2015).

4 Reese, T. S. & Karnovsky, M. J. Fine structural localization of a blood-brain barrier to exogenous peroxidase. *J. Cell. Biol.* 34, 207-217 (1967).

5 Brightman, M. W. & Reese, T. S. Junctions between intimately apposed cell membranes in the vertebrate brain. *J. Cell Biol.* 40, 648-677 (1969).

6 U Kniesel, H. W. Tight junctions of the blood-brain barrier. *Cell. Mol. Neurobiol.* 20, 57-76 (2000).

7 Ben-Zvi, A. et al. Mfsd2a is critical for the formation and function of the blood-brain barrier. *Nature* 509, 507-511 (2014).

8 Andreone, B. J. et al. Blood-Brain Barrier Permeability Is Regulated by Lipid Transport-Dependent Suppression of Caveolae-Mediated Transcytosis. *Neuron* 94, 581-594 e585 (2017).

9 Chow, B. W. & Gu, C. Gradual Suppression of Transcytosis Governs Functional Blood-Retinal Barrier Formation. *Neuron* 93, 1325-1333 e1323 (2017).

Yang, Y. R. et al. Mfsd2a (Major Facilitator Superfamily Domain Containing 2a) Attenuates Intracerebral Hemorrhage-Induced Blood-Brain Barrier Disruption by Inhibiting Vesicular Transcytosis. *J. Am. Heart Assoc.* 6 (2017).

11 Wang, J. Z. et al. Mfsd2a-based pharmacological strategies for drug delivery across the blood-brain barrier. *Pharmacol. Res.* 104, 124-131 (2016).

12 Nguyen, L. N. et al. Mfsd2a is a transporter for the essential omega-3 fatty acid docosahexaenoic acid. *Nature* 509, 503-506 (2014).

13 Quek, D. Q., Nguyen, L. N., Fan, H. & Silver, D. L. Structural Insights into the Transport Mechanism of the Human Sodium-dependent Lysophosphatidylcholine Transporter MFSD2A. *J. Biol. Chem.* 291, 9383-9394 (2016).

14 Demar, J. C., Jr., Ma, K., Chang, L., Bell, J. M. & Rapoport, S. I. alpha-Linolenic acid does not contribute appreciably to docosahexaenoic acid within brain phospholipids of adult rats fed a diet enriched in docosahexaenoic acid. *J. Neurochem.* 94, 1063-1076 (2005).

15 Lacombe, R. J. S., Chouinard-Watkins, R. & Bazinet, R. P. Brain docosahexaenoic acid uptake and metabolism. *Mol. Aspects Med.* 64, 109-134 (2018).

16 Ren, H. et al. Enriched Endogenous Omega-3 Fatty Acids in Mice Ameliorate Parenchymal Cell Death After Traumatic Brain Injury. *Mol. Neurobiol.* 54, 3317-3326 (2017).

17 Kidd, P. M. Omega-3 DHA and EPA for cognition, behavior, and mood: clinical findings and structural-functional synergies with cell membrane phospholipids. *Altern. Med. Rev.* 12, 207-227 (2007).

18 Singh, M. Essential fatty acids, DHA and human brain. *Indian J. Pediatr.,* 239-242 (2005).

19 Yeo, L. A. H. a. Y. K. Health benefits of docosahexaenoic acid (DHA). *Pharmacol. Res.* 40, 211-225 (1999).

20 Swanson, D., Block, R. & Mousa, S. A. Omega-3 fatty acids EPA and DHA: health benefits throughout life. *Adv. Nutr.* 3, 1-7 (2012).

21 Guemez-Gamboa, A. et al. Inactivating mutations in MFSD2A, required for omega-3 fatty acid transport in brain, cause a lethal microcephaly syndrome. *Nat. Genet.* 47, 809-813 (2015).

22 Alakbarzade, V. et al. A partially inactivating mutation in the sodium-dependent lysophosphatidylcholine transporter MFSD2A causes a non-lethal microcephaly syndrome. *Nat. Genet.* 47, 814-817 (2015).

23 Yan, N. Structural Biology of the Major Facilitator Superfamily Transporters. *Annu. Rev. Biophys.* 44, 257-283 (2015).

24 Ethayathulla, A. S. et al. Structure-based mechanism for Na(+)/melibiose symport by MelB. *Nat. Commun.* 5, 3009 (2014).

25 Granell, M., Leon, X., Leblanc, G., Padros, E. & Lorenz-Fonfria, V. A. Structural insights into the activation mechanism of melibiose permease by sodium binding. *Proc. Natl. Acad. Sci. USA* 107, 22078-22083 (2010).

26 Deng, D. et al. Crystal structure of the human glucose transporter GLUT1. *Nature* 510, 121-125 (2014).

27 Nomura, N. et al. Structure and mechanism of the mammalian fructose transporter GLUT5. *Nature* 526, 397-401 (2015).

28 Wisedchaisri, G., Park, M. S., Iadanza, M. G., Zheng, H. & Gonen, T. Proton-coupled sugar transport in the prototypical major facilitator superfamily protein XylE. *Nat. Commun.* 5, 4521 (2014).

29 Harding, M. M. Metal-ligand geometry relevant to proteins and in proteins: sodium and potassium. *Acta Crystallogr. D Biol. Crystallogr.* 58, 872-874 (2002).

30 Vu, T. M. et al. Mfsd2b is essential for the sphingosine-1-phosphate export in erythrocytes and platelets. *Nature* 550, 524-528 (2017).

31 Kobayashi, N. et al. MFSD2B is a sphingosine 1-phosphate transporter in erythroid cells. *Sci. Rep.* 8, 4969 (2018).

32 Drew, D. & Boudker, O. Shared Molecular Mechanisms of Membrane Transporters. *Annu. Rev. Biochem.* 85, 543-572 (2016).

33 Deng, D. et al. Molecular basis of ligand recognition and transport by glucose transporters. *Nature* 526, 391-396 (2015).

34 Pardridge, W. M. The blood-brain barrier: bottleneck in brain drug development. *NeuroRx* 2, 3-14 (2005).

35 Banks, W. A. From blood-brain barrier to blood-brain interface: new opportunities for CNS drug delivery. *Nat. Rev. Drug Discov.* 15, 275-292 (2016).

Example 2

Methods

Protein Expression, Purification and Sample Preparation.

*Mus musculus* Mfsd2a with a single point mutant (Q67H) was cloned into a modified BacMam expression vector[36] with an N-terminal GFP-his tag and a 3C protease cleavage site. The baculovirus was generated following the published protocol (Invitrogen LifeTechnologies). The recombinant protein was expressed in HEK293S cells grown in 293 Freestyle medium (LifeTechnologies) supplemented with 2% FBS. Cells were infected by baculovirus at a density of $2.5*10^6$ cells per ml. After 12 hours incubation at 37° C., 10 mM sodium butyrate was added to the culture, and the cells were moved to 30° C. for an additional 48 hours before harvesting. All protein purification steps were carried out at 4° C. unless specifically noted otherwise. Initially, the cell pellet was re-suspended in buffer containing 20 mM Tris-HCl pH 8.0 with the addition of a cocktail of protease inhibitors and DNase I, followed by a 30-minute incubation. The sample was then centrifuged at 18,000 g for 20 minutes. The crude membrane was homogenized by using either a glass Dounce tissue homogenizer or brief sonication in buffer A (20 mM Tris-HCl pH 8.0, 150 mM NaCl) supplemented with 2 mg/mL iodoacetamide, a cocktail of protease inhibitors and DNase I. The sample was incubated for 30 minutes prior to adding 1% lauryl maltose neopentyl glycol (LMNG, Anatrace) and 0.01% cholesteryl hemisuccinate (CHS, Anatrace). After additional 2 hours incubation, the sample was centrifuged at 18,000 g for 45 minutes. The supernatant was incubated with cobalt resin for a 1 hour. The resin was washed by buffer A+0.01% LMNG-0.001% CHS. The GFP-his tag was removed from Mfsd2a by overnight digestion with 3C protease. The sample was further purified by gel filtration (Superose 6, GE Healthcare) in buffer A plus 0.001% (w/v) LMNG-0.00033% (w/v) glyco-diosgenin (GDN, Anatrace)-0.00013% (w/v) CHS. The peak fraction was pooled and concentrated.

Anti-Mfsd2a ScFv was derived by phage display from chickens immunized with lipoparticles containing mouse Mfsd2a. ScFv was recombinantly expressed as a ScFv-Ig fusion protein with a human Fc and purified by protein-A chromatography. The ScFv fragment was generated by papain cleavage and the ScFv fragment was purified by ion-exchange chromatography using a HiTrap Q HP anion exchange column (GE Healthcare). Purified mouse Mfsd2a was mixed with the scFv at a 1:1 (w/w) ratio and incubated for 4 hours at 4° C. The complex was further purified by gel filtration (Superose 6, GE Healthcare) equilibrated in buffer A plus 0.001% (w/v) LMNG-0.00033% (w/v) GDN-0.00013% (w/v) CHS. The peak fraction was concentrated to 4 mg/ml for cryoEM studies.

Electron Microscopy Sample Preparation and Data Collection.

For cryo-EM, 3 μl of the purified complex was applied to glow discharged 300 mesh Quantifoil R2/1 holey carbon grids and blotted for 2.0 s at 96% humidity on a Leica EM GP2 before being plunge frozen in liquid ethane cooled by liquid nitrogen. Grids were imaged on a Titan Krios operated at 300 kV using a slit width a 20 eV on a GIF-Quantum Energy Filter. Images were collected on a K3 Summit detector (Gatan) in super-resolution counting mode at a magnification of 105,000×, corresponding to a physical pixel size of 0.86 Å. Serial EM[37] was used for data collection with a set of customized scripts enabling automated low-dose image acquisition. Data were collected using image shift to collect one image per hole by Multiple Record method (3×3 set of holes/stage movement).

Cryo-EM Data Processing

A total 8,669 movies were collected and subjected to beam-induced motion correction using the program MotionCor2[38]. A dose-weighted sum of all frames from each movie was used for all image processing steps. Contrast transfer function (CTF) parameters were estimated by Gctf[39]. Automated particle picking was first performed using cisTEM 1.0.0 Beta[40] using 500 images, the picked particles were extracted with box size of 232 pixels and subjected to 2D classification in cisTEM. The good classes, representing projections in different orientations, were selected and imported to Relion3.0-Beta-2[41] as templates for auto picking. All the picked particles were extracted with box size 232 pixels with original pixel size 0.86 Å in Relion and imported to CryoSparc (v2.13.2)[42] for further 2D classification. Rounds of 2D classifications yielded 460,956 particle images with clear features. With these particles, an initial 3D model was built by CryoSparc ab initio reconstruction without symmetry. The particles along with the initial model, which is imported as 3D template, were transferred back to Relion and subjected to 3D classification using k=4 and tau fudge (T) value 4. The two most populated classes with good features for the Mfsd2a region contained 307,951 particles after two rounds of classifications, with T=20 in the second round. The Relion Auto-Refine of these particles resulted in a 4.2 Å map without symmetry. To improve the map quality, local 3D classification focused on Mfsd2a region was performed. The signal of multiple domains except Mfsd2a, was subtracted from the particles with a mask covering the whole complex. The modified particle set was subjected to further local 3D classification without alignment using a mask around Mfsd2a and k=4, T=40. After classification, the class with best features of Mfsd2a was selected. The corresponding 90,577 particles were subjected to Bayesian Polishing and per particle CTF refinement, then imported back to CryoSparc for final Refinement. NU-Refinement of CryoSparc yield an improved map for the whole complex with nominal resolution of 3.7 Å. By applying a mask on the transporter only, the Mfsd2a domain was further refined to 3.5 Å in Relion, local resolution estimated by ResMap[43]. All refinements followed the gold-standard procedure, in which two half-datasets are refined independently. The overall resolutions were estimated based on the gold-standard Fourier shell correlation (FSC)=0.143 criterion.

Model Building and Refinement

The model was built into a 3.5 Å cryo-EM map using the Na(+)/melibiose symporter MelB (PDB 4M64) as template. Local parts were manually built in Coot[44]. The models were refined using Phenix real space refine[45] and the geometry of the models was evaluated by Molprobity[46]. All the figures were prepared in PyMol (Schrödinger)[47] or UCSF Chimera[48].

Lysophosphotidylcholine Uptake Assays.

Mfsd2a WT and variants were cloned into pmCherry-N1 vector (ClonTech) with an mCherry at C-terminus. The plasmids were transfected into HEK293S cells (ATCC, CRL-3022) using Lipofectamine 3000 (Invitrogen) according to the manufacturer's directions. Cells grown in 12-well plates were maintained in 293 Freestyle medium (LifeTechnologies) supplemented with 10% FBS in an incubator at 37° C. and 8% CO$_2$. The medium was replaced 24 hours post-transfection with 293 Freestyle Medium supplemented with 10% FBS and 10 mM sodium butyrate, and cells were incubated for an additional 24 hours. Mfsd2a transport activity was assayed by measuring TopFluor Lyso PC (Avanti) uptake in HEK293S cells. The cells were washed first with serum-free 293 Freestyle Medium and incubated in 293 Freestyle Medium supplemented with 10% FBS, 150 mM NaCl, and 1 μM TopFluor Lyso PC at 37° C. for 30 minutes. The cells were washed twice with ice-cold PBS and re-suspended in ice-cold PBS. The cells expressing Mfsd2a WT or variants were gated in the same range based on the mCherry level using the FL-3 channel of a BD Accuri C6 flow cytometer. The mean fluorescence of cells corresponding to TopFluor Lyso PC level was quantified using the FL-1 channel. WT and Mfsd2a variants showed similar surface localization.

Conservation Analysis of Mouse Mfsd2a Structure.

A multiple sequence alignment was performed with a cut-off of minimally 50% identity and maximally 90% identity to mouse Mfsd2a using the UniRef database on the ConSurf web server[49,50]. The conservation scores were generated and colored using a PyMOL script generated by the ConSurf web server.

System Setup for Molecular Dynamics Simulations

We initiated simulations of Mfsd2a without scFv. An initial sodium ion was placed near the center of the proposed Mfsd2a sodium binding site based on the cryo-EM map. The protein structure was aligned on the Orientations of Proteins in Membranes[51] entry for 6S7V[52] (MFS superfamily member LtaA) using PyMOL (Schrödinger)[47]. Prime (Schrödinger)[53] was used to model missing side chains, and to add capping groups to protein chain termini. Protonation states of all titratable residues were assigned at pH 7. Histidine residues were modeled as neutral, with a hydrogen atom bound to either the delta or epsilon nitrogen depending on which tautomeric state optimized the local hydrogen-bonding network. Dowser[54] was used to add water molecules to protein cavities. Using Dabble[55], the prepared protein structures were inserted into a pre-equilibrated palmitoyl-oleoyl-phosphatidylcholine (POPC) bilayer, the system was solvated, and sodium and chloride ions were added to neutralize the system and to obtain a final concentration of 150 mM. Final systems comprised approximately 90,000 atoms and system dimensions were approximately 120×120×100 Å. We performed ten independent simulations, each 1.2 μs in length. For each simulation, initial atom velocities were assigned randomly and independently.

Molecular Dynamics Simulation and Analysis Protocols

We used the CHARMM36m force field for proteins, the CHARMM36 force field for lipids and ions, and the TIP3P model for water[56-58]. All simulations were performed using the Compute Unified Device Architecture (CUDA) version of particle-mesh Ewald molecular dynamics (PMEMD) in AMBER18[59] on graphics processing units (GPUs).

Systems were first minimized using three rounds of minimization, each consisting of 500 cycles of steepest descent followed by 500 cycles of conjugate gradient optimization. 10.0 and 5.0 $kcal \cdot mol^{-1} \cdot Å^{-2}$ harmonic restraints were applied to protein and lipids for the first and second rounds of minimization, respectively. 1 $kcal \cdot mol^{-1} \cdot Å^{-2}$ harmonic restraints were applied to protein for the third round of minimization. Systems were then heated from 0 K to 100 K in the NVT ensemble over 12.5 ps and then from 100 K to 310 K in the NPT ensemble over 125 ps, using 10.0 $kcal \cdot mol^{-1} \cdot Å^{-2}$ harmonic restraints applied to protein heavy atoms. Subsequently, systems were equilibrated at 310 K and 1 bar in the NPT ensemble, with harmonic restraints on the protein non-hydrogen atoms tapered off by 1.0 $kcal \cdot mol^{-1} \cdot Å^{-2}$ starting at 5.0 $kcal \cdot mol^{-1} \cdot Å^{-2}$ in a stepwise fashion every 2 ns for 10 ns, and then by 0.1 $kcal \cdot mol^{-1} \cdot Å^{-2}$ every 2 ns for 20 ns. Production simulations were performed without restraints at 310 K and 1 bar in the NPT ensemble using the Langevin thermostat and the Monte Carlo barostat, and using a timestep of 4.0 fs with hydrogen mass repartitioning[60]. Bond lengths were constrained using the SHAKE algorithm[61]. Non-bonded interactions were cut off at 9.0 Å, and long-range electrostatic interactions were calculated using the particle-mesh Ewald (PME) method with an Ewald coefficient of approximately 0.31 Å, and 4th order B-splines. The PME grid size was chosen such that the width of a grid cell was approximately 1 Å. Trajectory frames were saved every 200 ps during the production simulations.

The AmberTools17 CPPTRAJ package was used to reimage trajectories[62]. Simulations were visualized and analyzed using Visual Molecular Dynamics (VMD)[63] and PyMOL (Schrödinger)[47]. In FIG. 4c, the first 0.1 μs of each simulation was discarded, and trajectories were aligned on the backbone atoms of the Mfsd2a cryo-EM structure Na$^+$ binding site residues D92, T95, D96, E159, T163, and K440. The position of Na$^+$ ions were recorded every 10 ns for each of the 10 simulations, each 1.2 μs in length. Each Na$^+$ ion position was then drawn as a point superimposed on the starting Mfsd2a structure. Na$^+$ ion positions corresponding to the initially placed Na$^+$ ion residue number were classified to be at the Na1 site. Na$^+$ ion positions that were within 3.6 Å of D92 and E159 were classified to be at the Na2 site. In Extended FIG. 7c, the same analysis was repeated taking into consideration only simulation #2, where both sodium ions are stably bound.

REFERENCES

36 Goehring, A. et al. Screening and large-scale expression of membrane proteins in mammalian cells for structural studies. *Nat. Protoc.* 9, 2574-2585 (2014).

37 Mastronarde, D. N. Automated electron microscope tomography using robust prediction of specimen movements. *J. Struct. Biol.* 152, 36-51 (2005).

38 Zheng, S. Q. et al. MotionCor2: anisotropic correction of beam-induced motion for improved cryo-electron microscopy. *Nat. Methods* 14, 331-332 (2017).

39 Zhang, K. Gctf: Real-time CTF determination and correction. *J. Struct. Biol.* 193, 1-12 (2016).

40 Grant, T., Rohou, A. & Grigorieff, N. cisTEM, user-friendly software for single-particle image processing. *Elife* 7 (2018).

41 Scheres, S. H. A Bayesian view on cryo-EM structure determination. *J. Mol. Biol.* 415, 406-418 (2012).

42 Punjani, A., Rubinstein, J. L., Fleet, D. J. & Brubaker, M. A. cryoSPARC: algorithms for rapid unsupervised cryo-EM structure determination. *Nat. Methods* 14, 290-296 (2017).

43 Swint-Kruse, L. & Brown, C. S. Resmap: automated representation of macromolecular interfaces as two-dimensional networks. *Bioinformatics* 21, 3327-3328 (2005).

44 Emsley, P., Lohkamp, B., Scott, W. G. & Cowtan, K. Features and development of Coot. *Acta Crystallogr. D Biol. Crystallogr.* 66, 486-501 (2010).

45 Adams, P. D. et al. PHENIX: a comprehensive Python-based system for macromolecular structure solution. *Acta Crystallogr. D Biol. Crystallogr.* 66, 213-221 (2010).

46 Chen, V. B. et al. MolProbity: all-atom structure validation for macromolecular crystallography. *Acta Crystallogr. D Biol. Crystallogr.* 66, 12-21 (2010).

47 The PyMOL Molecular Graphics System v.2.0. (Schrödinger, 2017).

48 Pettersen, E. F. et al. UCSF Chimera—a visualization system for exploratory research and analysis. *J. Comput. Chem.* 25, 1605-1612 (2004).

49 Ashkenazy, H. et al. ConSurf 2016: an improved methodology to estimate and visualize evolutionary conservation in macromolecules. *Nucleic Acids Res.* 44, W344-350 (2016).

50 Landau, M. et al. ConSurf 2005: the projection of evolutionary conservation scores of residues on protein structures. *Nucleic Acids Res.* 33, W299-302 (2005).

51 Lomize, M. A., Lomize, A. L., Pogozheva, I. D. & Mosberg, H. I. OPM: orientations of proteins in membranes database. *Bioinformatics* 22, 623-625 (2006).

52 Zhang, B. et al. Structure of a proton-dependent lipid transporter involved in lipoteichoic acids biosynthesis. *Nat Struct Mol Biol* 27, 561-569 (2020).

53 Jacobson, M. P., Friesner, R. A., Xiang, Z. & Honig, B. On the role of the crystal environment in determining protein side-chain conformations. *J Mol Biol* 320, 597-608 (2002).

54 Zhang, L. & Hermans, J. Hydrophilicity of cavities in proteins. *Proteins* 24, 433-438 (1996).

55 Betz, R. Dabble (v2.6.3). Zenodo (2017).

56 Huang, J. et al. CHARMM36m: an improved force field for folded and intrinsically disordered proteins. *Nat Methods* 14, 71-73 (2017).

57 Klauda, J. B. et al. Update of the CHARMM all-atom additive force field for lipids: validation on six lipid types. *J Phys Chem B* 114, 7830-7843 (2010).

58 Guvench, O., Hatcher, E., Venable, R. M., Pastor, R. W. & MacKerell, A. D. CHARMM Additive All-Atom Force Field for Glycosidic Linkages between Hexopyranoses. *J Chem Theory Comput* 5, 2353-2370 (2009).

59 AMBER 2018 (University of California, San Francisco).

60 Hopkins, C. W., Le Grand, S., Walker, R. C. & Roitberg, A. E. Long-Time-Step Molecular Dynamics through Hydrogen Mass Repartitioning. *J Chem Theory Comput* 11, 1864-1874 (2015).

61 Ryckaert, J., Ciccotti, G., Berendsen, H. J. Numerical integration of the cartesian equations of motion of a system with constraints: molecular dynamics of n-alkanes. *J. Comput. Phys.* 23, 327-341 (1977).

62 Roe, D. R. & Cheatham, T. E., 3rd. PTRAJ and CPPTRAJ: Software for Processing and Analysis of Molecular Dynamics Trajectory Data. *J. Chem. Theory Comput.* 9, 3084-3095 (2013).

63 Humphrey, W., Dalke, A. & Schulten, K. VMD: Visual molecular dynamics. *J Mol Graph Model* 14, 33-38 (1996).

Example 3

The epitope binding of the ScFv of SEQ ID NO: 7 was mapped. Mfsd2a residue interactions with the scFv Heavy chain are: N458, Q460, Q462, S465, Q466, P467, E468. Mfsd2a residue interactions with the scFv Light chain are: A223, V224, V225, S227, S465, E468.

Other accessible outward facing extracellular loops on Mfsd2a that can be targeted to block the function (within 5.0 Å of site-3 identified with SiteMap program and graphical evaluation) are: K75, E77, P136, D137, F138, T142, E143, Q234, S235, T236, A237, L239.

TABLE 1

| Light Chain CDR1 | SGARYGYG | SEQ ID NO: 1 |
|---|---|---|
| Light Chain CDR2 | ANNIRPS | SEQ ID NO: 2 |
| Light Chain CDR3 | GNEDSITYAA | SEQ ID NO: 3 |

TABLE 1-continued

| Heavy Chain CDR1 | GFTFSSYDMA | SEQ ID NO: 4 |
|---|---|---|
| Heavy Chain CDR2 | AGITSTGSYTNYGAAVKG | SEQ ID NO: 5 |
| Heavy Chain CDR3 | SSFGCPYSCWYDIAGSIDA | SEQ ID NO: 6 |
| Light Chain Variable region | ALTQPSSVSANPGETVKITCSGARYGYGWYQQ KSPGSALVTLIYANNIRPSAIPSRFSGSKSGSTAT LTITGVRAEDEAVYYCGNEDSITYAAFGAGTTL TVL | SEQ ID NO: 11 |
| Heavy Chain Variable region | AVTLDESGGGLQTPKGGLSLVCKASGFTFSSYD MAWVRQAPGKGLEWVAGITSTGSYTNYGAAV KGRATISRDNGQSTVRLQLNSLRAEDTATYFC AKSSFGCPYSCWYDIAGSIDAWGHGTEVIVSS | SEQ ID NO: 12 |

ScFv variable region Sequence
                                                            (SEQ ID NO: 7)
QPSSVSANPGETVKITCSGARYGYGWYQQKSPGSALVTLIYANNIRPSAIPSRFSGSKSGSTAT

LTITGVRAEDEAVYYCGNEDSITYAAFGAGTTLTVLGGSSRSSGGGGSSGGGGSAVTLDESG

GGLQTPKGGLSLVCKASGFTFSSYDMAWVRQAPGKGLEWVAGITSTGSYTNYGAAVKGRA

TISRDNGQSTVRLQLNSLRAEDTATYFCAKSSFGCPYSCWYDIAGSIDAWGHGTEVIVS

Mfsd2A polypeptide sequence NCBI Ref Seq: NP_001129965
                                                            SEQ ID NO: 9
    1  makgegaesg  saagllptsi  lqsterpaqv  kkepkkkkqq  lsvcnklcya  lggapyqvtg 61  calgfflqiy  lldvaqkdee  vvfcfssfqv  gpfsasiilf  vgrawdaitd  plvglcisks 121  pwtclgrlmp  wiifstplav  iayfliwfvp  dfphgqtywy  llfyclfetm  vtcfhvpysa 181  ltmfisteqt  erdsatayrm  tvevlgtvlg  taiqgqivgq  adtpcfqdln  sstvasqsan 241  hthgttshre  tqkayllaag  vivciyiica  vililgvreq  repyeaqqse  piayfrgirl 301  vmshgpyikl  itgflftsla  fmlvegnfvl  fctytlgfrn  efqnlllaim  lsatltipiw 361  qwfltrfgkk  tavyvgissa  vpflilvalm  esnliityav  avaagisvaa  afllpwsmlp 421  dviddfhlkq  phfhgtepif  fsfyvfftkf  asgvslgist  lsldfagyqt  rgcsqpervk 481  ftinmlvtma  pivlillgll  lfkmypidee  rrrqnkkalq  alrdeasssg  csetdstela 541  sil Mfsd2A mRNA sequence NCBI Ref Seq: NM_001136493
                                                            SEQ ID NO: 10
    1  agaactataa  gaggcgcgga  gggggcgtgc  agcagagtgc  gttcctcgtc  tgccagccgg 61  cttggctagc  gcgcggcggc  cgtggctaag  gctgctacga  agcgagcttg  ggaggagcag 121  cggcctgcgg  ggcagaggag  catcccgtct  accaggtccc  aagcggcgtg  gcccgcgggt 181  catggccaaa  ggagaaggcg  ccgagagcgg  ctccgcggcg  gggctgctac  ccaccagcat 241  cctccaaagc  actgaacgcc  cggcccaggt  gaagaaagaa  ccgaaaaaga  agaaacaaca 301  gttgtctgtt  tgcaacaagc  tttgctatgc  acttggggga  gcccctacc  aggtgacggg 361  ctgtgccctg  ggtttcttcc  ttcagatcta  cctattggat  gtggctcaga  aggatgagga 421  agttgtcttt  tgcttctcct  cattccaggt  gggccctttc  tctgcctcca  tcatcctgtt 481  tgtgggccga  gcctgggatg  ccatcacaga  ccccctggtg  ggcctctgca  tcagcaaatc 541  cccctggacc  tgcctgggtc  gccttatgcc  ctggatcatc  ttctccacgc  ccctggccgt 601  cattgcctac  ttcctcatct  ggttcgtgcc  cgacttccca  cacggccaga  cctattggta 661  cctgcttttc  tattgcctct  ttgaaacaat  ggtcacgtgt  ttccatgttc  cctactcggc 721  tctcaccatg  ttcatcagca  ccgagcagac  tgagcgggat  tctgccaccg  cctatcggat -continued
```
 781 gactgtggaa gtgctgggca cagtgctggg cacggcgatc cagggacaaa tcgtgggcca 841 agcagacacg ccttgtttcc aggacctcaa tagctctaca gtagcttcac aaagtgccaa 901 ccatacacat ggcaccacct cacacaggga aacgcaaaag gcatacctgc tggcagcggg 961 ggtcattgtc tgtatctata taatctgtgc tgtcatcctg atcctgggcg tgcgggagca 1021 gagagaaccc tatgaagccc agcagtctga gccaatcgcc tacttccggg gcctacggct 1081 ggtcatgagc cacggcccat acatcaaact tattactggc ttcctcttca cctccttggc 1141 tttcatgctg gtggagggga actttgtctt gttttgcacc tacaccttgg gcttccgcaa 1201 tgaattccag aatctactcc tggccatcat gctctcggcc actttaacca ttcccatctg 1261 gcagtggttc ttgacccggt ttggcaagaa gacagctgta tatgttggga tctcatcagc 1321 agtgccattt ctcatcttgg tggccctcat ggagagtaac ctcatcatta catatgcggt 1381 agctgtggca gctggcatca gtgtggcagc tgccttctta ctaccctggt ccatgctgcc 1441 tgatgtcatt gacgacttcc atctgaagca gccccacttc catggaaccg agcccatctt 1501 cttctccttc tatgtcttct tcaccaagtt tgcctctgga gtgtcactgg gcatttctac 1561 cctcagtctg gactttgcag ggtaccagac ccgtggctgc tcgcagccgg aacgtgtcaa 1621 gtttacactg aacatgctcg tgaccatggc toccatagtt ctcatcctgc tgggcctgct 1681 gctcttcaaa atgtaccca ttgatgagga gaggcggcgg cagaataaga aggccctgca 1741 ggcactgagg gacgaggcca gcagctctgg ctgctcagaa acagactcca cagagctggc 1801 tagcatcctc tagggcccgc cacgttgccc gaagccacca tgcagaaggc cacagaaggg 1861 atcaggacct gtctgccggc ttgctgagca gctggactgc aggtgctagg aagggaactg 1921 aagactcaag gaggtggccc aggacacttg ctgtgctcac tgtgggggccg gctgctctgt 1981 ggcctcctgc ctcccctctg cctgcctgtg gggccaagcc ctggggctgc cactgtgaat 2041 atgccaagga ctgatcgggc ctagcccgga acactaatgt agaaaccttt tttttttacag 2101 agcctaatta ataacttaat gactgtgtac atagcaatgt gtgtgtatgt atatgtctgt 2161 gagctattaa tgttattaat tttcataaaa gctggaaagc aaaaaaaaaa aaaaaaaaaa 2221 aaaaaaaaaa aaaaaa
```

Example 4—Structure and Mechanism of Blood-Brain Barrier Fatty Acid Transporter Mfsd2a Mfsd2a is a sodium-dependent lysophosphatidylcholine (LPC) symporter responsible for docosahexaenoic acid (DHA) uptake into the brain[1,2], which is crucial for brain development and performance[3]. Its mutations cause microcephaly syndromes[4,5]. Mfsd2a's ability to transport lipid is also a key mechanism underlying its function as a transcytosis inhibitor to regulate the blood-brain barrier (BBB)[6,7]. Specifically, we have shown previously that knock-in mouse harboring D96A mutation abolished Mfsd2a's lipid transport and caused BBB leakage[7], recapitulating the Mfsd2a knockout phenotype. Therefore, Mfsd2a lipid transport function is required for its ability to inhibit transcytosis to ensure BBB integrity. Thus, Mfsd2a represents an attractive target for modulating BBB permeability for drug delivery. Described herein is the cryo-electron microscopy structure of Mfsd2a. This structure defines this important transporter's architecture, reveals its unique extracellular domain, and uncovers the substrate-binding cavity. The structure, together with functional studies and molecular dynamics simulations, identifies a conserved sodium-binding site, reveals a potential lipid entry pathway, and helps rationalize Mfsd2a mutations that underlie microcephaly syndromes.

These results shed light on Mfsd2a's critical lipid transport function and aid the design of specific modulators for therapeutic purposes.

The blood-brain barrier is indispensable for normal brain function[8]. Historically, the restricted permeability of the brain vasculature has been attributed to specialized tight junctions between endothelial cells that prohibit passage of water-soluble molecules[9,10]. Recent evidence shows central nervous system (CNS) endothelial cells also actively inhibit transcytosis to ensure BBB integrity, and full barrier integrity requires restriction of both paracellular and transcellular leakage. A BBB-specific lipid transporter, Mfsd2a, is a key inhibitor of transcytosis[6,7,11]. Mice lacking Mfsd2a's lipid transport function have BBB leakage due to upregulated transcytosis without apparent tight junction disruption[6,7,11]. Mechanistically, Mfsd2a-translocated phospholipids inhibit caveolae vesicle formation, suppressing transcytosis[7,12]. Thus, Mfsd2a is a target for manipulating BBB permeability to facilitate CNS drug delivery[7].

As a lipid transporter[1,2], Mfsd2a is unique among mammalian major facilitator superfamily (MFS) members, which typically transport soluble substrates[13]. Moreover, Mfsd2a lacks significant sequence similarity to MFS transporters with known structures. The lack of a reliable structural model impedes mechanistic understanding of Mfsd2a. For example, it is unclear how Mfsd2a mediates lipid transport and how the transport is coupled to sodium.

Described herein is the structure of mouse Mfsd2a as determined by single-particle cryo-electron microscopy (cryo-EM). The structure, together with functional characterizations and molecular dynamics (MD) simulations, reveals the transporter's architecture and provides a blueprint to understand lipid translocation and sodium-dependent transport.

Figure 13:
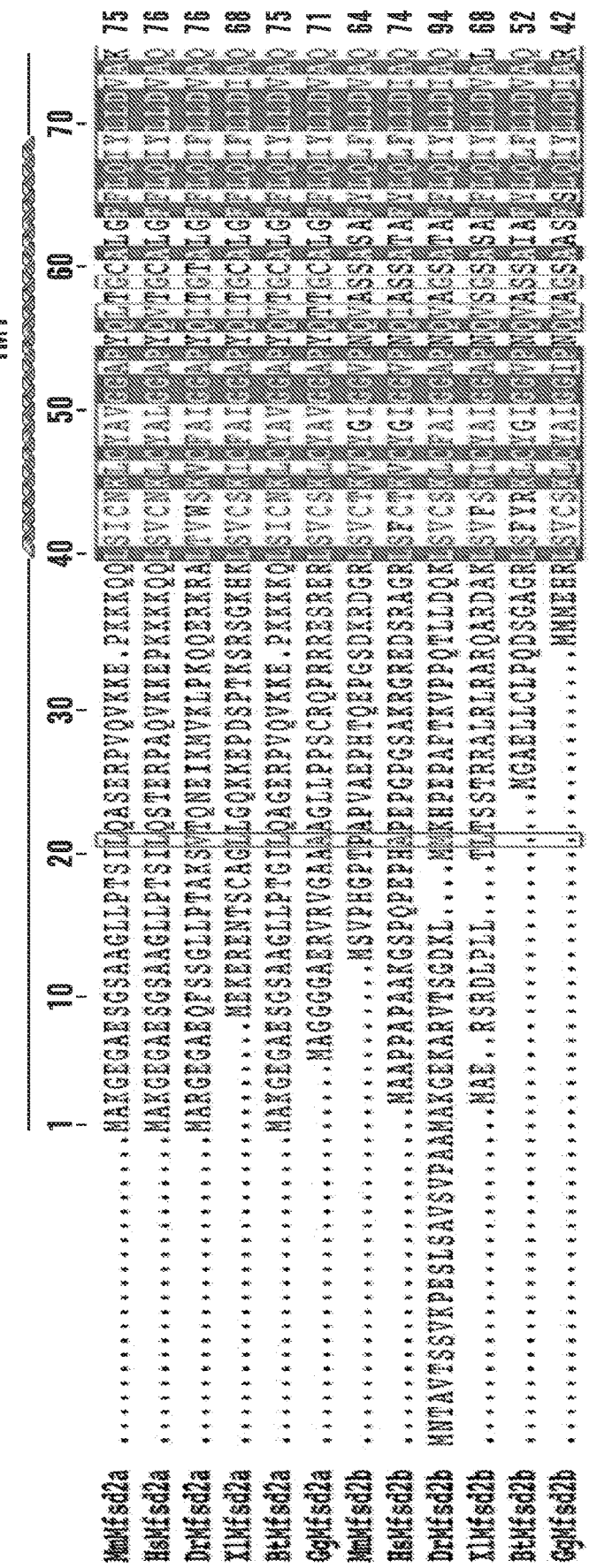
FIG. 13 depicts the sequence alignment of Mfsd2a and Mfsd2b homologs. Sequence alignment of Mfsd2a and Mfsd2b from *Mus musculus* (Mm), *Homo sapiens* (Hs), *Danio rerio* (Dr), *Xenopus laevis* (Xl), *Bos taurus* (Bt), and *Gallus gallus* (Gg) are shown. Fig. discloses SEQ ID NOS 15-26, respectively, in order of appearance.
Figure 13:
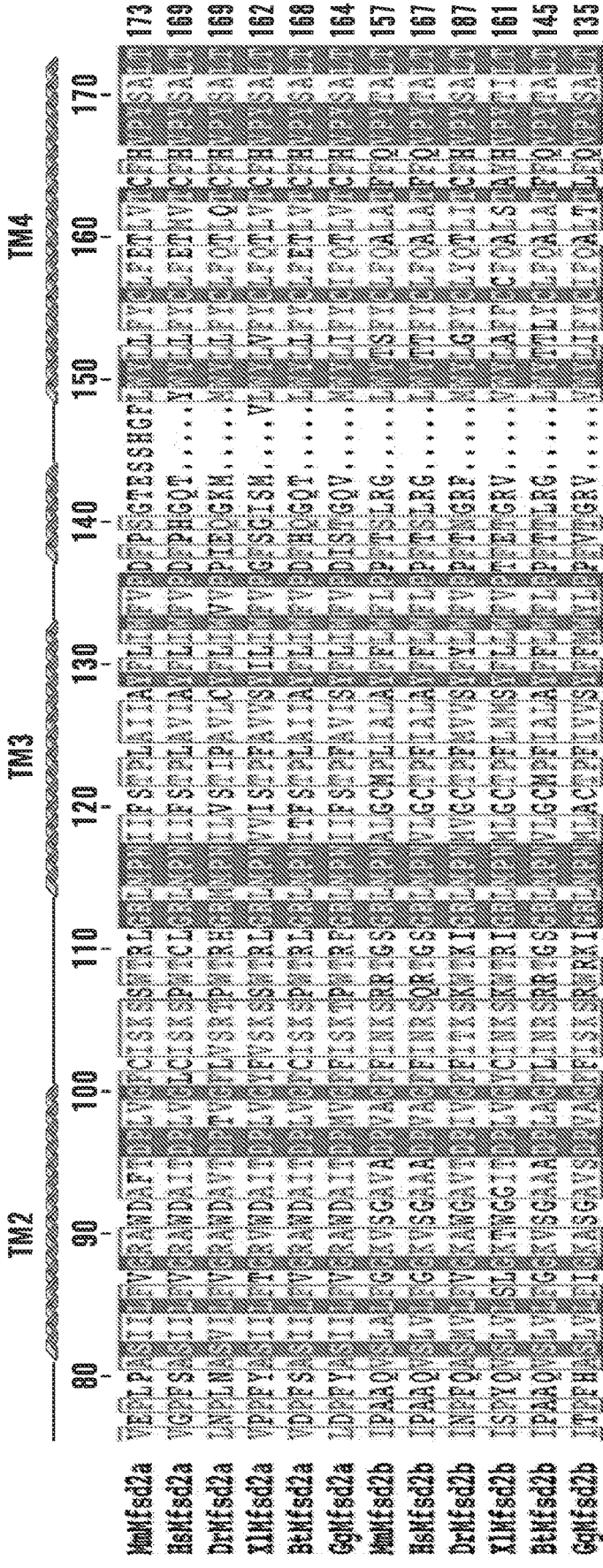
Figure 13:
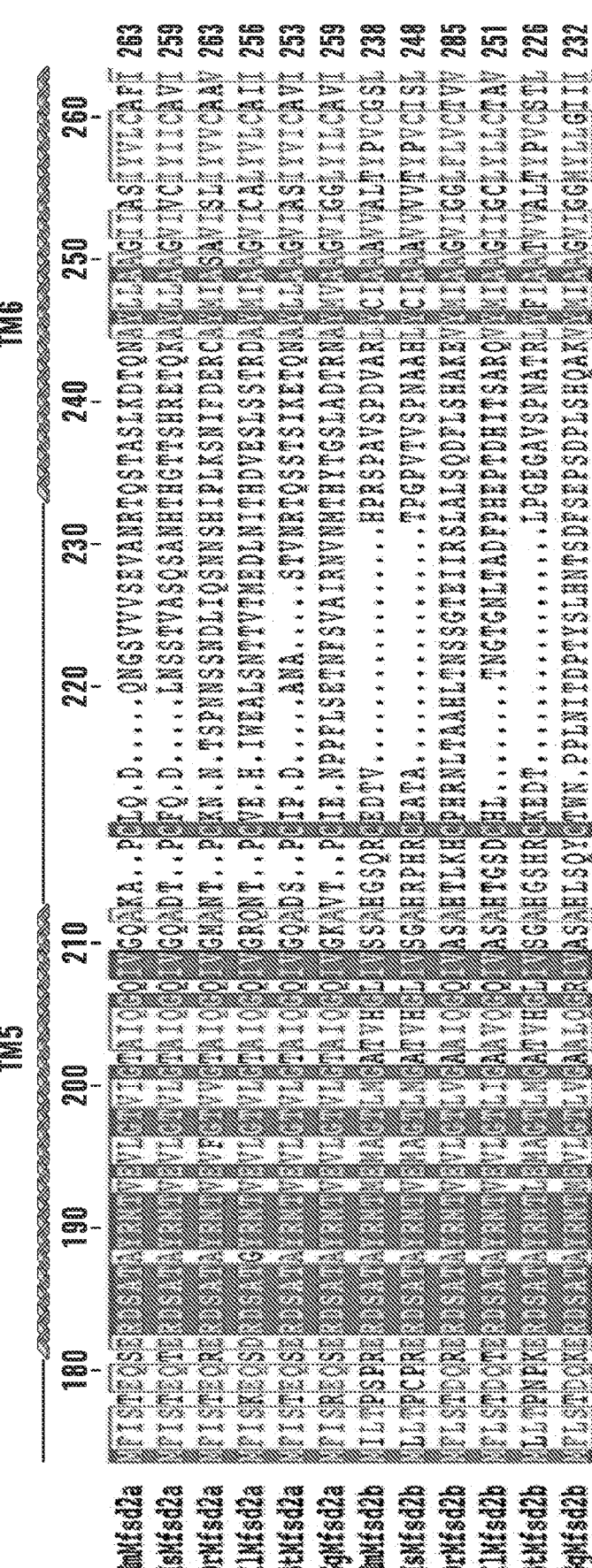
Figure 13:
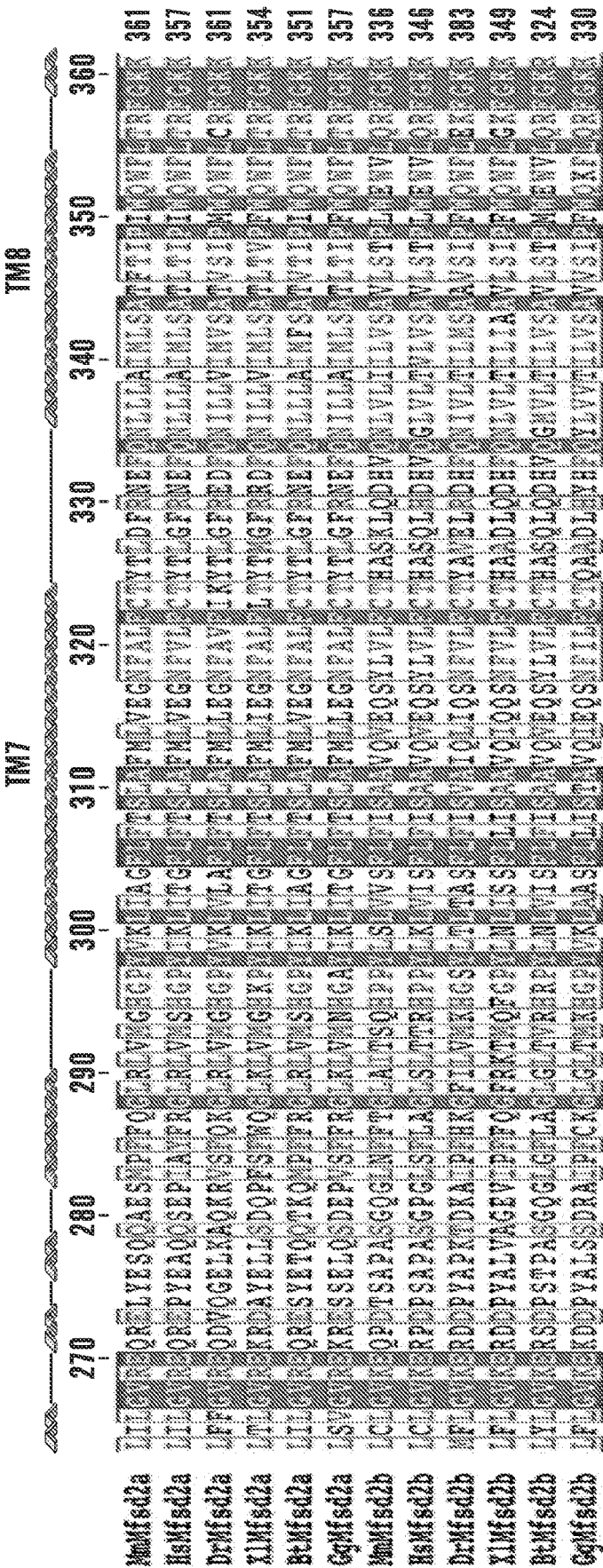
Figure 13:
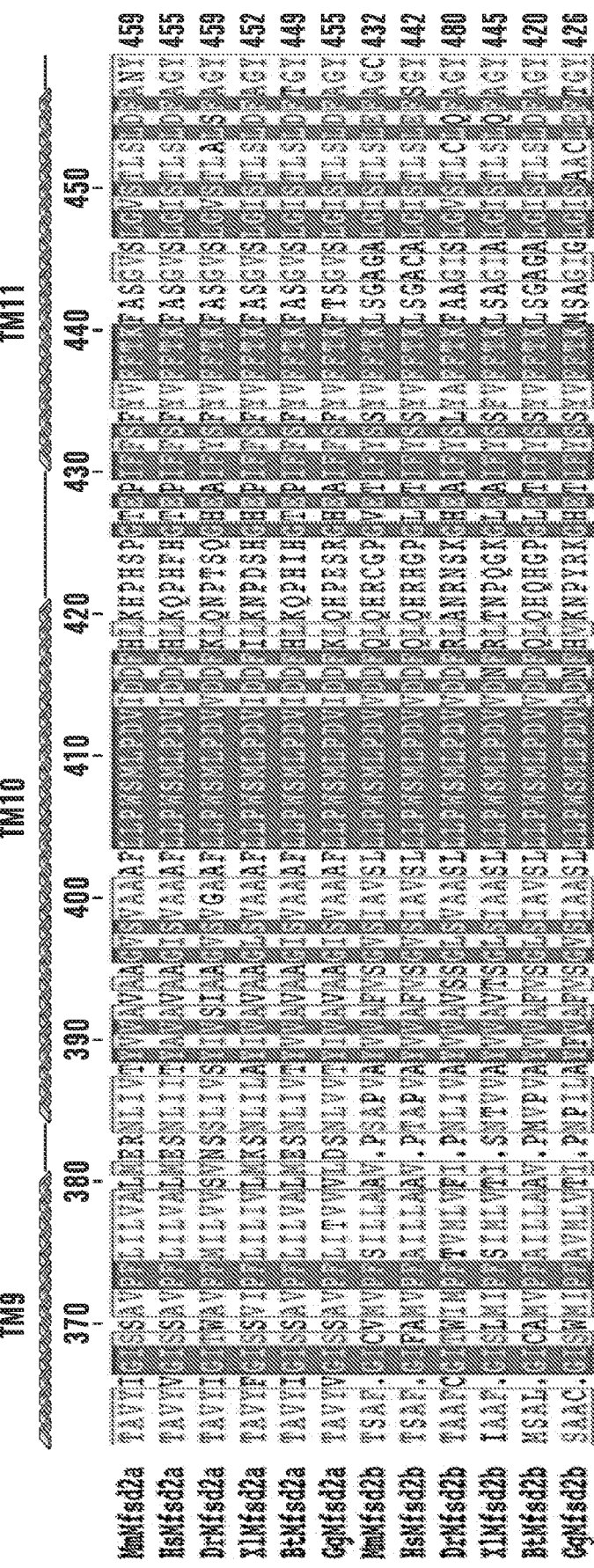
Figure 13:
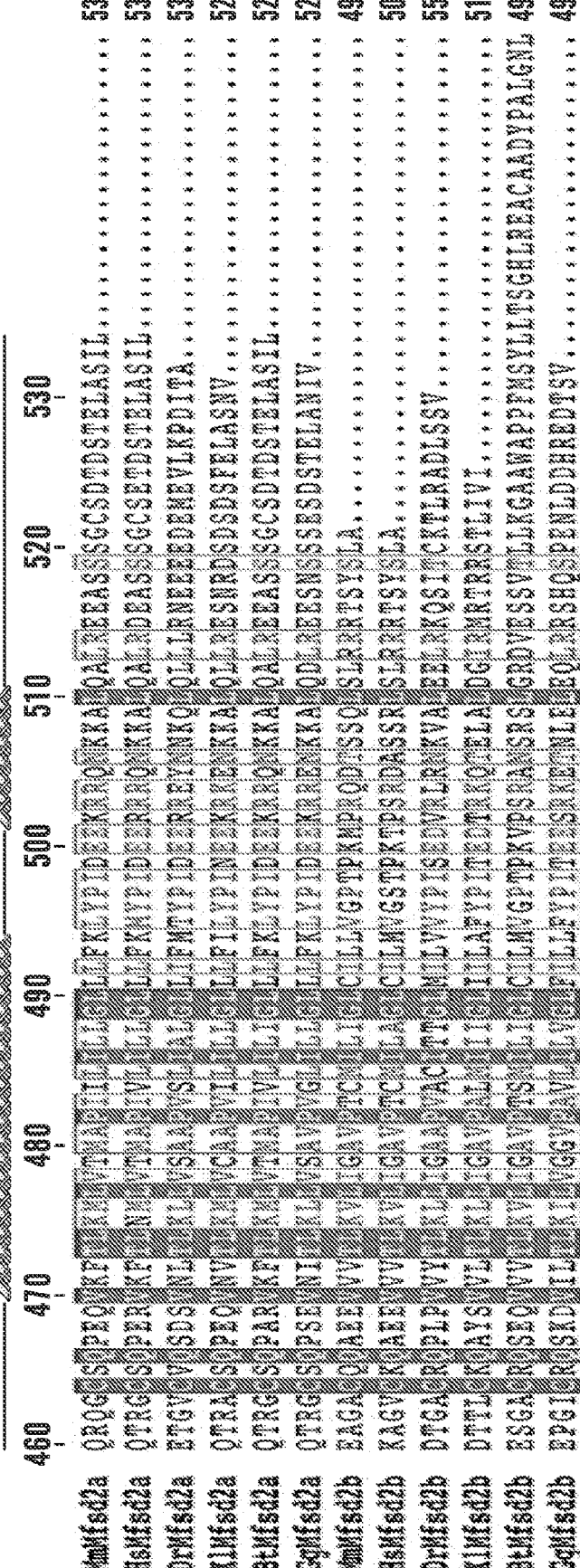

Structural determination and functional characterization. To elucidate the structure and transport mechanism of Mfsd2a, the mouse ortholog[6,7,12], which has optimal biochemical properties and shares 84% sequence identity and 90% similarity with human Mfsd2a was utilized (FIG. 13). Cells that overexpress wild-type mouse Mfsd2a showed significant TopFluor LPC (known Mfsd2a substrate[1,2]) uptake compared to control cells (FIG. 1A). Substituting D96, a residue critical for transport[1], substantially reduced uptake. These results confirm that mouse Mfsd2a is an LPC transporter with properties comparable to human Mfsd2a.

A loss-of-function point mutation, Q67H, was identified (FIGS. 6A-6D), that presumably arrests the transporter in an outward-facing conformation based on its location near the typical extracellular gate area in MFS. It was reasoned this might reduce conformational heterogeneity and this variant was selected for structural studies. Since Mfsd2a is small (59 kDa) with few features outside the micelle, a single-chain variable fragment that binds Mfsd2a was used as a fiducial marker to aid particle alignment. This strategy resulted in a 3.5 Å-resolution map (FIG. 1B, 7A-7F), showing clear side-chain densities (FIG. 8).

Overall structure. Mfsd2a adopts a canonical MFS fold with structurally related N-domain (TM1-6) and C-domain (TM7-12) (FIG. 1C). This structure captures Mfsd2a in an outward-facing conformation with a cavity at the N- and C-domain interface (FIG. 2C). One unique feature of Mfsd2a is its extracellular domain, primarily formed by an elongated, ordered loop between TM5 and TM6 (EL3) and a loop between TM11 and TM12 (EL6) (FIG. 1C). EL3 reaches across the N- and C-domain interface and interacts with EL6 and EL4 (between TM7 and TM8). A conserved disulfide bridge forms between C216 on EL3 and C464 on EL6, providing covalent linkage (FIG. 1C). The extracellular domain may potentially constrain relative movement between N- and C-domains. Mutating C216 or C464 to alanine substantially reduced transport (FIG. 2B), indicating an important role of the extracellular domain stabilized by the disulfide bridge. Intracellularly, the N- and C-domains are connected by a long linker between TM6 and TM7 (FIG. 10) that interacts with both domains and might stabilize the outward-open conformation. After the last TM helix, a short helix reaches from the C-domain to the domain interface on the intracellular surface, perhaps stabilizing the intracellular closed conformation. Unlike sugar transporters within MFS superfamily[14], no helical bundle domain forms on Mfsd2a's intracellular side.

Figure 2E:
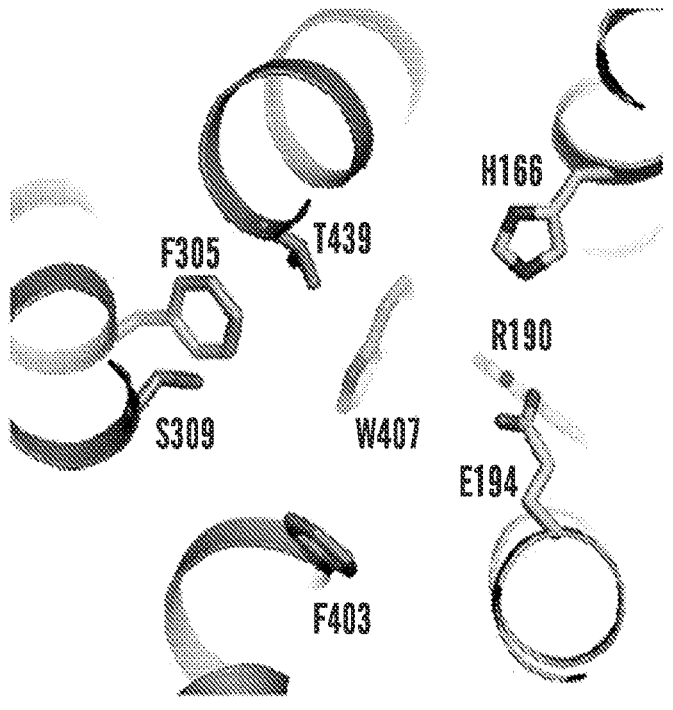

Translocation pathway. In the outward-facing conformation, the solvent-accessible cavity, traversing around half of the membrane, is surrounded mainly by TM1, TM2, TM4, TM5, TM7, TM8, TM10, and TM11 (FIG. 1C), which likely form a substrate translocation pathway. The cavity's bottom half has an overall highly negative electrostatic surface that becomes more neutral near the cavity's mouth (FIG. 2C). This electrostatic distribution can accommodate the amphipathic nature of LPC such that its positively charged headgroup settles in the cavity's base and its hydrophobic tail points to the extracellular side. To assess the functional roles of the residues near the bottom of the cavity, mutagenesis studies were performed (FIG. 2E, 2D). Majority alanine substitutions either abolished (R190A or H166A) or substantially reduced transport activity (S309A, F403A, W407A, E194A, or F305A) except T439A with no apparent effect. These results indicate important roles of the central pocket residues on both N- and C-domains. It is contemplated herein that highly conserved charged residues near the bottom of the cavity, such as H166, can directly interact with LPC's zwitterionic phosphatidylcholine headgroups.

Lateral entry and lipid-binding site. In the extracellular half of the membrane, Mfsd2a's N- and C-domains only loosely interact, leaving lateral "V"-shaped openings to the membrane between TM5 and TM8 on one side and between TM2 and TM11 on the other (FIG. 2C). Extra lipid-like density is wedged in both openings (FIGS. 3A, 3B, 3D) with the stronger density between TM5 and TM8 (TM5/TM8), indicating more stable interactions. Although the local resolution is insufficient to unambiguously resolve the lipid identity, LPC or LPC-like/containing molecule can be reasonably placed into the density between TM5 and TM8 (FIG. 3B). In this case, the LPC headgroup points to the cavity's center, and its C-terminal acyl chain extends out, parallel to the TM helices, matching the lipid bilayer environment. The density between TM2 and TM11 (TM2/TM11) shows some flatness features (FIG. 3D); its identity is less clear. The importance of residues constituting the potential lipid-binding sites were probed through mutagenesis (FIG. 3C). N335 on TM8 lies at the entrance of the lateral opening near the kink of the tentatively modelled LPC. Mutating N335 significantly reduced transport, consistent with its potential role in lipid docking. The T202 sidechain on TM5 points towards the lipid density. Mutation to a bulky residue (T202F; but not an alanine) substantially impaired transport, perhaps by sterically hindering lipid binding. In contrast, mutating Q334 on TM8 or Q207 on TM5, whose sidechains point away from the lipid density, only modestly impacted transport. Likewise, mutating residues near the TM2/TM11 lipid density (F64A, S82A, R89A, T451A, F86A, D455A, R461A) had modest or negligible impacts. Thus, it is contemplated herein that the TM5/TM8 lateral opening is more functionally important than the TM2/TM11 opening. It is proposed that the TM5/TM8 lateral opening constitutes an LPC binding site en route to the central cavity, facilitating LPC diffusion into/from the membrane. It is further contemplated that TM2/TM11 lateral opening could also be involved in lipid entry or exit.

Sodium-binding site. Mfsd2a's LPC transport activity depends on sodium[1,2]. Within the MFS superfamily, the bacterial melibiose transporter MelB is a well-characterized $Na^+$-coupled symporter[15,16]. Several key residues in MelB's $Na^+$-binding site are conserved in Mfsd2a, whose equivalent region likely also forms a sodium-binding site (FIG. 4A). In particular, side-chain oxygens of D92, D96, T95, and T163 form a pocket well-positioned to coordinate sodium at the center. In this region of the cryo-EM map, extra density above background levels (FIG. 4B) might be compatible with $Na^+$ given 150 mM NaCl in the sample. The resolution is insufficient to place the ion unambiguously, however.

To validate the proposed sodium-binding site and elucidate sodium coordination, all-atom MD simulations of Mfsd2a were performed. In all 13 independent simulations (~1.2 µs each) with a sodium ion placed in the putative binding pocket, the sodium quickly shifted ~2 Å towards TM2, forming polar interactions with D92, D96, T95, and T163. The sodium remained bound at this location ("Na1") for the remainder of each simulation (FIGS. 4C, 4D, 11A).

In four of five simulations initiated with no sodium present in the proposed binding pocket, a sodium ion from the extracellular solution diffused through the central cavity to spontaneously and stably bind at Na1, with coordination distances and geometry typical of sodium binding[17].

In many simulations, a sodium ion also bound at a second site ("Na2"), ~4 Å from Na1, further from TM2 and closer to the extracellular solvent (FIGS. 4C, 11E, 11C, 11D). The sodium at Na2 forms salt bridges with D92 and E159, with water molecules providing additional coordination. Sodium ions often bind simultaneously at Na1 and Na2. Because both sites are located beside a large, solvent-exposed cavity, sodium follows various pathways to reach them. After entering the cavity, sodium typically interacts briefly with Y55, Q56, E194, T198, and/or E316—in no particular order—before binding to Na1 or Na2. At Na2, sodium forms only two direct polar interactions with the protein, compared to six at Na1, resulting in weak and transient binding. Thus, it is proposed that Na1, which shows stable sodium binding, is the key sodium-binding site for the transport cycle.

To probe the functional significance of the Na$^+$-binding sites, mutagenesis studies were performed (FIG. 4E). For Na1, substituting alanine at D96 abolished transport, corroborating previous findings[1] and consistent with strong coordination by both oxygens of D96's carboxylate group for Na$^+$ at Na1. Mutating D92 or T95 also significantly impaired uptake, consistent with roles in coordinating Na$^+$. Substituting alanine for T163 had little effect, while substituting a longer side chain (methionine) that potentially interferes with Na$^+$ binding abolished uptake. In control experiments, mutating Q56 (central-cavity facing) had little effect. Together, these results indicate Na1 is functionally important and corroborate several critical residues found in human Mfsd2a[2]. For Na2, mutating E159 only modestly affected activity. Thus, Na2 likely is not involved directly in coupled transport of Na$^+$ and lipid. Sequence conservation analysis of Mfsd2a and its close relative Mfsd2b—an Na$^+$-independent sphingosine 1-phosphate transporter[18,19]—revealed D92 is conserved in Mfsd2a but is substituted by glycine in Mfsd2b, consistent with the differing Na$^+$ requirements. Notably, K440 is next to Na1, where it forms electrostatic interactions with D96 and D92, stabilizing closely spaced carboxylate groups and thus helping to uphold Na1. Mutating K440 abolished transport (FIG. 4E). Likewise, mutating Y55 significantly reduced uptake. Y55 is within distance to interact with K440, which might further stabilize Na1. Importantly, in a previous knock-in mouse study, D96A mutation abolished Mfsd2a's lipid transport and caused BBB leakage[7], recapitulating the Mfsd2a knock-out phenotype. This highlights the functional importance of the sodium-binding site and corroborates the link between Mfsd2a transport and BBB permeability.

Disease-causing mutations. Multiple Mfsd2a mutations cause lethal or progressive microcephaly syndromes[4,5,20-23]. For instance, T159M or S166L mutations (T163M and S170L in mouse) underlie a lethal microcephaly syndrome[4,20]. The present structure reveals that T163 is part of Na1. Its mutation to methionine thus likely disrupts Na$^+$ binding and impedes transport (FIG. 4d, 4E). S170 is below the cavity's base at the N- and C-domain interface (FIG. 5A), forms a hydrogen bond with R190, and closely contacts W407. S170 contributes to formation of the central binding pocket and possibly intracellular gate closing. As expected, S170L mutation reduced uptake close to background levels (FIG. 5C). A third mutation, S339L (S343L in mouse)[5], may affect TM8's helical bend (FIG. 5B), thereby affecting conformational transitions. The S343L mutation substantially reduced activity (FIG. 5C), consistent with decreased LPC uptake in patients[5]. A fourth mutation, T198M (T202M in mouse)[20,21] may interfere with substrate entry, as T202 lines the TM5/TM8 lateral opening (FIG. 3B). The T202M mutation indeed impaired transport. Several mutations likely affect protein structure or folding. Three proline point mutations (P402H, P493L, P164T, i.e., mouse P406H, P497L, P168T) are linked to microcephaly[20,22,23]. Given proline's unique properties, these mutations likely cause conformational changes or destabilize the structure. Additionally, an R326H/V250F double-mutation (R330H/A254F in mouse) underlies microcephaly[20]. Given A254F but not R330H affected uptake (FIG. 5C), the A254F mutation is likely responsible. Mutating A254 to a bulky residue presumably interferes with the packing interaction between TM3 and TM6, affecting structural stability or folding. These results corroborate that the mouse Mfsd2a structure provides a faithful model for interpreting function and disease-causing mutations of human Mfsd2a.

Discussion MFS transporters are thought to operate by a rocker-switch model[24]. Following a similar mechanism, opening or closing of Mfsd2a's lateral openings is expected to accompany opening or closing of the central cavity to the solution as the N- and C-domains rock during the transport cycle. For a Na$^+$-coupled transporter, a central question is how Na$^+$ is coupled to transport. The present structural analyses, MD simulations, and functional studies revealed a stable and functionally important Na$^+$-binding site, Na1, at a strategic position right around TM2's helical kink, encompassed by Na$^+$-binding residues D92 and D96. As TM2's kink gives rise to the "V"-shaped lateral opening between TM2 and TM11, Na$^+$ binding might be linked directly to its opening or closing, thus coupling Na$^+$ to the state transition between outward- and inward-open conformations. Additionally, the interaction between C-domain K440 and the N-domain D92 and D96 stabilizes the Na$^+$-binding site. This would also link Na$^+$ binding and conformational state transition, involving relative rocking between N- and C-domains. Moreover, the Na$^+$-binding sites are near the central cavity's base, where the LPC headgroup presumably binds. Thus, binding of LPC or sodium could induce local conformational changes, impacting binding of the other substrate and yielding transport coupling.

The Mfsd2a structure described herein represents the first for a eukaryotic lipid transporter within the MFS superfamily[13]. Compared with most known MFS transporters, whose soluble substrates diffuse directly into the cavity, it remains unknown how lipids enter and leave Mfsd2a. The present structure indicates a possible two-step mechanism: After the lipid diffuses laterally from the membrane to Mfsd2a, it docks onto the lipid-binding site at the lateral entry and then moves into the central cavity. Lateral openings were observed on both sides of Mfsd2a, at the N- and C-domain interface. The TM5/TM8 opening is more likely the LPC entrance in an outward-facing conformation: lipid density there matches reasonably with an LPC-like molecule, the density is relatively strong, and the surrounding residues are functionally important. In an inward-facing conformation, a simple scenario would be that the lateral opening on the same side also serves as the LPC entrance. This would potentially allow the LPC tail to remain in the lipid bilayer without being fully buried in the pocket during transport, helping explain how LPCs with relatively long tails can be transported[1,2]. The detailed mechanisms await future investigation. Interestingly, many other MFS transporters, such as GLUT3 (also in an outward-facing conformation)[25], have central cavities that are better shielded from the membrane.

This could reflect their different needs for substrate entry. The proposed lateral entry of lipids in Mfsd2a shows interesting parallels to other lipid transporters, such as ABC lipid transporters[26], P4 ATPase[27], and RND transporters[28]. This shared feature across structurally unrelated lipid transporter families may represent an optimal solution to overcome the high energy cost associated with moving lipids out of the membrane.

A major hurdle in developing therapeutics for CNS disorders is the limited permeability of most drug molecules across the BBB[29,30]. Given the critical role of Mfsd2a's lipid transport function in suppressing transcytosis thus ensuring the BBB's restrictive permeability, inhibiting Mfsd2a represents an attractive strategy for CNS drug delivery. In fact, mice lacking Mfsd2a activity exhibit leakage of diverse molecules, including IgG[6,7,11]. The present structure of Mfsd2a in an outward-facing conformation provides a blueprint for structure-based discovery of Mfsd2a inhibitors. In addition, biologics, such as an extracellular surface binder against Mfsd2a (FIGS. 12A-12B), are contemplated to inhibit transport by impeding conformational transitions during the transport cycle.

REFERENCES

1 Nguyen, L. N. et al. Mfsd2a is a transporter for the essential omega-3 fatty acid docosahexaenoic acid. *Nature* 509, 503-506 (2014).

2 Quek, D. Q., Nguyen, L. N., Fan, H. & Silver, D. L. Structural Insights into the Transport Mechanism of the Human Sodium-dependent Lysophosphatidylcholine Transporter MFSD2A. *J. Biol. Chem.* 291, 9383-9394 (2016).

3 Yeo, L. A. H. a. Y. K. Health benefits of docosahexaenoic acid (DHA). *Pharmacol. Res.* 40, 211-225 (1999).

4 Guemez-Gamboa, A. et al. Inactivating mutations in MFSD2A, required for omega-3 fatty acid transport in brain, cause a lethal microcephaly syndrome. *Nat. Genet.* 47, 809-813 (2015).

5 Alakbarzade, V. et al. A partially inactivating mutation in the sodium-dependent lysophosphatidylcholine transporter MFSD2A causes a non-lethal microcephaly syndrome. *Nat. Genet.* 47, 814-817 (2015).

6 Ben-Zvi, A. et al. Mfsd2a is critical for the formation and function of the blood-brain barrier. *Nature* 509, 507-511 (2014).

7 Andreone, B. J. et al. Blood-Brain Barrier Permeability Is Regulated by Lipid Transport-Dependent Suppression of Caveolae-Mediated Transcytosis. *Neuron* 94, 581-594 e585 (2017).

8 Andreone, B. J., Lacoste, B. & Gu, C. Neuronal and vascular interactions. *Annu. Rev. Neurosci.* 38, 25-46 (2015).

9 Reese, T. S. & Karnovsky, M. J. Fine structural localization of a blood-brain barrier to exogenous peroxidase. *J. Cell. Biol.* 34, 207-217 (1967).

10 Brightman, M. W. & Reese, T. S. Junctions between intimately apposed cell membranes in the vertebrate brain. *J. Cell Biol.* 40, 648-677 (1969).

11 Chow, B. W. & Gu, C. Gradual Suppression of Transcytosis Governs Functional Blood-Retinal Barrier Formation. *Neuron* 93, 1325-1333 e1323 (2017).

12 Yang, Y. R. et al. Mfsd2a (Major Facilitator Superfamily Domain Containing 2a) Attenuates Intracerebral Hemorrhage-Induced Blood-Brain Barrier Disruption by Inhibiting Vesicular Transcytosis. *J. Am. Heart Assoc.* 6 (2017).

13 Yan, N. Structural Biology of the Major Facilitator Superfamily Transporters. *Annu. Rev. Biophys.* 44, 257-283 (2015).

14 Deng, D. et al. Crystal structure of the human glucose transporter GLUT1. *Nature* 510, 121-125 (2014).

15 Ethayathulla, A. S. et al. Structure-based mechanism for Na(+)/melibiose symport by MelB. *Nat. Commun.* 5, 3009 (2014).

16 Granell, M., Leon, X., Leblanc, G., Padros, E. & Lorenz-Fonfria, V. A. Structural insights into the activation mechanism of melibiose permease by sodium binding. *Proc. Natl. Acad. Sci. USA* 107, 22078-22083 (2010).

17 Harding, M. M. Metal-ligand geometry relevant to proteins and in proteins: sodium and potassium. *Acta Crystallogr. D Biol. Crystallogr.* 58, 872-874 (2002).

18 Vu, T. M. et al. Mfsd2b is essential for the sphingosine-1-phosphate export in erythrocytes and platelets. *Nature* 550, 524-528 (2017).

19 Kobayashi, N. et al. MFSD2B is a sphingosine 1-phosphate transporter in erythroid cells. *Sci. Rep.* 8, 4969 (2018).

20 Scala, M. et al. Biallelic MFSD2A variants associated with congenital microcephaly, developmental delay, and recognizable neuroimaging features. *Eur. J. Hum. Genet.* 28, 1509-1519 (2020).

21 Riazuddin, S. et al. Exome sequencing of Pakistani consanguineous families identifies 30 novel candidate genes for recessive intellectual disability. *Mol. Psychiatry* 22, 1604-1614 (2017).

22 Hu, H. et al. Genetics of intellectual disability in consanguineous families. *Mol. Psychiatry* 24, 1027-1039 (2019).

23 Harel, T. et al. Homozygous mutation in MFSD2A, encoding a lysolipid transporter for docosahexanoic acid, is associated with microcephaly and hypomyelination. *Neurogenetics* 19, 227-235 (2018).

24 Drew, D. & Boudker, O. Shared Molecular Mechanisms of Membrane Transporters. *Annu. Rev. Biochem.* 85, 543-572 (2016).

25 Deng, D. et al. Molecular basis of ligand recognition and transport by glucose transporters. *Nature* 526, 391-396 (2015).

26 Plummer, A. M., Culbertson, A. T. & Liao, M. The ABCs of Sterol Transport. *Annu. Rev. Physiol.* 83, 153-181 (2021).

27 Andersen, J. P. et al. P4-ATPases as Phospholipid Flippases-Structure, Function, and Enigmas. *Front. Physiol.* 7, 275 (2016).

28 Nikaido, H. Structure and mechanism of RND-type multidrug efflux pumps. *Adv. Enzymol. Relat. Areas Mol. Biol.* 77, 1-60 (2011).

29 Pardridge, W. M. The blood-brain barrier: bottleneck in brain drug development. *NeuroRx* 2, 3-14 (2005).

30 Banks, W. A. From blood-brain barrier to blood-brain interface: new opportunities for CNS drug delivery. *Nat. Rev. Drug Discov.* 15, 275-292 (2016).

Methods

Protein Expression, Purification and Sample Preparation.

*Mus musculus* Mfsd2a with a point mutation (Q67H) was cloned into a modified BacMam™ expression vector[31] with an N-terminal GFP-his tag and a 3C protease cleavage site. The baculovirus was generated using sf9 insect cells following the published protocol (Invitrogen LifeTechnologies). Recombinant protein was expressed in HEK293S cells grown in 293 Freestyle medium (LifeTechnologies) supplemented with 2% FBS. Cells were infected with baculovirus at a density of $2.5*10^6$ cells per ml. After 12 hours' incubation at 37° C., 10 mM sodium butyrate was added to the culture, and the cells were moved to 30° C. for an additional 48 hours before harvesting. All protein purification steps were carried out at 4° C. unless specifically noted otherwise. Initially, the cell pellet was re-suspended in buffer containing 20 mM Tris-HCl pH 8.0 with the addition of a cocktail of protease inhibitors and DNase I, followed by a 30-minute incubation. The sample was then centrifuged at 18,000 g for 20 minutes. The crude membrane was homogenized by using either a glass Dounce tissue homogenizer or brief sonication in buffer A (20 mM Tris-HCl pH 8.0, 150 mM NaCl) supplemented with 2 mg/mL iodoacetamide, a cocktail of protease inhibitors and DNase I. The sample was incubated for 30 minutes prior to adding 1% lauryl maltose neopentyl glycol (LMNG, Anatrace) and 0.01% cholesteryl hemisuccinate (CHS, Anatrace). After an additional 2-hour incubation, the sample was centrifuged at 18,000 g for 45 minutes. The supernatant was incubated with cobalt resin for 1 hour. The resin was washed with buffer A+0.01% LMNG-0.001% CHS. The GFP-his tag was removed from Mfsd2a by overnight digestion with 3C protease. The sample was further purified by gel filtration (Superose 6, GE Healthcare) in buffer A plus 0.001% (w/v) LMNG-0.00033% (w/v) glyco-diosgenin (GDN, Anatrace)-0.00013% (w/v) CHS. The peak fraction was pooled and concentrated.

Anti-Mfsd2a scFv was generated as extracellular binders for Mfsd2a. ScFv was isolated by phage display from chickens immunized with virus-like particles (Lipoparticles)[32] that contain mouse Mfsd2a. The animal work was approved by Harvard University and followed the relevant ethical regulations. ScFv was recombinantly expressed as a scFv-Fc fusion protein with a human Fc and purified by protein-A chromatography. The scFv fragment was generated by papain cleavage and the scFv fragment was purified by ion-exchange chromatography using a HiTrap™ Q HP anion exchange column (GE Healthcare). Purified mouse Mfsd2a was mixed with the scFv at a 1:1 (w/w) ratio and incubated for 4 hours at 4° C. The complex was further purified by gel filtration (Superose 6™, GE Healthcare) equilibrated in buffer A plus 0.001% (w/v) LMNG-0.00033% (w/v) GDN-0.00013% (w/v) CHS. The peak fraction was concentrated to 4 mg/ml for cryoEM studies.

Electron Microscopy Sample Preparation and Data Collection.

For cryo-EM, 3 µl of the purified complex was applied to glow discharged 300 mesh Quantifoil™ R2/1 holey carbon grids and blotted for 2.0 s at 96% humidity on a Leica EM GP2 before being plunge frozen in liquid ethane cooled by liquid nitrogen. Grids were imaged on a Titan Krios™ operated at 300 kV using a slit width of 20 eV on a GIF-Quantum Energy Filter. Images were collected on a K3 Summit detector (Gatan) in super-resolution counting mode at a magnification of 105,000×, corresponding to a physical pixel size of 0.86 Å. Serial EM33 was used for data collection with a set of customized scripts enabling automated low-dose image acquisition. Data were collected using image shift to collect one image per hole by Multiple Record method (3×3 set of holes/stage movement).

Cryo-EM Data Processing

A total 8,669 movies were collected and subjected to beam-induced motion correction using the program Motion-Cor2™[34]. A dose-weighted sum of all frames from each movie was used for all image processing steps. Contrast transfer function (CTF) parameters were estimated by Gctf[35]. Automated particle picking was first performed using cisTEM 1.0.0 Beta[36] using 500 images; the picked particles were extracted with box size of 232 pixels and subjected to 2D classification in cisTEM™. The good classes, representing projections in different orientations, were selected and imported to Relion3.0-Beta-2[37] as templates for auto picking. All the picked particles were extracted with box size 232 pixels with original pixel size 0.86 Å in Relion and imported to CryoSparc™ (v2.13.2)[38] for further 2D classification. Rounds of 2D classifications yielded 460,956 particle images with clear features. With these particles, an initial 3D model was built by CryoSparc™ ab initio reconstruction without symmetry. The particles along with the initial model, which is imported as 3D template, were transferred back to Relion™ and subjected to 3D classification using k=4 and tau fudge (T) value 4. The two most populated classes with good features for the Mfsd2a region contained 307,951 particles after two rounds of classifications, with T=20 in the second round. The Relion™ Auto-Refine of these particles resulted in a 4.2 Å map without symmetry. To improve the map quality, local 3D classification focused on the Mfsd2a region was performed. The signal of multiple domains—except Mfsd2a—was subtracted from the particles with a mask covering the whole complex. The modified particle set was subjected to further local 3D classification without alignment using a mask around Mfsd2a and k=4, T=40. After classification, the class with the best features of Mfsd2a was selected. The corresponding 90,577 particles were subjected to Bayesian Polishing and per particle CTF refinement, then imported back to CryoSparc for final Refinement. NU-Refinement of CryoSparc yielded an improved map for the whole complex with nominal resolution of 3.7 Å. By applying a mask on the transporter only, the Mfsd2a domain was further refined to 3.5 Å in Relion, local resolution estimated by SAMUEL™[39]. All refinements followed the gold-standard procedure, in which two half-datasets are refined independently. The overall resolutions were estimated based on the gold-standard Fourier shell correlation (FSC)=0.143 criterion. The number of particles in each dataset and other details related to data processing are summarized in FIG. 13.

Model Building and Refinement

The model was built into a 3.5 Å cryo-EM map using the Na+/melibiose symporter MelB (PDB 4M64) as template. Local parts were manually built in Coot™[40]. The models were refined using Phenix real space refine[41] and the geometry of the models was evaluated by Molprobity[42]. All the figures were prepared in PyMol™ (Schrödinger)[43] or UCSF Chimera™[44].

Lysophosphotidylcholine Uptake Assays.

Mfsd2a WT and variants were cloned into pmCherry-N1 vector (ClonTech) with an mCherry fused at the C-terminus. Plasmids were transfected into HEK293S cells (ATCC, CRL-3022) using Lipofectamine™ 3000 (Invitrogen) according to the manufacturer's directions. Cells grown in 12-well plates were maintained in 293 Freestyle™ medium (LifeTechnologies) supplemented with 10% FBS in an incubator at 37° C. and 8% CO2. The medium was replaced 24 hours post-transfection with 293 Freestyle Medium supplemented with 10% FBS and 10 mM sodium butyrate, and cells were incubated for an additional 24 hours. Mfsd2a transport activity was assayed by measuring TopFluor Lyso PC (Avanti) uptake in HEK293S cells. The cells were washed first with serum-free 293 Freestyle Medium and incubated in 293 Freestyle Medium supplemented with 10% FBS, 150 mM NaCl, and 1 µM TopFluor™ Lyso PC at 37° C. for 30 minutes. The cells were washed twice with ice-cold PBS and re-suspended in ice-cold PBS. The cells expressing Mfsd2a WT or variants were gated in the same range based on the mCherry level using the FL-3 channel of a BD Accuri™ C6 flow cytometer. The mean fluorescence of cells corresponding to TopFluor Lyso PC level was quantified using the FL-1 channel. A one-way analysis of variance (ANOVA) test followed by Tukey's post hoc multiple comparison test was used to calculate statistical differences using Minitab™ Statistical Software[45] between wild-type Mfsd2a and mutant transport activities. p-values are indicated in the bar charts.

Conservation Analysis of Mouse Mfsd2a Structure.

A multiple sequence alignment was performed with a cut-off of minimally 50% identity and maximally 90% identity to mouse Mfsd2a using the UniRef database on the ConSurf™ web server[46,47]. The conservation scores were generated and colored using a PyMOL script generated by the ConSurf web server.

System Setup for Molecular Dynamics Simulations

Simulations of Mfsd2a without scFv in a hydrated lipid bilayer were performed under three conditions: (1) simulations with a sodium ion initially placed in the binding pocket at the position proposed on the basis of the cryo-EM density map, with a nonbonded interaction cutoff of 9 Å (10 independent simulations, 1.2 μs each), (2) simulations with a sodium ion initially placed in the binding pocket at the position proposed on the basis of the cryo-EM density map, with a nonbonded interaction cutoff of 12 Å (3 independent simulations, 1.2 μs each), (3) simulations with no sodium ions initially placed in the binding pocket, with a nonbonded interaction cutoff of 9 Å (5 independent simulations, 1.1 μs each). No substantial differences in simulation behavior were observed between the first two conditions. For all simulation conditions, the protein structure was aligned on the Orientations of Proteins in Membranes[48] entry for 6S7V[49] (MFS superfamily member LtaA) using PyMOL™ (Schrödinger)[43]. Prime™ (Schrödinger)[50] was used to model missing side chains, and to add capping groups to protein chain termini. Protonation states of all titratable residues were assigned at pH 7. Histidine residues were modeled as neutral, with a hydrogen atom bound to either the delta or epsilon nitrogen depending on which tautomeric state optimized the local hydrogen-bonding network. Dowser[51] was used to add water molecules to protein cavities. Using Dabble™[52], the prepared protein structures were inserted into a pre-equilibrated palmitoyl-oleoyl-phosphatidylcholine (POPC) bilayer, the system was solvated, and sodium and chloride ions were added to neutralize the system and to obtain a final concentration of 150 mM. Final systems comprised approximately 90,000 atoms and system dimensions were approximately 120×120×100 Å. For each simulation, initial atom velocities were assigned randomly and independently.

Molecular Dynamics Simulation and Analysis Protocols

The CHARMM36m force field was used for proteins, the CHARMM36 force field for lipids and ions, and the TIP3P model for water[53-55]. All simulations were performed using the Compute Unified Device Architecture (CUDA) version of particle-mesh Ewald molecular dynamics (PMEMD) in AMBER18[56] on graphics processing units (GPUs).

Systems were first minimized using three rounds of minimization, each consisting of 500 cycles of steepest descent followed by 500 cycles of conjugate gradient optimization. 10.0 and 5.0 kcal·mol$^{-1}$·Å$^{-2}$ harmonic restraints were applied to protein and lipids for the first and second rounds of minimization, respectively. 1 kcal·mol$^{-1}$·Å$^{-2}$ harmonic restraints were applied to protein for the third round of minimization. Systems were then heated from 0 K to 100 K in the NVT ensemble over 12.5 ps and then from 100 K to 310 K in the NPT ensemble over 125 ps, using 10.0 kcal·mol$^{-1}$·Å$^{-2}$ harmonic restraints applied to protein heavy atoms. Subsequently, systems were equilibrated at 310 K and 1 bar in the NPT ensemble, with harmonic restraints on the protein non-hydrogen atoms tapered off by 1.0 kcal·mol$^{-1}$·Å$^{-2}$ starting at 5.0 kcal·mol$^{-1}$·Å$^{-2}$ in a stepwise fashion every 2 ns for 10 ns, and then by 0.1 kcal·mol$^{-1}$·Å$^{-2}$ every 2 ns for 20 ns. Production simulations were performed without restraints at 310 K and 1 bar in the NPT ensemble using the Monte Carlo barostat, the Langevin thermostat with a collision frequency of 1.0 ps$^{-1}$, and a timestep of 4.0 fs with hydrogen mass repartitioning[57]. Bond lengths to hydrogen were constrained using the SHAKE algorithm[58]. Non-bonded interactions were cut off at either 9.0 or 12.0 Å (see "System setup for molecular dynamics simulations" section), and long-range electrostatic interactions were calculated using the particle-mesh Ewald (PME) method with an Ewald coefficient of approximately 0.31 Å, and 4th order B-splines. The PME grid size was chosen such that the width of a grid cell was approximately 1 Å. Trajectory frames were saved every 200 ps during the production simulations.

Figure 11C:
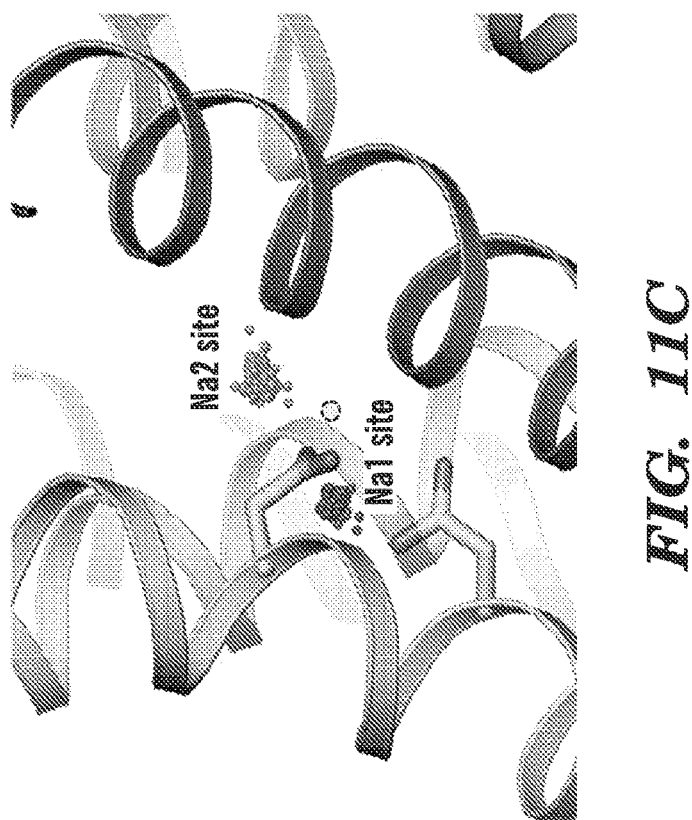
Figure 11E:
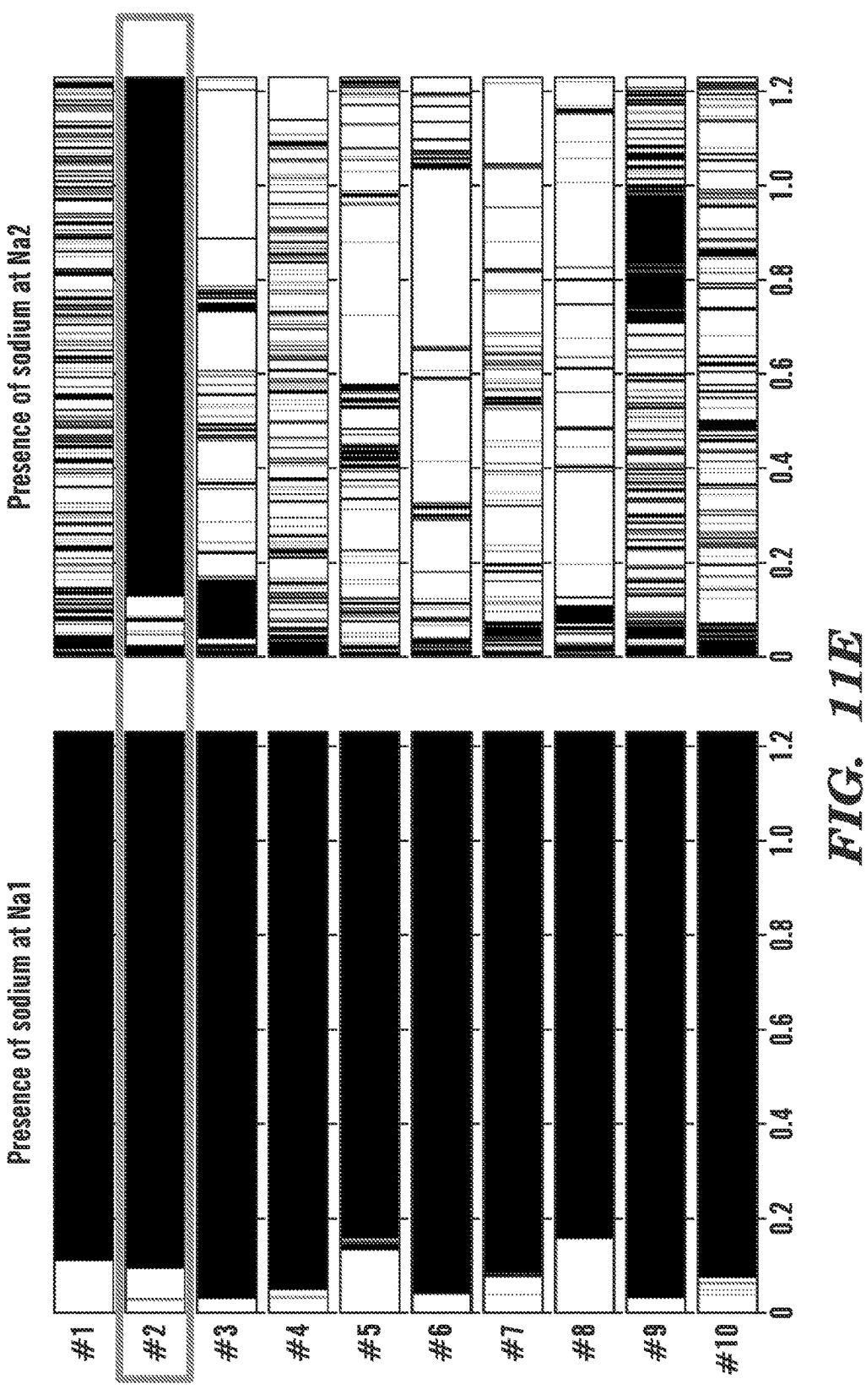
Figure 11E:
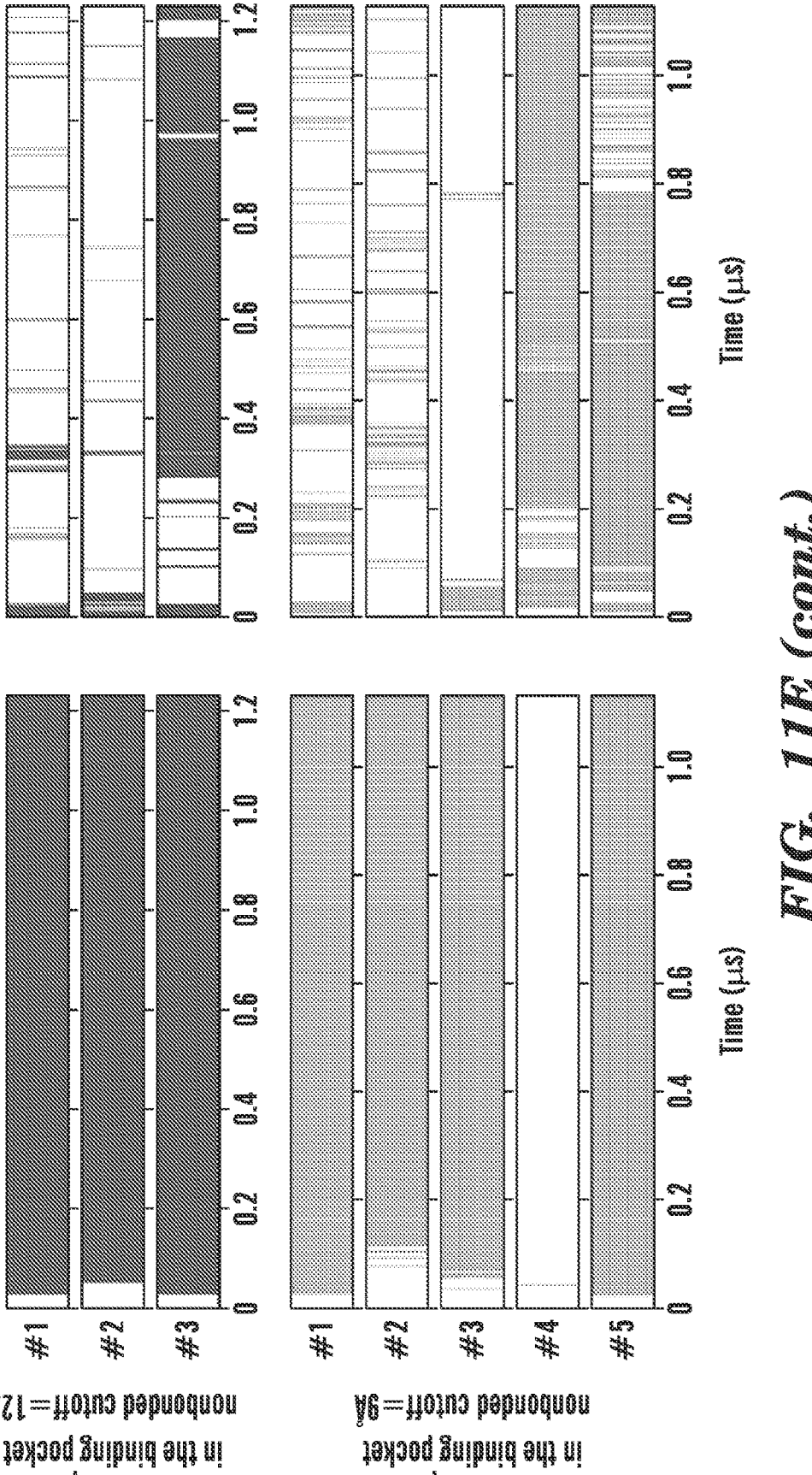

The AmberTools17 CPPTRAJ package was used to reimage trajectories[59]. Simulations were visualized and analyzed using Visual Molecular Dynamics (VMD)[60] and PyMOL (Schrödinger)[43]. In FIG. 4C, the first 0.1 μs of the production phase of each simulation of condition (1) was discarded (as well as the equilibration phase), and trajectories were aligned on the backbone atoms of the Mfsd2a cryo-EM structure Na$^+$-binding site residues D92, T95, D96, E159, T163, and K440. The positions of Na$^+$ ions were recorded every 10 ns for each of the 10 simulations. Each Na$^+$ ion position was then drawn as a point superimposed on the starting Mfsd2a structure. A sodium ion at a distance of 2-5 Å from the T95 side chain oxygen forming a salt bridge with D92 and/or D96 was considered to be present at the Na1 site. A sodium ion at a distance of 5-8 Å from the T95 side chain oxygen forming a salt bridge with D92 and/or E159 was considered to be present at the Na2 site. A salt bridge was considered to be formed if the sodium ion was within 3.5 Å of either side chain oxygen atoms of an aspartate or glutamate residue. In FIG. 11C, the same analysis was repeated taking into consideration only simulation #2 of condition (1), where both sodium ions were bound simultaneously. In FIG. 11E, the equilibration and the production phases are both plotted for each simulation. The same criteria as explained above for FIG. 11C are used to identify sodium ions present at the Na1 and Na2 sites.

Data Availability

The cryoEM map has been deposited into the Electron Microscopy Data Bank (accession number EMD-24252). The coordinates have been deposited into the Protein Data Bank (accession number 7N98).

REFERENCES

31 Goehring, A. et al. Screening and large-scale expression of membrane proteins in mammalian cells for structural studies. Nat. Protoc. 9, 2574-2585 (2014).

32 Tucker, D. F. et al. Isolation of state-dependent monoclonal antibodies against the 12-transmembrane domain glucose transporter 4 using virus-like particles. Proc. Natl. Acad. Sci. USA 115, E4990-E4999 (2018).

33 Mastronarde, D. N. Automated electron microscope tomography using robust prediction of specimen movements. J. Struct. Biol. 152, 36-51 (2005).

34 Zheng, S. Q. et al. MotionCor2: anisotropic correction of beam-induced motion for improved cryo-electron microscopy. Nat. Methods 14, 331-332 (2017).

35 Zhang, K. Gctf: Real-time CTF determination and correction. *J. Struct. Biol.* 193, 1-12 (2016).
36 Grant, T., Rohou, A. & Grigorieff, N. cisTEM, user-friendly software for single-particle image processing. *Elife* 7 (2018).
37 Scheres, S. H. A Bayesian view on cryo-EM structure determination. *J. Mol. Biol.* 415, 406-418 (2012).
38 Punjani, A., Rubinstein, J. L., Fleet, D. J. & Brubaker, M. A. cryoSPARC: algorithms for rapid unsupervised cryo-EM structure determination. *Nat. Methods* 14, 290-296 (2017).
39 Ru, H. et al. Molecular Mechanism of V(D)J Recombination from Synaptic RAG1-RAG2 Complex Structures. *Cell* 163, 1138-1152 (2015).
40 Emsley, P., Lohkamp, B., Scott, W. G. & Cowtan, K. Features and development of Coot. *Acta Crystallogr. D Biol. Crystallogr.* 66, 486-501 (2010).
41 Adams, P. D. et al. PHENIX: a comprehensive Python-based system for macromolecular structure solution. *Acta Crystallogr. D Biol. Crystallogr.* 66, 213-221 (2010).
42 Chen, V. B. et al. MolProbity: all-atom structure validation for macromolecular crystallography. *Acta Crystallogr. D Biol. Crystallogr.* 66, 12-21 (2010).
43 The PyMOL Molecular Graphics System v.2.0. (Schrödinger, 2017).
44 Pettersen, E. F. et al. UCSF Chimera—a visualization system for exploratory research and analysis. *J. Comput. Chem.* 25, 1605-1612 (2004).
45 Minitab 17 Statistical Software (Minitab, Inc. 2010).
46 Ashkenazy, H. et al. ConSurf 2016: an improved methodology to estimate and visualize evolutionary conservation in macromolecules. *Nucleic Acids Res.* 44, W344-350 (2016).
47 Landau, M. et al. ConSurf 2005: the projection of evolutionary conservation scores of residues on protein structures. *Nucleic Acids Res.* 33, W299-302 (2005).
48 Lomize, M. A., Lomize, A. L., Pogozheva, I. D. & Mosberg, H. I. OPM: orientations of proteins in membranes database. *Bioinformatics* 22, 623-625 (2006).
49 Zhang, B. et al. Structure of a proton-dependent lipid transporter involved in lipoteichoic acids biosynthesis. *Nat. Struct. Mol. Biol.* 27, 561-569 (2020).
50 Jacobson, M. P., Friesner, R. A., Xiang, Z. & Honig, B. On the role of the crystal environment in determining protein side-chain conformations. *J. Mol. Biol.* 320, 597-608 (2002).
51 Zhang, L. & Hermans, J. Hydrophilicity of cavities in proteins. *Proteins* 24, 433-438 (1996).
52 Betz, R. Dabble (v2.6.3). Zenodo (2017).
53 Huang, J. et al. CHARMM36m: an improved force field for folded and intrinsically disordered proteins. *Nat. Methods* 14, 71-73 (2017).
54 Klauda, J. B. et al. Update of the CHARMM all-atom additive force field for lipids: validation on six lipid types. *J. Phys. Chem. B* 114, 7830-7843 (2010).
55 Guvench, O., Hatcher, E., Venable, R. M., Pastor, R. W. & MacKerell, A. D. CHARMM Additive All-Atom Force Field for Glycosidic Linkages between Hexopyranoses. *J. Chem. Theory Comput.* 5, 2353-2370 (2009).
56 AMBER 2018 (University of California, San Francisco).
57 Hopkins, C. W., Le Grand, S., Walker, R. C. & Roitberg, A. E. Long-Time-Step Molecular Dynamics through Hydrogen Mass Repartitioning. *J. Chem. Theory Comput.* 11, 1864-1874 (2015).
58 Ryckaert, J., Ciccotti, G., Berendsen, H. J. Numerical integration of the cartesian equations of motion of a system with constraints: molecular dynamics of n-alkanes. *J. Comput. Phys.* 23, 327-341 (1977).
59 Roe, D. R. & Cheatham, T. E., 3rd. PTRAJ and CPPTRAJ: Software for Processing and Analysis of Molecular Dynamics Trajectory Data. *J. Chem. Theory Comput.* 9, 3084-3095 (2013).
60 Humphrey, W., Dalke, A. & Schulten, K. VMD: Visual molecular dynamics. *J. Mol. Graph. Model.* 14, 33-38 (1996).
61 Vilas, J. L. et al. MonoRes: Automatic and Accurate Estimation of Local Resolution for Electron Microscopy Maps. *Structure* 26, 337-344 e334 (2018).

Example 5

Figure 15:
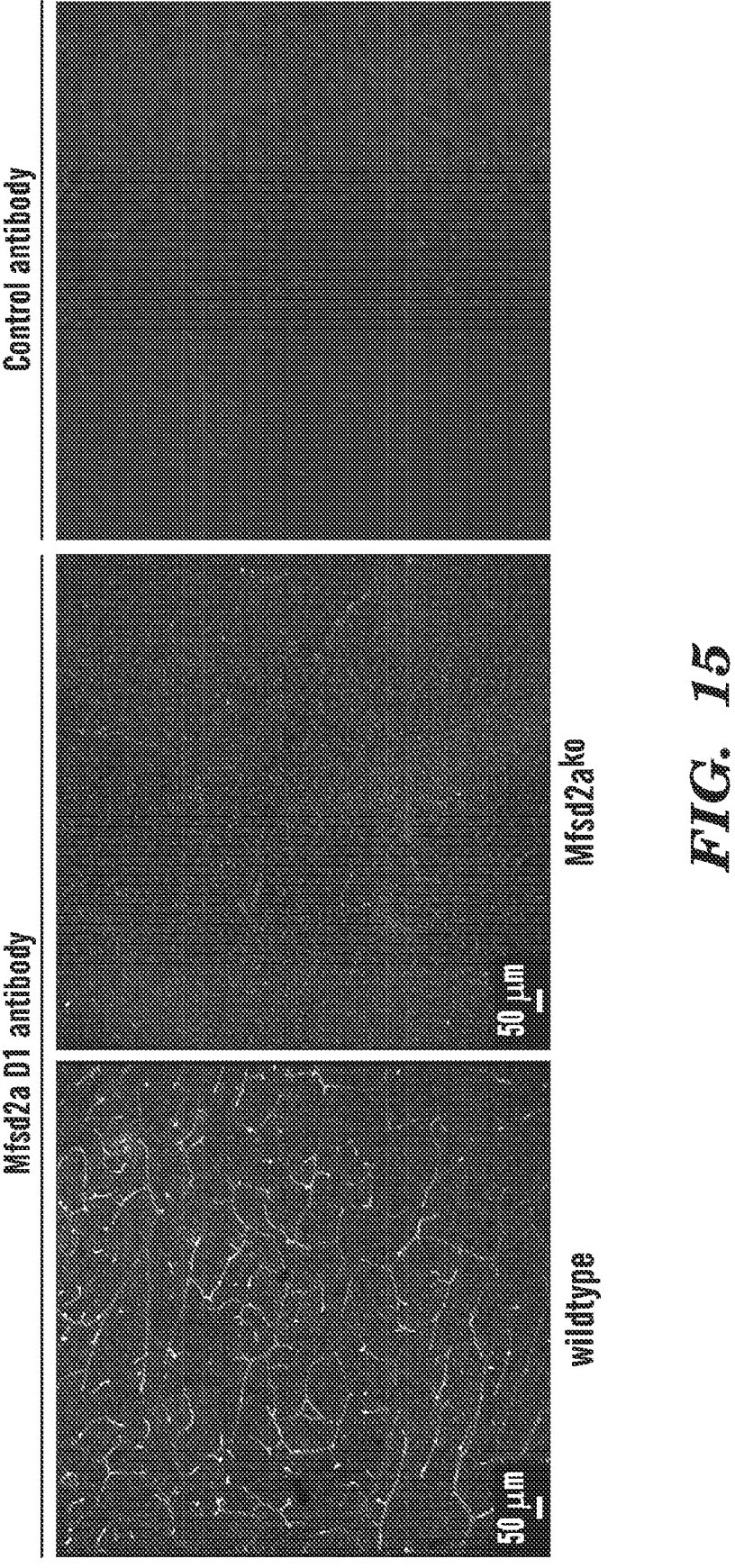
FIG. 15 depicts images of D1 antibody binding to the indicated cells.
Figure 16A:
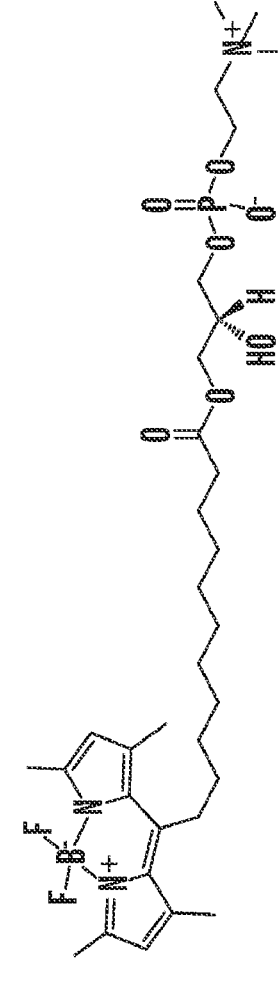
FIGS. 16A-16D demonstrate the effect of D1 antibody in cell-based Mfsd2a lipid transport assay.
Figure 16B:
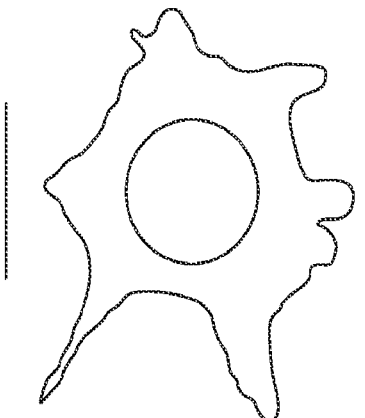
Figure 16B:
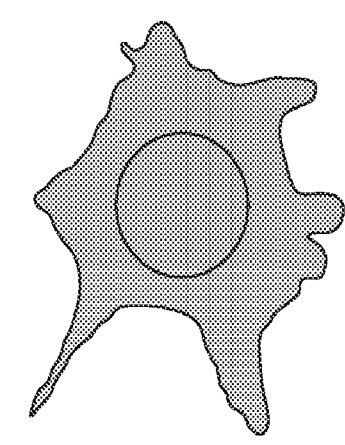
Figure 16C:
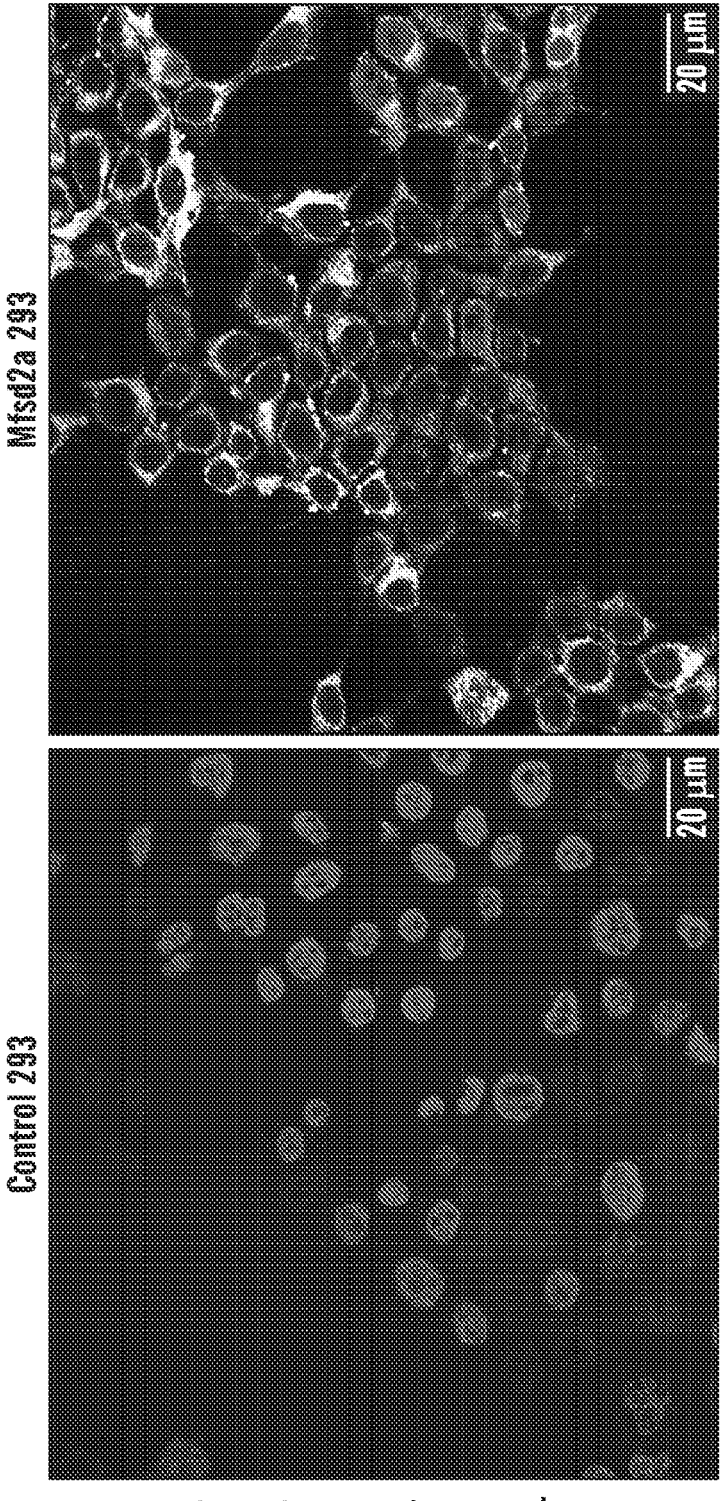
Figure 16D:
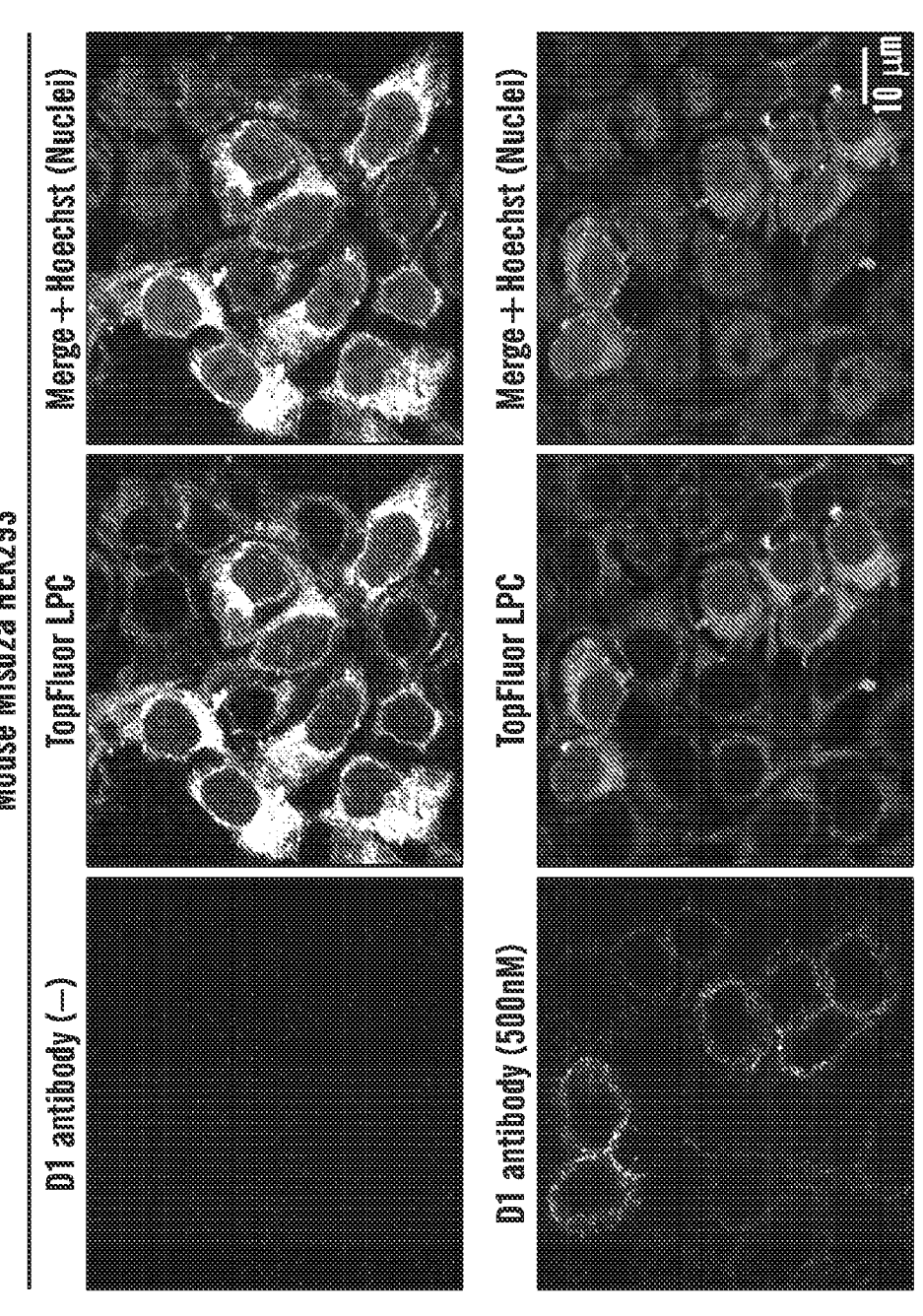

The specificity of the antibody described herein (D1, with CDRs of SEQ ID NOs: 1-6) was tested. IV-injection of D1 antibody or control antibody was IV injected at 10 ug/ml to adult mice. The antibodies were permitted to circulate for 15 minutes, followed by 10 ml PBS perfusion and fixation. Brains were sectioned and stained with fluorescent labeled secondary antibody. FIG. 15 demonstrate the specificity of the D1 antibody in vivo. It specifically binds to the endogenous Mfsd2a that is expressed on the luminal side of the brain endothelial cell plasma membrane in the wildtype mice, absence in the Mfsd2a knockout mice. Control antibody injected animals show no staining.

FIG. 16A-16D demonstrate that the D1 antibody is an inhibitor of Mfsd2A lipid transport, utilizing a fluorescent Mfsd2A substrate.

What is claimed herein is:

1. An antibody, antibody reagent, antigen-binding fragment thereof, or chimeric antigen receptor (CAR), that specifically binds a Mfsd2A polypeptide, said antibody reagent, antigen-binding portion thereof, or CAR comprising:
   (a) a heavy chain complementarity determining region (CDR) 1 having the amino acid sequence of SEQ ID NO: 4;
   (b) a heavy chain CDR2 having the amino acid sequence of SEQ ID NO: 5;
   (c) a heavy chain CDR3 having the amino acid sequence of SEQ ID NO: 6;
   (d) a light chain CDR1 having the amino acid sequence of SEQ ID NO: 1;
   (e) a light chain CDR2 having the amino acid sequence of SEQ ID NO: 2; and
   (f) a light chain CDR3 having the amino acid sequence of SEQ ID NO: 3.

2. The antibody, antibody reagent, antigen-binding portion thereof, or CAR of claim 1, which comprises a heavy chain variable domain comprising SEQ ID NO: 12 or a light chain variable domain comprising SEQ ID NO: 11.

3. The antibody, antibody reagent, antigen-binding portion thereof, or CAR of claim 1, which comprises the heavy chain variable domain comprising SEQ ID NO: 12 and the light chain variable domain comprising SEQ ID NO: 11.

4. The antibody, antibody reagent, antigen-binding portion thereof, or CAR of claim 1, comprising the sequence of SEQ ID NO: 7.

5. The antibody, antibody reagent, antigen-binding portion thereof, or CAR of claim 4, further comprising a conservative substitution in a sequence not comprised by a CDR.

6. The antibody, antibody reagent, antigen-binding portion thereof, or CAR of claim 1, wherein the antibody reagent or antigen-binding fragment thereof is fully humanized.

7. The antibody, antibody reagent, antigen-binding portion thereof, or CAR of claim 1, wherein the antibody reagent or antigen-binding fragment thereof is fully humanized except for the CDR sequences.

8. The antibody, antibody reagent, antigen-binding portion thereof, or CAR of claim 1, wherein the antibody reagent or antigen-binding fragment is selected from the group consisting of:

an immunoglobulin molecule, a monoclonal antibody, a chimeric antibody, a CDR-grafted antibody, a humanized antibody, a Fab, a Fab', a F(ab')2, a Fv, a disulfide linked Fv, a scFv, a single domain antibody, a diabody, a multispecific antibody, a dual specific antibody, and a bispecific antibody.

9. A composition, kit, or combination comprising:
(i) the antibody, antibody reagent, antigen-binding portion thereof, or CAR of claim 1; and
(ii) a central nervous system therapeutic agent.

10. The composition, kit, or combination of claim 9, wherein the antibody, antibody reagent, or antigen-binding portion thereof is conjugated to the central nervous system therapeutic agent.

11. A nucleic acid sequence encoding the antibody, antibody reagent, antigen-binding fragment thereof, or CAR of claim 1.

12. A cell comprising the antibody, antibody reagent, antigen-binding fragment thereof, or CAR of claim 1.

13. A pharmaceutical composition comprising the antibody, antibody reagent, antigen-binding fragment thereof, or CAR of claim 1 and a pharmaceutically acceptable carrier.

14. A method of increasing blood-brain barrier (BBB) permeability in a subject, the method comprising administering to the subject:

the antibody, antibody reagent, antigen-binding portion thereof, or CAR of claim 1.

* * * * *

SEQUENCE LISTING

<160> NUMBER OF SEQ ID NOS: 26

<210> SEQ ID NO 1
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 1

Ser Gly Ala Arg Tyr Gly Tyr Gly
1               5

<210> SEQ ID NO 2
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 2

Ala Asn Asn Ile Arg Pro Ser
1               5

<210> SEQ ID NO 3
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 3

Gly Asn Glu Asp Ser Ile Thr Tyr Ala Ala
1               5                   10

<210> SEQ ID NO 4
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 4

Gly Phe Thr Phe Ser Ser Tyr Asp Met Ala
1               5                   10

<210> SEQ ID NO 5
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 5

Ala Gly Ile Thr Ser Thr Gly Ser Tyr Thr Asn Tyr Gly Ala Ala Val
1               5                   10                  15

Lys Gly

<210> SEQ ID NO 6
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 6

Ser Ser Phe Gly Cys Pro Tyr Ser Cys Trp Tyr Asp Ile Ala Gly Ser
1               5                   10                  15

Ile Asp Ala

<210> SEQ ID NO 7
<211> LENGTH: 245
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 7

Gln Pro Ser Ser Val Ser Ala Asn Pro Gly Glu Thr Val Lys Ile Thr
1               5                   10                  15

Cys Ser Gly Ala Arg Tyr Gly Tyr Gly Trp Tyr Gln Gln Lys Ser Pro
            20                  25                  30

Gly Ser Ala Leu Val Thr Leu Ile Tyr Ala Asn Asn Ile Arg Pro Ser
        35                  40                  45

Ala Ile Pro Ser Arg Phe Ser Gly Ser Lys Ser Gly Ser Thr Ala Thr
    50                  55                  60

Leu Thr Ile Thr Gly Val Arg Ala Glu Asp Glu Ala Val Tyr Tyr Cys
65                  70                  75                  80

Gly Asn Glu Asp Ser Ile Thr Tyr Ala Ala Phe Gly Ala Gly Thr Thr
                85                  90                  95

Leu Thr Val Leu Gly Gly Ser Ser Arg Ser Ser Gly Gly Gly Gly Ser
            100                 105                 110

Ser Gly Gly Gly Gly Ser Ala Val Thr Leu Asp Glu Ser Gly Gly Gly
            115                 120                 125

Leu Gln Thr Pro Lys Gly Gly Leu Ser Leu Val Cys Lys Ala Ser Gly
    130                 135                 140

Phe Thr Phe Ser Ser Tyr Asp Met Ala Trp Val Arg Gln Ala Pro Gly
145                 150                 155                 160

Lys Gly Leu Glu Trp Val Ala Gly Ile Thr Ser Thr Gly Ser Tyr Thr
                165                 170                 175

Asn Tyr Gly Ala Ala Val Lys Gly Arg Ala Thr Ile Ser Arg Asp Asn
                180                 185                 190

Gly Gln Ser Thr Val Arg Leu Gln Leu Asn Ser Leu Arg Ala Glu Asp
            195                 200                 205

Thr Ala Thr Tyr Phe Cys Ala Lys Ser Ser Phe Gly Cys Pro Tyr Ser
    210                 215                 220

Cys Trp Tyr Asp Ile Ala Gly Ser Ile Asp Ala Trp Gly His Gly Thr
225                 230                 235                 240

Glu Val Ile Val Ser
                245

<210> SEQ ID NO 8

<400> SEQUENCE: 8

000

<210> SEQ ID NO 9
<211> LENGTH: 543
<212> TYPE: PRT
<213> ORGANISM: Homo sapiens

<400> SEQUENCE: 9

Met Ala Lys Gly Glu Gly Ala Glu Ser Gly Ser Ala Ala Gly Leu Leu
1               5                   10                  15

Pro Thr Ser Ile Leu Gln Ser Thr Glu Arg Pro Ala Gln Val Lys Lys

-continued

```
              20                    25                    30
Glu Pro Lys Lys Lys Lys Gln Gln Leu Ser Val Cys Asn Lys Leu Cys
        35                    40                    45

Tyr Ala Leu Gly Gly Ala Pro Tyr Gln Val Thr Gly Cys Ala Leu Gly
        50                    55                    60

Phe Phe Leu Gln Ile Tyr Leu Leu Asp Val Ala Gln Lys Asp Glu Glu
65                    70                    75                    80

Val Val Phe Cys Phe Ser Ser Phe Gln Val Gly Pro Phe Ser Ala Ser
                85                    90                    95

Ile Ile Leu Phe Val Gly Arg Ala Trp Asp Ala Ile Thr Asp Pro Leu
            100                   105                   110

Val Gly Leu Cys Ile Ser Lys Ser Pro Trp Thr Cys Leu Gly Arg Leu
            115                   120                   125

Met Pro Trp Ile Ile Phe Ser Thr Pro Leu Ala Val Ile Ala Tyr Phe
            130                   135                   140

Leu Ile Trp Phe Val Pro Asp Phe Pro His Gly Gln Thr Tyr Trp Tyr
145                   150                   155                   160

Leu Leu Phe Tyr Cys Leu Phe Glu Thr Met Val Thr Cys Phe His Val
                165                   170                   175

Pro Tyr Ser Ala Leu Thr Met Phe Ile Ser Thr Glu Gln Thr Glu Arg
            180                   185                   190

Asp Ser Ala Thr Ala Tyr Arg Met Thr Val Glu Val Leu Gly Thr Val
            195                   200                   205

Leu Gly Thr Ala Ile Gln Gly Gln Ile Val Gly Gln Ala Asp Thr Pro
            210                   215                   220

Cys Phe Gln Asp Leu Asn Ser Ser Thr Val Ala Ser Gln Ser Ala Asn
225                   230                   235                   240

His Thr His Gly Thr Thr Ser His Arg Glu Thr Gln Lys Ala Tyr Leu
                245                   250                   255

Leu Ala Ala Gly Val Ile Val Cys Ile Tyr Ile Ile Cys Ala Val Ile
            260                   265                   270

Leu Ile Leu Gly Val Arg Glu Gln Arg Glu Pro Tyr Glu Ala Gln Gln
            275                   280                   285

Ser Glu Pro Ile Ala Tyr Phe Arg Gly Leu Arg Leu Val Met Ser His
            290                   295                   300

Gly Pro Tyr Ile Lys Leu Ile Thr Gly Phe Leu Phe Thr Ser Leu Ala
305                   310                   315                   320

Phe Met Leu Val Glu Gly Asn Phe Val Leu Phe Cys Thr Tyr Thr Leu
                325                   330                   335

Gly Phe Arg Asn Glu Phe Gln Asn Leu Leu Leu Ala Ile Met Leu Ser
            340                   345                   350

Ala Thr Leu Thr Ile Pro Ile Trp Gln Trp Phe Leu Thr Arg Phe Gly
            355                   360                   365

Lys Lys Thr Ala Val Tyr Val Gly Ile Ser Ser Ala Val Pro Phe Leu
            370                   375                   380

Ile Leu Val Ala Leu Met Glu Ser Asn Leu Ile Ile Thr Tyr Ala Val
385                   390                   395                   400

Ala Val Ala Ala Gly Ile Ser Val Ala Ala Ala Phe Leu Leu Pro Trp
                405                   410                   415

Ser Met Leu Pro Asp Val Ile Asp Asp Phe His Leu Lys Gln Pro His
            420                   425                   430

Phe His Gly Thr Glu Pro Ile Phe Phe Ser Phe Tyr Val Phe Phe Thr
            435                   440                   445
```

```
Lys Phe Ala Ser Gly Val Ser Leu Gly Ile Ser Thr Leu Ser Leu Asp
    450                 455                 460

Phe Ala Gly Tyr Gln Thr Arg Gly Cys Ser Gln Pro Glu Arg Val Lys
465                 470                 475                 480

Phe Thr Leu Asn Met Leu Val Thr Met Ala Pro Ile Val Leu Ile Leu
                485                 490                 495

Leu Gly Leu Leu Leu Phe Lys Met Tyr Pro Ile Asp Glu Glu Arg Arg
                500                 505                 510

Arg Gln Asn Lys Lys Ala Leu Gln Ala Leu Arg Asp Glu Ala Ser Ser
            515                 520                 525

Ser Gly Cys Ser Glu Thr Asp Ser Thr Glu Leu Ala Ser Ile Leu
        530                 535                 540
```

<210> SEQ ID NO 10
<211> LENGTH: 2236
<212> TYPE: DNA
<213> ORGANISM: Homo sapiens

<400> SEQUENCE: 10

```
agaactataa gaggcgcgga gggggcgtgc agcagagtgc gttcctcgtc tgccagccgg      60
cttggctagc gcgcggcggc cgtggctaag gctgctacga agcgagcttg ggaggagcag     120
cggcctgcgg ggcagaggag catcccgtct accaggtccc aagcggcgtg gcccgcgggt     180
catggccaaa ggagaaggcg ccgagagcgg ctccgcggcg gggctgctac ccaccagcat     240
cctccaaagc actgaacgcc cggcccaggt gaagaaagaa ccgaaaaaga agaaacaaca     300
gttgtctgtt tgcaacaagc tttgctatgc acttggggga gcccctacc aggtgacggg     360 ctgtgccctg ggtttcttcc ttcagatcta cctattggat gtggctcaga aggatgagga     420
agttgtcttt tgcttctcct cattccaggt gggcccttc tctgcctcca tcatcctgtt     480
tgtgggccga gcctgggatg ccatcacaga cccctggtg ggcctctgca tcagcaaatc     540
cccctggacc tgcctgggtc gccttatgcc ctggatcatc ttctccacgc ccctggccgt     600
cattgcctac ttcctcatct ggttcgtgcc cgacttccca cacggccaga cctattggta     660 cctgctttc tattgcctct ttgaaacaat ggtcacgtgt ttccatgttc cctactcggc     720
tctcaccatg ttcatcagca ccgagcagac tgagcgggat tctgccaccg cctatcggat     780
gactgtggaa gtgctgggca cagtgctggg cacggcgatc cagggacaaa tcgtgggcca     840
agcagacacg ccttgtttcc aggacctcaa tagctctaca gtagcttcac aaagtgccaa     900
ccatacacat ggcaccacct cacacaggga aacgcaaaag gcatacctgc tggcagcggg     960
ggtcattgtc tgtatctata taatctgtgc tgtcatcctg atcctgggcg tgcgggagca    1020
gagagaaccc tatgaagccc agcagtctga gccaatcgcc tacttccggg gcctacggct    1080
ggtcatgagc cacggcccat acatcaaact tattactggc ttcctcttca cctccttggc    1140
tttcatgctg gtggagggga actttgtctt gttttgcacc tacaccttgg gcttccgcaa    1200
tgaattccag aatctactcc tggccatcat gctctcggcc actttaacca ttcccatctg    1260
gcagtggttc ttgacccggt ttggcaagaa gacagctgta tatgttggga tctcatcagc    1320
agtgccattt ctcatcttgg tggccctcat ggagagtaac ctcatcatta catatgcggt    1380
agctgtggca gctggcatca gtgtggcagc tgccttctta ctaccctggt ccatgctgcc    1440
tgatgtcatt gacgacttcc atctgaagca gccccacttc catggaaccg agcccatctt    1500
cttctccttc tatgtcttct tcaccaagtt tgcctctgga gtgtcactgg gcatttctac    1560
```

-continued

```
cctcagtctg acttttgcag ggtaccagac ccgtggctgc tcgcagccgg aacgtgtcaa    1620
gtttacactg aacatgctcg tgaccatggc tcccatagtt ctcatcctgc tgggcctgct    1680
gctcttcaaa atgtacccca ttgatgagga gaggcggcgg cagaataaga aggccctgca    1740
ggcactgagg gacgaggcca gcagctctgg ctgctcagaa acagactcca cagagctggc    1800
tagcatcctc tagggcccgc cacgttgccc gaagccacca tgcagaaggc cacagaaggg    1860
atcaggacct gtctgccggc ttgctgagca gctggactgc aggtgctagg aagggaactg    1920
aagactcaag gaggtggccc aggacacttg ctgtgctcac tgtggggccg gctgctctgt    1980
ggcctcctgc ctcccctctg cctgcctgtg gggccaagcc ctggggctgc cactgtgaat    2040
atgccaagga ctgatcgggc ctagcccgga acactaatgt agaaaccttt tttttttacag    2100 agcctaatta ataacttaat gactgtgtac atagcaatgt gtgtgtatgt atatgtctgt    2160
gagctattaa tgttattaat tttcataaaa gctggaaagc aaaaaaaaaa aaaaaaaaaa    2220
aaaaaaaaaa aaaaaa                                                    2236
```

```
<210> SEQ ID NO 11
<211> LENGTH: 103
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 11

Ala Leu Thr Gln Pro Ser Ser Val Ser Ala Asn Pro Gly Glu Thr Val
1               5                   10                  15

Lys Ile Thr Cys Ser Gly Ala Arg Tyr Gly Tyr Gly Trp Tyr Gln Gln
            20                  25                  30

Lys Ser Pro Gly Ser Ala Leu Val Thr Leu Ile Tyr Ala Asn Asn Ile
        35                  40                  45

Arg Pro Ser Ala Ile Pro Ser Arg Phe Ser Gly Ser Lys Ser Gly Ser
    50                  55                  60

Thr Ala Thr Leu Thr Ile Thr Gly Val Arg Ala Glu Asp Glu Ala Val
65                  70                  75                  80

Tyr Tyr Cys Gly Asn Glu Asp Ser Ile Thr Tyr Ala Ala Phe Gly Ala
                85                  90                  95

Gly Thr Thr Leu Thr Val Leu
            100
```

```
<210> SEQ ID NO 12
<211> LENGTH: 128
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 12

Ala Val Thr Leu Asp Glu Ser Gly Gly Gly Leu Gln Thr Pro Lys Gly
1               5                   10                  15

Gly Leu Ser Leu Val Cys Lys Ala Ser Gly Phe Thr Phe Ser Ser Tyr
            20                  25                  30

Asp Met Ala Trp Val Arg Gln Ala Pro Gly Lys Gly Leu Glu Trp Val
        35                  40                  45

Ala Gly Ile Thr Ser Thr Gly Ser Tyr Thr Asn Tyr Gly Ala Ala Val
```

-continued

```
        50                  55                  60

Lys Gly Arg Ala Thr Ile Ser Arg Asp Asn Gly Gln Ser Thr Val Arg
65                  70                  75                  80

Leu Gln Leu Asn Ser Leu Arg Ala Glu Asp Thr Ala Thr Tyr Phe Cys
                85                  90                  95

Ala Lys Ser Ser Phe Gly Cys Pro Tyr Ser Cys Trp Tyr Asp Ile Ala
                100                 105                 110

Gly Ser Ile Asp Ala Trp Gly His Gly Thr Glu Val Ile Val Ser Ser
        115                 120                 125

<210> SEQ ID NO 13
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 13

Gly Gly Gly Gly Ser
1               5

<210> SEQ ID NO 14
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic 6xHis tag"

<400> SEQUENCE: 14

His His His His His His
1               5

<210> SEQ ID NO 15
<211> LENGTH: 534
<212> TYPE: PRT
<213> ORGANISM: Mus musculus

<400> SEQUENCE: 15

Met Ala Lys Gly Glu Gly Ala Glu Ser Gly Ser Ala Ala Gly Leu Leu
1               5                   10                  15

Pro Thr Ser Ile Leu Gln Ala Ser Glu Arg Pro Val Gln Val Lys Lys
                20                  25                  30

Glu Pro Lys Lys Lys Gln Gln Leu Ser Ile Cys Asn Lys Leu Cys Tyr
                35                  40                  45

Ala Val Gly Gly Ala Pro Tyr Gln Leu Thr Gly Cys Ala Leu Gly Phe
        50                  55                  60

Phe Leu Gln Ile Tyr Leu Leu Asp Val Ala Lys Val Glu Pro Leu Pro
65                  70                  75                  80

Ala Ser Ile Ile Leu Phe Val Gly Arg Ala Trp Asp Ala Phe Thr Asp
                85                  90                  95

Pro Leu Val Gly Phe Cys Ile Ser Lys Ser Ser Trp Thr Arg Leu Gly
                100                 105                 110

Arg Leu Met Pro Trp Ile Ile Phe Ser Thr Pro Leu Ala Ile Ile Ala
        115                 120                 125

Tyr Phe Leu Ile Trp Phe Val Pro Asp Phe Pro Ser Gly Thr Glu Ser
        130                 135                 140
```

-continued

```
Ser His Gly Phe Leu Trp Tyr Leu Leu Phe Tyr Cys Leu Phe Glu Thr
145                 150                 155                 160

Leu Val Thr Cys Phe His Val Pro Tyr Ser Ala Leu Thr Met Phe Ile
                165                 170                 175

Ser Thr Glu Gln Ser Glu Arg Asp Ser Ala Thr Ala Tyr Arg Met Thr
                180                 185                 190

Val Glu Val Leu Gly Thr Val Ile Gly Thr Ala Ile Gln Gly Gln Ile
                195                 200                 205

Val Gly Gln Ala Lys Ala Pro Cys Leu Gln Asp Gln Asn Gly Ser Val
        210                 215                 220

Val Val Ser Glu Val Ala Asn Arg Thr Gln Ser Thr Ala Ser Leu Lys
225                 230                 235                 240

Asp Thr Gln Asn Ala Tyr Leu Leu Ala Ala Gly Ile Ile Ala Ser Ile
                245                 250                 255

Tyr Val Leu Cys Ala Phe Ile Leu Ile Leu Gly Val Arg Glu Gln Arg
                260                 265                 270

Glu Leu Tyr Glu Ser Gln Gln Ala Glu Ser Met Pro Phe Phe Gln Gly
                275                 280                 285

Leu Arg Leu Val Met Gly His Gly Pro Tyr Val Lys Leu Ile Ala Gly
        290                 295                 300

Phe Leu Phe Thr Ser Leu Ala Phe Met Leu Val Glu Gly Asn Phe Ala
305                 310                 315                 320

Leu Phe Cys Thr Tyr Thr Leu Asp Phe Arg Asn Glu Phe Gln Asn Leu
                325                 330                 335

Leu Leu Ala Ile Met Leu Ser Ala Thr Phe Thr Ile Pro Ile Trp Gln
                340                 345                 350

Trp Phe Leu Thr Arg Phe Gly Lys Lys Thr Ala Val Tyr Ile Gly Ile
                355                 360                 365

Ser Ser Ala Val Pro Phe Leu Ile Leu Val Ala Leu Met Glu Arg Asn
        370                 375                 380

Leu Ile Val Thr Tyr Val Val Ala Val Ala Ala Gly Val Ser Val Ala
385                 390                 395                 400

Ala Ala Phe Leu Leu Pro Trp Ser Met Leu Pro Asp Val Ile Asp Asp
                405                 410                 415

Phe His Leu Lys His Pro His Ser Pro Gly Thr Glu Pro Ile Phe Phe
                420                 425                 430

Ser Phe Tyr Val Phe Phe Thr Lys Phe Ala Ser Gly Val Ser Leu Gly
                435                 440                 445

Val Ser Thr Leu Ser Leu Asp Phe Ala Asn Tyr Gln Arg Gln Gly Cys
        450                 455                 460

Ser Gln Pro Glu Gln Val Lys Phe Thr Leu Lys Met Leu Val Thr Met
465                 470                 475                 480

Ala Pro Ile Ile Leu Ile Leu Leu Gly Leu Leu Leu Phe Lys Leu Tyr
                485                 490                 495

Pro Ile Asp Glu Glu Lys Arg Arg Gln Asn Lys Lys Ala Leu Gln Ala
                500                 505                 510

Leu Arg Glu Glu Ala Ser Ser Ser Gly Cys Ser Asp Thr Asp Ser Thr
                515                 520                 525

Glu Leu Ala Ser Ile Leu
        530
```

<210> SEQ ID NO 16
<211> LENGTH: 530
<212> TYPE: PRT

<213> ORGANISM: Homo sapiens

<400> SEQUENCE: 16

```
Met Ala Lys Gly Glu Gly Ala Glu Ser Gly Ser Ala Ala Gly Leu Leu
1               5                   10                  15

Pro Thr Ser Ile Leu Gln Ser Thr Glu Arg Pro Ala Gln Val Lys Lys
            20                  25                  30

Glu Pro Lys Lys Lys Lys Gln Gln Leu Ser Val Cys Asn Lys Leu Cys
        35                  40                  45

Tyr Ala Leu Gly Gly Ala Pro Tyr Gln Val Thr Gly Cys Ala Leu Gly
    50                  55                  60

Phe Phe Leu Gln Ile Tyr Leu Leu Asp Val Ala Gln Val Gly Pro Phe
65                  70                  75                  80

Ser Ala Ser Ile Ile Leu Phe Val Gly Arg Ala Trp Asp Ala Ile Thr
                85                  90                  95

Asp Pro Leu Val Gly Leu Cys Ile Ser Lys Ser Pro Trp Thr Cys Leu
            100                 105                 110

Gly Arg Leu Met Pro Trp Ile Ile Phe Ser Thr Pro Leu Ala Val Ile
        115                 120                 125

Ala Tyr Phe Leu Ile Trp Phe Val Pro Asp Phe Pro His Gly Gln Thr
    130                 135                 140

Tyr Trp Tyr Leu Leu Phe Tyr Cys Leu Phe Glu Thr Met Val Thr Cys
145                 150                 155                 160

Phe His Val Pro Tyr Ser Ala Leu Thr Met Phe Ile Ser Thr Glu Gln
                165                 170                 175

Thr Glu Arg Asp Ser Ala Thr Ala Tyr Arg Met Thr Val Glu Val Leu
            180                 185                 190

Gly Thr Val Leu Gly Thr Ala Ile Gln Gly Gln Ile Val Gly Gln Ala
        195                 200                 205

Asp Thr Pro Cys Phe Gln Asp Leu Asn Ser Ser Thr Val Ala Ser Gln
    210                 215                 220

Ser Ala Asn His Thr His Gly Thr Thr Ser His Arg Glu Thr Gln Lys
225                 230                 235                 240

Ala Tyr Leu Leu Ala Ala Gly Val Ile Val Cys Ile Tyr Ile Ile Cys
                245                 250                 255

Ala Val Ile Leu Ile Leu Gly Val Arg Glu Gln Arg Glu Pro Tyr Glu
            260                 265                 270

Ala Gln Gln Ser Glu Pro Ile Ala Tyr Phe Arg Gly Leu Arg Leu Val
        275                 280                 285

Met Ser His Gly Pro Tyr Ile Lys Leu Ile Thr Gly Phe Leu Phe Thr
    290                 295                 300

Ser Leu Ala Phe Met Leu Val Glu Gly Asn Phe Val Leu Phe Cys Thr
305                 310                 315                 320

Tyr Thr Leu Gly Phe Arg Asn Glu Phe Gln Asn Leu Leu Leu Ala Ile
                325                 330                 335

Met Leu Ser Ala Thr Leu Thr Ile Pro Ile Trp Gln Trp Phe Leu Thr
            340                 345                 350

Arg Phe Gly Lys Lys Thr Ala Val Tyr Val Gly Ile Ser Ser Ala Val
        355                 360                 365

Pro Phe Leu Ile Leu Val Ala Leu Met Glu Ser Asn Leu Ile Ile Thr
    370                 375                 380

Tyr Ala Val Ala Val Ala Ala Gly Ile Ser Val Ala Ala Ala Phe Leu
385                 390                 395                 400
```

Leu Pro Trp Ser Met Leu Pro Asp Val Ile Asp Asp Phe His Leu Lys
            405             410             415

Gln Pro His Phe His Gly Thr Glu Pro Ile Phe Phe Ser Phe Tyr Val
            420             425             430

Phe Phe Thr Lys Phe Ala Ser Gly Val Ser Leu Gly Ile Ser Thr Leu
            435             440             445

Ser Leu Asp Phe Ala Gly Tyr Gln Thr Arg Gly Cys Ser Gln Pro Glu
    450             455             460

Arg Val Lys Phe Thr Leu Asn Met Leu Val Thr Met Ala Pro Ile Val
465             470             475             480

Leu Ile Leu Leu Gly Leu Leu Leu Phe Lys Met Tyr Pro Ile Asp Glu
            485             490             495

Glu Arg Arg Arg Gln Asn Lys Lys Ala Leu Gln Ala Leu Arg Asp Glu
            500             505             510

Ala Ser Ser Ser Gly Cys Ser Glu Thr Asp Ser Thr Glu Leu Ala Ser
            515             520             525

Ile Leu
    530

<210> SEQ ID NO 17
<211> LENGTH: 532
<212> TYPE: PRT
<213> ORGANISM: Danio rerio

<400> SEQUENCE: 17

Met Ala Arg Gly Glu Gly Ala Glu Gln Phe Ser Ser Gly Leu Leu Pro
1               5               10              15

Thr Ala Lys Ser Val Thr Gln Asn Glu Ile Lys Met Val Lys Leu Pro
            20              25              30

Lys Gln Gln Glu Arg Lys Arg Ala Leu Thr Val Trp Ser Lys Val Cys
            35              40              45

Phe Ala Ile Gly Gly Ala Pro Tyr Gln Ile Thr Gly Thr Ala Leu Gly
    50              55              60

Phe Phe Leu Gln Ile Phe Leu Leu Asp Val Ala Gln Leu Asn Pro Leu
65              70              75              80

Asn Ala Ser Val Ile Leu Phe Val Gly Arg Ala Trp Asp Ala Val Thr
            85              90              95

Asp Pro Thr Val Gly Phe Leu Val Ser Arg Thr Pro Trp Thr Arg His
            100             105             110

Gly Arg Met Met Pro Trp Ile Leu Val Ser Thr Ile Pro Ala Val Leu
            115             120             125

Cys Tyr Phe Leu Ile Trp Val Val Pro Pro Ile Glu Gln Gly Lys Met
    130             135             140

Met Trp Tyr Leu Leu Phe Tyr Cys Leu Phe Gln Thr Leu Gln Thr Cys
145             150             155             160

Phe His Val Pro Tyr Ser Ala Leu Thr Met Phe Ile Ser Thr Glu Gln
            165             170             175

Arg Glu Arg Asp Ser Ala Thr Ala Tyr Arg Met Thr Val Glu Val Phe
            180             185             190

Gly Thr Val Val Gly Thr Ala Ile Gln Gly Gln Ile Val Gly Met Ala
            195             200             205

Asn Thr Pro Cys Lys Asn Asn Thr Ser Pro Asn Asn Ser Ser Asn Asp
    210             215             220

Leu Ile Gln Ser Asn Asn Ser His Ile Pro Leu Lys Ser Asn Ile Phe
225             230             235             240

```
Asp Glu Arg Cys Ala Tyr Met Ile Ala Ser Ala Val Ile Ser Leu Ile
            245                 250                 255

Tyr Val Val Cys Ala Ala Val Leu Phe Phe Gly Val Arg Glu Gln Asp
            260                 265                 270

Val Gln Gly Glu Leu Lys Ala Gln Lys Arg Val Ser Phe Gln Lys Gly
            275                 280                 285

Leu Arg Leu Val Met Gly His Gly Pro Tyr Val Lys Leu Val Leu Ala
            290                 295                 300

Phe Leu Phe Thr Ser Leu Ala Phe Met Leu Leu Glu Gly Asn Phe Ala
305                 310                 315                 320

Val Phe Ile Lys Tyr Thr Leu Gly Phe Arg Glu Asp Phe Gln Asn Ile
                    325                 330                 335

Leu Leu Val Ile Met Val Ser Ala Thr Val Ser Ile Pro Met Trp Gln
                    340                 345                 350

Trp Phe Leu Cys Arg Phe Gly Lys Lys Thr Ala Val Tyr Ile Gly Ile
                    355                 360                 365

Thr Trp Ala Val Pro Phe Met Ile Leu Val Val Ser Val Asn Ser Ser
            370                 375                 380

Leu Ile Val Ser Tyr Ile Val Ser Ile Ala Ala Gly Val Ser Val Gly
385                 390                 395                 400

Ala Ala Phe Leu Leu Pro Trp Ser Met Leu Pro Asp Val Val Asp Asp
                    405                 410                 415

Phe Lys Leu Gln Asn Pro Thr Ser Gln Gly His Glu Ala Ile Phe Tyr
                    420                 425                 430

Ser Phe Tyr Val Phe Phe Thr Lys Phe Ala Ser Gly Val Ser Leu Gly
            435                 440                 445

Val Ser Thr Leu Ala Leu Ser Phe Ala Gly Tyr Glu Thr Gly Val Cys
            450                 455                 460

Val Gln Ser Asp Ser Val Asn Leu Thr Leu Lys Leu Leu Val Ser Ala
465                 470                 475                 480

Ala Pro Val Ser Leu Ile Ala Leu Gly Leu Leu Ile Phe Met Thr Tyr
                    485                 490                 495

Pro Ile Asp Glu Glu Arg Arg Glu Tyr Asn Asn Lys Gln Leu Gln Leu
            500                 505                 510

Leu Leu Arg Asn Glu Glu Glu Glu Asp Glu Met Glu Val Leu Lys Pro
            515                 520                 525

Asp Ile Thr Ala
    530
```

```
<210> SEQ ID NO 18
<211> LENGTH: 524
<212> TYPE: PRT
<213> ORGANISM: Xenopus laevis

<400> SEQUENCE: 18
```

```
Met Glu Lys Glu Arg Glu Asn Thr Ser Cys Ala Gly Leu Leu Gly Gln
1                   5                   10                  15

Lys Lys Glu Pro Asp Ser Pro Thr Lys Ser Arg Ser Gly Lys His Lys
            20                  25                  30

Leu Ser Val Cys Ser Lys Ile Cys Phe Ala Ile Gly Gly Ala Pro Tyr
            35                  40                  45

Gln Ile Thr Gly Cys Ala Leu Gly Phe Phe Leu Gln Ile Phe Leu Leu
    50                  55                  60

Asp Ile Ala Gln Val Pro Pro Phe Tyr Ala Ser Ile Ile Leu Phe Thr
```

-continued

```
65                    70                   75                   80

Gly Arg Val Trp Asp Ala Ile Thr Asp Pro Leu Val Gly Tyr Phe Val
                85                    90                   95

Ser Lys Ser Ser Trp Thr Arg Leu Gly Arg Leu Met Pro Trp Val Val
                100                   105                  110

Ile Ser Thr Pro Phe Ala Val Val Ser Tyr Ile Leu Ile Trp Phe Val
                115                   120                  125

Pro Gly Phe Ser Gly Ile Ser Met Val Leu Trp Tyr Leu Val Phe Tyr
        130                   135                  140

Cys Leu Phe Gln Thr Leu Val Thr Cys Phe His Val Pro Tyr Ser Ala
145                   150                  155                  160

Leu Thr Met Phe Ile Ser Lys Glu Gln Ser Asp Arg Asp Ser Ala Thr
                165                   170                  175

Gly Tyr Arg Met Thr Val Glu Val Leu Gly Thr Val Leu Gly Thr Ala
                180                   185                  190

Ile Gln Gly Gln Ile Val Gly Arg Gln Asn Thr Pro Cys Val Glu His
        195                   200                  205

Ile Trp Glu Ala Leu Ser Asn Thr Thr Val Thr Met Glu Asp Leu Asn
        210                   215                  220

Ile Thr His Asp Val Glu Ser Leu Ser Ser Thr Arg Asp Ala Tyr Met
225                   230                  235                  240

Ile Ala Ala Gly Val Ile Cys Ala Leu Tyr Val Leu Cys Ala Ile Ile
                245                   250                  255

Leu Thr Leu Gly Val Arg Glu Lys Arg Asp Ala Tyr Glu Leu Leu Ser
                260                   265                  270

Asp Gln Pro Phe Ser Phe Trp Gln Gly Leu Lys Leu Val Met Gly His
        275                   280                  285

Lys Pro Tyr Ile Lys Leu Ile Thr Gly Phe Leu Phe Thr Ser Leu Ala
        290                   295                  300

Phe Met Leu Ile Glu Gly Asn Phe Ala Leu Phe Leu Thr Tyr Thr Met
305                   310                  315                  320

Gly Phe Arg Arg Asp Phe Gln Asn Ile Leu Leu Val Ile Met Leu Ser
                325                   330                  335

Ala Thr Leu Thr Val Pro Phe Trp Gln Trp Phe Leu Thr Arg Phe Gly
                340                   345                  350

Lys Lys Thr Ala Val Tyr Phe Gly Ile Ser Ser Val Ile Pro Phe Leu
                355                   360                  365

Ile Leu Ile Val Leu Met Lys Ser Asn Leu Ile Leu Ala Tyr Ile Val
        370                   375                  380

Ala Val Ala Ala Gly Leu Ser Val Ala Ala Ala Phe Leu Leu Pro Trp
385                   390                  395                  400

Ser Met Leu Pro Asp Val Ile Asp Asp Phe Ile Leu Lys Asn Pro Asp
                405                   410                  415

Ser His Gly His Glu Pro Ile Phe Phe Ser Phe Tyr Val Phe Phe Thr
                420                   425                  430

Lys Phe Ala Ser Gly Val Ser Leu Gly Ile Ser Thr Leu Ser Leu Asp
        435                   440                  445

Phe Ala Gly Tyr Gln Thr Arg Ala Cys Ser Gln Pro Glu Gln Val Asn
        450                   455                  460

Val Thr Leu Lys Met Leu Val Cys Ala Ala Pro Val Ile Leu Ile Leu
465                   470                  475                  480

Leu Gly Leu Leu Leu Phe Ile Leu Tyr Pro Ile Asn Glu Glu Lys Arg
                485                   490                  495
```

-continued

```
Lys Glu Asn Lys Lys Ala Leu Gln Leu Leu Arg Glu Ser Asn Arg Asp
            500                 505                 510

Ser Asp Ser Asp Ser Phe Glu Leu Ala Ser Asn Val
        515                 520

<210> SEQ ID NO 19
<211> LENGTH: 524
<212> TYPE: PRT
<213> ORGANISM: Bos taurus

<400> SEQUENCE: 19

Met Ala Lys Gly Glu Gly Ala Glu Ser Gly Ser Ala Ala Gly Leu Leu
1               5                   10                  15

Pro Thr Gly Ile Leu Gln Ala Gly Glu Arg Pro Val Gln Val Lys Lys
            20                  25                  30

Glu Pro Lys Lys Lys Lys Gln Leu Ser Ile Cys Asn Lys Leu Cys Tyr
        35                  40                  45

Ala Val Gly Gly Ala Pro Tyr Gln Val Thr Gly Cys Ala Leu Gly Phe
        50                  55                  60

Phe Leu Gln Ile Tyr Leu Leu Asp Val Ala Gln Val Asp Pro Phe Ser
65                  70                  75                  80

Ala Ser Ile Ile Leu Phe Val Gly Arg Ala Trp Asp Ala Ile Thr Asp
            85                  90                  95

Pro Leu Val Gly Phe Cys Ile Ser Lys Ser Pro Trp Thr Arg Leu Gly
            100                 105                 110

Arg Leu Met Pro Trp Ile Thr Phe Ser Thr Pro Leu Ala Ile Ile Ala
            115                 120                 125

Tyr Phe Leu Ile Trp Phe Val Pro Asp Phe His Gln Gly Gln Thr Leu
        130                 135                 140

Trp Tyr Leu Leu Phe Tyr Cys Leu Phe Glu Thr Leu Val Thr Cys Phe
145                 150                 155                 160

His Val Pro Tyr Ser Ala Leu Thr Met Phe Ile Ser Thr Glu Gln Ser
            165                 170                 175

Glu Arg Asp Ser Ala Thr Ala Tyr Arg Met Thr Val Glu Val Leu Gly
            180                 185                 190

Thr Val Leu Gly Thr Ala Ile Gln Gly Gln Ile Val Gly Gln Ala Asp
            195                 200                 205

Ser Pro Cys Ile Pro Asp Ala Asn Ala Ser Thr Val Asn Arg Thr Gln
        210                 215                 220

Ser Ser Thr Ser Ile Lys Glu Thr Gln Asn Ala Tyr Leu Leu Ala Ala
225                 230                 235                 240

Gly Val Ile Ala Ser Ile Tyr Val Ile Cys Ala Val Ile Leu Ile Leu
            245                 250                 255

Gly Val Arg Glu Gln Arg Glu Ser Tyr Glu Thr Gln Gln Thr Lys Gln
            260                 265                 270

Met Pro Phe Phe Arg Gly Leu Arg Leu Val Met Ser His Gly Pro Tyr
        275                 280                 285

Ile Lys Leu Ile Ala Gly Phe Leu Phe Thr Ser Leu Ala Phe Met Leu
        290                 295                 300

Val Glu Gly Asn Phe Ala Leu Phe Cys Thr Tyr Thr Leu Gly Phe Arg
305                 310                 315                 320

Asn Glu Phe Gln Asn Leu Leu Leu Ala Ile Met Phe Ser Ala Thr Val
            325                 330                 335

Thr Ile Pro Ile Trp Gln Trp Phe Leu Thr Arg Phe Gly Lys Lys Thr
```

-continued

```
                340               345               350
Ala Val Tyr Ile Gly Ile Ser Ser Ala Val Pro Phe Leu Ile Leu Val
        355               360               365
Ala Leu Met Glu Ser Asn Leu Ile Val Thr Tyr Val Val Ala Val Ala
    370               375               380
Ala Gly Ile Ser Val Ala Ala Ala Phe Leu Leu Pro Trp Ser Met Leu
385               390               395               400
Pro Asp Val Ile Asp Asp Phe His Leu Lys Gln Pro His Ile His Gly
            405               410               415
Thr Glu Pro Ile Phe Phe Ser Phe Tyr Val Phe Phe Thr Lys Phe Ala
            420               425               430
Ser Gly Val Ser Leu Gly Ile Ser Thr Leu Ser Leu Asp Phe Thr Gly
            435               440               445
Tyr Gln Thr Arg Gly Cys Ser Gln Pro Ala Arg Val Lys Phe Thr Leu
        450               455               460
Lys Met Leu Val Thr Met Ala Pro Ile Val Leu Ile Leu Ile Gly Leu
465               470               475               480
Leu Leu Phe Lys Leu Tyr Pro Ile Asp Glu Glu Lys Arg Arg Gln Asn
            485               490               495
Lys Lys Ala Leu Gln Ala Leu Arg Glu Glu Ala Ser Ser Ser Gly Cys
            500               505               510
Ser Asp Thr Asp Ser Thr Glu Leu Ala Ser Ile Leu
            515               520
```

```
<210> SEQ ID NO 20
<211> LENGTH: 528
<212> TYPE: PRT
<213> ORGANISM: Gallus gallus

<400> SEQUENCE: 20
```

```
Met Ala Gly Gly Gly Gly Ala Glu Arg Val Arg Val Gly Ala Ala Ala
1               5                10               15
Ala Gly Leu Leu Pro Pro Ser Cys Arg Gln Pro Arg Arg Arg Glu Ser
            20               25               30
Arg Glu Arg Leu Ser Val Cys Ser Lys Leu Cys Tyr Ala Val Gly Gly
        35               40               45
Ala Pro Tyr Gln Thr Thr Gly Cys Ala Leu Gly Phe Phe Leu Gln Ile
    50               55               60
Tyr Leu Leu Asp Val Ala Gln Leu Asp Pro Phe Tyr Ala Ser Ile Ile
65               70               75               80
Leu Phe Val Gly Arg Ala Trp Asp Ala Ile Thr Asp Pro Met Val Gly
            85               90               95
Phe Phe Ile Ser Lys Thr Pro Trp Thr Arg Phe Gly Arg Leu Met Pro
            100              105              110
Trp Ile Ile Phe Ser Thr Pro Phe Ala Val Ile Ser Tyr Phe Leu Ile
            115              120              125
Trp Phe Val Pro Asp Ile Ser Thr Gly Gln Val Met Trp Tyr Leu Ile
            130              135              140
Phe Tyr Cys Ile Phe Gln Thr Leu Val Thr Cys Phe His Val Pro Tyr
145              150              155              160
Ser Ala Leu Thr Met Phe Ile Ser Arg Glu Gln Ser Glu Arg Asp Ser
            165              170              175
Ala Thr Ala Tyr Arg Met Thr Val Glu Val Leu Gly Thr Val Leu Gly
            180              185              190
```

Thr Ala Ile Gln Gly Gln Ile Val Gly Lys Ala Val Thr Pro Cys Ile
        195                 200                 205

Glu Asn Pro Pro Phe Leu Ser Glu Thr Asn Phe Ser Val Ala Ile Arg
    210                 215                 220

Asn Val Asn Met Thr His Tyr Thr Gly Ser Leu Ala Asp Thr Arg Asn
225                 230                 235                 240

Ala Tyr Met Val Ala Ala Gly Val Ile Gly Gly Leu Tyr Ile Leu Cys
                245                 250                 255

Ala Val Ile Leu Ser Val Gly Val Arg Glu Lys Arg Glu Ser Ser Glu
                260                 265                 270

Leu Gln Ser Asp Glu Pro Val Ser Phe Phe Arg Gly Leu Lys Leu Val
        275                 280                 285

Met Asn His Gly Ala Tyr Ile Lys Leu Ile Thr Gly Phe Leu Phe Thr
    290                 295                 300

Ser Leu Ala Phe Met Leu Leu Glu Gly Asn Phe Ala Leu Phe Cys Thr
305                 310                 315                 320

Tyr Thr Leu Gly Phe Arg Asn Glu Phe Gln Asn Ile Leu Leu Ala Ile
                325                 330                 335

Met Leu Ser Ala Thr Leu Thr Ile Pro Phe Trp Gln Trp Phe Leu Thr
                340                 345                 350

Arg Phe Gly Lys Lys Thr Ala Val Tyr Val Gly Ile Ser Ser Ala Val
        355                 360                 365

Pro Phe Leu Ile Thr Val Val Val Leu Asp Ser Asn Leu Val Val Thr
    370                 375                 380

Tyr Ile Val Ala Val Ala Ala Gly Ile Ser Val Ala Ala Ala Phe Leu
385                 390                 395                 400

Leu Pro Trp Ser Met Leu Pro Asp Val Ile Asp Asp Phe Lys Leu Gln
                405                 410                 415

His Pro Glu Ser Arg Gly His Glu Ala Ile Phe Phe Ser Phe Tyr Val
                420                 425                 430

Phe Phe Thr Lys Phe Thr Ser Gly Val Ser Leu Gly Ile Ser Thr Leu
        435                 440                 445

Ser Leu Asp Phe Ala Gly Tyr Gln Thr Arg Gly Cys Ser Gln Pro Ser
    450                 455                 460

Glu Val Asn Ile Thr Leu Lys Leu Leu Val Ser Ala Val Pro Val Gly
465                 470                 475                 480

Leu Ile Leu Leu Gly Leu Leu Leu Phe Lys Leu Tyr Pro Ile Asp Glu
                485                 490                 495

Glu Lys Arg Arg Glu Asn Lys Lys Ala Leu Gln Asp Leu Arg Glu Glu
        500                 505                 510

Ser Asn Ser Ser Ser Glu Ser Asp Ser Thr Glu Leu Ala Asn Ile Val
        515                 520                 525

<210> SEQ ID NO 21
<211> LENGTH: 494
<212> TYPE: PRT
<213> ORGANISM: Mus musculus

<400> SEQUENCE: 21

Met Ser Val Pro His Gly Pro Thr Pro Ala Pro Val Ala Glu Pro His
1                   5                   10                  15

Thr Gln Glu Pro Gly Ser Asp Lys Arg Asp Gly Arg Leu Ser Val Cys
                20                  25                  30

Thr Lys Val Cys Tyr Gly Ile Gly Gly Val Pro Asn Gln Val Ala Ser
        35                  40                  45

-continued

```
Ser Ala Ser Ala Phe Tyr Leu Gln Leu Phe Leu Leu Asp Val Ala Gln
    50              55              60

Ile Pro Ala Ala Gln Val Ser Leu Ala Leu Phe Gly Gly Lys Val Ser
65              70              75              80

Gly Ala Val Ala Asp Pro Val Ala Gly Phe Phe Ile Asn Lys Ser Arg
                85              90              95

Arg Thr Gly Ser Gly Arg Leu Met Pro Trp Ala Leu Gly Cys Met Pro
            100             105             110

Leu Ile Ala Leu Ala Tyr Phe Phe Leu Trp Phe Leu Pro Pro Phe Thr
            115             120             125

Ser Leu Arg Gly Leu Trp Tyr Thr Ser Phe Tyr Cys Leu Phe Gln Ala
    130             135             140

Leu Ala Thr Phe Phe Gln Val Pro Tyr Thr Ala Leu Thr Met Ile Leu
145             150             155             160

Thr Pro Ser Pro Arg Glu Arg Asp Ser Ala Thr Ala Tyr Arg Met Thr
                165             170             175

Met Glu Met Ala Gly Thr Leu Met Gly Ala Thr Val His Gly Leu Ile
            180             185             190

Val Ser Ser Ala His Gly Ser Gln Arg Cys Glu Asp Thr Val His Pro
    195             200             205

Arg Ser Pro Ala Val Ser Pro Asp Val Ala Arg Leu Tyr Cys Ile Ala
    210             215             220

Ala Ala Val Val Ala Leu Thr Tyr Pro Val Cys Gly Ser Leu Leu Cys
225             230             235             240

Leu Gly Val Lys Glu Gln Pro Asp Thr Ser Ala Pro Ala Ser Gly Gln
            245             250             255

Gly Leu Asn Phe Phe Thr Gly Leu Ala Ile Thr Ser Gln His Pro Pro
            260             265             270

Tyr Leu Ser Leu Val Val Ser Phe Leu Phe Ile Ser Ala Ala Val Gln
    275             280             285

Val Glu Gln Ser Tyr Leu Val Leu Phe Cys Thr His Ala Ser Lys Leu
    290             295             300

Gln Asp His Val Gln Asn Leu Val Leu Ile Ile Leu Val Ser Ala Val
305             310             315             320

Leu Ser Thr Pro Leu Trp Glu Trp Val Leu Gln Arg Phe Gly Lys Lys
            325             330             335

Thr Ser Ala Phe Gly Ile Cys Val Met Val Pro Phe Ser Ile Leu Leu
            340             345             350

Ala Ala Val Pro Ser Ala Pro Val Ala Tyr Val Val Ala Phe Val Ser
            355             360             365

Gly Val Ser Ile Ala Val Ser Leu Leu Leu Pro Trp Ser Met Leu Pro
    370             375             380

Asp Val Val Asp Asp Phe Gln Leu Gln His Arg Cys Gly Pro Gly Val
385             390             395             400

Glu Thr Ile Phe Tyr Ser Ser Tyr Val Phe Phe Thr Lys Leu Ser Gly
                405             410             415

Ala Gly Ala Leu Gly Ile Ser Thr Leu Ser Leu Glu Phe Ala Gly Cys
            420             425             430

Glu Ala Gly Ala Cys Gln Gln Ala Glu Glu Val Val Val Thr Leu Lys
            435             440             445

Val Leu Ile Gly Ala Val Pro Thr Cys Met Ile Leu Ile Gly Leu Cys
    450             455             460
```

-continued

```
Ile Leu Leu Val Gly Pro Thr Pro Lys Met Pro Arg Gln Asp Thr Ser
465             470             475             480

Ser Gln Leu Ser Leu Arg Arg Arg Thr Ser Tyr Ser Leu Ala
                485             490

<210> SEQ ID NO 22
<211> LENGTH: 504
<212> TYPE: PRT
<213> ORGANISM: Homo sapiens

<400> SEQUENCE: 22

Met Ala Ala Pro Pro Ala Pro Ala Ala Lys Gly Ser Pro Gln Pro Glu
1               5               10              15

Pro His Ala Pro Glu Pro Gly Pro Gly Ser Ala Lys Arg Gly Arg Glu
                20              25              30

Asp Ser Arg Ala Gly Arg Leu Ser Phe Cys Thr Lys Val Cys Tyr Gly
        35              40              45

Ile Gly Gly Val Pro Asn Gln Ile Ala Ser Ser Ala Thr Ala Phe Tyr
    50              55              60

Leu Gln Leu Phe Leu Leu Asp Ile Ala Gln Ile Pro Ala Ala Gln Val
65              70              75              80

Ser Leu Val Leu Phe Gly Gly Lys Val Ser Gly Ala Ala Ala Asp Pro
                85              90              95

Val Ala Gly Phe Phe Ile Asn Arg Ser Gln Arg Thr Gly Ser Gly Arg
                100             105             110

Leu Met Pro Trp Val Leu Gly Cys Thr Pro Phe Ile Ala Leu Ala Tyr
                115             120             125

Phe Phe Leu Trp Phe Leu Pro Pro Phe Thr Ser Leu Arg Gly Leu Trp
    130             135             140

Tyr Thr Thr Phe Tyr Cys Leu Phe Gln Ala Leu Ala Thr Phe Phe Gln
145             150             155             160

Val Pro Tyr Thr Ala Leu Thr Met Leu Leu Thr Pro Cys Pro Arg Glu
                165             170             175

Arg Asp Ser Ala Thr Ala Tyr Arg Met Thr Val Glu Met Ala Gly Thr
                180             185             190

Leu Met Gly Ala Thr Val His Gly Leu Ile Val Ser Gly Ala His Arg
                195             200             205

Pro His Arg Cys Glu Ala Thr Ala Thr Pro Gly Pro Val Thr Val Ser
        210             215             220

Pro Asn Ala Ala His Leu Tyr Cys Ile Ala Ala Ala Val Val Val Val
225             230             235             240

Thr Tyr Pro Val Cys Ile Ser Leu Leu Cys Leu Gly Val Lys Glu Arg
                245             250             255

Pro Asp Pro Ser Ala Pro Ala Ser Gly Pro Gly Leu Ser Phe Leu Ala
                260             265             270

Gly Leu Ser Leu Thr Thr Arg His Pro Pro Tyr Leu Lys Leu Val Ile
        275             280             285

Ser Phe Leu Phe Ile Ser Ala Ala Val Gln Val Glu Gln Ser Tyr Leu
    290             295             300

Val Leu Phe Cys Thr His Ala Ser Gln Leu His Asp His Val Gln Gly
305             310             315             320

Leu Val Leu Thr Val Leu Val Ser Ala Val Leu Ser Thr Pro Leu Trp
                325             330             335

Glu Trp Val Leu Gln Arg Phe Gly Lys Lys Thr Ser Ala Phe Gly Ile
        340             345             350
```

-continued

```
Phe Ala Met Val Pro Phe Ala Ile Leu Leu Ala Ala Val Pro Thr Ala
        355                 360                 365

Pro Val Ala Tyr Val Val Ala Phe Val Ser Gly Val Ser Ile Ala Val
    370                 375                 380

Ser Leu Leu Leu Pro Trp Ser Met Leu Pro Asp Val Val Asp Asp Phe
385                 390                 395                 400

Gln Leu Gln His Arg His Gly Pro Gly Leu Glu Thr Ile Phe Tyr Ser
            405                 410                 415

Ser Tyr Val Phe Phe Thr Lys Leu Ser Gly Ala Cys Ala Leu Gly Ile
            420                 425                 430

Ser Thr Leu Ser Leu Glu Phe Ser Gly Tyr Lys Ala Gly Val Cys Lys
            435                 440                 445

Gln Ala Glu Glu Val Val Val Thr Leu Lys Val Leu Ile Gly Ala Val
    450                 455                 460

Pro Thr Cys Met Ile Leu Ala Gly Leu Cys Ile Leu Met Val Gly Ser
465                 470                 475                 480

Thr Pro Lys Thr Pro Ser Arg Asp Ala Ser Ser Arg Leu Ser Leu Arg
                485                 490                 495

Arg Arg Thr Ser Tyr Ser Leu Ala
            500

<210> SEQ ID NO 23
<211> LENGTH: 551
<212> TYPE: PRT
<213> ORGANISM: Danio rerio

<400> SEQUENCE: 23

Met Asn Thr Ala Val Thr Ser Ser Val Lys Pro Glu Ser Leu Ser Ala
1               5                   10                  15

Val Ser Val Pro Ala Ala Met Ala Lys Gly Glu Lys Ala Arg Val Thr
            20                  25                  30

Ser Gly Asp Lys Leu Met Met Lys His Pro Glu Pro Ala Phe Thr Lys
        35                  40                  45

Val Pro Pro Gln Thr Leu Leu Asp Gln Lys Leu Ser Val Cys Ser Lys
    50                  55                  60

Leu Cys Phe Ala Ile Gly Gly Ala Pro Asn Gln Val Ala Gly Ser Ala
65                  70                  75                  80

Thr Ala Phe Phe Leu Gln Ile Tyr Leu Leu Asp Ile Ala Gln Ile Asn
                85                  90                  95

Pro Phe Gln Ala Ser Met Val Leu Phe Val Gly Lys Ala Trp Gly Ala
            100                 105                 110

Val Thr Asp Pro Ile Val Gly Phe Phe Ile Thr Lys Ser Lys Trp Thr
            115                 120                 125

Lys Ile Gly Arg Leu Met Pro Trp Met Val Gly Cys Thr Pro Phe Met
    130                 135                 140

Val Val Ser Tyr Phe Tyr Leu Trp Phe Val Pro Pro Phe Thr Asn Gly
145                 150                 155                 160

Arg Phe Met Trp Tyr Leu Gly Phe Tyr Cys Leu Tyr Gln Thr Leu Ile
                165                 170                 175

Thr Cys Phe His Val Pro Tyr Ser Ala Leu Thr Met Phe Leu Ser Thr
            180                 185                 190

Asp Gln Arg Glu Arg Asp Ser Ala Thr Ala Tyr Arg Met Thr Val Glu
        195                 200                 205

Val Leu Gly Thr Leu Val Gly Ala Ala Ile Gln Gly Gln Ile Val Ala
```

-continued

```
        210             215             220
Ser Ala His Thr Leu Lys His Cys Pro His Arg Asn Leu Thr Ala Ala
225             230             235             240

His Leu Thr Asn Ser Ser Gly Thr Glu Ile Ile Arg Ser Leu Ala Leu
                245             250             255

Ser Gln Asp Phe Leu Ser His Ala Lys Glu Val Tyr Met Ile Ala Ala
                260             265             270

Gly Val Ile Gly Gly Leu Phe Leu Val Cys Thr Val Val Met Phe Leu
            275             280             285

Gly Val Lys Glu Arg Asp Asp Pro Tyr Ala Pro Lys Thr Asp Lys Ala
            290             295             300

Ile Pro Phe His Lys Gly Phe Ile Leu Val Met Lys His Gly Ser Tyr
305             310             315             320

Leu Thr Leu Thr Ala Ser Phe Leu Phe Ile Ser Val Ala Ile Gln Leu
                325             330             335

Ile Gln Ser Asn Phe Val Leu Phe Cys Thr Tyr Ala Val Glu Leu Arg
                340             345             350

Asp His Phe Gln Asn Ile Val Leu Thr Ile Leu Met Ser Ala Ala Val
                355             360             365

Ser Ile Pro Phe Trp Gln Trp Phe Leu Glu Lys Phe Gly Lys Lys Thr
370             375             380

Ala Ala Phe Cys Gly Ile Thr Trp Ile Met Pro Phe Thr Val Met Leu
385             390             395             400

Val Phe Ile Pro Asn Leu Ile Val Ala Tyr Val Val Ala Val Ser Ser
                405             410             415

Gly Leu Ser Val Ala Ala Ser Leu Leu Leu Pro Trp Ser Met Leu Pro
            420             425             430

Asp Val Val Asp Asp Phe Arg Leu Ala Asn Arg Asn Ser Lys Gly His
            435             440             445

Glu Ala Ile Phe Tyr Ser Leu Tyr Ala Phe Phe Thr Lys Phe Ala Ala
            450             455             460

Gly Ile Ser Leu Gly Val Ser Thr Leu Cys Leu Gln Phe Ala Gly Tyr
465             470             475             480

Asp Thr Gly Ala Cys Arg Gln Pro Leu Pro Val Val Tyr Thr Leu Lys
                485             490             495

Leu Leu Ile Gly Ala Ala Pro Val Ala Cys Ile Thr Thr Gly Leu Met
            500             505             510

Ile Leu Val Val Tyr Pro Ile Ser Glu Asp Val Arg Leu Arg Asn Lys
            515             520             525

Val Ala Leu Glu Glu Leu Arg Lys Gln Ser Ile Thr Cys Lys Thr Leu
            530             535             540

Arg Ala Asp Leu Ser Ser Val
545             550
```

<210> SEQ ID NO 24
<211> LENGTH: 511
<212> TYPE: PRT
<213> ORGANISM: Xenopus laevis

<400> SEQUENCE: 24

```
Met Ala Glu Arg Ser Arg Asp Leu Pro Leu Leu Thr Leu Thr Ser Ser
1               5               10              15

Thr Arg Arg Ala Leu Arg Leu Arg Ala Arg Gln Ala Arg Asp Ala Lys
                20              25              30
```

```
Leu Ser Val Phe Ser Lys Ile Cys Tyr Ala Ile Gly Gly Ala Pro Asn
        35                  40                  45

Gln Val Ser Gly Ser Ala Ser Ala Phe Phe Leu Gln Ile Tyr Leu Leu
    50                  55                  60

Asp Val Ala Leu Ile Ser Pro Tyr Gln Val Ser Leu Val Leu Ser Leu
65                  70                  75                  80

Gly Lys Thr Trp Gly Gly Ile Thr Asp Pro Leu Val Gly Tyr Cys Ile
                85                  90                  95

Asn Lys Ser Lys Trp Thr Arg Ile Gly Arg Leu Met Pro Trp Met Leu
            100                 105                 110

Gly Cys Thr Pro Phe Leu Met Met Ser Tyr Phe Leu Leu Trp Phe Val
            115                 120                 125

Pro Thr Phe Glu Thr Gly Arg Val Val Trp Tyr Leu Ala Phe Phe Cys
    130                 135                 140

Cys Phe Gln Ala Leu Ser Thr Ala Tyr His Val Pro Tyr Thr Ile Leu
145                 150                 155                 160

Thr Met Phe Leu Ser Thr Asp Gln Thr Glu Arg Asp Ser Ala Thr Ala
                165                 170                 175

Tyr Arg Met Thr Val Glu Val Leu Gly Thr Leu Ile Gly Ala Ala Val
            180                 185                 190

Gln Gly Gln Ile Val Ala Ser Ala His Thr Gly Ser Asp Cys His Leu
            195                 200                 205

Thr Asn Gly Thr Gly Asn Leu Thr Ala Asp Phe Pro His Glu Pro Thr
    210                 215                 220

Asp His Ile Thr Ser Ala Arg Gln Val Tyr Met Ile Ala Ala Gly Ile
225                 230                 235                 240

Ile Gly Cys Leu Tyr Leu Leu Cys Thr Ala Val Leu Phe Leu Gly Val
                245                 250                 255

Lys Glu Arg Asp Asp Pro Tyr Ala Leu Val Ala Gly Glu Val Ile Pro
            260                 265                 270

Phe Phe Gln Gly Phe Arg Lys Thr Met Gln Phe Gly Pro Tyr Leu Asn
            275                 280                 285

Leu Ile Ser Ser Phe Leu Leu Ile Ser Ala Ala Val Gln Ile Gln Gln
    290                 295                 300

Ser Asn Phe Val Leu Phe Cys Thr His Ala Ala Asp Leu Gln Asp His
305                 310                 315                 320

Phe Gln Asn Leu Val Leu Thr Ile Leu Ile Ala Ala Val Leu Ser Ile
                325                 330                 335

Pro Phe Trp Gln Trp Phe Leu Gly Lys Phe Gly Lys Lys Ile Ala Ala
            340                 345                 350

Phe Gly Ile Ser Leu Met Ile Pro Phe Ser Ile Met Leu Val Thr Ile
            355                 360                 365

Ser Asn Thr Val Val Ala Tyr Val Val Ala Val Thr Ser Gly Leu Ser
    370                 375                 380

Ile Ala Ala Ser Leu Leu Leu Pro Trp Ser Met Leu Pro Asp Val Val
385                 390                 395                 400

Asp Asn Phe Arg Leu Thr Asn Pro Gln Gly Lys Gly Leu Glu Ala Ile
                405                 410                 415

Phe Tyr Ser Ser Phe Val Phe Phe Thr Lys Leu Ser Ala Gly Ile Ala
            420                 425                 430

Leu Gly Ile Ser Thr Leu Ser Leu Gln Phe Ala Gly Tyr Asp Thr Thr
            435                 440                 445

Leu Cys Lys Gln Ala Tyr Ser Val Val Leu Thr Leu Lys Leu Leu Ile
```

-continued

```
        450               455               460
Gly Ala Val Pro Ala Leu Met Ile Ile Ile Gly Leu Ile Ile Leu Ala
465               470               475               480

Phe Tyr Pro Ile Thr Glu Asp Thr Arg Lys Gln Thr Glu Leu Ala Leu
              485               490               495

Asp Gly Ile Arg Met Arg Thr Arg Arg Ser Thr Leu Ile Val Ile
              500               505               510

<210> SEQ ID NO 25
<211> LENGTH: 515
<212> TYPE: PRT
<213> ORGANISM: Bos taurus

<400> SEQUENCE: 25

Met Gly Ala Glu Leu Leu Cys Leu Pro Gln Asp Ser Gly Ala Gly Arg
1               5               10               15

Leu Ser Phe Tyr Arg Lys Leu Cys Tyr Gly Ile Gly Gly Val Pro Asn
              20               25               30

Gln Val Ala Ser Ser Ala Ile Ala Phe Tyr Leu Gln Leu Phe Leu Leu
        35               40               45

Asp Val Ala Gln Ile Pro Ala Ala Gln Val Ser Leu Val Leu Phe Gly
        50               55               60

Gly Lys Val Ser Gly Ala Ala Ala Asp Pro Leu Ala Gly Phe Leu Ile
65               70               75               80

Asn Arg Ser Arg Arg Thr Gly Ser Gly Arg Leu Met Pro Trp Val Leu
              85               90               95

Gly Cys Met Pro Phe Ile Ala Leu Ala Tyr Phe Phe Leu Trp Phe Leu
              100               105               110

Pro Pro Phe Thr Thr Leu Arg Gly Leu Trp Tyr Thr Thr Leu Tyr Cys
              115               120               125

Leu Phe Gln Ala Leu Ala Thr Phe Phe Gln Val Pro Tyr Thr Ala Leu
        130               135               140

Thr Met Leu Leu Thr Pro Asn Pro Lys Glu Arg Asp Ser Ala Thr Ala
145               150               155               160

Tyr Arg Met Thr Leu Glu Met Ala Gly Thr Leu Met Gly Ala Thr Val
              165               170               175

His Gly Leu Ile Val Ser Gly Ala His Gly Ser His Arg Cys Lys Glu
              180               185               190

Asp Thr Leu Pro Gly Glu Gly Ala Val Ser Pro Asn Ala Thr Arg Leu
              195               200               205

Tyr Phe Ile Ala Ala Thr Val Val Ala Leu Thr Tyr Pro Val Cys Ser
        210               215               220

Thr Leu Leu Tyr Leu Gly Val Lys Glu Arg Ser Asp Pro Ser Thr Pro
225               230               235               240

Ala Ser Gly Gln Gly Leu Gly Phe Leu Ala Gly Leu Gly Leu Thr Val
              245               250               255

Arg His Arg Pro Tyr Leu Asn Leu Val Ile Ser Phe Leu Phe Ile Ser
              260               265               270

Ala Ala Val Gln Val Glu Gln Ser Tyr Leu Val Leu Phe Cys Thr His
        275               280               285

Ala Ser Gln Leu Gln Asp His Val Gln Gly Met Val Leu Thr Ile Leu
        290               295               300

Val Ser Ala Val Leu Ser Thr Pro Met Trp Glu Trp Val Leu Gln Arg
305               310               315               320
```

```
Phe Gly Lys Arg Met Ser Ala Leu Gly Ile Cys Ala Met Val Pro Phe
                325                 330                 335

Ala Ile Leu Leu Ala Ala Val Pro Met Val Pro Val Ala Tyr Val Val
                340                 345                 350

Ala Phe Val Ser Gly Leu Ser Ile Ala Val Ser Leu Leu Leu Pro Trp
                355                 360                 365

Ser Met Leu Pro Asp Val Val Asp Asp Phe Gln Leu Gln His Gln His
        370                 375                 380

Gly Pro Gly Leu Glu Thr Ile Phe Tyr Ser Ser Tyr Val Phe Phe Thr
385                 390                 395                 400

Lys Leu Ser Gly Ala Gly Ala Leu Gly Ile Ser Thr Leu Ser Leu Asp
                405                 410                 415

Phe Ala Gly Tyr Glu Ser Gly Ala Cys Arg Gln Ser Glu Gln Val Val
                420                 425                 430

Val Thr Leu Lys Val Leu Ile Gly Ala Val Pro Thr Ser Met Ile Leu
                435                 440                 445

Ile Gly Leu Cys Ile Leu Met Val Gly Pro Thr Pro Lys Val Pro Ser
        450                 455                 460

Arg Ala Asn Ser Arg Ser Leu Gly Arg Asp Val Glu Ser Ser Val Thr
465                 470                 475                 480

Leu Leu Lys Gly Ala Ala Trp Ala Pro Pro Phe Met Ser Tyr Leu Leu
                485                 490                 495

Thr Ser Gly His Leu Arg Glu Ala Cys Ala Ala Asp Tyr Pro Ala Leu
                500                 505                 510

Gly Asn Leu
        515

<210> SEQ ID NO 26
<211> LENGTH: 499
<212> TYPE: PRT
<213> ORGANISM: Gallus gallus

<400> SEQUENCE: 26

Met Met Met Glu His Arg Leu Ser Val Cys Ser Lys Leu Cys Tyr Ala
1               5                   10                  15

Ile Gly Gly Ile Pro Asn Gln Val Ala Gly Ser Ala Ala Ser Phe Ser
                20                  25                  30

Leu Gln Ile Tyr Leu Leu Asp Ile Ala Arg Ile Thr Pro Phe His Ala
        35                  40                  45

Ser Leu Val Leu Phe Ile Gly Lys Ala Ser Gly Ala Val Ser Asp Pro
        50                  55                  60

Val Ala Gly Phe Phe Ile Ser Lys Ser Arg Trp Arg Lys Ile Gly Arg
65                  70                  75                  80

Leu Met Pro Trp Met Leu Ala Cys Thr Pro Phe Ile Val Val Ser Tyr
                85                  90                  95

Phe Phe Met Trp Tyr Leu Pro Pro Phe Val Thr Gly Arg Val Val Trp
                100                 105                 110

Tyr Leu Ile Phe Tyr Cys Ile Phe Gln Ala Leu Thr Thr Leu Phe Gln
        115                 120                 125

Val Pro Tyr Ser Ala Leu Thr Met Phe Leu Ser Thr Asp Gln Lys Glu
        130                 135                 140

Arg Asp Ser Ala Thr Ala Tyr Arg Met Thr Met Glu Val Leu Gly Thr
145                 150                 155                 160

Leu Val Gly Ala Ala Leu Gln Gly Arg Ile Val Ala Ser Ala His Leu
                165                 170                 175
```

-continued

```
Ser Gln Tyr Cys Thr Trp Asn Pro Pro Leu Asn Ile Thr Asp Pro Thr
            180                 185                 190

Tyr Ser Leu His Asn Thr Ser Asp Phe Ser Glu Pro Ser Asp Pro Leu
        195                 200                 205

Ser His Gln Ala Lys Val Tyr Met Ile Ala Ala Gly Val Ile Gly Gly
    210                 215                 220

Met Tyr Leu Leu Gly Ile Ile Ile Leu Phe Leu Gly Val Lys Glu Lys
225                 230                 235                 240

Asp Asp Pro Tyr Ala Leu Ser Ser Asp Arg Ala Ile Pro Phe Cys Lys
                245                 250                 255

Gly Leu Gly Leu Thr Met Lys His Gly Pro Tyr Val Lys Leu Ala Ala
            260                 265                 270

Ser Phe Leu Leu Ile Ser Thr Ala Val Gln Ile Glu Gln Ser Asn Phe
        275                 280                 285

Ile Leu Phe Cys Thr Gln Ala Ala Asp Leu His Tyr His Phe Gln Tyr
    290                 295                 300

Leu Val Val Thr Ile Leu Val Ser Ala Val Val Ser Ile Pro Phe Trp
305                 310                 315                 320

Gln Lys Phe Leu Gln Arg Phe Gly Lys Lys Ser Ala Ala Cys Gly Ile
            325                 330                 335

Ser Trp Met Ile Pro Phe Ala Val Met Leu Val Thr Ile Pro Asn Pro
            340                 345                 350

Ile Leu Ala Tyr Phe Val Ala Phe Val Ser Gly Val Ser Ile Ala Ala
            355                 360                 365

Ser Leu Leu Leu Pro Trp Ser Met Leu Pro Asp Val Ala Asp Asn Phe
    370                 375                 380

His Val Lys Asn Pro Tyr Arg Lys Gly His Glu Thr Ile Phe Tyr Ser
385                 390                 395                 400

Ser Tyr Val Phe Phe Thr Lys Met Ser Ala Gly Ile Gly Leu Gly Ile
            405                 410                 415

Ser Ala Ala Cys Leu Glu Phe Thr Gly Tyr Glu Pro Gly Ile Cys Arg
            420                 425                 430

Gln Ser Lys Asp Val Ile Leu Thr Leu Lys Ile Leu Val Gly Gly Val
        435                 440                 445

Pro Ala Val Leu Ile Leu Val Gly Leu Phe Ile Leu Leu Phe Tyr Pro
    450                 455                 460

Ile Thr Glu Glu Ser Arg Lys Glu Thr Asn Leu Glu Leu Glu Gln Leu
465                 470                 475                 480

Arg Arg Ser His Gln Ser Pro Glu Asn Leu Asp Asp His Arg Glu Asp
                485                 490                 495

Thr Ser Val
```